United States Patent
Yu et al.

(10) Patent No.: US 6,774,134 B2
(45) Date of Patent: Aug. 10, 2004

(54) HETEROCYCLIC SUBSTITUTED 2-METHYL-BENZIMIDAZOLE ANTIVIRAL AGENTS

(75) Inventors: Kuo-Long Yu, Zionsville, IN (US); Rita L. Civiello, Killingworth, CT (US); Keith D. Combrink, Wallingford, CT (US); Hatice Belgin Gulgeze, Middletown, CT (US); Ny Sin, Meriden, CT (US); Xiangdong Wang, Guilford, CT (US); Nicholas Meanwell, East Hampton, CT (US); Brian Lee Venables, Milford, CT (US); Yi Zhang, Evansville, IN (US); Bradley C. Pearce, East Hampton, CT (US); Zhiwei Yin, Meriden, CT (US); Jan Willem Thuring, Hamden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 98 days.

(21) Appl. No.: 09/994,012

(22) Filed: Nov. 16, 2001

(65) Prior Publication Data

US 2002/0099208 A1 Jul. 25, 2002

Related U.S. Application Data

(60) Provisional application No. 60/257,139, filed on Dec. 20, 2000.

(51) Int. Cl.$^7$ ................. A61K 31/4709; C07D 401/06
(52) U.S. Cl. ................. 514/312; 546/153; 546/155; 546/157
(58) Field of Search ................. 546/153, 155, 546/157; 514/312

(56) References Cited

U.S. PATENT DOCUMENTS

| | | |
|---|---|---|
| 3,394,141 A | 7/1968 | Sparatore |
| 4,324,794 A | 4/1982 | Tidwell et al. |
| 5,256,668 A | 10/1993 | Hsu et al. |

FOREIGN PATENT DOCUMENTS

| | | |
|---|---|---|
| AU | A-14704 | 12/1998 |
| EP | 058146 A1 | 8/1982 |
| WO | WO 00/04900 | 2/2000 |
| WO | WO 00/38508 | 7/2000 |
| WO | WO 01/00611 | 1/2001 |
| WO | WO 01/00612 | 1/2001 |
| WO | WO 01/00615 | 1/2001 |
| WO | WO 01/36395 | 5/2001 |

OTHER PUBLICATIONS

E. J. Dubovi, et al, Antimicrobial Agents and Chemotherapy, 19(4), pp. 649–656, 1981.
P. R. Wyde, et al, Antiviral Research, 38, pp. 31–42, 1998.
F. Pagani, et al, Boll. Chim. Farm., 104, pp. 427–431, 1965.
G. Paglietti, et al, IL. Farmaco–Ed. Sc., 30, pp. 505–511, 1975.
S. Shigeta, et al, Antiviral Chemistry & Chemotherapy, 3(3), pp. 171–177, 1992.
W. R. Roderick, et al, J. Med. Chem., 15(6), pp. 655–658, 1972.
B. Cakir, et al, Gazi Eczacilik Fak. Der., 5(1), pp. 71–77, 1988.
H. R. Howard, et al, Eur. J. Med. Chem., 27, pp. 779–789, 1992.
F. Sparatore, et al, Il Farmaco Ed. Sci., 33, pp. 901–923, 1978.
Jama, 277(1), pp. 12–13, 1997.
E. De Clercq, Int. J. Antimicrobial Agents, 7, pp. 193–202, 1996.
R. R. Tidwell, et al, J. Med. Chem., 26, pp. 294–298, 1983.

*Primary Examiner*—Joseph K. McKane
*Assistant Examiner*—Rebecca Anderson
(74) *Attorney, Agent, or Firm*—Samuel J. DuBoff

(57) ABSTRACT

The present invention concerns antiviral compounds, their methods of preparation and their compositions, and use in the treatment of viral infections. More particularly, the invention provides heterocyclic substituted 2-methylbenzimidazole derivatives for the treatment of respiratory syncytial virus infection.

7 Claims, No Drawings

HETEROCYCLIC SUBSTITUTED 2-METHYL-BENZIMIDAZOLE ANTIVIRAL AGENTS

This application claims the benefit under 35 USC 119(e) of U.S. Provisional Application No. 60/257,139 filed Dec. 20, 2000.

BACKGROUND OF THE INVENTION

1. Field of the Invention

The present invention concerns antiviral compounds, their methods of preparation and their compositions, and use in the treatment of viral infections. More particularly, the invention provides heterocyclic substituted 2-methylbenzimidazole derivatives for the treatment of respiratory syncytial virus infection.

2. Background Art

Respiratory syncytial virus (RSV) is the leading cause of serious lower respiratory tract infection in infants, children, elderly and immunocompromised persons. A severe viral infection may result in bronchiolitis or pneumonia which may require hospitalization or result in death. (*JAMA*, 1997, 277, 12). Currently only Ribavirin is approved for the treatment of this viral infection. Ribavirin is a nucleoside analogue which is administered intranasally as an aerosol. The agent is quite toxic, and its efficacy has remained controversial. RespiGam, approved for prophylaxis in high risk pediatric patients, is an intravenous immunoglobulin which effectively neutralizes the virus. Recently, Synagis, a monoclonal antibody administered through intramuscular injection has also been approved for use in high risk pediatric patients. However, both drugs are very expensive. Accordingly, inexpensive, safe and effective antiviral agents against respiratory syncytial virus will be beneficial for patients.

Many agents are known to inhibit respiratory syncytial virus (De Clercq, *Int. J. Antiviral Agents*, 1996, 7, 193). Y. Tao et al. (EP 0 058 146 A1, 1998) disclosed that Ceterizine, a known antihistamine, exhibited anti-RSV activity. Tidwell et al., *J. Med. Chem.* 1983, 26, 294 (U.S. Pat. No. 4,324,794, 1982), and Dubovi et al., *Antimicrobial Agents and Chemotherapy*, 1981, 19, 649, reported a series of amidino compounds with the formula shown below as inhibitors of RSV.

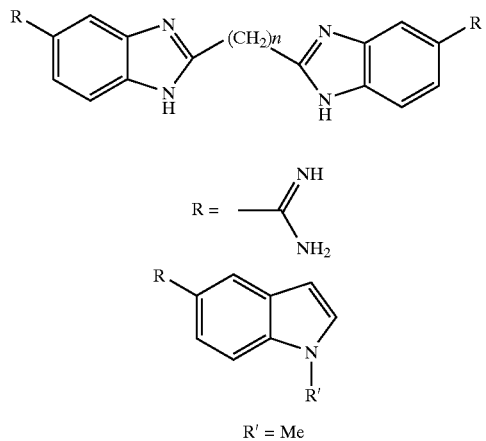

Hsu et al., U.S. Pat. No. 5,256,668 (1993) also disclosed a series of 6-aminopyrimidones that possess anti-viral activity against RSV.

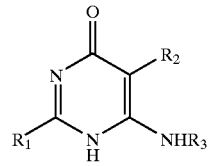

Y. Gluzman, et al., (AU Patent, Au-A-14,704, 1997) and P. R. Wyde et al. (*Antiviral Res.* 1998, 38, 31) disclosed a series of triazine containing compounds that were useful for the treatment and/or prevention of RSV infection.

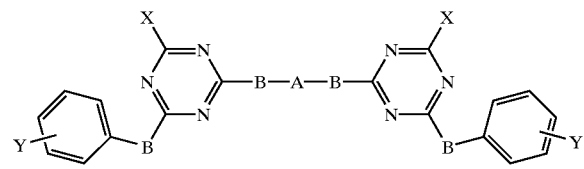

In addition, T. Nitz, et al., (WO Patent, WO 00/38508, 1999) disclosed a series of triaryl containing compounds that were useful for the treatment and/or prevention of RSV and related pneumoviral infections.

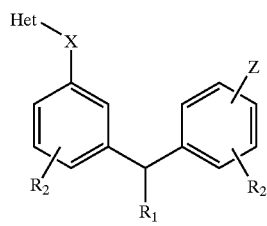

Moreover, Yu et al. (WO 020004900) also disclosed a series of substituted benzimidazoles that is useful for the treatment and prevention of RSV infection.

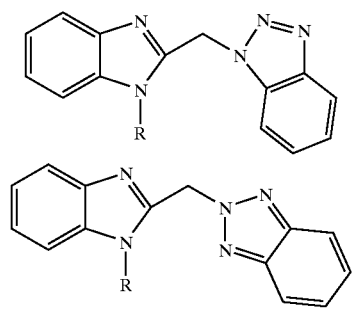

A related series of compounds were first disclosed by F. Pagani and F. Sparatore in *Boll Chim Farm.* 1965, 104, 427 and by G. Paglietti, et al. in *Il Farmaco, Ed. Sci.* 1975, 30, 505, and found to possess analgesic and anti-arrhythmic activity. The structural formula for these compounds are depicted in Formula Ia and Ib.

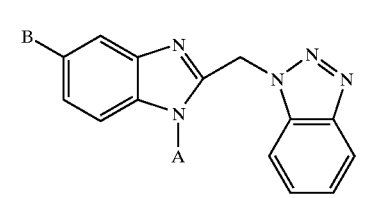
Formula Ia

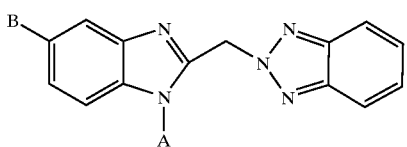
Formula Ib

In Formula Ia and Ib, A is —(CH$_2$)n-N(R)$_2$, n=2 or 3, R=Me or Et, or A is

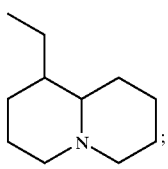

B=H, Cl, CF$_3$, CH$_3$CO, NO$_2$.

Another series of closely related compounds that Sparatore had disclosed were in *Il Farmaco Ed. Sci.* 1967, 23, 344 (U.S. Pat. No. 3,394,141, 1968). Some of the compounds were reported to have analgesic, anti-inflammatory or antipyretic activities. The structure of these compounds is depicted in Formula Ic. In Formula Ic, C=H, CF$_3$, or NO$_2$. D is —(CH$_2$)n-NR$_2$, n=2 or 3, R=Me or Et, or D=

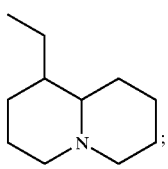

E is H, Cl or OEt.

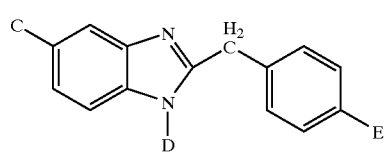
Formula Ic

Another series of compounds structurally related to this invention are pyrido[1,2-a]benzoazoles and pyrimidio[1,2a] benzimidazoles disclosed by S. Shigeta et al in *Antiviral Chem. & Chemother.* 1992, 3, 171. These compounds have demonstrated inhibition of orthomyxovirus and paramyxovirus replication in HeLa cells. The structures of these compounds are shown in Formulas Id and Ie, in which F=NH, S, or O; Q=—NHCOPh, —COOH, COOEt, or CN; T=COMe, CN, or COOEt; G=O or NH.

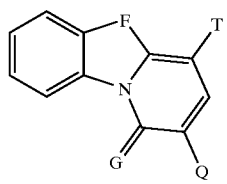
Formula Id

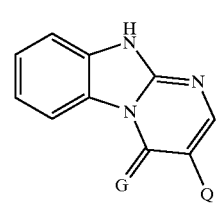
Formula Ie

A bis-benzimidazole with an ethylenediol linker shown below has also been reported as a potent inhibitor of rhinoviruses (Roderick, et al. *J. Med. Chem.* 1972, 15, 655).

A series of 2-aminobenzimidazoles have been reported by E. Janssens, et al. as inhibitors of RSV in a series of recent publications and representative examples formula 1f–1h are shown below from PCT WO 01/00611 A1; PCT WO 01/00612 and PCT WO 01/00615, respectively all published on Jan. 4, 2001.

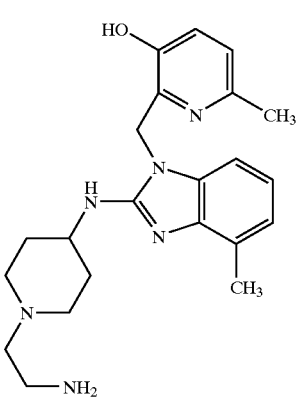
Formula 1f

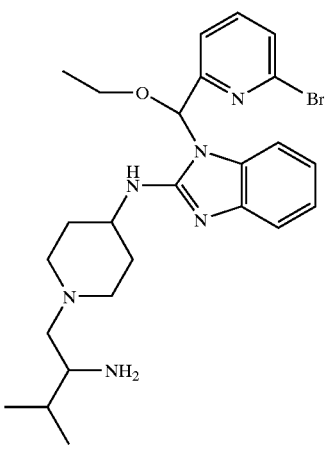
Formula 1g

Formula 1h

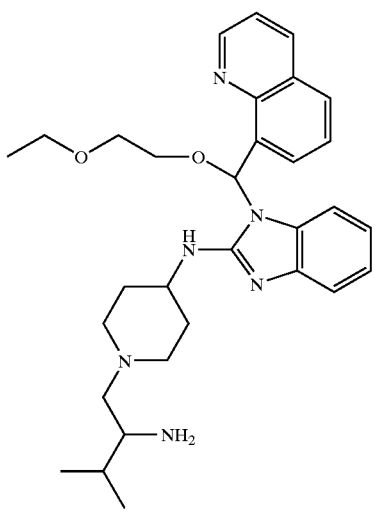

A series of triazole containing compounds have been reported by Janssen as inhibitors of RSV in PCT WO 01/36395 (May 25, 2001) and a representative example is shown below.

Formula 1i

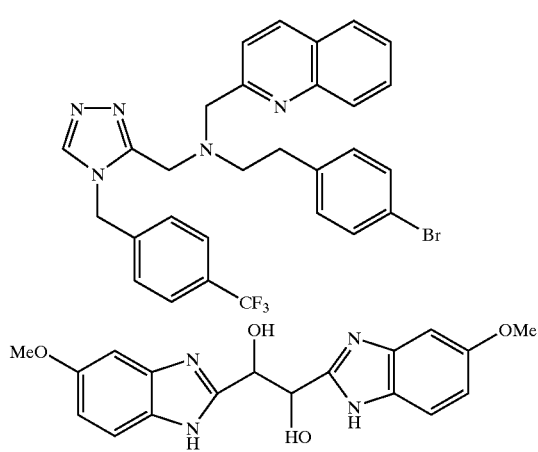

Other structurally related compounds are bis-benzimidazoles which possess antifungal activity (B. Cakir, et al. *Eczacilik Fak. Derg.* 1988, 5, 71).

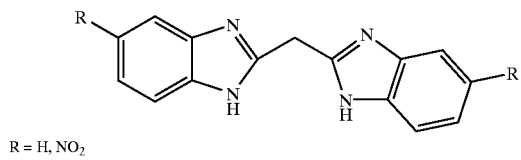

Also, H. R. Howard et al. reported a series of benzimidazolone-1-acetic acids that possessed aldolase reductase inhibitory activity (*Eur. J. Med. Chem.* 1992, 27, 779–789).

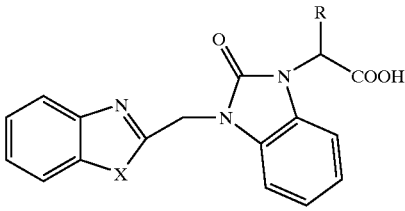

X = O, S

Other prior art related to the chemical structure of the present invention:

(1) F. Sparatore, et al, "Derivati Benzotriazolici Attivi Sull'accrescimento Delle Piante," *Il Farmaco Ed. Sci.* 1978, 33, 901.
(2) Katritzky, A. R. et al, "Synthesis and Transformations Of Substituted Benzazolyl- and Tetrazolyl(benzotriazol-1-yl) methanes," *J. Heterocyclic Chem.* 1996, 33, 1107.
(3) Terri A. Fairley, et al. "Structure, DNA Minor Groove Binding, And Base Pair Specificity of Alkyl and Aryl-Linked Bis(amidinobenzimidazoles) and Bis (amidinoindoles), *J. Med. Chem.* 1993, 36, 1746.
(4) R. K. Upadhyay et al, "New Synthesis and Biological Evaluation," *Indian J. Heterocyclic Chem.* 1994, 4, 121.
(5) A. R. Katritzky, et al, "A New Route to N-substituted Heterocycles," *Tetrahedron*, 1993, 49, 2829.
(6) K. Yu et al. in Substituted Benzimidazole Anti-viral Agents, PCT WO00/04900 published Feb. 3, 2000.

SUMMARY OF THE INVENTION

This invention relates to novel heterocyclic substituted 2-methylbenzimidazoles and the antiviral activity against RSV. The structural formula for these compounds are depicted in Formula I, and includes pharmaceutically acceptable salts thereof, Formula I

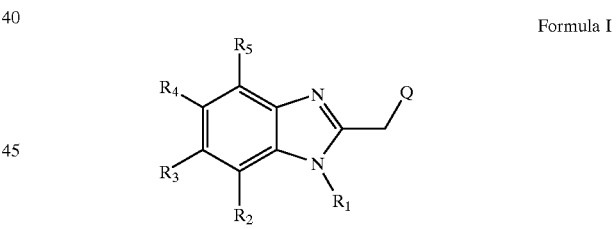

wherein:

$R_1$ is $-(CR^aR^b)_n-X$;

$R^a$, $R^b$ are each independently selected from the group consisting of H, $C_{1-6}$ alkyl; each of said $C_{1-6}$ alkyl being optionally substituted with one to six same or different halogen;

X is H or $C_{1-6}$ alkyl; said $C_{1-6}$ alkyl being optionally substituted with a member selected from the group consisting of (1) one to six same or different halogen or hydroxy, (2) heteroaryl, (3) non-aromatic heterocyclic ring and (4) a member selected from Group A;

n is 1–6;

Group A is a member selected from the group consisting of halogen, CN, $OR^x$, $N^+R^cR^dR^e[T^-]$, $NR^cR^d$, $COR^c$, $CO_2R^x$, $CONR^xR^y$ and $S(O)_mR^c$;

$R^x$ and $R^y$ are independently H or $C_{1-6}$ alkyl;

$R^c$, $R^d$ and $R^e$ are independently $C_{1-6}$ alkyl;

m is 0–2

$T^-$ is halogen, $CF_3SO_3^-$ or $CH_3SO_3^-$;

$R_2$ and $R_5$ are independently halogen or H;

$R_3$ and $R_4$ are each independently selected from the group consisting of H, halogen and $C_{1-6}$ alkyl; said $C_{1-6}$ alkyl can be optionally substituted with one to six same or different halogen;

Q is a member selected from the group consisting of

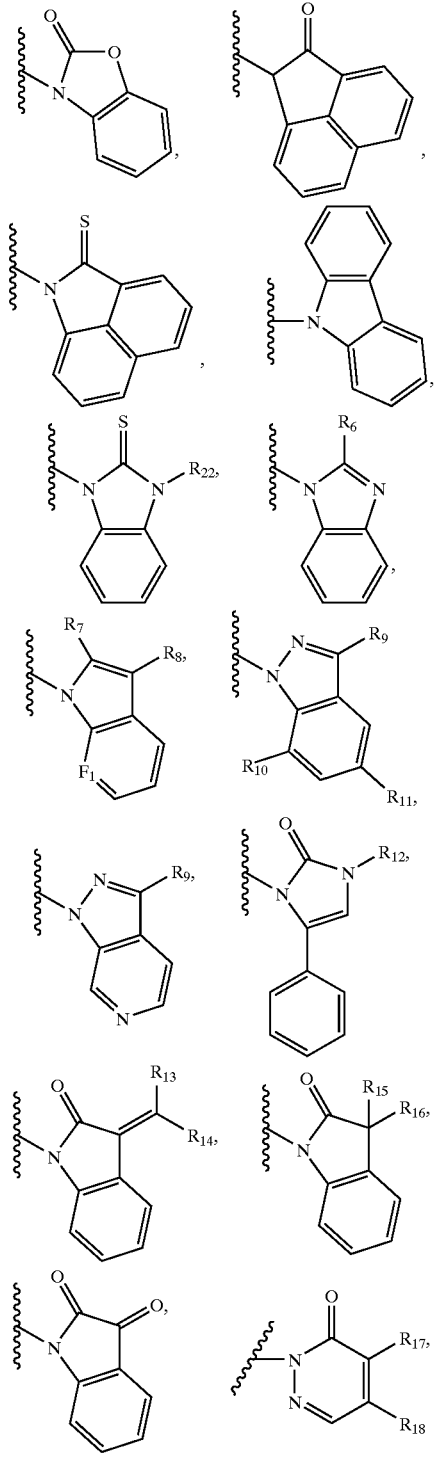

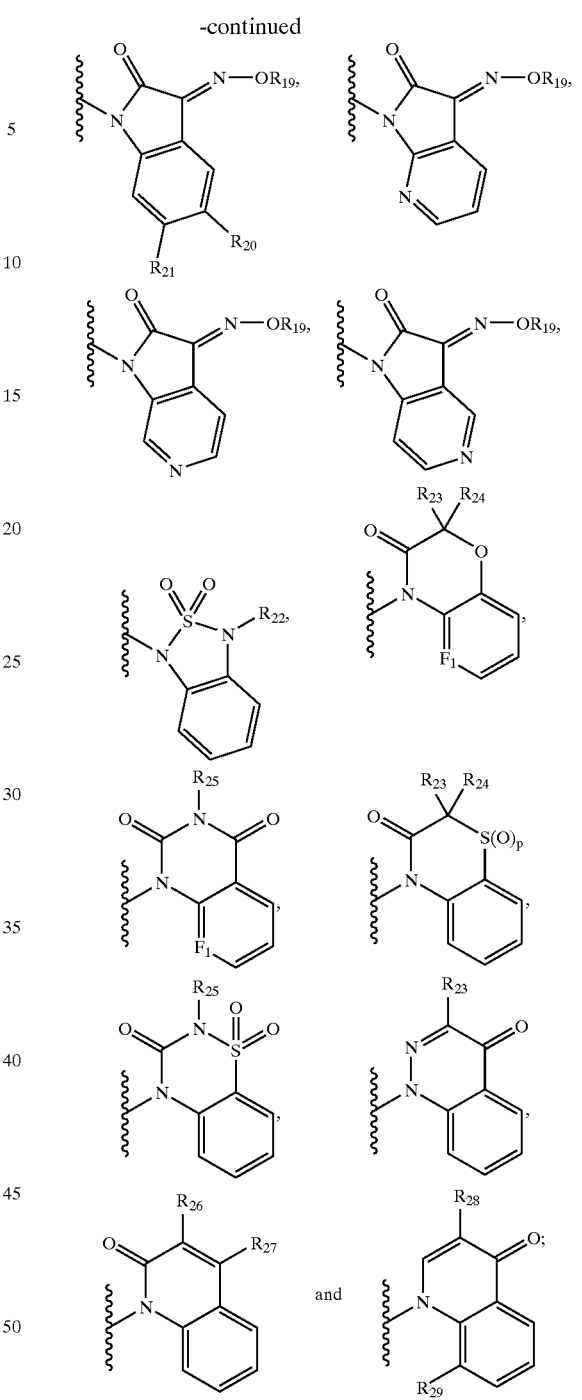

$F_1$ is CH or N;

$R_6$ is selected from the group consisting of H, halogen, $NR^fR^g$, $SR^n$ and a five-membered heteroaryl containing one to two of the same or different heteroatoms selected from the group consisting of O, S and N;

$R^f$ and $R^g$ are independently H, $C_{1-6}$ alkyl or $C_{1-6}$ alkyl; said $C_{1-6}$ alkyl optionally substituted with $OR^h$ or $CO_2R^h$;

$R^h$ and $R^i$ are independently H or $C_{1-6}$ alkyl;

$R^n$ is $C_{1-6}$ alkyl optionally substituted with $CO_2R^h$;

$R_7$ is H, or $CO_2R^h$;

$R_8$ is H, $COR^h$, $CO_2R^h$ or $C_{1-6}$ alkyl; said $C_{1-6}$ alkyl optionally substituted with $OR^h$;

$R_9$ is H, halogen, heteroaryl, phenyl, phenyl substituted with a halogen group, phenyl substituted with a methanesulfonyl group, $COR^h$, $CO_2R^h$, $C_{1-6}$ alkyl, $C_{2-6}$ alkenyl, and $C_{2-4}$ alkynyl; said $C_{2-4}$ alkynyl optionally substituted with $C_{1-6}$ cycloalkyl;

$R_{10}$ and $R_{11}$ are independently H, $NO_2$ or $NR^hR^i$;

$R_{12}$ is H, $CO_2R^h$ or $C_{1-2}$ alkyl; said $C_{1-2}$ alkyl optionally substituted with phenyl;

$R_{13}$ and $R_{14}$ are independently selected from the group consisting of H, $OR^h$, $CONR^jR^k$, $NR^lR^m$ and pyrrolidine; wherein said pyrrolidine is attached at the nitrogen atom;

$R^j$ and $R^k$ are independently H or $C_{1-6}$ alkyl optionally substituted with phenyl;

$R^l$ and $R^m$ are independently $C_{1-6}$ alkyl;

$R_{15}$ and $R_{16}$ are independently selected from the group consisting of H, $OR^h$, phenyl, pyridyl and $C_{1-6}$ alkyl; said $C_{1-6}$ alkyl optionally substituted with $CO_2R^h$;

$R_{17}$ and $R_{18}$ are independently selected from the group consisting of halogen, $NR^lR^m$, $SR^h$ and morpholine; wherein said morpholine is attached at the nitrogen atom;

$R_{19}$ is selected from the group consisting of H, phenyl, $C_{2-6}$ alkenyl and $C_{1-6}$ alkyl; said $C_{1-6}$ alkyl optionally substituted with one to six same or different halogen, $CO_2R^h$, $CONR^hR^i$, pyridyl and one to three phenyl groups; wherein in the case of $C_{1-6}$ alkyl substituted with one phenyl group, said phenyl group is optionally substituted with a member selected from the group consisting of halogen, $PO(OR^h)_2$, $CO_2R^h$, $SO_2R^n$ and $CONR^hR^i$;

$R^n$ is $C_{1-6}$ alkyl;

$R_{20}$ and $R_{21}$ are independently H or halogen;

$R_{22}$ is $C_{1-6}$ alkyl;

$R_{23}$ and $R_{24}$ are independently H or $C_{1-6}$ alkyl;

$R_{25}$ is $C_{1-6}$ cycloalkyl or $C_{1-6}$ alkyl; said $C_{1-6}$ alkyl group optionally substituted with a member selected from the group consisting of $CO_2R^h$, $PhCO_2R^h$ and one to six same or different halogens;

$R_{26}$ is selected from the group consisting of H, halogen, $C_{1-6}$ alkyl; $C_{2-6}$ alkenyl, $OR^h$ and $COR^h$; said $C_{2-6}$ alkenyl being optionally substituted with $OR^h$;

$R_{27}$ is H, $OR^h$ or $CO_2R^h$;

$R_{28}$ is $CO_2R^h$;

$R_{29}$ is H or halogen;

heteroaryl is a 5- or 6-membered aromatic ring containing at least one and up to four non-carbon atoms selected from the group consisting of O, N and S;

non-aromatic heterocyclic ring is a 3 to 7-membered non-aromatic ring containing at least one and up to four non-carbon atoms selected from the group consisting of O, N and S; and p is 0–2.

In a preferred embodiment, heteroaryl is selected from the group consisting of pyridyl, thiazolyl, 1,2,3-oxadiazolyl, 1,2,4-oxadiazolyl, 1,2,4-oxadiazol-5-one and tetrazole.

In another preferred embodiment, non-aromatic heterocyclic ring is selected from the group consisting of pyrrolidine and piperidine.

$R^a$ and $R^b$ are hydrogen.

In another preferred embodiment, $R_1$ is —$(CH_2)_n$—X and n is 2–4.

In another preferred embodiment, $R_3$ and $R_4$ are each independently selected from the group consisting of H, fluorine and $C_{1-2}$ alkyl; said $C_{1-2}$ alkyl being optionally substituted with one to three fluorine atoms.

In another preferred embodiment $R_1$ is 3-methyl-2-butyl or —$(CH_2)_n$—X wherein n is 2–4;

X is a member selected from the group consisting of —F, —CN, —$SR^c$, $SO_2R^c$, —$OR^x$, —$COR^c$, $CO_2R^x$, $CONR^xR^y$, $[NR^cR^dR^e][T^-]$,

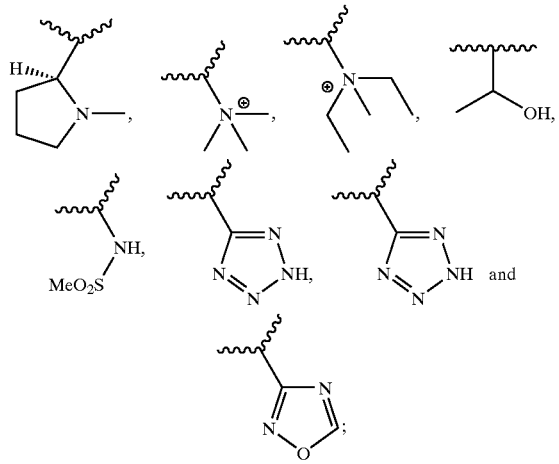

$R^c$, $R^d$ and $R^e$ are independently $C_{1-4}$ alkyl; and $R^x$ and $R^y$ are independently H or $C_{1-4}$ alkyl.

In another preferred embodiment, $R_2$ and $R_5$ are independently H.

Another preferred embodiment includes a pharmaceutical composition which comprises a therapeutically effective amount of one or more of the aforementioned compounds of Formula I, including pharmaceutically acceptable salts thereof, and a pharmaceutically acceptable carrier.

Another preferred embodiment includes method for treating mammals infected with RSV, and in need thereof, which comprises administering to said mammal a therapeutically effective amount of a compound of Formula I, including pharmaceutically acceptable salts thereof.

The term pharmaceutically acceptable salt includes solvates, hydrates, acid addition salts and quarternary salts. The acid addition salts are formed from a compound of Formula I and a pharmaceutically acceptable inorganic acid including but not limited to hydrochloric, hydrobromic, sulfuric, phosphoric, methanesulfonic, acetic, citric, malonic, fumaric, maleic, sulfamic, or tartaric acids. Quaternary salts include chloride, bromide, iodide, sulfate, phosphate, methansulfonate, citrate, acetate, malonate, fumarate, sulfamate, and tartrate.

Halogen means bromine, chlorine, iodine and fluorine.

DETAILED DESCRIPTION OF THE INVENTION

Compounds of Formula I may be prepared using the procedures outlined in Schemes I–X.

Compounds of Formula I can be prepared as shown in Scheme I. Treatment of substituted or unsubstituted 2-hydroxymethylbenzimidazole Ia with thionyl chloride provides 2-chloromethylbenzimidazole Ib. Coupling of chloride Ib with a heterocycle in the presence of base, preferred cesium carbonate, sodium hydride, or phosphazene base such as BTPP gives compounds of Formula I.

Scheme I

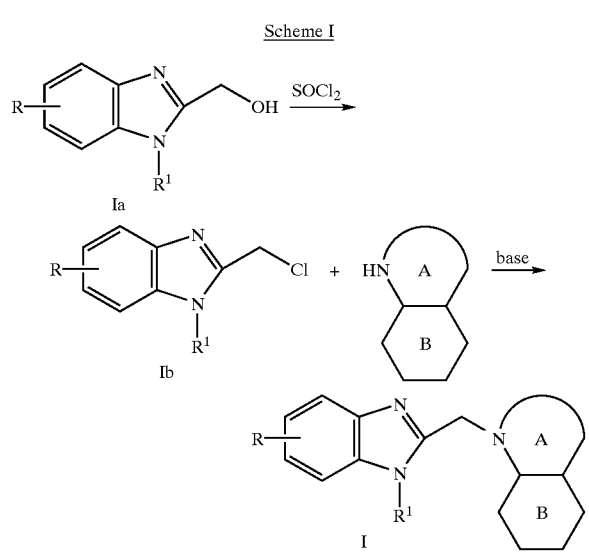

The synthesis of compounds of Formula Ia is described in Schemes Ia and Ib. Coupling of substituted or unsubstituted 2-fluoro-nitrobenzene (III) with an appropriate amine followed by reduction under catalytic hydrogenation conditions gives diamines of Formula IV. Cyclization of diamine IV with glycolic acid in 4–6 N HCl gives compounds of Formula Ia (Scheme Ia). Alternatively, a diamine of Formula V can be cyclized with glycolic acid in 4–6 N HCl to give 2-hydroxymethyl benzimidazole VI which is treated with base preferably cesium carbonate or sodium hydride followed by the addition of an appropriate halide to give compound Ia (Scheme Ib).

Scheme Ia

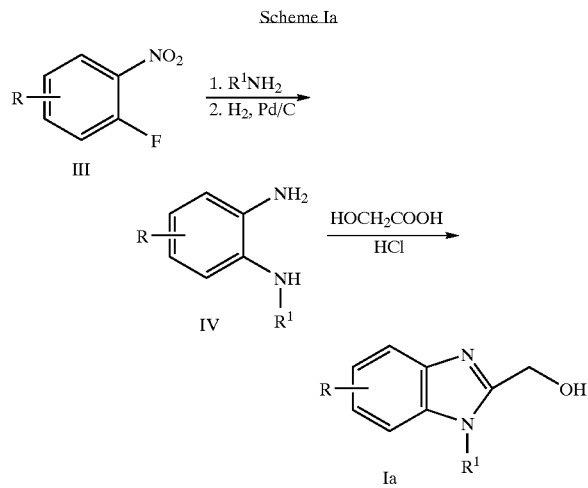

Scheme Ib

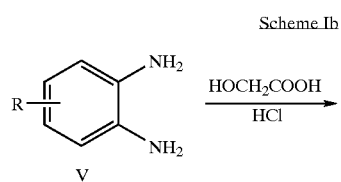

Compounds of Formula I can also be prepared as shown in Scheme II. Coupling of the mesylate VII and an appropriate heterocycle in the presence of base such as sodium hydride or BTPP followed by cleavage of the mesylate with tetrabutylammonium fluoride or hydrazine gives intermediate VIII. Alkylation of compound VIII with an appropriate halide in the presence of base such as sodium hydride, BTPP or cesium carbonate gives compound of Formula I. Alternatively, compounds of Formula I can be obtained through a Michael addition of VIII with acrylonitrile, methyl vinyl ketone, or methyl vinyl sulfone.

Scheme II

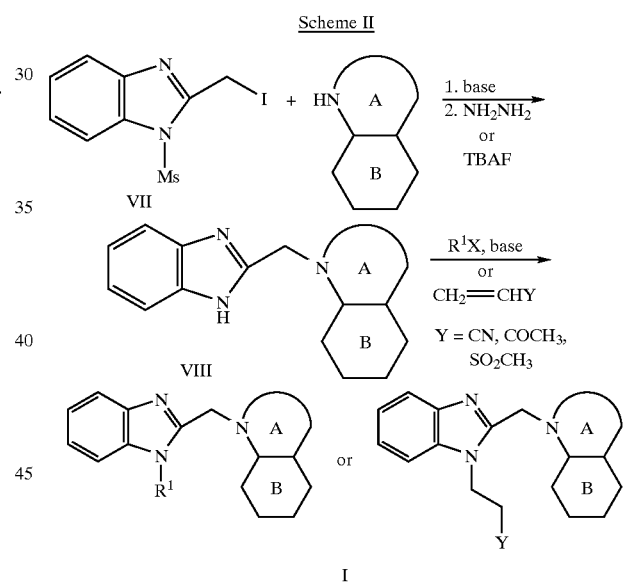

The compound VII can be prepared using the reaction sequence depicted in Scheme Ia. In Scheme IIa, 2-chloromethylbenzimidazole reacts with methanesulfonyl chloride (MsCl) and triethylamine to give compound of Formula VIIa. The chloride can be refluxed with potassium iodide in acetone to produce the compound of Formula VII, as described in PCT WO 00/04900.

Scheme IIa

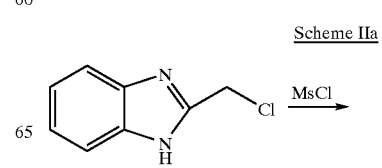

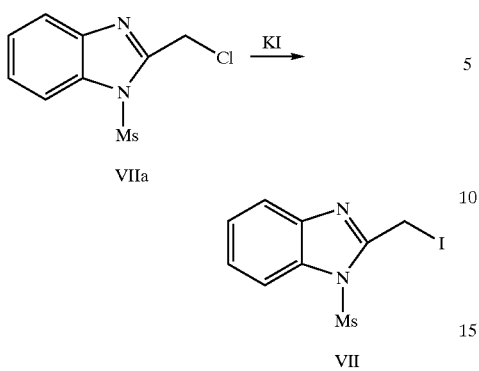

Alternatively, compounds of Formula I can be obtained through Mitsunobu coupling of Ia with an appropriate heterocycle in the presence of tributylphosphine and 1,1'-(azodicarbonyl)dipiperidine (ADDP) as depicted in Scheme III.

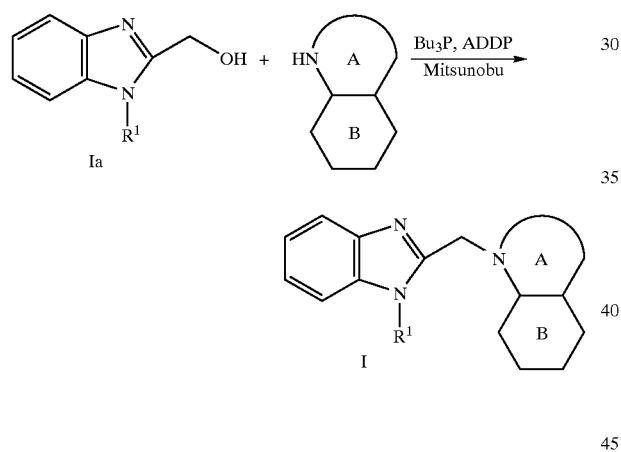

In a different approach, compounds of Formula I were prepared using the synthetic route illustrated in Scheme IV. The diamine IV is first coupled either with acid IXa through an amide coupling reagent such as EDAC and HOBT or 2-chloro-1-methyl pyridinium iodide or with acid chloride IXb in the prescence of base. The crude intermediate is directly cyclized to the benzimidazole in refluxing acetic acid providing compounds of Formula I.

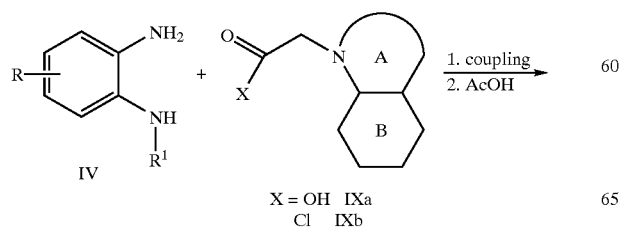

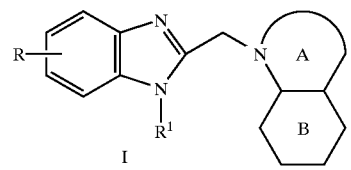

Scheme IVa describes the synthesis of compounds of formulas IXa and IXb. An appropriate heterocycle is alkylated with either t-butyl bromoacetate or ethyl bromoacetate followed by hydrolysis of the ester with trifluoroacetic acid or sodium hydroxide gives acid IXa. Conversion of the acid to the acid chloride with thionyl chloride or oxalyl chloride provides a compound of Formula IXb.

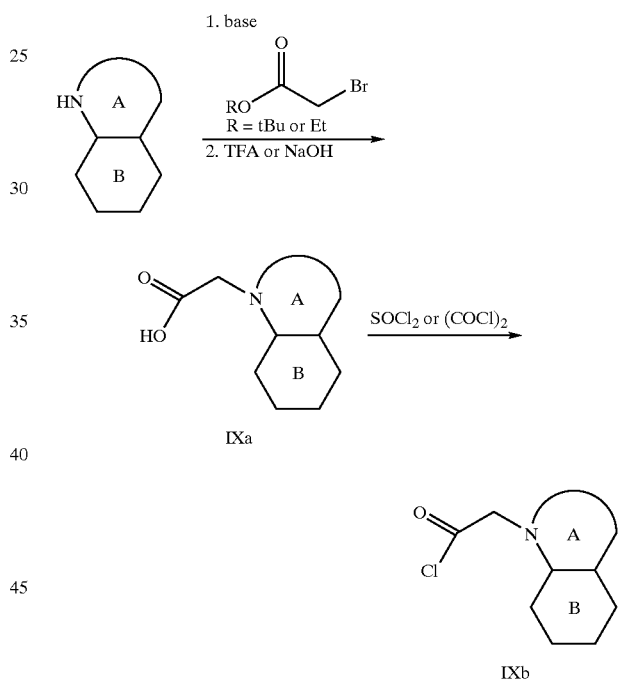

Some compounds of Formula I can be further derivatized with a specific example being the isatin and oxime series. Derivative compounds of Formula XII can be prepared as outlined in Schemes V, VI, and VII.

In Scheme V, chloride Ib reacts with isatin in the presence of a base, such as sodium hydride or BTPP, to give compounds of Formula X. The isatin derivative X and an appropriate hydroxylamine are refluxed with an acid catalyst to provide oximes of Formula XII. The chloride Ib also can react directly with an oxime of Formula XI to afford compounds of Formula XII.

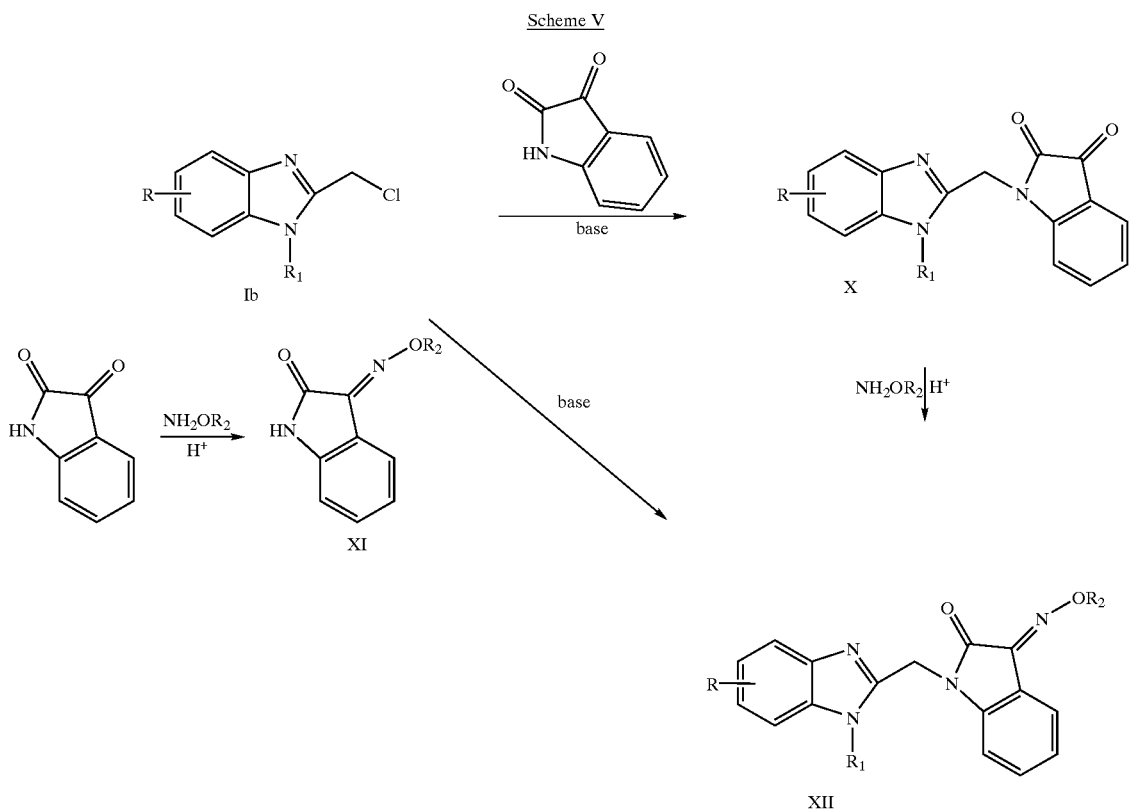

Alternatively, phenylenediamine of Formula IV was coupled to an isatin or oxime acetyl chloride of Formula XIIIa or XIIIb, followed by ring closure in refluxing acetic acid to provide compounds of Formula X or XII (Scheme VI). The corresponding isatin or oxime acetyl chloride intermediates XIIIa or XIIIb were synthesized using standard procedures as shown in Scheme VIa.

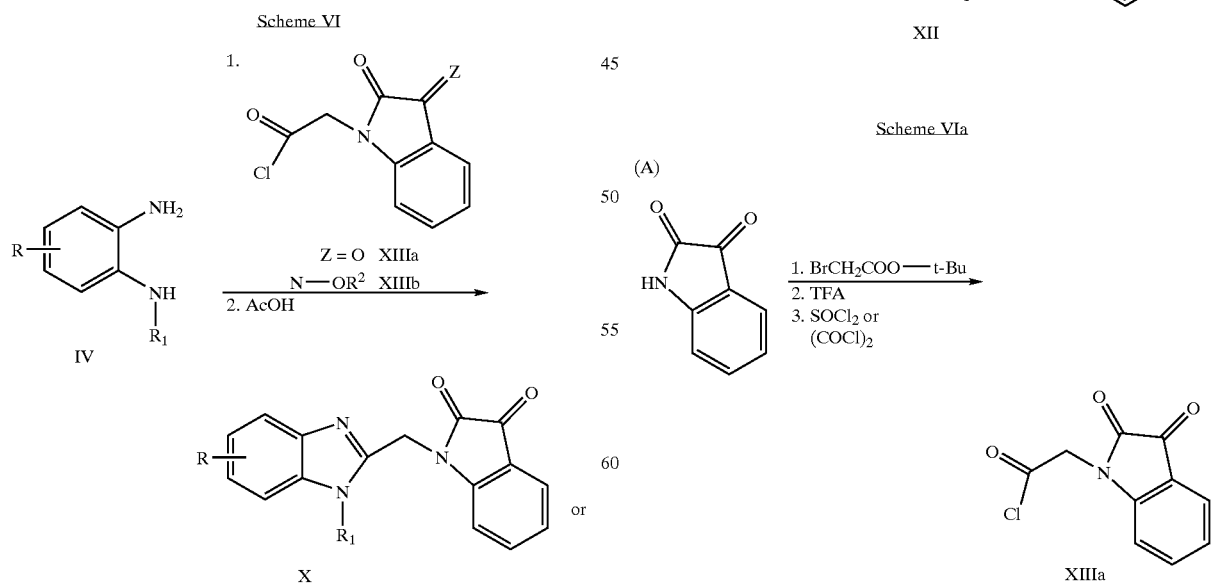

(B)

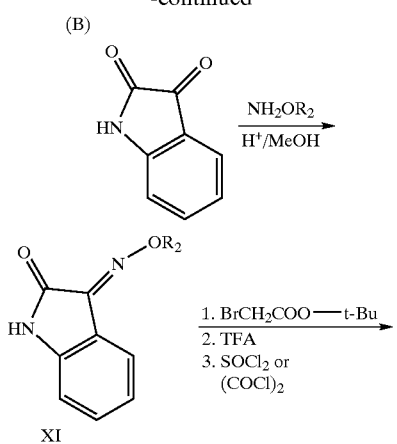

In an alternative approach depicted in Scheme VII, isatin is refluxed with O-tritylhydoxylamine. The resulting oxime XIV is coupled to chloride Ib and subsequently hydrolyzed to give oxime derivative of Formula XV. Alkylation of the oxime with an appropriate halide in the presence of BEMP on polystyrene yields compounds of Formula XII.

Scheme VII

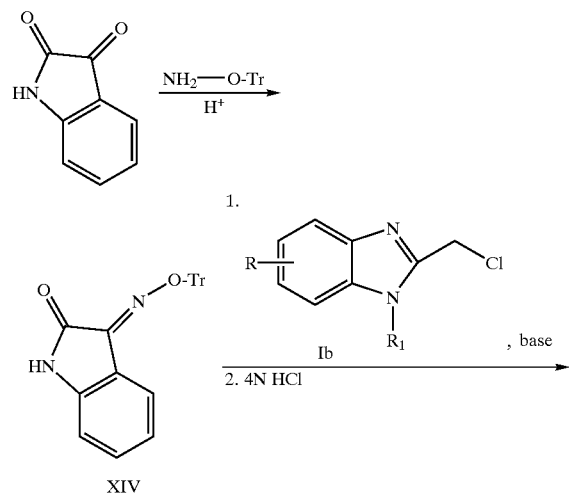

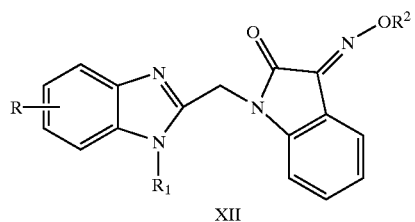

In addition to oxime derivatives, isatin compound X can be converted to derivatives XVI, XVII, and XVIII through Wittig reaction, reaction with organolithium reagent, or Aldol condensation as depicted in Scheme VIII.

Scheme VIII (A)

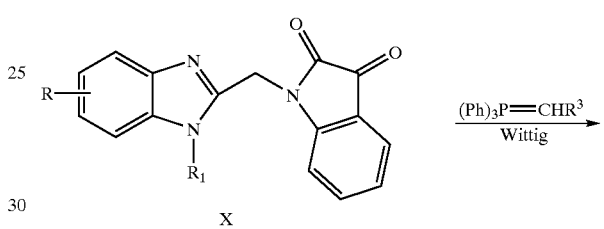

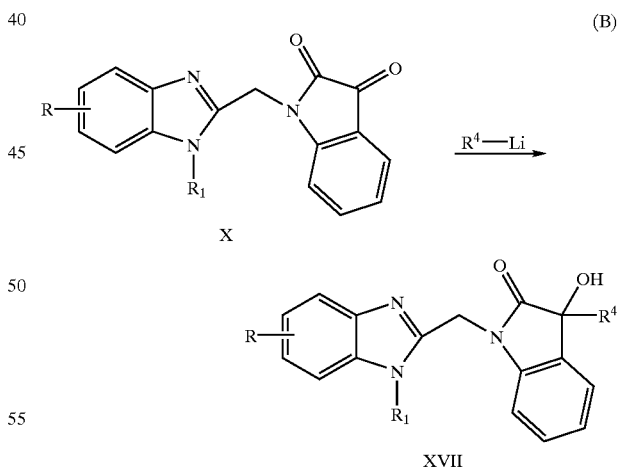

(C)

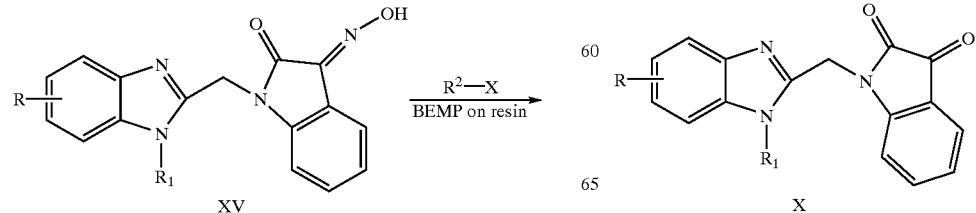

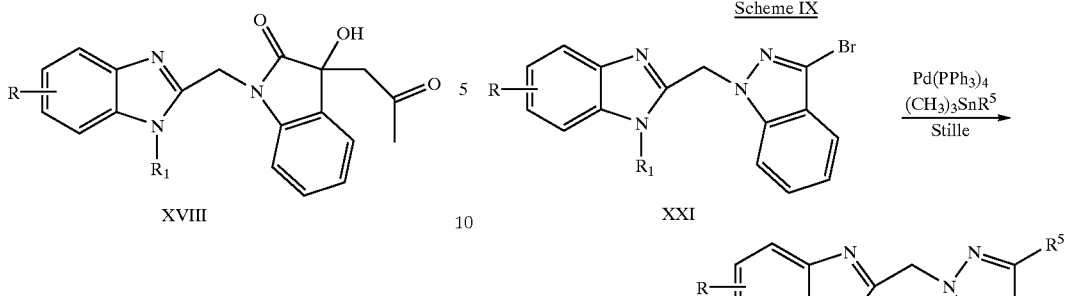

In addition, compounds of Formula X can be converted to 2-quinolone derivatives by reaction of the isatin X with ethyl diazoacetate to give derivative XIX.

(A)

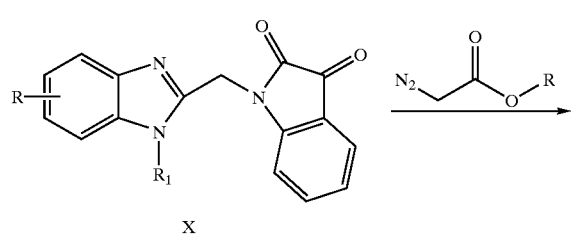

Derivatives of Formula XXIV are prepared by formation of the heterocyclic ring as described in Scheme X. Compound XXIII, prepared according to Scheme I with phthalimide as the heterocycle, is treated with hydrazine to afford the amine XXIV which is coupled to a 2-fluoro-nitrobenzene. Reduction under catalytic hydrogenation conditions followed by cyclization with 1,1'-thiocarbonyldiimidazole provides compound of Formula XXVI which can be further derivatized by alkylation with an appropriate halide to compound XXVII.

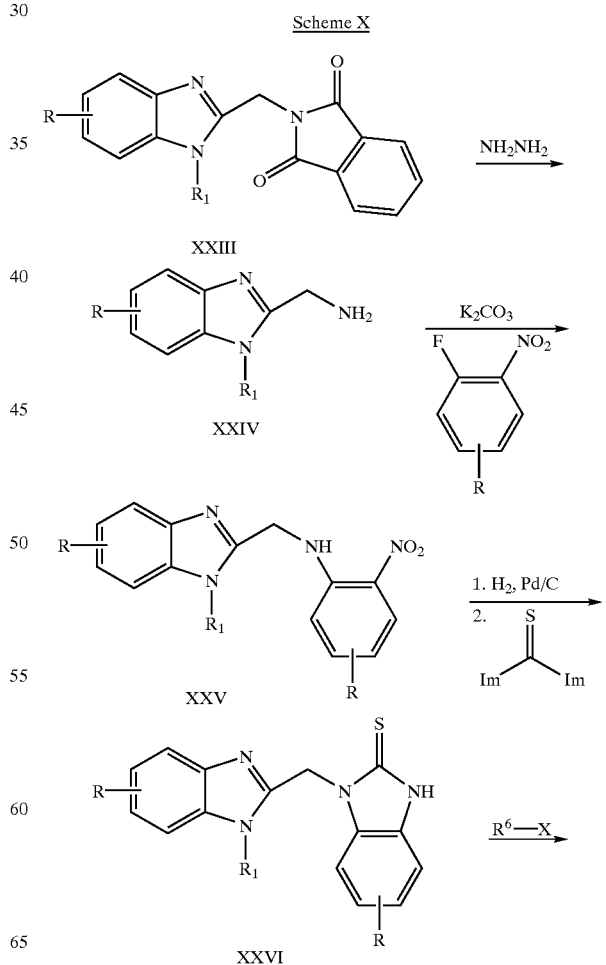

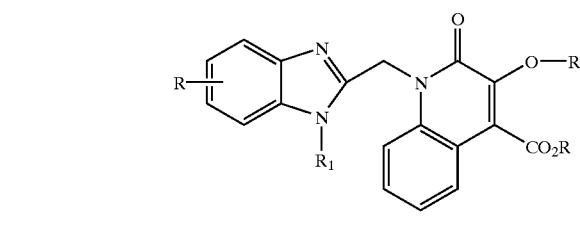

Compound of Formula XXII, prepared according to Scheme I, II, III, or IV, can be further derivatized through Stille coupling as shown in Scheme IX.

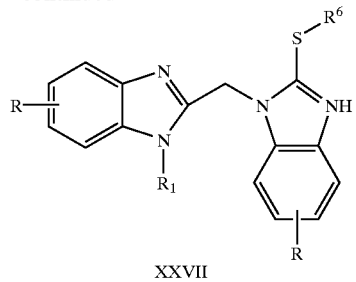

XXVII

Im = 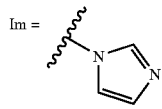

Abbreviations Used in Schemes I–X and Experimental Section

AcOH: glacial acetic acid
BEMP: 2-t-butylimino-2-diethylamino-1,3-dimethyl-perhydro-1,3,2-diazaphosphorine
BTPP: t-butylimino-tri(pyrrolidino)phosphorane
DIEA: N,N-diisopropylethylamine
DMF: dimethylformamide
EDAC: 1-[3-(dimethyl amino)propyl]-3-ethylcarbodiimide hydrochloride
EtOH: ethyl alcohol
EtOAc: ethyl acetate
$Et_2O$: diethyl ether
HOBT: 1-hydroxybenzotriazole hydrate
MeOH: methyl alcohol
Ph: phenyl
Prep HPLC: preparative high performance liquid chromatography
TFA: trifluoroacetic acid
THF: tetrahydrofuran.
Tr: trityl or triphenylmethyl
TBDMS: t-butyldimethylsilyl
TMS: trimethylsilyl It will be appreciated by those skilled in the art that reference herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient, and will ultimately be at the discretion of the attendant physician or veterinarian. In general however, a suitable dose will be in the range of from about 0.01 to 750 mg/kg of body weight per day preferably in the range of 0.1 to 100 mg/kg/day, most preferably in the range of 0.5 to 25 mg/kg/day.

Treatment is preferably commenced before or at the time of infection and continued until virus is no longer present in the respiratory tract. However, the treatment can also be commenced when given post-infection, for example after the appearance of established symptoms.

Suitable treatment is given 1–4 times daily and continued for 3–7, e.g. 5 days post infection depending upon the particular compound used.

The desired dose may be presented in a single dose or as divided doses administered at appropriate intervals, for example as two, three, four or more sub-doses per day.

The compound is conveniently administered in unit dosage form, for example, containing 10 to 1500 mg, conveniently 20 to 1000 mg, most conveniently 50 to 700 mg of active ingredient per unit dosage form.

While it is possible that, for use in therapy, a compound of the invention may be administered as the raw chemical, it is preferable to present the active ingredient as a pharmaceutical formulation.

The invention thus further provides a pharmaceutical formulation comprising a compound of the Formula I, or a pharmaceutically acceptable salt or derivative thereof together with a pharmaceutically acceptable carrier thereof.

The carrier must be "acceptable" in the sense of being compatible with the other ingredients of the formulation and not deleterious to the recipient thereof.

The pharmaceutical formulations may be in the form of conventional formulations for the intended mode of administration.

For intranasal administration according to the method of the invention the compounds of the invention may be administered by any of the methods and formulations employed in the art for intranasal administration.

Thus in general the compounds may be administered in the form of a solution or a suspension or as a dry powder.

Solutions and suspensions will generally be aqueous, for example prepared from water alone (for example sterile or pyrogen-free water), or water and a physiologically acceptable co-solvent (for example ethanol, propylene glycol, and polyethylene glycols such as PEG 400).

Such solutions or suspensions may additionally contain other excipients, for example, preservatives (such as benzalkonium chloride), solubilizing agents/surfactants such as polysorbates (e.g. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomizing spray pump.

Intranasal administration may also be achieved by means of an aerosol formulation in which the compound is provided in a pressurized pack with a suitable propellant such as a chlorofluorocarbon (CFC), for example dichlorodifluoromethane, trichlorofluoromethane or dichlorotetrafluroroethane, carbon dioxide or other suitable gas. The aerosol may conveniently also contain a surfactant such as lecithin. The dose of drug may be controlled by provision of a metered valve.

Experimental Section

Proton nuclear magnetic resonance ($^1H$ NMR) spectra were recorded on a Bruker Avance 500, AC-300, Bruker DPX-300 or a Varian Gemini 300 spectrometer. All spectra were determined in $CDCl_3$, $CD_3OD$, d-acetone or DMSO-$d_6$ and chemical shifts are reported in δ units relative to tetramethylsilane (TMS). Splitting patterns are designated as follows: s, singlet; d, doublet; t, triplet; m, multiplet; b, broad peak; dd, doublet of doublets; dt, doublet of triplets. Mass spectroscopy was performed on a Finnigan SSQ 7000 quadrupole mass spectrometer in both positive and negative electrospray ionization (ESI) modes or on a LC-MS using Shimadzu LC-10AS with micromass platform LC single quadrupole mass spectrometer in positive electrospray ionization. High resolution mass spectroscopy was recorded using Finnigan MAT 900. Infrared (IR) spectra were recorded on a Perkin-Elmer system 2000 FT-IR. Elemental analysis was performed with Perkin-Elmer series II, model 2400 CHN/O/S analyzer. Column chromatography was performed on silica gel from VWR Scientific. Preparative HPLC was performed using Shimadzu LC-8A on a C18 column eluted with mixture of MeOH in water with 0.1% trifluoroacetic acid.

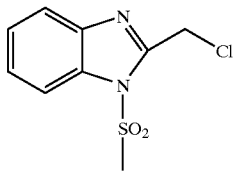

1a

To a solution of 2-(chloromethyl)benzimidazole (80 g, 0.48 mol) and methanesulfonyl chloride (58.3 mL, 0.75 mol) in methylene chloride (0.5 L), triethylamine (136 mL, 0.97 mol) was added dropwise under nitrogen. The resulting mixture was stirred at room temperature for 6 hours. The mixture was filtered and the filtrate was evaporated. The residue was triturated in methanol and filtered to afford 74.9 g of compound 1a as a brown solid:

$^1$H NMR (CDCl$_3$) δ3.44 (s, 3H), 5.11 (s, 2H), 7.40–7.49 (m, 2H), 7.76–7.82 (m, 1H), 7.85–7.91 (m, 1H);

IR(KBr, cm$^{-1}$) 3027, 2920, 1371, 1349, 1177, 1144, 1059;

MS m/e 245 (MH$^+$);

Anal. Calcd for C$_9$H$_9$ClN$_2$O$_2$S: C, 44.18; H, 3.71; N, 11.45

Found: C, 44.09; H, 3.57; N, 11.49.

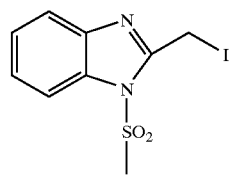

1b

A solution of potassium iodide (206 g, 1.24 mol) and compound 1a (74.8 g, 0.414 mol) in acetone (1 L) was stirred at reflux under nitrogen for 4 hours. The solid was filtered and the filtrate was evaporated. The crude product was triturated in MeOH and filtered to give 83 g of compound 1b as a solid:

$^1$H NMR (CDCl$_3$) δ3.48 (s, 3H), 4.97 (s, 2H), 7.40–7.50 (m, 2H), 7.75–7.85 (m, 2H);

IR (KBr, cm$^{-1}$) 3022, 2916, 1366, 1173, 1055, 966, 763, 745;

MS m/e 336 (MH$^+$);

Anal. Calcd for C$_9$H$_9$IN$_2$O$_2$S: C, 32.16; H, 2.70; N, 8.33

Found: C, 32.05; H, 2.63; N, 8.22.

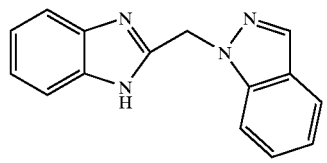

1c

To a solution of indazole (591 mg, 5.00 mmol) in DMF (7 mL) was added NaH (60% suspension in mineral oil, 200 mg, 5.00 mmol). After stirring for 30 minutes, compound 1b (1.51 g, 4.50 mmol) was added and the resulting solution was stirred at room temperature overnight. The mixture was diluted with saturated aqueous NaHCO$_3$, and extracted with Et$_2$O. The combined extracts were dried over MgSO$_4$ and evaporated. Purification by flash column chromatography (gradient, EtOAc:hexanes=1:4 to 2:1) gave an intermediate which was subsequently treated with hydrazine (2 mL) in MeOH (10 mL) and stirred at 65° C. for 2 hours. The solvent was evaporated and the residue was purified by column chromatography (gradient, EtOAc:hexanes=1:1 to straight EtOAc to EtOAc:MeOH=10:1). Recrystallization from EtOAc and hexanes gave 359 mg (29% yield) of compound 1c:

$^1$H NMR (CDCl$_3$) δ5.88 (s, 2H), 7.20 (t, J=4.5 Hz, 1H), 7.24–7.27 (m, 2H), 7.41 (t, J=4.5 Hz, 1H), 7.55 (bs over d, J=5.2 Hz, 2H), 7.75 (d, J=4.9 Hz, 1H), 8.11 (s, 2H);

MS m/e 249 (MH$^+$).

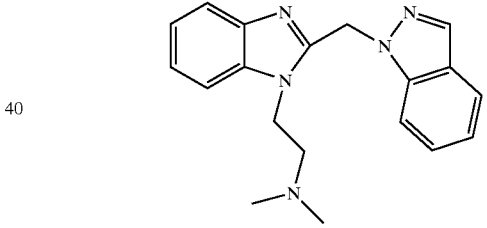

1

To a mixture of compound 1c (248 mg, 1.00 mmol) and NaH (60% suspension in mineral oil, 96 mg, 2.40 mmol) in DMF (3 mL) was added 2-chloro-N,N-dimethylethylamine hydrochloride (158 mg, 1.10 mmol) and the mixture was stirred at 65° C. for 4 hours. The reaction was quenched with saturated aqueous NaHCO$_3$ and extracted with Et$_2$O. The combined extracts were dried over MgSO$_4$ and evaporated. The resulting residue was purified by flash column chromatography (gradient, EtOAc:hexanes=1:1 to straight EtOAc to EtOAc:MeOH=10:1) to give 27 mg (14% yield) of compound 1 as a light yellow gum:

$^1$H NMR (CDCl$_3$) δ2.24 (bs, 8H), 4.29 (bt, J=6.8 Hz, 2H), 5.90 (s, 2H), 7.07 (t, J=7.7 Hz, 1H), 7.19–7.29 (m, 4H), 7.62 (t, J=7.6 Hz, 2H), 7.71–7.75 (m, 1H), 7.96 (s, 1H);

IR (KBr, cm$^{-1}$) 2944, 2772, 1616, 1464, 1418, 1333, 1164, 743;

MS m/e 320 (MH$^+$).

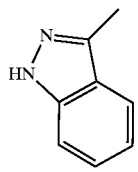

2a

A mixture of 2'-bromoacetophenone (2.00 g, 10.05 mmol) and hydrazine (322 mg, 10.05 mmol) in EtOH (10 mL) was refluxed for 48 hours. The solvent was evaporated. To the residue in THF (75 mL) was added 1 N HCl (15 mL). The resulting emulsion was warmed and stirred for 10 minutes. The mixture was neutralized with saturated NaHCO$_3$. The organic layer was dried over MgSO$_4$ and evaporated. The residue was subjected to column chromatography (EtOAc/hexanes, 1:1) to give 363 mg (27% yield) of compound 2a which was used immediately upon isolation.

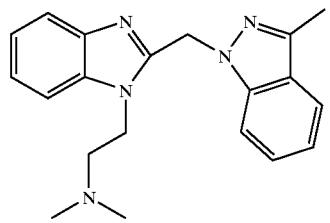

2

Compound 2 was prepared using the same procedure as compound 1 starting with compound 2a:

$^1$H NMR (CDCl$_3$) δ2.24 (bs, 8H), 2.57 (s, 3H), 4.35 (t, J=7.2 Hz, 2H), 5.86 (s, 2H), 7.09 (dt, J=0.8, 7.9 Hz, 1H), 7.24–7.32 (m, 4H), 7.56 (d, J=8.9 Hz, 1H), 7.61 (d, J=8.0 Hz, 1H), 7.77–7.81 (m, 1H);

IR (KBr, cm$^{-1}$) 3406, 2824, 1615, 1508, 1456, 1351, 1332, 744;

MS m/e 334 (MH$^+$);

Anal. Calcd for C$_{20}$H$_{23}$N$_5$·0.25H$_2$O: C, 71.08; H, 7.01; N, 20.72

Found: C, 71.05; H, 7.06; N, 20.70.

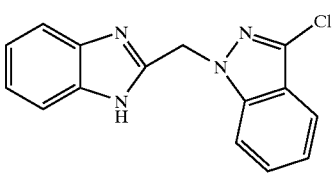

3a

Compound 3a was prepared using the same procedure as compound 1c with 3-chloroindazole in 44% yield:

$^1$H NMR (CDCl$_3$) δ5.79 (s, 2H), 7.17–7.27 (m, 3H), 7.40–7.60 (m, 1H), 7.51–7.54 (m, 3H), 7.66 (d, J=8.2 Hz, 1H);

IR (KBr, cm$^{-1}$) 2864, 2751, 1615, 1464, 1445, 1336, 1279, 1176, 989, 749.

MS m/e 283 (MH$^+$);

Anal. Calcd for C$_{15}$H$_{11}$ClN$_4$: C, 63.72; H, 3.92; N, 19.82

Found: C, 63.47; H, 3.98; N, 19.83.

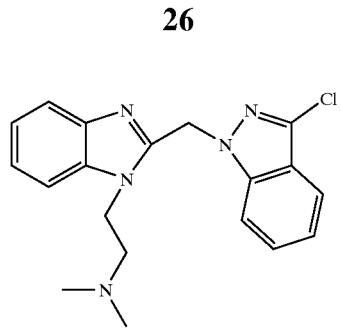

3

Compound 3 was prepared using the same procedure as compound 1 in 63% yield:

$^1$H NMR (CD$_3$OD) δ2.28 (s, 6H), 2.34 (t, J=7.0 Hz, 2H), 4.38 (t, J=7.0 Hz, 2H), 5.88 (s, 2H), 7.15–7.25 (m, 1H), 7.26–7.40 (m, 3H), 7.62–7.68 (m, 3H), 7.76–7.80 (m, 1H);

IR (KBr, cm$^{-1}$) 2945, 2825, 2773, 1616, 1496, 1466, 1336, 1253, 1172, 1006, 992, 746;

MS m/e 353 (MH$^+$);

Anal. Calcd for C$_{19}$H$_{20}$ClN$_5$: C, 64.49; H, 5.70, N, 19.79

Found: C, 64.54; H, 5.72, N, 19.80.

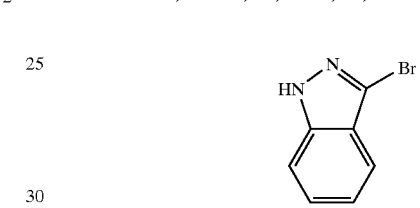

4a

3-Bromoindazole 4a was prepared using a procedure described by Boulton, B. E. and Coller, A. W (Aust. J. Chem., 1974, 27, 2343–2346):

A solution of bromine (0.99 g, 6.19 mmol) in 10% NaOH was slowly added to a suspension of indazole (1 g, 8.50 mmol) in 2 N NaOH (25 mL). The reaction mixture became a thick white slurry. After stirring for 2 hours, a small amount of sodium bisulfite was added and the solution was neutralized with 1 N HCl. The white solid was filtered and washed with water. Recrystallization from water gave 0.76 g (45% yield) of 3-bromoindazole 4a:

$^1$H NMR (CDCl$_3$) δ7.22–7.27 (m, 1H), 7.43–7.52 (m, 2H), 7.60–7.67 (m, 1H);

IR (KBr, cm$^{-1}$) 3154, 2944, 2915, 1624, 1479, 1331, 1242, 1026, 901, 770, 735, 639;

MS m/e 195 (MH$^-$);

Anal. Calcd for C$_7$H$_5$BrN$_2$: C, 42.67; H, 2.56; N, 14.22

Found: C, 42.37; H, 2.55; N, 14.06.

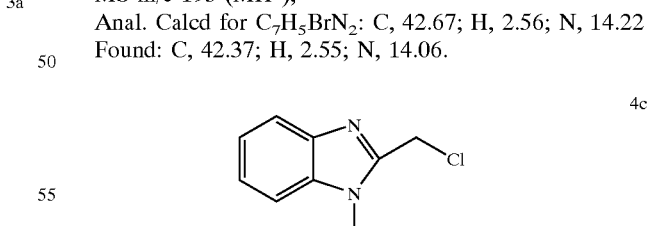

4c

To a solution of 2-hydroxymethylbenzimidazole (27.1 g, 182.9 mmol) in a 1:1 mixture of DMF/THF (200 mL) was added NaH (60% in mineral oil, 8.05 g, 201.2 mmol) at room temperature. After stirring for 1.5 hour, 1-bromo-3-methylbutane (29 g, 192 mmol) was added and the mixture was stirred at 75° C. overnight. The mixture was adjusted to neutral pH with concentrated HCl and the solvent was evaporated. The residue was diluted with EtOAc, washed with water, dried over MgSO₄, and evaporated. The residue was crystallized from EtOAc/hexane to give 29 g of compound 4b as white solid. The mother liquor was purified by flash chromatography (EtOAc:hexane=1:1 to 2:1 and then EtOAc:MeOH=10:0 to 10:1) to give additional 5.24 g (total 86% yield) of 4b.

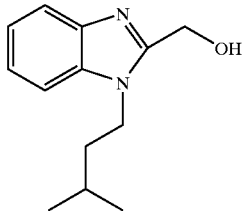

4b

To a solution of compound 4b (34.24 g, 156.9 mmol) in CH₂Cl₂ (100 mL) was slowly added SOCl₂ (28 g, 235.4 mmol) with ice-bath cooling. The resulting solution was stirred at room temperature for 1 hour and evaporated. The residue was dried in vacuo and then triturated with a mixture of CH₂Cl₂/Et₂O to give 41.25 g (96% yield) of compound 4c as a white solid:

$^1$H NMR (DMSO-d$_6$) δ0.99 (d, J=6.3 Hz, 6H), 1.72–1.79 (m, 3H), 4.47–4.52 (m, 2H), 5.36 (s, 2H), 7.52–7.61 (m, 2H), 7.82–7.92 (m, 2H);

MS m/e 237 (MH⁺).

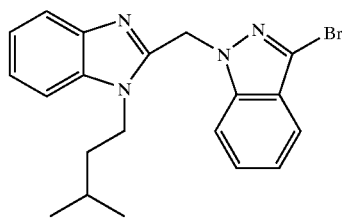

4

To a solution of 3-bromoindazole (4a, 303 mg, 1.54 mmol) in CH₃CN (15 mL) was added NaH (60% suspension in mineral oil, 68 mg, 1.69 mmol). After stirring for 30 minutes at room temperature, compound 4c was added and the reaction was stirred at room temperature for 22 hours. The reaction was quenched with saturated aqueous NaHCO₃ and extracted with Et₂O. The combined organic extracts were dried over MgSO₄ and evaporated. Purification of the resulting residue by column chromatography (hexanes/EtOAc, 1.5:1) followed by trituration with hexanes gave 191 mg (31% yield) of compound 4:

$^1$H NMR (CDCl₃) δ: 0.91 (d, J=6.6 Hz, 6H), 1.11–1.18 (m, 1H), 1.58–1.72 (m, 1H), 4.20–4.26 (m, 2H), 5.90 (s, 2H), 7.16–7.21 (m, 1H), 7.25–7.29 (m, 3H), 7.34–7.39 (m, 1H), 7.57 (dt, J=1.0, 8.2, 1H), 7.57 (d, J=8.5, 1H), 7.77–7.82 (m, 1H);

IR (KBr, cm⁻¹) 2951, 1615, 1472, 1460, 1325, 1247, 1168, 973, 766, 738;

MS m/e 399 (MH⁺);

Anal. Calcd for C₂₀H₂₁BrN₄: C, 60.46; H, 5.33; N, 14.10
Found: C, 60.30; H, 5.46; N, 14.05.

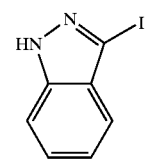

5a 3-iodoindazole (5a) was prepared using the same procedure as compound 4a with iodine in 89% yield:

$^1$H NMR (CDCl₃) δ7.21–7.27 (m, 1H), 7.43–7.60 (m, 3H);

IR (KBr, cm⁻¹) 3153, 2933, 2903, 1620, 1472, 1344, 1321, 1239, 1013, 899, 769, 747, 738;

MS m/e 243 (MH⁻);

Anal. Calcd for C₇H₅IN₂: C, 34.45; H, 2.07; N, 11.45
Found: C, 34.62; H, 1.97; N, 11.38.

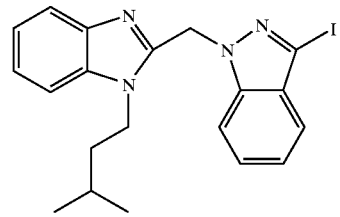

5

Compound 5 was prepared as an off-white solid using the same procedure as compound 4 with 3-iodoindazole (5a) in 54% yield:

$^1$H NMR (CDCl₃) δ0.90 (d, J=6.6 Hz, 6H), 1.07–1.15 (m, 2H), 1.60–1.66 (m, 1H), 4.18–4.24 (m, 2H), 5.94 (s, 2H), 7.18 (t, J=7.5 Hz, 1H), 7.25–7.28 (m, 3H), 7.37 (td, J=7.7, 1.0 Hz, 1H), 7.44 (d, J=8.2 Hz, 1H), 7.65 (d, J=8.5 Hz, 1H), 7.78–7.81 (m, 1H);

IR (KBr, cm⁻¹) 2951, 1614, 1505, 1462, 1167, 967, 740;

MS m/e 445 (MH⁺);

Anal. Calcd for C₂₀H₂₁IN₄: C, 54.06; H, 4.76; N, 12.61
Found: C, 53.90; H, 4.82; N, 12.35.

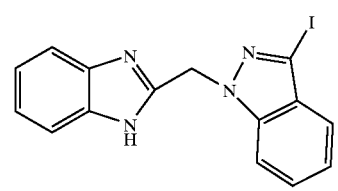

6a

Compound 6a was prepared using the same procedure as compound 1c with 3-iodoindazole (5a) in 34% yield:

$^1$H NMR (DMSO-d$_6$) δ5.92 (s, 2H), 7.15–7.18 (m, 2H), 7.27 (t, J=4.7 Hz, 1H), 7.46–7.53 (m, 4H), 7.82 (d, J=5.2 Hz, 1H);

IR (KBr, cm⁻¹) 2830, 2625, 1613, 1538, 1490, 1457, 1445, 1276, 749;

MS m/e 375 (MH⁺);

Anal. Calcd for C₁₅H₁₁I.0.25H₂O: C, 47.57; H, 3.06, N, 14.79
Found: C, 47.47; H, 2.93; N, 14.52.

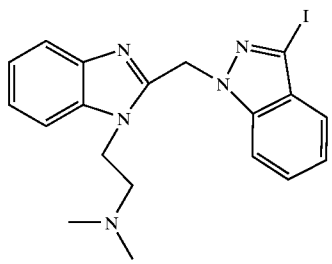

6

Compound 6 was prepared as a yellow solid using the same procedure as compound 1 with compound 6a and 2-chloro-N,N-dimethylethylamine hydrochloride in 51% yield:

$^1$H NMR (CDCl$_3$) δ2.27 (s, 6H), 2.31 (t, J=7.2 Hz, 2H), 4.36 (t, J=7.0 Hz, 2H), 5.96 (s, 2H), 7.18–7.46 (m, 6H), 7.67 (bd, J=9.3 Hz, 1H), 7.77–7.80 (m, 1H);

IR (KBr, cm$^{-1}$) 3435, 1613, 1460, 1423, 1248, 1165, 740;

MS m/e 446 (MH$^+$);

Anal. Calcd for C$_{19}$H$_{20}$IN$_5$: C, 51.25; H, 4.53; N, 15.73

Found: C, 51.25; H, 4.51; N, 15.38.

The amine 6 and excess 4N HCl in dioxane were stirred in MeOH. The solvent was evaporated and the residue dried under vacuum to give the HCl salt of compound 6:

$^1$H NMR (CD$_3$OD) δ3.13 (s, 6H), 3.76–3.82 (m, 2H), 5.17–5.23 (m, 2H), 6.41 (s, 2H), 7.35–7.40 (m, 1H), 7.56–7.76 (m, 5H), 7.92 (d, J=8.5 Hz, 1H), 8.09 (d, J=7.9 Hz, 1H);

IR (KBr, cm$^{-1}$) 3400, 2675, 1613, 1489, 1460, 1316, 1172, 970, 755;

MS m/e 446 (MH$^+$);

Anal. Calcd for C$_{19}$H$_{20}$IN$_5$.2HCl.0.5H$_2$O: C, 43.28; H, 4.40, N, 13.28

Found: C, 43.22; H, 4.53, N, 13.17.

7

A mixture of the compound 6 (50 mg, 0.11 mmol) and methyl iodide (16 mg, 0.11 mmol) in acetone (1 mL) was stirred at room temperature for 17 hours. Collection of the solid by filtration gave 50 mg (77% yield) of compound 7 as a pale yellow solid:

$^1$H NMR (CD$_3$OD) δ3.32 (s, 9H), 3.70–3.75 (m, 2H), 5.01–5.07 (m, 2H), 6.07 (s, 2H), 7.27–7.59 (m, 5H), 7.64 (d, J=7.8 Hz, 1H), 7.70 (d, J=7.5 Hz, 1H), 7.85 (d, J=8.6 Hz, 1H);

IR (KBr, cm$^{-1}$) 3435, 3011, 1615, 1489, 1475, 1459, 1414, 1248, 1168, 965, 755;

MS m/e 459 (M$^+$);

Anal. Calcd for C$_{20}$H$_{23}$I$_2$N$_5$: C, 40.91; H, 3.95; N, 11.93

Found: C, 40.87; H, 3.96; N, 11.65.

8

Compound 8 was prepared using the same procedure as compound 1 with compound 6a and 2-chloroethyl methyl sulfide in 70% yield:

$^1$H NMR (CDCl$_3$) δ2.14 (s, 3H), 2.63 (t, J=7.1 Hz, 2H), 4.61 (t, J=7.1 Hz, 2H), 6.14 (s, 2H), 7.20 (t, J=7.1 Hz, 1H), 7.36–7.47 (m, 5H), 7.84–7.89 (m, 2H);

IR(KBr, cm$^{-1}$) 1613, 1460, 1426, 1331, 1163, 755, 743;

MS m/e 449 (MH$^+$);

Anal. Calcd for C$_{18}$H$_{17}$IN$_4$S.0.25H$_2$O: C, 47.74; H, 3.90; N, 12.37

Found: C, 47.64; H, 3.77; N, 12.23.

9

A mixture of compound 8 (75 mg, 0.17 mmol) and magnesium monoperoxyphthalate hexahydrate (MMPP, 165 mg, 0.33 mmol) in DMF (3 mL) was stirred at room temperature for 17 hours. The reaction mixture was diluted with EtOAc and washed with water. The organic layer was separated, dried over MgSO$_4$, and evaporated. Column chromatography (EtOAc/hexanes, 2:1) gave compound 9:

$^1$H NMR (CDCl$_3$) δ2.97 (s, 3H), 3.26 (bt, J=7.6 Hz, 2H), 4.88 (bt, J=7.6 Hz, 2H), 5.97 (s, 2H), 6.92–7.51 (m, 6H), 7.74–7.82 (m, 2H);

IR (KBr, cm$^{-1}$) 1458, 1318, 1294, 1167, 1133, 966, 766, 742;

MS m/e 481 (MH$^+$);

Anal. Calcd for C$_{18}$H$_{17}$IN$_4$O$_2$S.0.25H$_2$O: C, 45.01; H, 3.57; N, 11.66

Found: C, 44.83; H, 3.58; N, 11.38.

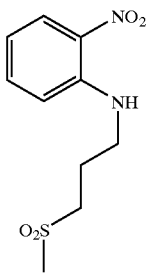

10a

2-Fluoronitrobenzene (35.4 g, 250.9 mmol), 3-(methylthio)propylamine (24.0 g, 228.1 mmol) and potassium carbonate (47.3 g, 342 mmol) were stirred in CH$_3$CN (100 mL) at room temperature for 18 hours. After stirring for an additional hour at reflux, the mixture was cooled to room temperature and filtered. The filtrate was evaporated. To the residue in DMF (150 mL), monoperoxyphthalic acid magnesium hexahydrate (168 g, 340 mmol) was added in several portions with ice-water cooling. The mixture was stirred at room temperature for 3 hours and the solvent was evaporated. The residue was dissolved in CH$_2$Cl$_2$ and washed with 1 N NaOH, water, brine, dried over MgSO$_4$, and evaporated. The residue was triturated in hot EtOAc to give 10a (48.7 g, 75% yield) as an orange solid:

$^1$H NMR (CDCl$_3$) δ2.25–2.35 (m, 2H), 2.97 (s, 3H), 3.17 (t, J=7.2 Hz, 2H), 3.59 (t, J=6.9 Hz, 2H), 6.68–6.74 (m, 1H), 6.89 (d, J=8.1 Hz, 1H), 7.45–7.51 (m, 1H), 8.20 (dd, J=1.5, 8.7 Hz, 1H);

MS m/e 259 (MH$^+$);

Anal. Calcd for C$_{10}$H$_{14}$N$_2$O$_4$S: C, 46.50; H, 5.46; N, 10.84

Found: C, 46.53; H, 5.54; N, 10.90.

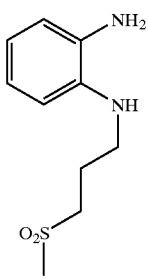

10b

To a suspension of 10a (48.5 g, 187.8 mmol) in a mixture of CHCl$_3$ and MeOH (150 mL, 1:3) was added 10% palladium on carbon (6 g) under nitrogen. The reduction was carried out in a Parr shaker with hydrogen pressure maintained between 40 and 60 psi for 25 min. The catalyst was removed by filtration and the filtrate was evaporated to give crude 10b:

$^1$H NMR (CD$_3$OD) δ2.11–2.21 (m, 2H), 2.98 (s, 3H), 3.28–3.36 (m, 4H), 6.75 (dt, J=0.9, 7.2 Hz, 1H), 6.85 (d, J=7.5 Hz, 1H), 7.06–7.12 (m, 2H);

MS m/e 229 (MH$^+$).

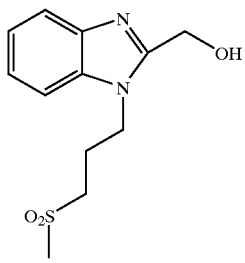

10c

Diamine 10b was stirred at reflux for 18 hours with glycolic acid (15.7 g, 207 mmol) in 6 N HCl (150 mL). The solution was cooled in an ice bath and neutralized with concentrated NH$_4$OH solution, extracted with EtOAc, dried over MgSO$_4$, and evaporated. The residue was purified by chromatography (gradient, EtOAc:hexane=1:1, EtOAc, then EtOAc: MeOH=10:1) to give a product which crystallized from EtOAc/MeOH to afford 25.7 g (51% yield over two steps) of compound 10c:

$^1$H NMR (CD$_3$OD) δ2.38–2.44 (m, 2H), 2.97 (s, 3H), 3.24 (t, J=7.6 Hz, 2H), 4.54 (t, J=7.6 Hz, 2H), 7.27 (t, J=1.1, 8.1 Hz, 1H), 7.33 (dt, J=1.1, 8.0 Hz, 1H), 7.62 (d, J=8.1 Hz, 1H), 7.64 (dd, J=1.0, 8.0 Hz, 1H);

MS m/e 269 (MH$^+$).

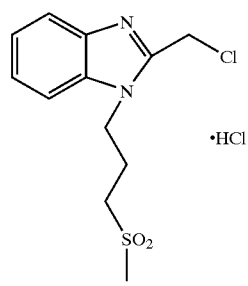

10d

Compound 10d was prepared using the same procedure as compound 4c with alcohol 10c:

$^1$H NMR (CD$_3$OD) δ2.46–2.52 (m, 2H), 3.03 (s, 3H), 3.37 (t, J=7.1 Hz, 2H), 4.77 (t, J=7.8 Hz, 2H), 5.31 (s, 2H), 7.68–7.73 (m, 2H), 7.86 (dd, J=2.8, 6.9 Hz, 1H), 8.03 (dd, J=1.7, 6.1 Hz, 1H);

MS m/e 287 (MH$^+$).

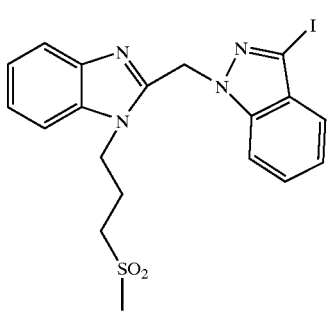

10

Compound 10 was prepared using the same procedure as compound 4 with compound 5a and compound 10d:

$^1$H NMR (CDCl$_3$) δ1.88–2.00 (m, 2H), 2.85 (s, 3H), 3.05–3.10 (m, 2H), 4.76–4.81 (m, 2H), 6.35 (s, 2H), 7.08–7.27 (m, 1H), 7.25 (d, J=8.4 Hz, 1H), 7.37–7.44 (m, 3H), 7.54–7.57 (m, 1H), 7.77–7.80 (m, 1H), 8.34 (d, J=8.7 Hz, 1H);

MS m/e 495 (MH⁺).

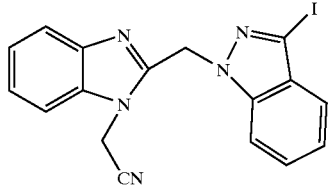

11

Compound 11 was prepared using the same procedure as compound 1 with compound 6a and bromoacetonitrile in 42% yield:

¹H NMR (CDCl₃) δ5.42 (s, 2H), 5.93 (s, 2H), 7.19–7.47 (6H), 7.67 (d, J=8.7 Hz, 1H), 7.79 (dd, J=2.1, 6.6 Hz, 1H);
IR (KBr, cm⁻¹) 3435, 1615, 1464, 1412, 1198, 752, 741.

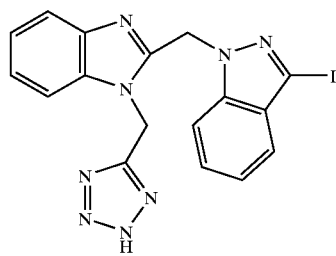

12

A mixture of compound 11 (310 mg, 0.75 mmol), sodium azide (146 mg, 2.25 mmol), and ammonium chloride (120 mg, 2.25 mmol) in DMF (15 mL) was stirred at 110° C. for 16 hours. The solid was filtered and the filtrate was evaporated under vacuum. The residue was dissolved in 1N NaOH and the aqueous solution was washed with EtOAc. The aqueous solution was adjusted to pH 7 and then extracted with EtOAc. The organic extracts were dried over MgSO₄ and evaporated to give 260 mg of crude product which was converted to sodium salt by adding 1N NaOH (0.54 mL, 0.54 mmol) in MeOH (5 mL). The solvent was evaporated and the residue was purified by C18 column chromatography to give 40 mg of compound 12 as the sodium salt:

¹H NMR (CD₃OD) δ5.84 (s, 2H), 6.19 (s, 2H), 7.20–7.30 (m, 3H), 7.47–7.60 (m, 4H), 7.70 (d, J=8.9 Hz, 1H);
IR (KBr, cm⁻¹) 3368, 1615, 1462, 1321, 1247, 1168, 741;
MS m/e 457 (MH⁺);
Anal. Calcd for C₁₇H₁₃IN₈Na.1.75H₂O: C, 40.06; H, 3.06; N, 21.98
Found: C, 40.30; H, 3.33; N, 21.66.

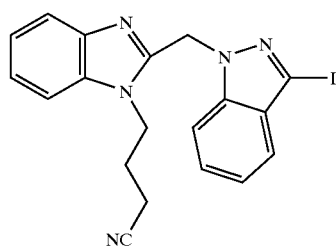

13

Compound 13 was prepared using the same procedure as compound 1 with compound 6a and 4-bromobutyronitrile:

¹H NMR (CDCl₃) δ1.59–1.69 (m, 2H), 2.38 (t, J=7.0 Hz, 2H), 4.45 (t, J=8.7 Hz, 2H), 5.94 (s, 2H), 7.20–7.48 (m, 6H), 7.72 (d, J=8.5 Hz, 1H), 7.79–7.84 (m, 1H);

IR (KBr, cm⁻¹) 3424, 2943, 1614, 1459, 1418, 1166, 742;

MS m/e 442 (MH⁺);

Anal. Calcd for C₁₉H₁₆IN₅: C, 51.72; H, 3.65; N, 15.87

Found: C, 51.63; H, 3.87; N, 15.61.

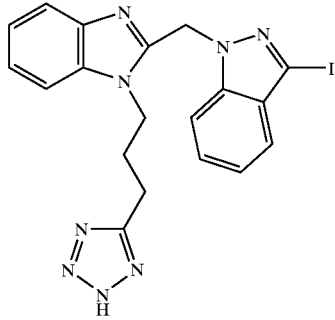

14

Compound 14 was prepared using the same procedure as compound 12 with compound 13:

¹H NMR (CD₃OD) δ1.94–2.03 (m, 2H), 2.85 (t, J=7.2 Hz, 2H), 4.37 (t, J=7.7 Hz, 2H), 5.98 (s, 2H), 7.23–7.32 (m, 3H)), 7.39–7.52 (m, 3H), 7.60–7.69 (m, 2H);

IR (KBr, cm⁻¹) 3395, 1615, 1459, 1327, 1167, 743;

MS m/e 485 (MH⁺);

Anal. Calcd for C₁₉H₁₆IN₈Na.3.00H₂O: C, 41.05; H, 4.08; N, 19.54

Found: C, 41.03; H, 3.87; N, 19.24.

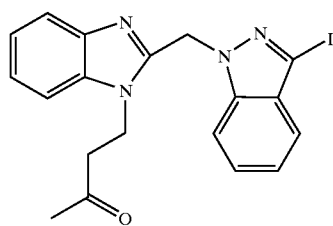

15

Compound 6a (800 mg, 2.14 mmol) and methyl vinyl ketone (600 mg, 8.55 mmol) were refluxed in EtOH (25 mL) for 18 hours. The solvent was evaporated to give a tan solid. This solid was triturated with Et₂O and filtered to give 825 mg (87% yield) of compound 15:

¹H NMR (CDCl₃) δ2.09 (s, 3H), 2.58 (t, J=7.1 Hz, 2H), 4.59 (t, J=7.1 Hz, 2H), 6.03 (s, 2H), 7.20–7.30 (m, 4H), 7.41–7.48 (m, 2H), 7.77–7.81 (m, 2H);

IR (KBr, cm⁻¹) 3396, 1702, 1614, 1420, 1461, 1368, 1323, 1247, 1166, 1151, 742;

MS m/e 445 (MH⁺);

Anal. Calcd for C₁₉H₁₇IN₄O: C, 51.37; H, 3.86; N, 12.61

Found: C, 51.48; H, 3.91; N, 12.50.

16

Ketone 15 (300 mg, 0.68 mmol) was suspended in MeOH (10 mL) and cooled to 0° C. with an ice bath. Sodium borohydride (25 mg, 0.68 mmol) was added and the reaction mixture was allowed to stir while warming to room temperature. The solvent was evaporated. The residue was diluted with water and extracted with Et$_2$O. The organic extracts were dried over MgSO$_4$ and evaporated. Trituration with Et$_2$O followed by filtration gave 210 mg (70% yield) of compound 16:

$^1$H NMR (CDCl$_3$) δ1.18 (d, J=6.2 Hz, 3H), 1.52–1.56 (m, 2H), 3.78–3.82 (m, 1H), 4.12–4.53 (m, 2H), 5.99 (q, J=15.2 Hz, 2H), 7.21 (t, J=7.6 Hz, 1H), 7.27–7.30 (m, 1H), 7.37–7.39 (m, 1H), 7.42–7.46 (m, 2H), 7.77–7.81 (m, 2H);

IR (KBr, cm$^{-1}$) 3392, 2960, 2925, 1614, 1461, 1421, 1323, 1248, 1165, 742;

MS m/e 447 (MH$^+$);

Anal. Calcd for C$_{19}$H$_{19}$IN$_4$O: C, 51.13; H, 4.29; N, 12.55
Found: C, 50.93; H, 4.22; N, 12.27.

17

Compound 17 was prepared using the same procedure as compound 4 with 7-nitroindazole in 20% yield:

$^1$H NMR (CDCl$_3$) δ0.82 (d, J=6.6 Hz, 6H), 1.25–1.40 (m, 2H), 1.53–1.68 (m, 1H), 4.27–4.32 (m, 2H), 6.00 (s, 2H), 7.12 (t, J=7.9 Hz, 1H), 7.19–7.30 (m, 3H), 7.69–7.73 (m, 1H), 7.92 (dd, J=0.8, 8.3 Hz, 1H), 8.28 (dd, J=0.9, 7.6 Hz, 1H), 8.31 (s, 1H);

IR (KBr, cm$^{-1}$) 2957, 1728, 1516, 1455, 1407, 1335, 1301, 1138, 737;

MS m/e 364 (MH$^+$).

18

Compound 18 was prepared using the same procedure as compound 4 with 3-chloro-5-nitroindazole in 33% yield:

$^1$H NMR (CDCl$_3$) δ0.90 (d, J=6.6 Hz, 6H), 1.18–1.28 (m, 2H), 1.58–1.71 (m, 1H), 4.19–4.25 (m, 2H), 5.82 (s, 2H), 7.19–7.25 (m, 3H), 7.69–7.72 (m, 1H), 7.79 (d, J=9.3 Hz, 1H), 8.19 (dd, J=2.1, 9.3 Hz, 1H), 8.57 (d, J=2.1, 1H);

IR (KBr, cm$^{-1}$) 2956, 1586, 1616, 1524, 1459, 1339, 794, 749;

MS m/e 398 (MH$^+$);

Anal. Calcd for C$_{20}$H$_{20}$N$_5$O$_2$Cl: C, 60.38; H, 5.07; N, 17.60
Found: C, 60.67; H, 5.42; N, 17.03.

19a

Compound 19a was prepared using the same procedures as compound 1c with 3-bromo-5-nitroindazole and was used without further purification.

19

Compound 19 was prepared using the same procedures as compound 1 with compound 19a and 2-chloro-N,N-dimethylethylamine hydrochloride in 25% yield:

$^1$H NMR (CDCl$_3$) δ2.32 (s, 6H), 2.49 (bt, 2H), 4.42 (bt, 2H), 5.97 (s, 2H), 7.28–7.33 (m, 3H), 7.75–7.79 (m, 1H), 7.88 (d, J=9.3 Hz, 1H), 8.27 (dd, J=2.1, 9.3 Hz, 1H), 8.57 (d, J=2.1 Hz, 1H);

IR (KBr, cm$^{-1}$) 2943, 2772, 1616, 1517, 1456, 1340, 1277, 737;

MS m/e 443 (MH$^+$);

Anal. Calcd for C$_{19}$H$_{21}$BrN$_6$O$_2$: C, 51.25; H, 4.75, N, 18.87
Found: C, 51.38; H, 4.45, N, 18.88.

20

Compound 19 (40 mg, 0.09 mmol) was reduced in a Parr apparatus under H$_2$ in the presence of 10% palladium on carbon (40 mg) in a mixture of MeOH and CHCl$_3$ (2.4 mL, 5:1) for 2 hours at 35 psi. The catalyst was removed by filtration through a pad of celite and the filtrate was evaporated to give compound 20:

$^1$H NMR (CDCl$_3$) δ3.12 (s, 6H), 3.57–3.65 (m, 2H), 5.00–5.06 (m, 2H), 6.19 (s, 2H), 7.35–7.49 (m, 2H), 7.67 (d, J=7.8 Hz, 1H), 7.79 (d, J=8.0 Hz, 1H), 7.87 (s, 1H), 8.06 (d, J=8.9 Hz, 1H), 8.29 (s, 1H);

MS m/e 335 (MH$^+$).

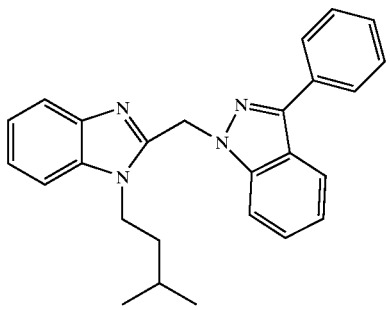

21

A mixture of compound 4 (40 mg, 0.10 mmol), phenyltrimethyltin (29 mg, 0.12 mmol), and palladium tetrakistriphenylphosphine (12 mg, 0.01 mmol) in toluene (2 ml) was heated to reflux for 3 hours. The reaction mixture was diluted with EtOAc (10 ml), washed with saturated NaHCO₃, dried over MgSO₄, and concentrated. The residue was purified by prep-HPLC (gradient, 10% MeOH in H₂O with 0.1% TFA to 90% MeOH in H₂O with 0.1% TFA) to give 34 mg (86% yield) of compound 21 as a pale yellow solid:

$^1$H NMR (CD$_3$OD) δ0.77 (d, J=6.6 Hz, 6H), 1.30–1.40 (m, 2H), 1.40–1.56 (m, 1H), 4.45–4.50 (m, 2H), 6.26 (s, 2H), 7.32–7.58 (m, 8H), 7.75 (m, 3H), 7.91 (d, J=6.9 Hz, 1H), 8.07 (d, J=8.1 Hz, 1H);

IR (KBr, cm$^{-1}$) 2960, 1683, 1492, 1188, 1136, 749;

MS m/e 395 (MH$^+$).

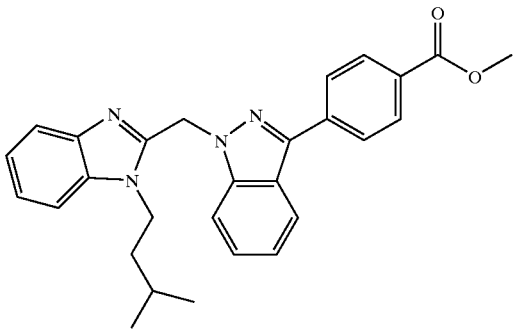

22

Compound 22 was prepared using the same procedure as compound 21 with 4-trimethylstannyl-benzoic acid methyl ester prepared according to the procedure described by Wursthorn, K. R. and Kuivila, H. G. (*J. Organomet. Chem.*, 1977, 140 (1), 29–39):

$^1$H NMR (CDCl$_3$) δ0.82 (d, J=6.6 Hz, 6H), 1.18–1.25 (m, 2H), 1.71–1.79 (m, 1H), 3.97 (s, 3H), 4.21–4.38 (m, 2H), 6.00 (s, 2H), 7.25–7.42 (m, 6H), 7.71–7.48 (m, 2H), 8.02–8.21 (m, 4H);

MS m/e 453 (MH$^+$).

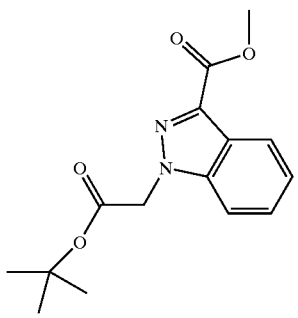

23a

A solution of indazole-3-carboxylic acid (Fluka, 3.0 g, 18.5 mmol) in MeOH (50 ml) with concentrated sulfuric acid (0.1 ml) was heated to reflux for 12 hours, cooled and concentrated. The residue was dissolved in EtOAc and washed with saturated NaHCO₃, dried over MgSO₄ and concentrated to give 2.32 g (70% yield) of the methyl ester as a dark solid. The ester was dissolved in CH₃CN (50 mL), treated with K₂CO₃ (0.83 g, 6.0 mmol) and t-butyl bromoacetate (0.84 mL, 5.7 mmol), and stirred at room temperature for 12 hours. The solution was filtered and concentrated. The residue was purified by flash chromatography (gradient, hexanes:EtOAc=20:1 to 5:1) to give 1.44 g (87% yield) of compound 23a:

$^1$H NMR (DMSO-d$_6$) δ1.41 (s, 9H), 3.93 (s, 3H), 5.44 (s, 2H), 7.36 (t, J=7.1 Hz, 1H), 7.51 (J=7.2 Hz, 1H), 7.78 (d, J=8.1 Hz, 1H), 8.08 (d, J=8.1 Hz, 1H);

IR (KBr, cm$^{-1}$) 2986, 1746, 1720, 1230;

MS m/e 290 (MH$^+$);

Anal. Calcd for C$_{15}$H$_{18}$N$_2$O$_4$: C, 62.06; H, 6.25; N, 9.65

Found: C, 62.23; H, 6.27; N, 9.63.

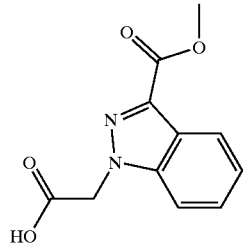

23b

Compound 23a (1.2 g, 4.13 mmol) was dissolved in TFA (5 mL) and stirred for 12 hours. The solution was concentrated to give 0.96 g (99% yield) of compound 23b:

$^1$H NMR (DMSO-d$_6$) δ3.93 (s, 3H), 5.44 (s, 2H), 7.36 (t, J=7.1 Hz, 1H), 7.50 (t, J=7.1 Hz, 1H), 7.80 (d, J=8.2 Hz, 1H), 8.09 (d, J=8.2 Hz, 1H);

IR (KBr, cm$^{-1}$) 1716, 1323, 1149, 747;

MS m/e 234 (MH$^+$).

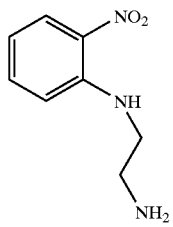

23c

A solution of 2-fluoronitrobenzene (30 mL, 2.84 mmol) in $CH_3CN$ (30 mL) was added to a solution of ethylenediamine (76 mL, 1.14 mmol) in $CH_3CN$ (50 mL). The mixture was stirred at room temperature for 12 hours then concentrated to give 51 g (99% yield) of the product 23c as an orange oil:

$^1$H NMR (DMSO-$d_6$) δ2.82 (t, J=6.0 Hz, 2H), 3.30 (t, J=6.0 Hz, 2H), 6.66 (t, J=8.4 Hz, 1H), 7.05 (d, J=8.7 Hz, 1H), 7.53 (d, J=8.4 Hz, 1H), 8.30–8.34 (m, 1H);

IR (film, $cm^{-1}$) 1621, 1514, 1347, 740;

MS m/e 182 ($MH^+$);

Anal. Calcd for $C_8H_{11}N_3O_2 \cdot 0.20H_2O$: C, 51.99; H, 6.22; N, 22.74

Found: C, 51.99; H, 6.29; N, 22.46.

23d

To a mixture of amine 23c (2.0 g, 11 mmol) in $CH_2Cl_2$ (50 mL) was added triethyl amine (1.53 mL, 11 mol) and the mixture was cooled to 0° C. Methanesulfonyl chloride (0.85 mL, 11 mmol) was added slowly. Once the addition was complete the reaction mixture was warmed to room temperature and stirred for 12 hours. The mixture was poured into water and the aqueous layer separated, dried over $MgSO_4$, and evaporated. The residue was chromatographed (3% MeOH in $CH_2Cl_2$) to give 2.55 g (89% yield) of 23d as an orange oil:

$^1$H NMR (DMSO-$d_6$) δ2.91 (s, 3H), 3.18 (dd, J=6.1, 11.6 Hz, 2H), 3.39–3.42 (m, 2H), 6.70 (t, J=9.0 Hz, 1H), 7.08 (d, J=8.5 Hz, 1H), 7.28 (t, J=6.1 Hz, exchanges with $D_2O$, 1H), 7.55 (td, J=1.0, 6.0, Hz, 1H); 8.07 (dd, J=1.0, 8.7 Hz, 1H); 8.23 (bs, 1H exchanges with $D_2O$);

IR (film, $cm^{-1}$) 1511, 1354, 1317, 1151;

MS m/e 260 ($MH^+$);

Anal. Calcd for $C_9H_{13}N_3O_4S \cdot 0.5H_2O \cdot 0.08$ EtOAc: C, 40.66; H, 5.36; N, 15.26

Found: C, 40.58; H, 5.29; N, 14.88.

23e

A mixture of compound 23d (1.0 g, 3.9 mmol) and 10% palladium on carbon (100 mg) in EtOH (50 mL) was hydrogenated at 50 psi for 12 hours. The mixture was filtered and the filtrate was evaporated to give an orange oil. The residue was chromatographed (1% MeOH in $CH_2Cl_2$) to give 0.55 g (62% yield) of compound 23e as a dark oil:

$^1$H NMR (DMSO-$d_6$) δ2.91 (s, 3H), 3.17 (bs, 2H), 4.45 (bs, 3H, 1H exchanges with $D_2O$), 6.40–6.56 (m, 4H), 7.11 (bs, 1H, exchanges with $D_2O$);

IR (film, $cm^{-1}$) 3326, 1625, 1510, 1315, 1148, 738;

MS m/e 230 ($MH^+$);

Anal. Calcd for $C_9H_{15}N_3O_2S$: C, 46.78; H, 6.63; N, 18.18

Found: C, 46.81; H, 6.79; N, 17.81.

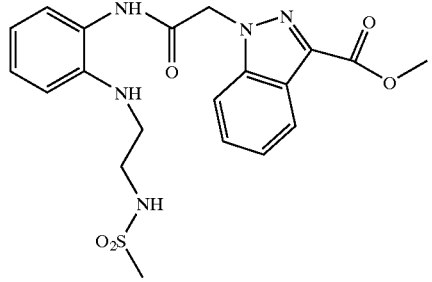

23F

Compound 23b (0.4 g, 1.7 mmol) and thionyl chloride (5 mL) were stirred at reflux for 30 minutes. The excess thionyl chloride was evaporated in vacuo to give the corresponding acid chloride. Diamine 23e was dissolved in $CH_2Cl_2$ (10 mL), treated with $Et_3N$ (0.21 g, 2.0 mmol) and cooled to −78° C. A solution of the acid chloride in $CH_2Cl_2$ (10 mL) was added dropwise. The reaction mixture was stirred at −78° C. for 1 hour, then warmed to room temperature and stirred for 12 hours. The precipitate was filtered to give 0.33 g (44% yield) of compound 23f:

$^1$H NMR (DMSO-$d_6$) δ2.91 (s, 3H), 3.13–3.17 (m, 2H), 3.21–3.32 (m, 2H), 3.93 (s, 3H), 5.26 (t, J=5.6 Hz, 1H, exchanges with $D_2O$), 5.49 (s, 2H), 6.57 (t, J=7.6 Hz, 1H), 6.68 (d, J=8.0, 1H), 7.02–7.18 (m, 4H, 1H exchanges with $D_2O$), 7.36 (t, J=7.7 Hz, 1H), 7.52 (t, J=7.8 Hz, 1H), 7.80 (d, J=8.5 Hz, 1H), 8.09 (d, J=8.2 Hz, 1H), 9.57 (s, 1H, exchanges with $D_2O$);

IR (KBr, $cm^{-1}$) 1730, 1681, 1541, 1311, 1169;

MS m/e 445 ($MH^+$);

Anal. Calcd for $C_{20}H_{23}N_5O_5S$: C, 53.92; H, 5.20; N, 15.72

Found: C, 53.57 ; H, 5.22; N, 15.58.

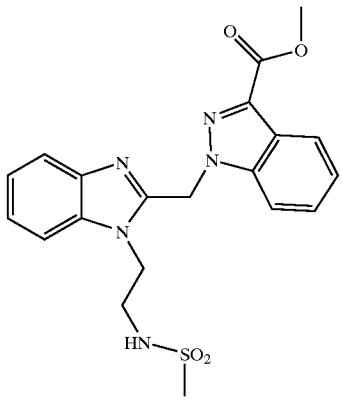

23

Compound 23f was dissolved in AcOH (20 mL) and heated to reflux for 4 hours. The mixture was cooled and concentrated. The residue was purified by flash chromatography (gradient, MeOH/CH$_2$Cl$_2$, 3% to 5%) to give 240 mg (85% yield) of compound 23 as a white foam:

$^1$H NMR (DMSO-d$_6$) δ2.83 (s, 3H), 3.34–3.39 (m, 2H), 4.48–4.52 (m, 2H), 6.21 (s, 2H), 7.16 (t, J=7.9 Hz, 1H), 7.26 (t, J=7.2 Hz, 1H), 7.35–7.45 (m, 2H), 7.48–7.53 (m, 2H), 7.61 (d, J=8.0 Hz, 1H), 8.11 (d, J=8.2 Hz, 1H), 11.97 (s, 1H, exchanges with D$_2$O);

IR (KBr, cm$^{-1}$) 1716, 1323, 1149, 747;

MS m/e 427 (MH$^+$);

Anal. Calcd for C$_{20}$H$_{21}$N$_5$O$_4$.0.35H$_2$O.53 AcOH: C, 54.33; H, 5.16; N, 15.04

Found: C, 54.33; H, 5.16; N, 15.16.

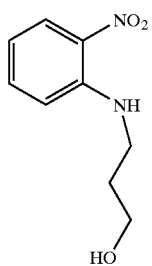

24a

A solution of 2-fluoronitrobenzene (5.0 g, 35.5 mmol) and 1-amino-3-propanol (2.65 g, 35.5 mmol) in CH$_3$CN (100 mL) and triethylamine (4.1 g, 40 mmol) was heated to reflux for 12 hours, then cooled and concentrated. The residue was dissolved in EtOAc and washed with 1N HCl. The organic layer was dried over MgSO$_4$ and concentrated to give 6.5 g (93% yield) of compound 24a as a dark orange solid:

$^1$H NMR (DMSO-d$_6$) δ1.95–2.10 (m, 2H), 3.48 (t, J=6.7 Hz, 2H), 3.86 (t, J=6.7 Hz, 2H), 6.61–6.67 (m, 1H), 6.90 (d, J=9 Hz, 1H), 7.41–7.47 (m, 1H), 8.17 (d, J=7.8 Hz, 1H);

IR (KBr cm$^{-1}$) 3378, 1512, 1353, 1069;

MS m/e 196 (MH$^+$).

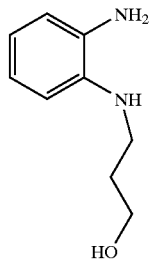

24b

A solution of compound 24a (6.5 g, 33.1 mmol) in EtOH (50 mL) was hydrogenated at 40 psi with 10% palladium on carbon (100 mg) for 4 hours. The catalyst was removed by filtration and the filtrate was evaporated to give 2.7 g (38% yield) of compound 24b as a dark oil:

$^1$H NMR(DMSO-d$_6$) δ1.90–1.94 (m, 2H), 3.27 (t, J=6.4 Hz, 2H), 3.83 (t, J=5.9 Hz, 2H), 6.67–6.73 (m, 3H) 6.81–6.85 (m, 1H);

MS m/e 166 (MH$^+$).

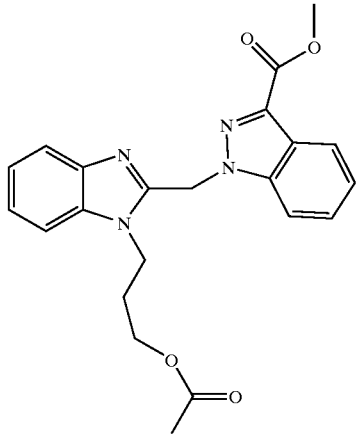

24

Compound 24 was prepared using the same sequence as compound 23 with compound 23b and compound 24b:

$^1$H NMR (DMSO-d$_6$) δ1.86–1.98 (m, 2H), 1.99 (s, 3H), 3.91 (s, 3H), 3.98 (t, J=6.2 Hz, 2H), 4.42 (t, J=7.4 Hz, 2H), 6.18 (s, 2H), 7.15–7.28 (m, 2H), 7.38 (t, J=7.5 Hz, 1H), 7.50–7.58 (m, 2H), 7.90 (d, J=8.5 Hz, 1H), 8.10 (d, J=8.1 Hz, 1H);

IR (KBr, cm$^{-1}$) 1740, 1723, 740;

MS m/e 406 (MH$^+$);

Anal. Calcd for C$_{22}$H$_{22}$N$_4$O$_4$: C, 65.01; H, 5.46; N, 13.78

Found: C, 64.87; H, 5.56; N, 13.66.

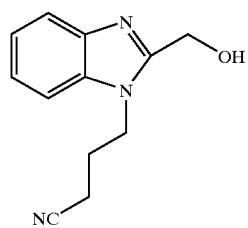

25a

To a solution of 2-hydroxymethylbenzimidazole (29.63 g, 200 mmol) in a mixture of DMF/THF (150 mL, 1:1) was added sodium hydride (60% in mineral oil, 8.4 g, 210 mmol) in several portions at room temperature. After stirring for 1 hour, 4-bromobutyronitrile (29.6 g, 200 mmol) was added and the resulting solution was stirred at 80° C. for 18 hours. The solvent was evaporated. The residue was diluted with H₂O and extracted with EtOAc. The combined extracts were dried over MgSO₄ and evaporated. The residue was purified by flash chromatography (EtOAc:hexane=1:1 to 2:1, then EtOAc: MeOH=10:1) to give 22.11 g (51% yield) of 25a as a white solid:

¹H NMR (CDCl₃) δ2.27–2.32 (m, 2H), 2.41 (t, J=6.0 Hz, 2H), 4.41 (t, J=7.2 Hz, 2H), 7.26–7.38 (m, 3H), 7.67–7.70 (m, 1H);

MS m/e 216 (MH⁺).

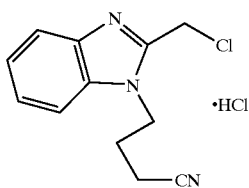

25b

To alcohol 25a (22 g, 102.2 mmol) suspended in CH₂Cl₂ (100 mL) was slowly added thionyl chloride (15.81 g, 132.9 mmol) while cooling at 0° C. with an ice bath. The ice bath was removed and the solution was stirred at room temperature for 1 hour. The solvent was evaporated. The residue was triturated with EtOAc to give a nearly quantitative yield of 25b as light gray powder:

¹H NMR (CDCl₃) δ2.32–2.38 (m, 2H), 2.70 (t, J=7.3 Hz, 2H), 4.69 (t, J=7.6 Hz, 2H), 5.33 (s, 2H), 7.69–7.74 (m, 2H), 7.85–7.87 (m, 1H), 8.00–8.02 (m, 1H);

MS m/e 234 (MH⁺);

Anal. Calcd for C₁₂H₁₂N₃.HCl.0.25H₂O: C, 52.48; H, 4.95; N, 15.30

Found: C, 52.52; H, 4.88; N, 15.26.

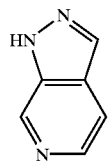

25c 1H-pyrazolo[3,4-c]pyridine 25c was prepared according to the procedure described by D. Chapman et al. (*Journal of the Chemical Society, Perkin Transactions I*, 1980, 2398).

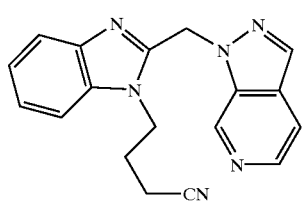

25

A suspension of 1H-pyrazolo[3,4-c]pyridine (25c, 24 mg, 0.20 mmol) and Cs₂CO₃ (196 mg, 0.60 mmol) in DMF (4 ml) was pre-mixed for 2 hours before compound 25b (54 mg, 0.20 mmol) was added to the mixture. The reaction mixture was stirred at room temperature for 18 hours. The mixture was diluted with EtOAc (10 ml), washed with H₂O and brine, dried over MgSO₄, and concentrated. The crude product was purified by preperative HPLC (gradient, 10% MeOH in H₂O with 0.1% TFA to 90% MeOH in H₂O with 0.1% TFA) to yield 35 mg (55% yield) of compound 25 as a viscous oil:

¹H NMR (CD₃OD) δ2.20–2.26 (m, 2H), 2.64 (t, J=7.2 Hz, 2H), 4.68 (t, J=7.6 Hz, 2H), 6.44 (s, 2H), 7.39–7.42 (m, 1H), 7.46–7.49 (m, 1H), 7.65 (d, J=8.1 Hz, 1H), 7.75 (d, J=8.2 Hz, 1H), 8.38 (d, J=6.2 Hz, 1H), 8.47 (d, J=6.2 Hz, 1H), 8.64 (s, 1H), 9.77 (s, 1H);

MS m/e 317 (MH⁺).

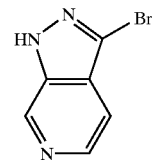

26a

3-Bromo-1H-pyrazolo[3,4-c]pyridine 26a was prepared the procedure described by D. Chapman et al. (*Journal of the Chemical Society, Perkin Transactions I*, 1980, 2398).

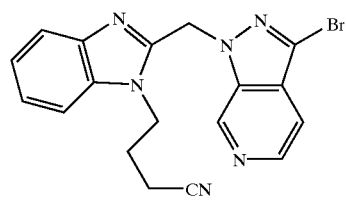

26

Compound 26 was prepared using the same procedure as compound 25 with compound 25b and compound 26a:

¹H NMR (CDCl₃) δ1.83–1.89 (m, 2H), 2.42 (t, J=7.0 Hz, 2H), 4.47 (t, J=7.6 Hz, 2H), 5.97 (s, 2H), 7.28–7.37 (m, 3H), 7.48–7.49 (m, 1H), 7.78–7.79 (m, 1H), 8.39 (d, J=5.6 Hz, 1H), 9.29 (d, J=0.4 Hz, 1H);

MS m/e 394, 396 (MH⁺).

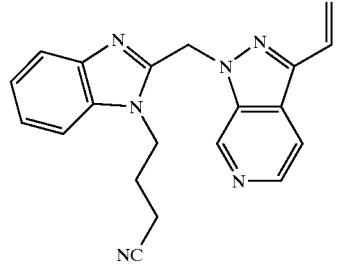

Compound 27 was prepared using the same procedure as Compound 21 starting with compound 26 and tributylvinyl-tin.

¹H NMR (CDCl₃) δ1.73–1.79 (m, 2H), 2.33 (t, J=7.0 Hz, 2H), 4.45 (t, J=7.6 Hz, 2H), 5.63 (d, J=11.4 Hz, 1H), 5.99 (s, 2H), 6.14 (d, J=18 Hz, 1H), 6.99–7.04 (m, 1H), 7.29–7.34 (m, 3H), 7.75 (d, J=5.6 Hz, 1H), 7.80–7.82 (m, 1H), 8.37 (d, J=5.6 Hz, 1H), 9.27 (s, 1H);

MS m/e 343 (MH⁺).

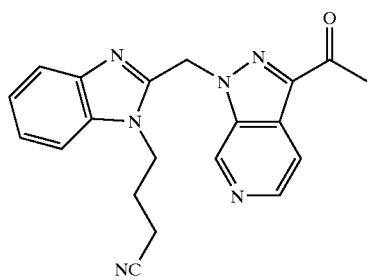

Compound 28 was prepared using the same procedure as compound 21 starting with compound 26 and tributyl(1-ethoxyvinyl)tin. The crude product formed was stirred in 25% HCl—MeOH for 2 h and purified by preparative-HPLC (gradient, 10% MeOH in H$_2$O with 0.1% TFA to 90% MeOH in H$_2$O with 0.1% TFA) to give the desired product (78%).

$^1$H NMR (CD$_3$OD) δ2.31–2.38 (m, 2H), 2.69–2.73 (m, 5H), 4.76 (t, J=7.5 Hz, 2H), 6.59 (s, 2H), 7.44–7.48 (m, 1H), 7.52–7.55 (m, 1H), 7.66–7.69 (m, 1H), 7.38–7.85 (m, 1H), 8.61–8.65 (m, 2H), 9.80 (s, 1H);

MS m/e 359 (MH$^+$).

29a

To a solution of 5-chloropentyne (2.05 g, 20.0 mmol) in THF (20 ml) at −28° C. was added butyllithium (2.5 M in hexane, 16.4 ml, 41.0 mmol) dropwise. The formed solution was kept at 0° C. for 1 h before addition of tributyltin chloride (6.44 g, 19.8 mmol). The final solution was heated to reflux for 2 h, cooled down to the ambient temperature, diluted with EtOAc (200 ml). The organic layer was washed with aqueous NaHCO$_3$ saturated aqueous NaCl respectively, dried over MgSO$_4$, concentrated and was used as crude without further purification.

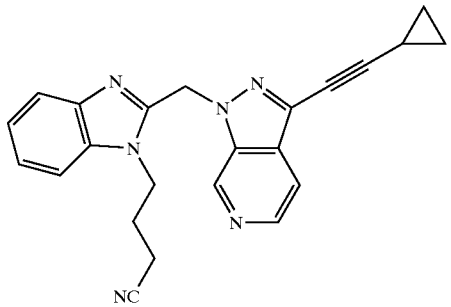

Compound 29 was prepared using the same procedure as compound 21 starting with compound 26 and tributyl-cyclopropylethynyl-stannane.

$^1$H NMR (CD$_3$OD) δ0.88–0.90 (m, 2H), 0.98–1.02 (m, 2H), 1.60–1.65 (m, 1H), 2.19–2.25 (m, 2H), 2.66 (t, J=7.2 Hz, 2H), 4.68 (t, J=7.5 Hz, 2H), 6.38 (s, 2H), 7.42–7.45 (m, 1H), 7.48–7.51 (m, 1H), 7.66 (d, J=8.1 Hz, 1H), 7.78 (d, J=8.2 Hz, 1H), 8.18–8.19 (m, 1H), 8.47 (d, J=6.0 Hz, 1H), 9.66 (s, 1H);

MS m/e 382 (MH$^+$).

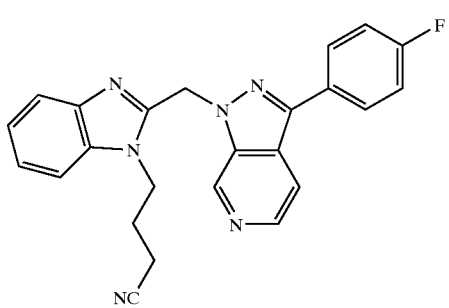

30

A mixture of compound 26 (40 mg, 0.1 mmol), 4-fluorophenylboronic acid (15 mg, 0.11 mmol), Cs$_2$CO$_3$ (49 mg, 0.15 mmol) and PdCl$_2$(PPh$_3$)$_2$ (7 mg, 0.01 mmol) in DMF (1 ml) was heated to 100° C. for 4 h. Diluted with EtOAc (20 ml), washed with NaHCO$_3$, H$_2$O, and brine. Dried over MgSO$_4$ and concentrated. The residue was purified by prep-HPLC (gradient, 10% MeOH in H$_2$O with 0.1% TFA to 90% MeOH in H$_2$O with 0.1% TFA) to give compound 30 16 mg (39%).

$^1$H NMR (CD$_3$OD) δ2.24–2.30 (m, 2H), 2.64 (t, J=7.1 Hz, 2H), 4.72 (t, J=7.6 Hz, 2H), 6.45 (s, 2H), 7.30–7.34 (m, 2H), 7.39–7.42 (m, 1H), 7.46–7.49 (m, 1H), 7.64 (d, J=8.1 Hz, 1H), 7.76 (d, J=8.2 Hz, 1H), 8.07–8.10 (m, 1H), 8.51 (d, J=6.2 Hz, 1H), 8.55 (d, J=6.2 Hz, 1H), 9.72 (s, 1H);

MS m/e 411 (MH$^+$).

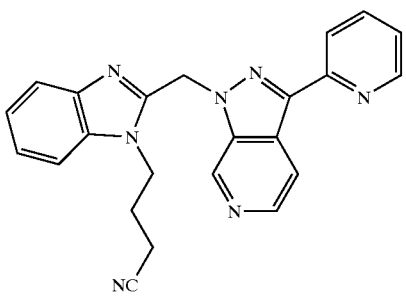

31

Compound 31 was prepared using the same procedure as compound 21 starting with compound 26 and tributyl(2-pyridio)tin.

$^1$H NMR (CD$_3$OD) δ2.30–2.36 (m, 2H), 2.71 (t, J=7.1 Hz, 2H), 4.77 (t, J=7.6 Hz, 2H), 6.57 (s, 2H), 7.44–7.49 (m, 2H), 7.50–7.54 (m, 1H), 7.67 (d, J=8.1 Hz, 1H), 7.83 (d, J=8.2 Hz, 1H), 7.94–7.98 (m, 1H), 8.28 (d, J=8.0 Hz, 1H), 8.57–8.59 (m, 1H), 8.79 (d, J=4.3 Hz, 1H), 9.17–9.18 (m, 1H), 9.83 (s, 1H);

MS m/e 394 (MH$^+$).

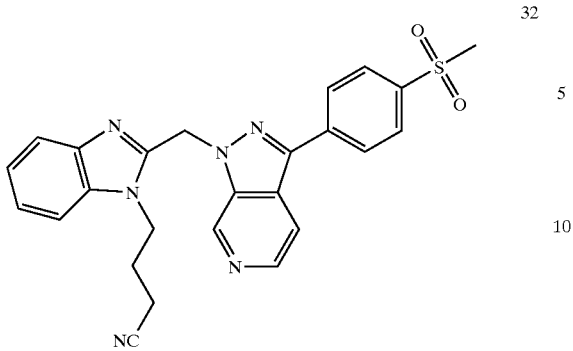

32

Compound 32 was prepared using the same procedure as compound 21 starting with compound 26 and 4-methylsulfonylphenylboronic acid.

$^1$H NMR (CD$_3$OD) δ2.27–2.33 (m, 2H), 2.67 (t, J=7.1 Hz, 2H), 4.75 (t, J=7.6 Hz, 2H), 6.53 (s, 2H), 7.42–7.45 (m, 1H), 7.49–7.52 (m, 1H), 7.66 (d, J=8.1 Hz, 1H), 7.79 (d, J=8.2 Hz, 1H), 8.10–8.13 (m, 2H), 8.29–8.32 (m, 2H), 8.57–8.60 (m, 2H), 9.77 (s, 1H);

MS m/e 471 (MH$^+$).

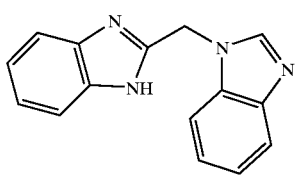

33

Compound 33 was prepared using the same procedure as compound 1c starting with compound 1b and benzimidazole:

$^1$H NMR (CDCl$_3$) δ5.65 (s, 2H), 6.90–7.18 (m, 6H), 7.44 (s, 1H), 7.65 (bs, 2H);
IR (KBr, cm$^{-1}$) 1493, 1459, 1437, 1330, 1273, 745;
MS m/e 249 (MH$^+$);
Anal. Calcd for C$_{15}$H$_{12}$N$_4$·0.3H$_2$O: C, 71.02; H, 5.01; N, 22.08
Found: C, 70.96; H, 4.86; N, 21.93.

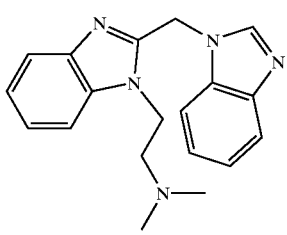

34

Compound 34 was prepared using the same procedure as compound 1 with compound 33 and 2-chloro-N,N-dimethylethylamine hydrochloride:

$^1$H NMR (CD$_3$OD) δ3.14 (s, 6H), 3.94 (t, J=7.6 Hz, 2H), 5.14 (t, J=7.6 Hz, 2H), 6.79 (s, 2H), 7.52–7.80 (m, 6H), 7.80–8.12 (m, 2H);
IR (KBr, cm$^{-1}$) 3400, 2680, 1617, 1551, 1464, 1368, 756;
MS m/e 320 (MH$^+$).

35

To a solution of 2-chlorobenzimidazole (71 mg, 0.46 mmol) and NaH (60% suspension in mineral oil, 19 mg, 0.46 mmol) in DMF (2 mL) was added compound 4c and the reaction was stirred at room temperature for 5 days. The solvent was evaporated in vacuo and the residue was diluted with EtOAc, washed with water and brine, dried over MgSO$_4$, and concentrated. Purification by flash column chromatography (hexanes/EtOAc, 3:1) gave 43 mg (29% yield) of compound 35 as a white solid:

$^1$H NMR (CDCl$_3$) δ0.83 (d, J=6.7 Hz, 6H), 1.06–1.14 (m, 2H), 1.47–1.56 (m, 1H), 4.05–4.11 (m, 2H), 5.99 (s, 2H), 7.21–7.30 (m, 2H), 7.34–7.45 (m, 3H), 7.54 (d, J=7.1 Hz, 1H), 7.69–7.72 (m, 1H), 7.89–7.92 (m, 1H);

IR (KBr, cm$^{-1}$) 3435, 2954, 1470, 1458, 1381, 744;

MS m/e 353 (MH$^+$);

Anal. Calcd for C$_{20}$H$_{21}$ClN$_4$: C, 68.08; H, 6.00; N, 15.88
Found: C, 67.82; H, 5.84; N, 15.58.

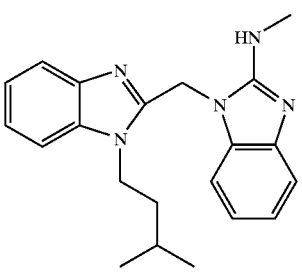

36

Compound 35 (150 mg, 0.43 mmol) and methylamine (165 mg, 2.13 mmol) were mixed in EtOH (2 mL) in a sealed tube. The reaction mixture was stirred at 125° C. for 18 hours. The EtOH was evaporated to give a light brown solid which was triturated with water to give 197 mg (100% yield) of compound 36:

$^1$H NMR (DMSO-d$_6$) δ0.90 (d, J=6.6 Hz, 6H), 1.32–1.40 (m, 2H), 1.57–1.64 (m, 1H), 2.94 (d, J=4.4 Hz, 3H), 4.21–4.27 (m, 2H), 5.57 (s, 2H), 6.84 (t, J=7.2 Hz, 1H), 6.96 (t, J=7.2 Hz, 1H), 7.10–7.26 (m, 4H), 7.50 (d, J=7.7 Hz, 1H), 7.56 (d, J=7.6 Hz, 1H);

IR (KBr, cm$^{-1}$) 3375, 2955, 1668, 1622, 1577, 1462, 1331, 739;

MS m/e 348 (MH$^+$).

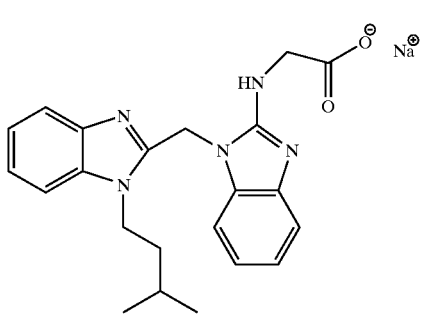

37

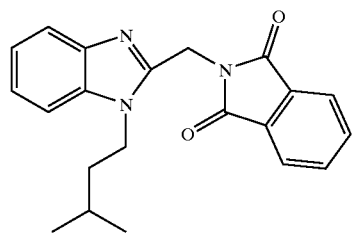

39

A mixture of glycine sodium salt hydrate (285 mg, 2.94 mmol) and compound 35 (207 mg, 0.59 mmol) in a mixture of water and EtOH (3 mL, 2:1) were stirred in a sealed tube at 120° C. for 9 days. The solvent was evaporated. The resulting solid was dissolved in water and the pH was adjusted to 7. The aqueous solution was extracted with EtOAc and the combined extracts were dried over $MgSO_4$ and evaporated. To the residue in MeOH was added 1 equivalent of 1N NaOH. The solvent was evaporated to give compound 37 as a brown solid:

$^1$H NMR (DMSO-$d_6$) δ0.82 (d, J=6.6 Hz, 6H), 1.20–1.31 (m, 2H), 1.48–1.54 (m, 1H), 3.52 (d, J=3.8 Hz, 2H), 4.18–4.24 (m, 2H), 5.57 (s, 2H), 6.22 (t, J=4.0 Hz, 1H), 6.78–6.82 (m, 1H), 6.89–6.94 (m, 1H), 7.06–7.28 (m, 4H), 7.47 (d, J=7.5 Hz, 1H), 7.58 (d, J=8.4 Hz, 1H);

MS m/e 392 (MH$^+$).

Compound 39 was prepared using the same procedure as compound 4 with phthalimide in 26% yield:

$^1$H NMR (CDCl$_3$) δ1.00 (d, J=6.2 Hz, 6H), 1.67–1.81 (m, 3H), 4.30 (t, J=7.9 Hz, 2H), 5.11 (s, 1H), 7.17–7.32 (m, 4H), 7.68–7.76 (m, 2H), 7.85–7.91 (m, 2H);

IR (KBr, cm$^{-1}$) 2953, 1774, 1718, 1469, 1424, 1394, 1323, 1115, 950, 749, 723;

MS m/e 348 (MH$^+$);

Anal. Calcd for $C_{21}H_{21}N_3O_2 \cdot 0.5H_2O$: C, 70.77; H, 6.22; N, 11.79

Found: C, 70.76; H, 6.39; N, 11.62.

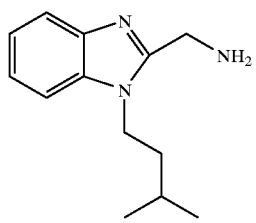

40a

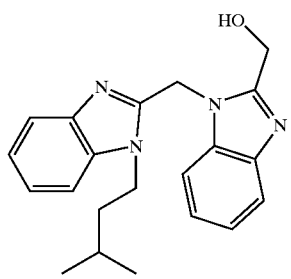

38

Compound 38 was prepared using the same procedure as compound 4 with 2-benzimidazolemethanol:

$^1$H NMR (CDCl$_3$) δ0.87 (d, J=6.5 Hz, 6H), 1.32–1.40 (m, 2H), 1.48–1.55 (m, 1H), 4.14–4.19 (m, 2H), 4.87 (s, 2H), 5.72 (s, 2H), 7.28–7.40 (m, 6H), 7.72–7.79 (m, 2H);

IR (KBr, cm$^{-1}$) 2948, 1473, 1458, 1438, 1400, 1035, 740;

MS m/e 349 (MH$^+$);

Anal. Calcd for $C_{21}H_{24}N_4 \cdot 0.25H_2O$: C, 71.46; H, 7.00; N, 15.87

Found: C, 71.23; H, 6.99; N, 15.90.

Compound 39 (2.0 g, 6.00 mmol) was stirred at reflux with excess hydrazine hydrate (617 mg, 17.61 mmol) in EtOH for 2 hours. The reaction mixture was diluted with EtOH and the precipitate was filtered and washed with EtOH. The filtrate was concentrated, diluted with EtOAc, washed with water and brine, dried over $MgSO_4$, and concentrated to give 967 mg (74% yield) of compound 40a as a brown oil which was used without further purification.

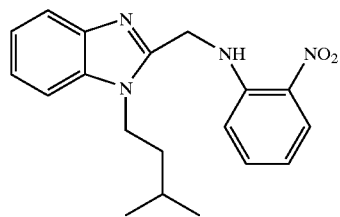

40b

A mixture of amine 40a (960 mg, 4.42 mmol), 1-fluoro-2-nitrobenzene (811 mg, 5.75 mmol), and $K_2CO_3$ (732 mg, 5.03 mmol) in $CH_3CN$ was stirred at reflux for 18 hours. The reaction mixture was filtered and washed with EtOAc. The filtrate was concentrated, subjected to flash column chromatography (gradient, hexanes/EtOAc, 3:1 to 2:1), and recrystallized from $Et_2O$/hexanes to give 486 mg (32% yield) of compound 40b as an orange solid.

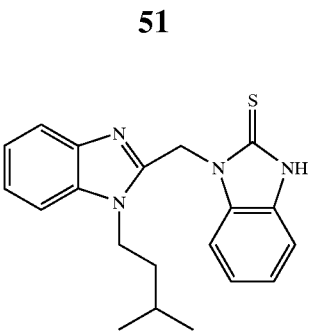

40

Compound 40b (1.0 g, 2.96 mmol) was reduced under H$_2$ in a Parr apparatus in the presence of 10% palladium on carbon (150 mg) in a mixture of EtOAc and MeOH (22 mL, 10:1) at 60 psi for 45 minutes. The catalyst was removed by filtration through a pad of celite and the filtrate was concentrated. This diamine was then treated with 1,1'-thiocarbonyldiimidazole (686 mg, 3.85 mmol) in THF and stirred at reflux for 5 hours. The solvent was concentrated and the residue was subjected to flash column chromatography (hexanes/EtOAc, 2:1) to give 835 mg (81% yield) of compound 40:

$^1$H NMR (CDCl$_3$) δ0.91 (d, J=6.6 Hz, 6H), 1.34–1.42 (m, 2H), 1.64–1.73 (m, 2H), 4.39 (bt, J=8.0 Hz, 2H), 5.83 (s, 2H), 7.10–7.27 (m, 5H), 7.37 (d, J=7.4 Hz, 1H), 7.50 (d, J=7.7 Hz, 1H), 7.57 (d, J=7.5 Hz, 1H), 13.03 (s, 1H);

MS m/e 351 (MH$^+$).

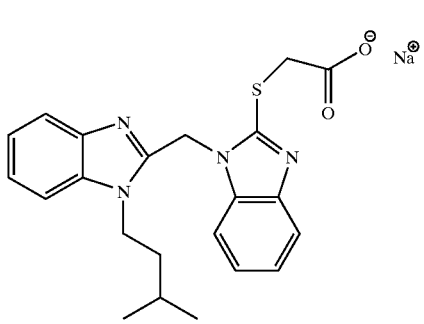

41

A mixture of compound 40 (150 mg, 0.43 mmol), bromoacetic acid (65 mg, 0.47 mmol) and K$_2$CO$_3$ (65 mg, 0.47 mmol) in CH$_3$CN (2 mL) were stirred at room temperature for 3 days. Additional bromoacetic acid (60 mg, 0.43 mmol) in CH$_3$CN (2 mL) was added and the reaction mixture was refluxed for 4 hours. The solvent was evaporated. The residue was diluted with saturated aqueous NaHCO$_3$ and extracted with EtOAc. The aqueous layer was then neutralized to pH 7 and extracted with EtOAc. The extracts were dried over MgSO$_4$ and evaporated to give 77 mg (44% yield) of compound 41 as a pale brown solid.

A mixture of acid 41 (125 mg, 0.31 mmol) and 1N NaOH (0.31 mL, 0.31 mmol) in MeOH (3 mL) was stirred at room temperature and was evaporated to give a light green product. This material was dissolved in water, treated with active carbon and filtered. The filtrate was concentrated to give 107 mg (80% yield) of the sodium salt of compound 41:

$^1$H NMR (DMSO-d$_6$) δ0.85 (d, J=6.6 Hz, 6H), 1.23–1.33 (m, 2H), 1.51–1.60 (m, 2H), 3.82 (s, 2H), 4.22–4.28 (m, 2H), 5.72 (s, 2H), 7.03–7.26 (m, 4H), 7.36 (d, J=7.0 Hz, 1H), 7.48–7.57 (m, 3H);

MS m/e 409 (MH$^+$).

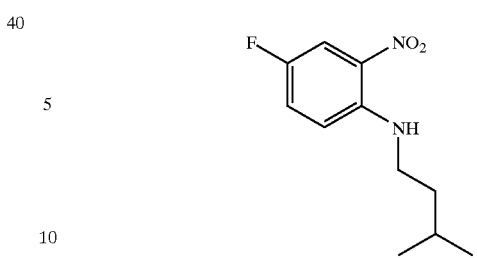

42a

To a solution of 2,5-difluoronitrobenzene (45 g, 282.86 mmol) in CH$_3$CN (500 mL) was added potassium carbonate (78 g, 565.72 mmol) and isoamylamine (25 g, 282.86 mmol). The reaction mixture was stirred at room temperature for 18 hours with the aid of a mechanical stirrer. The potassium carbonate was filtered and the filtrate was evaporated to give an orange oil. The oil was diluted with EtOAc, washed with water and brine, dried over MgSO$_4$, and evaporated. Purification by flash column chromatography (hexanes/EtOAc, 20:1) gave 53 g (83% yield) of compound 42a:

$^1$H NMR (CDCl$_3$) δ0.98 (d, J=6.5 Hz, 6H), 1.61–1.65 (m, 2H), 1.74–1.78 (m, 1H), 3.30 (t, J=7.3 Hz, 2H), 6.83 (dd, J=4.6, 9.5 Hz, 1H), 7.23–7.27 (m, 1H), 7.85 (dd, J=3.1, 9.2 Hz, 1H);

MS m/e 226 (MH$^+$).

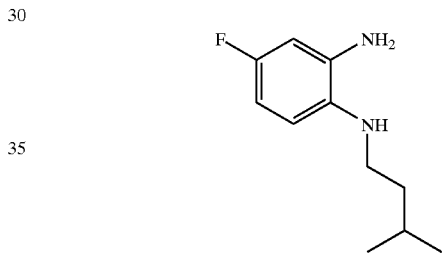

42b

To a solution of compound 42a (53 g, 235.14 mmol) and concentrated HCl (15 mL) in MeOH (200 mL) was added 10% palladium on carbon (5 g) and the mixture was reduced under H$_2$ at 55 psi for 1.5 hours. The catalyst was removed by filtration through a pad of celite and the filtrate was concentrated to give 47 g (87% yield) of diamine 42b as the HCl salt:

$^1$H NMR (CDCl$_3$) δ0.97 (d, J=6.2 Hz, 6H), 1.65–1.77 (m, 3H), 3.36 (t, J=8.0 Hz, 2H), 6.50–6.57 (m, 1H), 6.71 (dd, J=2.7, 10.5 Hz, 1H), 7.28 (dd, J=5.5, 8.8 Hz, 1H);

MS m/e 197 (MH$^+$).

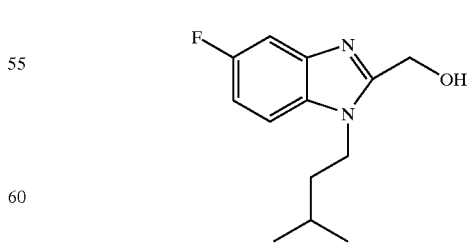

42c

A mixture of diamine 42b (47 g, 200.66 mmol) and glycolic acid (16 g, 210.70 mmol) in 4N HCl (500 mL) were stirred at reflux for 18 hours. The reaction mixture was cooled to 0° C. and was adjusted to pH 8 by adding concentrated ammonium hydroxide. The product was extracted with EtOAc, dried over MgSO$_4$, and evaporated. The crude product was recrystallized with EtOAc/hexanes to give 27 g (37% yield) of compound 42c as brown crystals:

$^1$H NMR (CDCl$_3$) δ1.02 (d, J=6.0 Hz, 6H), 1.68–1.75 (m, 3H), 3.19 (bs, 1H), 4.22 (t, J=7.7 Hz, 2H), 4.93 (s, 2H), 7.06 (dt, J=2.2, 9.1 Hz, 1H), 7.26–7.28 (m, 1H), 7.37 (dd, J=2.1, 8.9 Hz, 1H);

MS m/e 237 (MH$^+$).

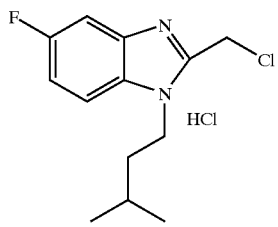

42d

To a solution of alcohol 42c (27 g, 112.99 mmol) in CH$_2$Cl$_2$ (100 mL) was slowly added thionyl chloride (27 g, 225.99 mmol) and the reaction mixture was stirred at 65° C. for 2.5 hours. The solvent and excess thionyl chloride were evaporated to give a grey solid. The solid was suspended in Et$_2$O and evaporated several times to ensure removal of the solvent and reagent. The solid was then dissolved in a minimal amount of CH$_2$Cl$_2$ and precipitated by addition of hexanes. The solid was collected by filtration and triturated with Et$_2$O to give 32 g (96% yield) of compound 42d as a grey solid:

$^1$H NMR (CDCl$_3$) δ1.08 (d, J=6.4 Hz, 6H), 1.79–1.90 (m, 3H), 4.44 (bt, J=8.2 Hz, 2H), 5.32 (s, 2H), 7.36 (dt, J=2.2, 8.9, 1H), 7.54–7.59 (m, 2H);

MS m/e 255 (MH$^+$).

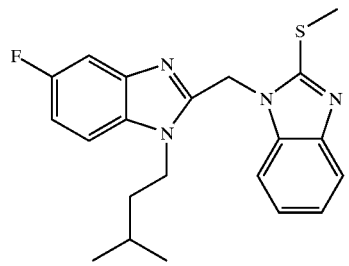

42

Compound 42 was prepared using the same procedure as compound 4 with compound 42d and 2-(methylmercapto)benzimidazole in 95% yield:

$^1$H NMR (CD$_3$OD) δ0.99 (d, J=6.5 Hz, 6H), 1.61–1.66 (m, 2H), 1.66–1.71 (m, 1H), 2.91 (s, 3H), 4.40–4.43 (m, 2H), 6.05 (s, 2H), 7.21 (td, J=2.4, 9.2 Hz, 1H), 7.27 (dd, J=2.4, 8.9 Hz, 1H), 7.43–7.51 (m, 2H), 7.63–7.65 (m, 2H), 7.76 (d, J=7.8 Hz, 1H);

MS m/e 384 (MH$^+$).

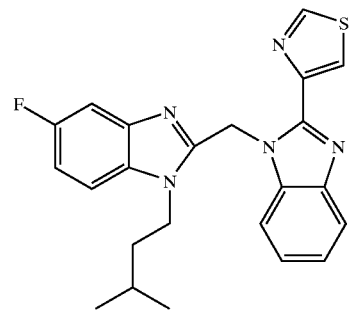

43

Compound 43 was prepared using the same procedure as compound 4 with compound 42d and thiabenazole in 67% yield:

$^1$H NMR (CD$_3$OD) δ1.02 (d, J=6.2 Hz, 6H), 1.72–1.74 (m, 3H), 4.45–4.48 (m, 2H), 6.56 (s, 2H), 7.17–7.21 (m, 2H), 7.46–7.53 (m, 2H), 7.62–7.64 (m, 1H), 7.72 (d, J=8.1 Hz, 1H), 7.84 (d, J=7.8 Hz, 1H), 8.61 (s, 1H), 9.09 (s, 1H);

MS m/e 420 (MH$^+$).

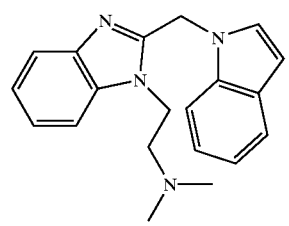

44

Compound 44 was prepared using the same procedure sequence as compound 1 starting with indole:

$^1$H NMR (CDCl$_3$) δ2.01 (bs, 8H), 4.02 (t, J=7.3 Hz, 2H), 5.64 (s, 2H), 6.55 (dd, J=0.8, 3.2 Hz, 1H), 7.08–7.29 (m, 6H), 7.48 (d, J=8.6 Hz, 1H), 7.62 (d, J=7.5 Hz, 1H), 7.80–7.84 (m, 1H);

IR (KBr, cm$^{-1}$) 2943, 2824, 1613, 1463, 1420, 1323, 741;
MS m/e 319 (MH$^+$).

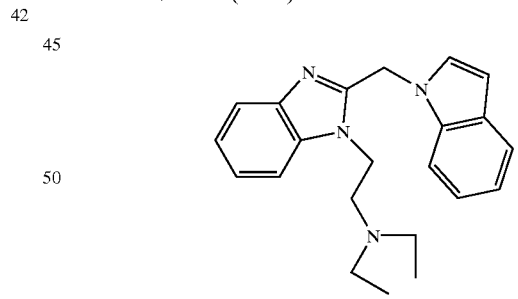

45

Compound 45 was prepared using the same procedure sequence as compound 1 starting with indole and 2-chloro-N,N-diethylethylamine hydrochloride:

$^1$H NMR (CD$_3$OD) δ1.31 (t, J=7.3 Hz, 6H), 3.10 (t, J=8.1 Hz, 2H), 3.60–3.75 (m, 4H), 4.94 (s, 2H), 4.99–5.04 (m, 2H), 6.75 (d, J=8.0 Hz, 1H), 6.81 (t, J=7.5 Hz, 1H), 7.10 (t, J=7.4 Hz, 1H), 7.19 (d, J=7.2 Hz, 1H), 7.62–7.72 (m, 4H), 7.82 (d, J=7.2 Hz, 8.06 (d, J=7.4 Hz, 1H);

IR (KBr, cm$^{-1}$) 3396, 2925, 1728, 1606, 1523, 1464, 1253, 1136, 753;
MS m/e 349 (MH$^+$).

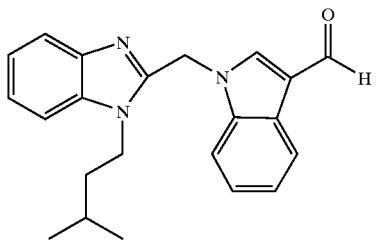

46

To a suspension of indole-3-carboxaldehyde (129 mg, 0.89 mmol) in CH$_3$CN was added NaH (60% suspension in mineral oil, 39 mg, 0.98 mmol). After stirring for 15 minutes, the neutral form of compound 4c (232 mg, 0.98 mmol) was added. The reaction mixture was stirred at room temperature for 2.5 hours and then heated to 70° C. for 1.5 hours. After evaporation of the solvent, the resulting residue was diluted with aqueous saturated NaHCO$_3$ and extracted with EtOAc. The organic extracts were dried over MgSO$_4$ and evaporated. Column chromatography (gradient, hexanes/EtOAc, 1:1 to EtOAc/hexanes, 2:1) gave 199 mg (65% yield) of compound 46:

$^1$H NMR (CDCl$_3$) δ0.68 (d, J=6.6 Hz, 6H), 1.05–1.13 (m, 2H), 1.23–1.36H), 3.87–3.93 (m, 2H), 5.60 (s, 2H), 7.22–7.33 (m, 4H), 7.47–7.54 (m, 1H), 7.70 (s, 1H), 7.75–7.80 (m, 1H), 8.23–8.27 (m, 1H), 9.90 (s, 1H);

IR (KBr, cm$^{-1}$) 3432, 2961, 1662, 1651, 1526, 1463, 1386, 1189, 1171, 1038, 778, 739;

MS m/e 346 (MH$^+$);

Anal. Calcd for C$_{22}$H$_{23}$N$_3$O.0.25H$_2$O: C, 75.51; H, 6.77; N, 12.01

Found: C, 75.60; H, 6.59; N, 11.83.

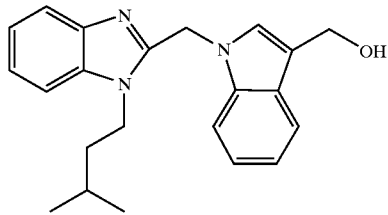

47

Sodium borohydride (10 mg, 0.26 mmol) was added to a solution of aldehyde 46 (70 mg, 0.20 mmol) in MeOH (5 mL) at 0° C. The reaction was monitored by thin layer chromatography and when complete, the solvent was evaporated. The resulting residue was subjected to flash column chromatography (straight EtOAc) to give 50 mg (70% yield) of compound 47 as a white solid:

$^1$H NMR (CDCl$_3$) δ0.71 (d, J=6.6 Hz, 6H), 1.04–1.12 (m, 2H), 1.22–1.33 (m, 1H), 3.87–3.92 (m, 2H), 4.82 (s, 2H), 5.56 (s, 2H), 7.12 (s, 1H), 7.14–7.31 (m, 5H), 7.47 (d, J=8.2 Hz, 1H), 7.71–7.74 (m, 1H), 7.80–7.83 (m, 1H);

IR (KBr, cm$^{-1}$) 3247, 2950, 2867, 1612, 1465, 1309, 1038, 743;

MS m/e 348 (MH$^+$);

Anal. Calcd for C$_{22}$H$_{25}$N$_3$O.0.25H$_2$O: C, 75.08; H, 7.30; N, 11.94

Found: C, 74.86; H, 7.17; N, 11.82.

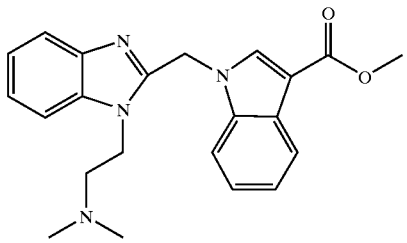

48

Compound 48 was prepared using the same procedure sequence as compound 1 starting with methyl indole-4-carboxylate:

$^1$H NMR (CDCl$_3$) δ2.00 (s, 6H), 2.13 (t, J=6.9 Hz, 2H), 3.81 (s, 3H), 4.00 (t, J=6.9 Hz, 2H), 5.63 (s, 2H), 7.21–7.26 (m, 5H), 7.50 (dd, J=2.4, 5.9 Hz, 1H), 7.76 (dd, J=4.5, 7.5 Hz, 1H), 7.79 (s, 1H), 8.13 (dd, J=0.3, 6.2 Hz, 1H);

MS m/e 377 (MH$^+$).

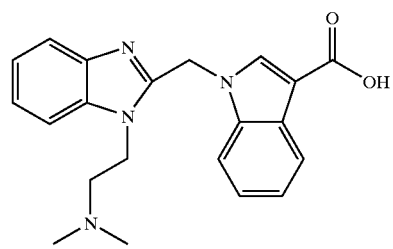

49

A mixture of methyl ester 48 (45 mg, 0.12 mmol) and sodium hydroxide (480 mg, 12.00 mmol) in MeOH (15 mL) was stirred at room temperature for 2 hours and then heated at reflux for 4 days. The solution was neutralized with 1N HCl and the solvent was evaporated. The product was dissolved in cold MeOH and decanted from the solids. The solvent was evaporated to give compound 49:

$^1$H NMR (CD$_3$OD) δ2.93 (s, 6H), 3.30–3.34 (m, 2H), 4.87–4.92 (m, 2H), 6.16 (s, 2H), 7.27–7.30 (m, 2H), 7.42–7.54 (m, 2H), 4.63 (dd, J=3.0, 6.8 Hz, 1H), 7.67 (d, J=7.5 Hz, 1H), 7.89 (d, J=6.4 Hz, 1H), 8.17–8.20 (m, 1H), 8.23 (s, 1H);

MS m/e 361 (MH$^-$).

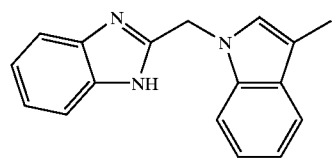

50

To a solution of 3-methylindole (390 mg, 2.97 mmol) in CH$_3$CN was added NaH (60% suspension in mineral oil, 72 mg, 2.97 mmol) and the mixture was stirred at room temperature for 1 hour. Compound 1b was added and the mixture was stirred at room temperature for 17 hours. The solvent was evaporated and the residue was diluted with CH$_2$Cl$_2$, washed with water, dried over MgSO$_4$, and concentrated. Purification by flash column chromatography (hexanes/EtOAc, 4:1) gave the mesyl protected intermediate.

The mesyl protecting group was removed by stirring the mesyl protected intermediate (25 mg, 0.07 mmol) with excess hydrazine hydrate (2 mL) in MeOH (5 mL) at reflux. The solvent was evaporated and the residue was diluted with CH$_2$Cl$_2$, washed with water, dried over MgSO$_4$, and concentrated. Intermediate 50 was used without further purification.

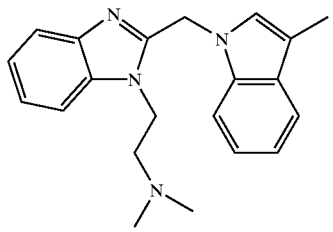

51

To a mixture of 50 (10 mg, 0.04 mmol) and NaH (60% suspension in mineral oil, 4 mg, 0.1 mmol) in THF (1 mL) was added 2-chloro-N,N-dimethylethylamine hydrochloride (6 mg, 0.04 mmol) and the mixture was stirred at reflux for 24 hours. The solvent was evaporated and the residue was diluted with CH$_2$Cl$_2$, washed with water, dried over MgSO$_4$, and concentrated. Purification by flash column chromatography (straight EtOAc) gave 6 mg (46% yield) of compound 51:

$^1$H NMR (CDCl$_3$) δ2.00 (s over t, J=7.5 Hz, 8H), 2.27 (s, 3H), 4.01–4.06 (t, J=7.5 Hz, 2H), 5.57 (s, 2H), 6.89 (s, 1H), 6.89–7.32 (m, 5H), 7.44 (d, J=8.9 Hz, 1H), 7.56 (d, J=8.7 Hz, 1H), 7.80–7.83 (m, 1H);

MS m/e 333 (MH$^+$).

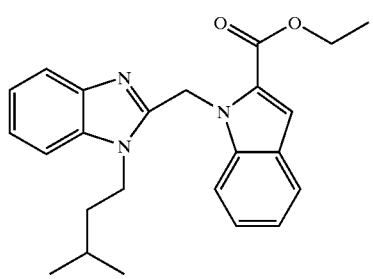

52

Compound 52 was prepared using the same procedure as compound 4 with compound 4c and ethyl indole-2-carboxylate:

$^1$H NMR (CDCl$_3$) δ0.80 (d, J=6.6 Hz, 6H), 1.02–1.09 (m, 3H), 1.41 (t, J=7.1 Hz, 3H), 4.02–4.07 (m, 2H), 4.39 (q, J=7.1 Hz, 2H), 6.30 (s, 2H), 7.11 (t, J=7.1 Hz, 1H), 7.19–7.25 (m, 4H), 7.44 (s, 1H), 7.60–7.66 (m, 2H), 7.76–7.80 (m, 1H);

IR (KBr, cm$^{-1}$) 2956, 2871, 1699, 1519, 1458, 1325, 1257, 1194, 1139, 1096, 743;

MS m/e 390 (MH$^+$).

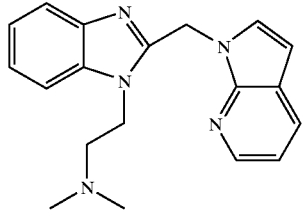

53

Compound 53 was prepared using the same procedure as compound 4 with compound 4c and 7-azaindole:

$^1$H NMR (CDCl$_3$) δ0.57 (d, J=6.6 Hz, 6H), 0.86–0.97 (m, 2H), 1.04–1.13 (m, 1H), 3.99–4.05 (m, 2H), 5.77 (s, 2H), 6.41 (d, J=3.6 Hz, 1H), 7.05 (dd, J=4.7, 7.8 Hz, 1H), 7.19–7.25 (m, 4H), 7.33–7.76 (m, 1H), 7.86 (dd, J=1.6, 7.8 Hz, 1H), 8.31 (dd, J=1.4, 4.7 Hz, 1H);

MS m/e 319 (MH$^+$).

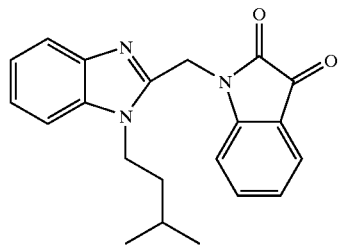

54

To a solution of isatin (7.35 g, 50.0 mmol) in DMF (250 ml) at 0° C. was added NaH (5.0 g, 60% dispersion, 125 mmol). The resulting mixture was stirred at 0° C. for 30 minutes and then chloride 4c (13.0 g, 55.0 mmol) was added. After stirring for additional 2 hours, the mixture was diluted with EtOAc (250 ml), washed with saturated NH$_4$Cl and water (250 ml×2), brine, dried over MgSO$_4$, and concentrated. The residue was purified by flash chromatography (gradient, hexane:EtOAc=3:1 to 1:2) to give 11.6 g (67% yield) of compound 54 as an orange solid:

$^1$H NMR (CD$_3$OD) δ0.96 (d, J=6.6 Hz, 6H), 1.54–1.57 (m, 2H), 1.65–1.75 (m, 1H), 4.21–4.26 (m, 2H), 5.24 (s, 2H), 7.10–7.11 (m, 1H), 7.26–7.32 (m, 3H), 7.54–7.59 (m, 3H), 7.76–7.78 (m, 1H);

MS m/e 348 (MH$^+$).

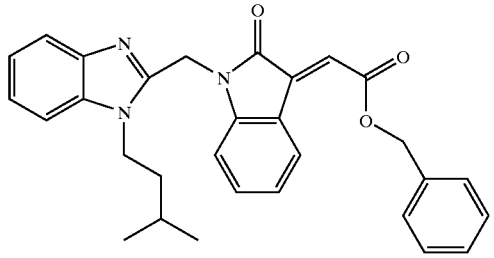

55

The isatin compound 54 (416 mg, 1.20 mmol) and benzyl (triphenylphosphoranylidene) acetate (540 mg, 1.32 mmol) were stirred in CH$_2$Cl$_2$ for 1 hour. The solvent was evaporated and column chromatography (20% EtOAc in hexanes) gave 350 mg (60% yield) of compound 55:

$^1$H NMR (CDCl$_3$) δ0.91 (d, J=6.6 Hz, 6H), 1.39–1.47 (m, 2H), 1.59–1.73 (m, 2H), 4.19–4.24 (m, 2H), 5.29 (s, 2H), 5.31 (s, 2H), 6.99–7.04 (m, 2H), 7.25–7.32 (m, 4H), 7.35–7.43 (m, 6H), 7.27–7.80 (m, 1H), 8.50 (d, J=7.5 Hz, 1H);

MS m/e 480 (MH⁺).

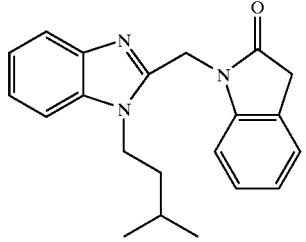

56

Compound 55 (100 mg, 0.21 mmol) was treated with hydrazine (13 mg, 0.42 mmol) in ethanol (5 mL) and heated at 60° C. for 16 hours. Solvent was evaporated and column chromatography (10% EtOAc in hexanes) gave compound 56 as a white solid:

¹H NMR (CDCl₃) δ0.97 (d, J=6.5 Hz, 6H), 1.45–1.52 (m, 2H), 1.65–1.76 (m, 1H), 3.59 (s, 2H), 4.23–4.29 (m, 2H), 5.27 (s, 2H), 7.01 (t, J=7.0 Hz, 1H), 7.18–7.33 (m, 5H), 7.41 (d, J=7.9 Hz, 1H), 7.76–7.80 (m, 1H);

MS m/e 334 (MH⁺).

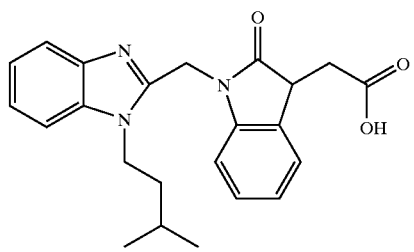

57

To a solution of compound 55 (100 mg, 0.21 mmol) in EtOAc (7 mL) was added 10% palladium on carbon (25 mg). The solution was agitated under H₂ at 50 psi for 3 hours. The reaction mixture was diluted with MeOH and the catalyst was filtered through a pad of celite. The filtrate was concentrated and the residue was washed with EtOAc to give 60 mg (73% yield) of compound 57 as a light green solid:

¹H NMR (CDCl₃) δ0.94 (d, J=6.5 Hz, 6H), 1.46–1.70 (m, 3H), 2.81 (dd, J=6.8, 17.0 Hz, 1H), 2.97 (dd, J=4.8, 17.0 Hz, 1H), 3.81 (t, J=5.6 Hz, 1H), 4.25–4.30 (m, 2H), 5.09 (d, J=16.0 Hz, 1H), 5.24 (d, J=16.0 Hz, 1H), 6.95–7.01 (m, 1H), 7.06–7.25 (m, 4H), 7.29 (d, J=7.2 Hz, 1H), 7.49 (d, J=7.7 Hz, 1H), 7.59 (d, J=7.6 Hz, 1H), 12.41 (s, 1H);

MS m/e 392 (MH⁺).

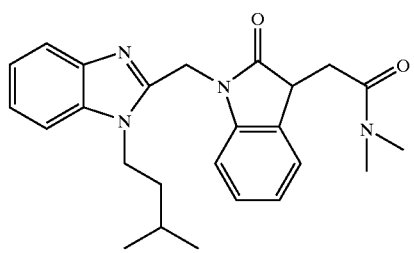

58

Acid 57 (120 mg, 0.31 mmol), dimethyl amine hydrochloride (25 mg, 0.31 mmol), HOBT (46 mg, 0.34 mmol), N-methylmorpholine (85 mg, 0.84 mmol), and EDAC (65 mg, 0.34 mmol) were stirred in anhydrous DMF (1 mL) for 16 hours at room temperature. The reaction mixture was diluted with EtOAc and water. An insoluble white solid was filtered and triturated in EtOAc to give compound 58:

¹H NMR (CDCl₃) δ0.96 (d, J=6.4 Hz, 3H), 0.98 (d, J=6.4 Hz, 3H), 1.41–1.76 (m, 3H), 2.75 (dd, J=9.0, 16.5 Hz, 1H), 2.98 (s, 3H), 2.99 (s, 3H), 3.16 (dd, J=3.1, 16.6 Hz, 1H), 4.01 (dd, J=3.0, 9.0 Hz, 1H), 4.27 (t, J=8.2 Hz, 2H), 5.08 (d, J=15.4 Hz, 1H), 5.42 (d, J=15.4 Hz, 1H), 6.95–7.00 (m, 1H), 7.16–7.32 (m, 5H), 7.41 (d, J=7.8 Hz, 1H), 7.74–7.78 (m, 1H);

MS m/e 419 (MH⁺).

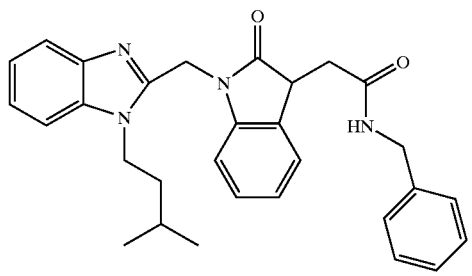

59

Compound 59 was prepared using the same procedure as compound 58 with benzyl amine:

¹H NMR (CDCl₃) δ0.96 (d, J=6.4 Hz, 3H), 0.98 (d, J=6.4 Hz, 3H), 1.42–1.75 (m, 3H), 2.70 (dd, J=7.2, 15.4 Hz, 1H), 3.02 (dd, J=5.7, 15.4 Hz, 1H), 3.95 (t, J=6.3 Hz, 1H), 4.28 (t, J=8.1 Hz, 2H), 4.45(t, J=5.0 Hz, 2H), 5.11 (d, J=15.4 Hz, 1H), 5.42 (d, J=15.4 Hz, 1H), 6.49–6.61 (m, 1H), 6.94–7.02 (m, 1H), 7.21–7.33 (m, 10H), 7.44 (d, J=7.9 Hz, 1H), 7.74–7.66 (m, 1H);

MS m/e 481 (MH⁺).

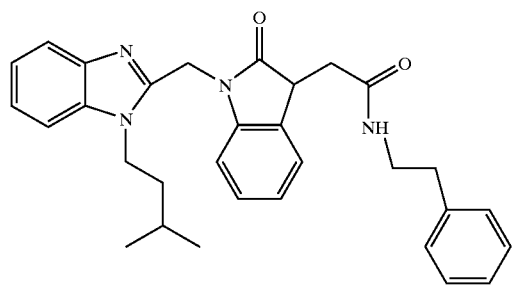

60

Compound 60 was prepared using the same procedure as compound 58 with phenethylamine:

¹H NMR (CDCl₃) δ0.97 (d, J=6.5 Hz, 6H), 1.40–1.93 (m, 3H), 2.51 (q, J=7.9 Hz, 1H), 2.78–2.96 (m, 3H), 3.50–3.62 (m, 2H), 3.91–3.96 (m, 1H), 4.24 (t, J=8.1 Hz, 2H), 5.04 (d, J=15.4 Hz, 1H), 5.35 (d, J=15.4 Hz, 1H), 6.07 (t, J=5.6 Hz, 1H), 7.00 (t, J=7.5 Hz, 1H), 7.15–7.32 (m, 10H), 7.40 (d, J=7.6 Hz, 1H), 7.72–7.77 (m, 1H);

MS m/e 495 (MH⁺).

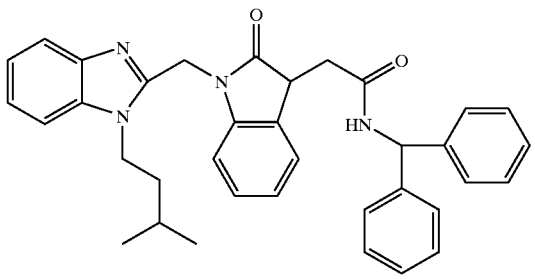

61

Compound 61 was prepared using the same procedure as compound 58 with aminodiphenylmethane:

$^1$H NMR (CDCl$_3$) δ0.94 (d, J=6.4 Hz, 3H), 0.96 (d, J=6.4 Hz, 3H), 1.39–1.71 (m, 3H), 2.70 (dd, J=7.1, 15.4 Hz, 1H), 3.03 (dd, J=6.2, 15.4 Hz, 1H), 3.97 (t, J=6.6 Hz, 1H), 4.22 (t, J=8.2 Hz, 1H), 5.03 (d, J=15.4 Hz, 1H), 5.34 (d, J=15.4 Hz, 1H), 6.27 (d, J=8.0 Hz, 1H), 6.90–7.05 (m, 2H), 7.15–7.36 (m, 14H), 7.41 (d, J=7.8 Hz, 1H), 7.72–7.77 (m, 1H);

MS m/e 557 (MH$^+$).

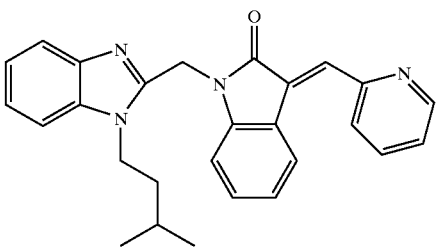

62

To a solution of 1,3-dihydro-3,3-dimethyl-2H-indol-2-one (100 mg, 0.62 mmol) in THF (20 mL) was added BTPP (0.61 g, 1.98 mmol). The solution was stirred for 15 minutes and then the compound 25b (168 mg, 0.61 mmol) was added and the mixture was stirred for 3 days at room temperature. The solvent was removed and the residue was washed with water. (20 mL, 10×) to give 110 mg (50% yield) of compound 62 as a clear glass:

$^1$H NMR (DMSO-d$_6$) δ1.41 (s, 6H), 2.05–2.08 (m, 2H), 2.48 (t, J=4.3 Hz, 2H), 4.25–4.56 (m, 2H), 5.25 (s, 2H), 7.07 (t, J=4.47 Hz, 1H), 7.18–7.39 (m, 4H), 7.55 (d, J=4.7 Hz, 2H), 7.81 (d, J=4.1 Hz, 1H);

MS m/e 357 (MH$^+$).

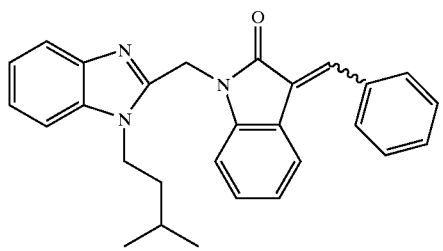

63

To a solution of benzyltriphenylphosphonium chloride (129 mg, 0.33 mmol) in CH$_2$Cl$_2$ was added NaH (16 mg, 0.39 mmol) and the mixture was stirred for 30 minutes. This solution was added dropwise to a solution of the isatin compound 54 in CH$_2$Cl$_2$. The reaction mixture was allowed to stir for 1 hour, was diluted with EtOAc, and washed with H$_2$O. The organic layer was dried over MgSO$_4$ and evaporated. Column chromatography (20% EtOAc in hexanes) gave compound 63 as a 2:1 mixture of regioisomers:

$^1$H NMR (CDCl$_3$) δ0.82, 0.93 (d, J=6.6 Hz, 6H), 1.32–1.46 (m, 2H), 1.53–1.77 (m, 1H), 4.20–4.31 (m, 2H), 6.85, 7.03 (td, J=1.0, 7.7 Hz, 1H), 7.15–7.21 (m, 1H), 7.25–7.39 (m, 4H), 7.43–7.50 (m, 3H), 7.63 (bs, 1H), 7.60,7.93 (s, 1H), 7.62–7.66, 8.29–8.33 (m, 1H);

MS m/e 422 (MH$^+$).

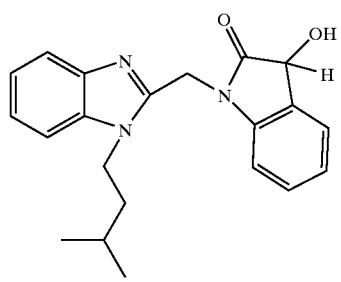

64

Compound 64 was prepared using the same procedure as compound 63 with triphenyl(2-pyridylmethyl)-phosphonium chloride hydrochloride:

$^1$H NMR (CDCl$_3$) δ0.89 (d, J=6.6 Hz, 6H), 1.39–1.47 (m, 2H), 1.64–1.73 (m, 1H), 4.25–4.31 (m, 2H), 5.38 (s, 2H), 7.03 (t, J=7.2 Hz, 1H), 7.22–7.41 (m, 6H), 7.63 (d, J=7.8 Hz, 1H), 7.78–7.83 (m, 3H), 8.86 (d, J=3.7 Hz, 1H), 9.02 (d, J=7.5 Hz, 1H);

MS m/e 423 (MH$^+$).

65

To a solution of compound 54 (102 mg, 0.29 mmol) in MeOH (5 mL) was added 10% palladium on carbon (20 mg) and the mixture was aggitated on a Parr apparatus under H$_2$ at 50 psi for 18 hours. The catalyst was filtered through a pad of celite and the filtrate was evaporated. The residue was triturated in a mixture of Et$_2$O and hexanes and then filtered to give 70 mg (69% yield) of compound 65:

$^1$H NMR (CDCl$_3$) δ0.98 (d, J=6.6 Hz, 6H), 1.48–1.76 (m, 3H), 3.28 (bs, 1H), 4.19–4.25 (m, 2H), 5.10 (s, 1H), 5.13 (d, J=15.5 Hz, 1H), 5.22 (d, J=15.5 Hz, 1H), 7.07 (t, J=7.0 Hz, 1H), 7.23–7.30 (m, 4H), 7.35 (d, J=7.7 Hz, 1H), 7.42 (d, J=7.4 Hz, 1H), 7.73–7.77 (m, 1H);

IR (KBr, cm$^{-1}$) 3423, 2956, 1720, 1615, 1468, 1369, 1172, 743;

MS m/e 378 (MH$^+$);

Anal. Calcd for C$_{21}$H$_{24}$N$_3$O$_2$: C, 71.98; H, 6.90; N, 11.99 Found: C, 71.67; H, 6.57; N, 11.66.

66

To a round bottom flask charged with methyl lithium in ether (1.4 M, 1.18 mL, 1.65 mmol) was added ZnCl$_2$ in ether (1.0 M, 1.27 mL, 1.27 mmol) at −78° C. The mixture was allowed to stir for 1 hour. Compound 54 (442 mg, 1.27 mmol) was added and the mixture was stirred at −78° C. for 1 hour. The temperature was raised to 21° C. Column chromatography (gradient, 15–20% EtOAc in hexanes) gave compound 66 as a yellow solid:

$^1$H NMR (CDCl$_3$) δ1.05 (d, J=6.2 Hz, 6H), 1.65 (s, 3H), 1.69–1.82 (m, 3H), 4.19–4.30 (m, 2H), 4.88 (d, J=16.4 Hz, 1H), 5.44 (d, J=16.4 Hz, 1H), 6.90 (d, J=7.8 Hz, 1H), 7.09 (t, J=7.5 1H), 7.18–7.37 (m, 4H), 7.46 (dd, J=1.0, 7.3 Hz, 1H), 7.62 (d, J=7.1 Hz, 1H).

MS m/e 364 (MH$^+$).

67

A mixture of compound 54 (200 mg, 0.58 mmol) and K$_2$CO$_3$ (1.5 g, 10.85 mmol) in acetone were stirred at reflux for 30 minutes. The solvent was evaporated and the residue was taken up in EtOAc. Column chromatography (gradient, 30–50% EtOAc in hexanes) gave compound 67 as a yellow solid:

$^1$H NMR (CDCl$_3$) δ0.98 (t, J=6.2 Hz, 6H), 1.53–1.77 (m, 3H), 2.15 (s, 3H), 3.06 (d, J=17.2 Hz, 1H), 3.25 (d, J=17.2 Hz, 1H), 4.19 (t, J=8.1 Hz, 2H), 4.98 (d, J=15.7 Hz, 1H), 5.26 (d, J=15.7 Hz, 1H), 7.00 (dt, J=1.4, 7.3 Hz, 1H), 7.18–7.32 (m, 6H), 7.67–7.71 (m, 1H);

MS m/e 406 (MH$^+$).

68

A mixture of lithium (30% dispersion in mineral oil, 0.5% sodium, 27 mg, 1.17 mmol) and ZnCl$_2$(1 M, 0.58 mL, 0.58 mmol) were stirred at 0° C. for 15 minutes. To this solution, t-butyl bromoacetate (76 mg, 0.39 mmol) was added and the resulting mixture was stirred for 15 minutes followed by addition of compound 54 (135 mg, 0.39 mmol) in THF. The mixture was stirred for an additional 15 minutes. The reaction was quenched with 1 N HCl and extracted with EtOAc. Column chromatography (20% EtOAc in hexanes) gave compound 68 as a brown solid:

$^1$H NMR (CDCl$_3$) δ0.99 (t, J=6.4 Hz, 6H), 1.35 (s, 9H), 1.55–1.64 (m, 2H), 1.68–1.79(m, 1H), 2.86 (d,J=15.6 Hz, 1H), 2.94 (d,J=15.6 Hz, 1H), 4.17–4.30 (m, 2H), 5.04 (d, J=15.6 Hz, 1H), 5.34 (d, J=15.6 Hz, 1H), 7.05 (td, J=0.8, 7.5 Hz, 1H), 7.23–7.39 (m, 6H), 7.74–7.78 (m, 1H);

MS m/e 464 (MH$^+$).

69a

Compound 69a was prepared using Michael addition conditions described by Popov, I. I. (*Khim Geterotskl. Soedin.* 1996 (6), 781–792):

$^1$H NMR (CDCl$_3$) δ3.08 (t, J=6.8 Hz, 2H), 4.63 (t, J=6.8 Hz, 2H), 4.77 (d, J=5.7 Hz, 2H), 5.73 (t, J=5.7 Hz, 1H), 7.17–7.28 (m, 2H), 7.64 (d, J=1.2 Hz, 1H), 7.70 (d, J=1.2 Hz, 1H);

MS m/e 202 (MH$^+$);

Anal. Calcd for C$_{11}$H$_{11}$N$_3$O: C$_{65.66}$; H, 5.51; N, 20.88

Found: C, 65.94; H, 5.57; N, 21.08.

69b

To a solution of alcohol 69a (20 g, 99.4 mmol) in CH$_2$Cl$_2$ (50 mL) was slowly added thionyl chloride (15.4 g, 129.2 mmol). The solution was stirred at room temperature for 3 hours. The solvent was evaporated. The residue was diluted with water and neutralized with saturated aqueous sodium bicarbonate solution, and extracted with EtOAc. The combined extracts were washed with water, dried over MgSO$_4$, and evaporated. The residue was triturated with Et$_2$O and hexane to give 19.78 g (91% yield) of compound 69b as a white solid:

$^1$H NMR (CDCl$_3$) δ3.02 (t, J=7.0 Hz, 2H), 4.65 (t, J=7.0 Hz, 2H), 4.99 (s, 2H), 7.34–7.44 (m, 3H), 7.79–7.82 (m, 1H);

MS m/e 220 (MH$^+$);

Anal. Calcd for C$_{11}$H$_{10}$ClN$_3$: C, 60.09; H, 4.65; N, 19.13

Found: C, 60.09; H, 4.65; N, 19.11.

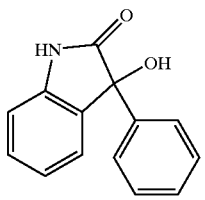

69c

To a solution of isatin (2.94 g, 20.00 mmol) in THF (50 mL) was slowly added phenyllithium (1.8 M in hexanes, 33 mL, 60.00 mmol) at 0° C. The resulting solution was stirred at room temperature for 1 hour. The reaction was quenched with saturated aqueous NH$_4$Cl and extracted with EtOAc. The combined extracts were dried over MgSO$_4$ and concentrated. Purification of the crude product by flash column chromatography (gradient, hexanes:EtOAc=2:1 to straight EtOAc) gave 3.55 g (79% yield) of compound 69c:

$^1$H NMR (CDCl$_3$) δ6.96 (d, J=8.1 Hz, 1H), 7.03 (t, J=6.0 Hz, 1H), 7.16 (t, J=6.9 Hz, 1H), 7.27–7.38 (m, 6H);

MS m/e 226 (MH$^+$);

Anal. Calcd for C$_{14}$H$_{11}$NO$_2$: C, 74.65; H, 4.92; N, 6.22

Found: C, 74.25; H, 4.99; N, 5.85.

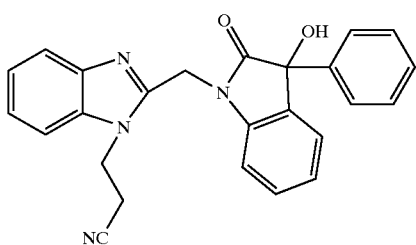

69

A mixture of compound 69c (371 mg, 1.65 mmol), BTPP (609 mg, 1.95 mmol), and chloride 69b (330 mg, 1.50 mmol) were stirred together in THF (10 mL) at room temperature for 1 hour. The solvent was evaporated and the residue was diluted with water and extracted with EtOAc. The combined organic extracts were washed with water, dried over MgSO$_4$, and evaporated. Purification by flash column chromatography (gradient, EtOAc/hexanes=2:1 to EtOAc/MeOH =10:1) gave 540 mg (88% yield) of compound 69 as a white solid:

$^1$H NMR (CDCl$_3$) δ2.62–2.90 (m, 2H), 4.50–4.80 (m, 2H), 5.12 (d, J=16.0 Hz, 1H), 5.47 (bd, J=16.0 Hz, 1H), 7.05–7.80 (m, 13H);

IR (KBr, cm$^{-1}$) 3409, 2252, 1720, 1613, 1467, 1361, 1170, 746;

MS m/e 409 (MH$^+$).

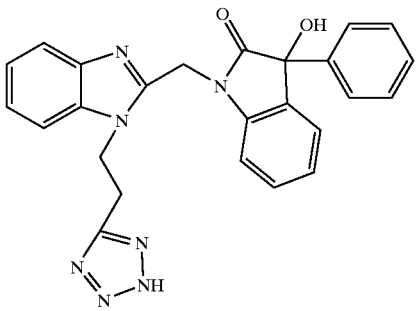

70

A mixture of compound 69 (450 mg, 1.10 mmol), sodium azide (215 mg, 3.50 mmol) and ammonium chloride (176 mg, 3.30 mmol) were stirred in DMF (15 mL) at 115° C. for 40 hours. The solvent was evaporated and the residue was diluted with 1 N NaOH and washed with Et$_2$O. The aqueous layer was then acidified with concentrated HCl and the solid collected by filtration. The solid was dissolved in a mixture of Et$_2$O and THF, dried over MgSO$_4$, and evaporated. The resulting residue was triturated in Et$_2$O and filtered. The solid was then treated with 1 equivalent of 1 N NaOH in MeOH. The solvent was evaporated and the residue was triturated in Et$_2$O to give 258 mg (50% yield) of compound 70 as sodium salt:

$^1$HNMR (DMSO-d$_6$) δ2.83–2.88 (m, 1H), 3.10–3.15 (m, 1H), 4.46–4.56 (m, 2H), 5.04 (d, J=16.5 Hz, 1H), 5.18 (d, J=16.5 Hz, 1H), 6.93 (d, J=8.0 Hz, 1H), 6.98 (d, J=7.3 Hz, 1H), 7.11 (d, J=7.5 Hz, 1H), 7.15–7.21 (m, 6H), 7.48 (d, J=7.9 Hz, 2H), 7.54 (d, J=8.9 Hz, 2H);

IR (KBr, cm$^{-1}$) 3202, 1716, 1613, 1487, 1467, 1424, 1365, 1171, 745;

MS m/e 452 (MH$^+$).

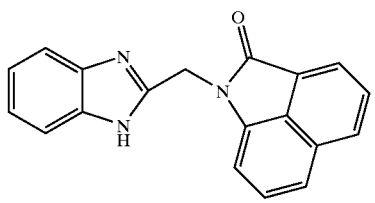

71a

A mixture of benz[c,d]indol-2(1H)-one (2.00 g, 11.82 mmol) and NaH (60% suspension in mineral oil, 567 mg, 14.19 mmol) in CH$_3$CN (30 mL) was stirred at room temperature for 30 minutes. Compound 1b (4.77 g, 14.19 mmol) was added and the reaction was stirred at 60° C. for 72 hours. The reaction was quenched with saturated aqueous NaHCO$_3$ and extracted with CH$_2$Cl$_2$. The organic extracts were dried over MgSO$_4$ and evaporated to give 5.00 g of a crude mesyl protected product. The crude material was treated with excess hydrazine hydrate (20.42 g, 0.64 mol) in a mixture of MeOH and CH$_2$Cl$_2$, and the mixture was stirred at reflux for 18 hours. The solvent was evaporated and the residue was diluted with water and extracted with EtOAc. The extracts were dried over MgSO$_4$ and concentrated. Purification by flash column chromatography (gradient, CH$_2$Cl$_2$/EtOAc, 4:1 to 1:4) gave 2 g (57% yield) of compound 71a:

$^1$H NMR (CDCl$_3$) δ5.39 (s, 2H), 7.19–7.25 (m, 3H), 7.42–7.64 (m, 5H), 7.95–8.00 (m, 2H);

IR (KBr, cm$^{-1}$) 3227, 1686, 1625, 1492, 1318, 776, 737;

MS m/e 300 (MH+);
Anal. Calcd for $C_{19}H_{13}N_3O \cdot 0.2H_2O$: C, 75.33; H, 4.46; N, 13.87
Found: C, 75.57; H, 4.26; N, 13.81.

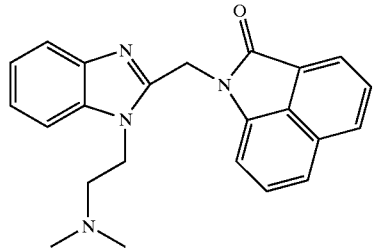

71

Compound 71a (600 mg, 2.00 mmol) and NaH (60% suspension in mineral oil, 240 mg, 6.00 mmol) in a mixture of toluene and DMF (30 mL, 3:1) were stirred at room temperature for 30 minutes. 2-Chloro-N,N-dimethylethylamine hydrochloride (317 mg, 2.20 mmol) was added and the reaction mixture was stirred at 55° C. for 18 hours. The reaction was diluted with saturated aqueous NaHCO$_3$ and extracted with Et$_2$O. The organic extracts were dried over MgSO$_4$ and evaporated. Purification by flash column chromatography (EtOAc/acetone, 3.5:1) gave 248 mg (33% yield) of compound 71. Treatment of the free amine in MeOH with excess 4N HCl in dioxane followed by evaporation of the solvent gave the HCl salt of compound 71:

$^1$H NMR (CD$_3$OD) δ3.14 (s, 6H), 3.84–3.89 (m, 2H), 5.16–5.22 (m, 2H), 5.92 (s, 2H), 7.43 (d, J=7.1 Hz, 1H), 7.60–7.74 (m, 4H), 7.88–7.93 (m, 2H), 8.09 (d, J=8.1 Hz, 1H), 8.20 (d, J=6.9 Hz, 1H), 8.27 (d, J=8.1 Hz, 1H);

IR (KBr, cm$^{-1}$) 3391, 1706, 1633, 1470, 1305, 964, 828, 756;

MS m/e 371 (MH+);

Anal. Calcd for $C_{23}H_{22}N_4O \cdot 2HCl \cdot 3H_2O$: C, 55.54; H, 6.08; N, 11.26
Found: C, 55.73; H, 6.14; N, 11.03.

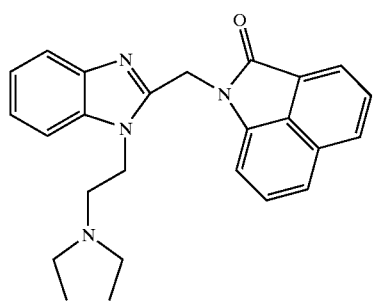

72

Compound 72 was prepared using the same procedure as compound 71 with 2-(diethylamino)ethyl chloride hydrochloride in 63% yield:

$^1$H NMR (CD$_3$OD) δ1.45 (t, J=7.3 Hz, 6H), 3.46–3.51 (m, 4H), 3.82 (t, J=8.1 Hz, 2H), 5.23 (t, J=8.0 Hz, 2H), 5.91 (s, 2H), 7.42 (d, J=7.1 Hz, 1H), 7.59–7.78 (m, 5H), 7.86–7.92 (m, 1H), 8.10 (d, J=8.2 Hz, 1H), 8.19 (d, J=7.0 Hz, 1H), 8.26 (d, J=8.2 Hz, 1H);

IR (KBr, cm$^{-1}$) 3445, 2947, 1717, 1633, 1473, 1394, 1303, 966, 830, 781, 749;

MS m/e 399 (MH+);

Anal. Calcd for $C_{25}H_{26}N_4O \cdot 2HCl \cdot 3H_2O$: C, 57.14; H, 6.52; N, 10.66
Found: C, 56.96; H, 6.48; N, 10.40.

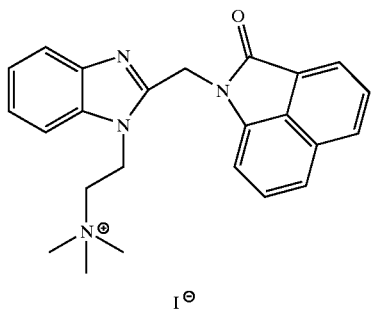

73

To a solution of amine 71 (50 mg, 0.14 mmol) in acetone (1.5 mL) was added methyl iodide (19 mg, 0.14 mmol). The reaction mixture was stirred under N$_2$ atmosphere at ambient temperature for 16 hours. The precipitate was filtered, washed with ether and dried to give 17 mg (24% yield) of compound 73:

$^1$H NMR (CD$_3$OD) δ3.43 (s, 9H), 3.85–3.90 (m, 2H), 5.00–5.05 (m, 2H), 5.56 (s, 2H), 7.33–7.42 (m, 3H), 7.51–7.56 (m, 1H), 7.63–7.71 (m, 3H), 7.81–7.86 (m, 1H), 8.14–8.20 (m, 2H);

MS m/e 385 (MH+).

Anal. Calcd for $C_{24}H_{25}IN_4O \cdot 0.50H_2O$: C, 55.29; H, 5.03; N, 10.75

Found: C, 55.10; H, 5.01; N, 10.59.

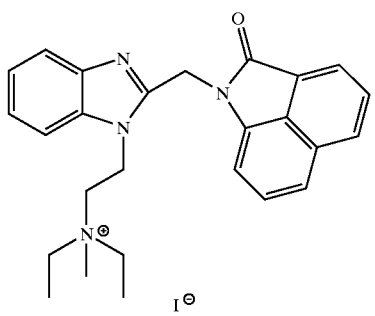

74

Compound 74 was prepared using the same procedure as compound 73 with compound 72 and methyl iodide in 49% yield:

$^1$H NMR (CDCl$_3$) δ1.44 (t, J=7.2 Hz, 6H), 3.31 (s, 3H), 3.64 (q, J=7.2 Hz, 4H), 3.75–3.81 (m, 2H), 4.97–5.03 (m, 2H), 5.56 (s, 2H), 7.31–7.43 (m, 3H), 7.51–7.72 (m, 4H), 7.81–7.86 (m, 1H), 8.14–8.20 (m, 2H);

IR (KBr, cm$^{-1}$) 3011, 1693, 1634, 1493, 1460, 1427, 1092, 774, 747;

MS m/e 413 (MH+);

Anal. Calcd for $C_{26}H_{29}IN_4O$: C, 57.79; H, 5.41; N, 10.37

Found: C, 57.67; H, 5.38; N, 10.37.

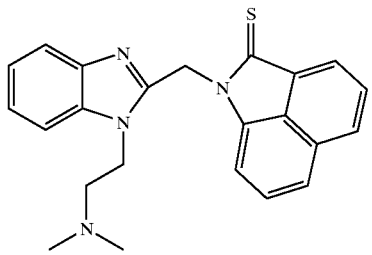

75

To a solution of compound 71 (74 mg, 0.20 mmol) in toluene (7 mL) was added 2,4-bis(4-methoxyphenyl)-1,3-dithia-2,4-diphosphetane-2,4-disulfide (Lawesson's reagent, 51 mg, 0.13 mmol). The reaction mixture was stirred at reflux for 4 hours. The solvent was evaporated and the residue was subjected to column chromatography (gradient, straight EtOAc to EtOAc/acetone, 2:1). The product was triturated with ether and then dried in vacuo to give 65 mg (77% yield) of compound 75:

$^1$H NMR (DMSO-$d_6$) δ2.20 (s, 6H), 2.58–2.64 (m, 2H), 4.48–4.52 (m, 2H), 5.97 (s, 2H), 7.11–7.16 (m, 1H), 7.19–7.25 (m, 1H), 7.40 (d, J=7.2 Hz, 1H), 7.46 (d, J=7.9 Hz, 1H), 7.55–7.62 (m, 2H), 7.83 (d, J=8.3 Hz, 1H), 7.89 (d, J=7.9 Hz, 1H), 8.23 (d, J=7.1 Hz, 1H), 8.32 (d, J=8.1 Hz, 1H);

IR (KBr, cm$^{-1}$) 3436, 1493, 1471, 1373, 1313, 1280, 1231, 970, 818, 767, 745;

MS m/e 387 (MH$^+$).

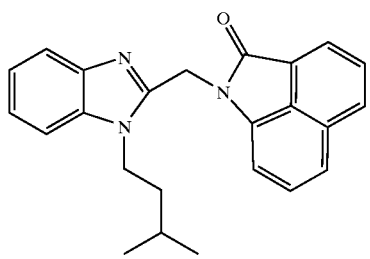

76

Compound 76 was prepared using the same procedure as compound 71 with 1-bromo-3-methylbutane in 35% yield:

$^1$H NMR (CD$_3$OD) δ0.92 (d, J=6.2 Hz, 6H), 1.65–1.69 (m, 3H); 4.56–4.62 (m, 2H), 5.79 (s, 2H), 7.24 (d, J=7.2 Hz, 1H), 7.56–7.67 (m, 2H), 7.71–7.77 (m, 2H), 7.86–7.89 (m, 1H), 7.91 (d, J=7.1 Hz, 1H), 8.19 (d, J=7.0 Hz, 1H), 8.26 (d, J=8.1 Hz, 1H);

IR (KBr, cm$^{-1}$) 3449, 2453, 1709, 1493, 1470, 1293, 831, 781, 750;

MS m/e 370 (MH$^+$);

Anal. Calcd for C$_{24}$H$_{23}$N$_3$O.HCl.1.5H$_2$O: C, 66.58; H, 6.29; N, 9.71

Found: C, 66.68; H, 6.20; N, 9.53.

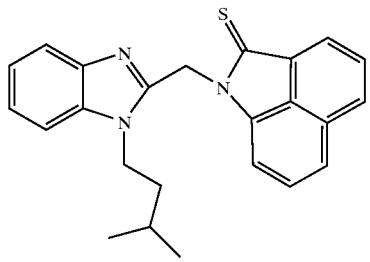

77

Compound 77 was prepared using the same procedure as compound 75 with compound 76:

$^1$H NMR (CD$_3$OD) δ0.71 (d, J=6.6 Hz, 6H), 1.14–1.25 (m, 2H), 1.50–1.57 (m, 1H), 4.22–4.28 (m, 2H), 6.05 (s, 2H), 7.25–7.35 (m, 2H), 7.38 (d, J=7.8 Hz, 1H), 7.47 (d, J=7.2 Hz, 1H), 7.47 (d, J=7.2 Hz, 1H), 7.59 (d, J=8.3 Hz, 1H), 7.72 (d, J=7.6 Hz, 1H), 7.83–7.86 (m, 1H), 8.05 (d, J=8.1 Hz, 1H), 8.28 (d, J=7.1 Hz, 1H);

IR (KBr, cm$^{-1}$) 3441, 2959, 1610, 1493, 1471, 1372, 1281, 1231, 1208, 969, 819, 744;

MS m/e 386 (MH$^+$);

Anal. Calcd for C$_{24}$H$_{23}$N$_3$S.0.4H$_2$O: C, 73.40; H, 6.11; N, 10.70

Found: C, 73.60; H, 5.83; N, 10.53.

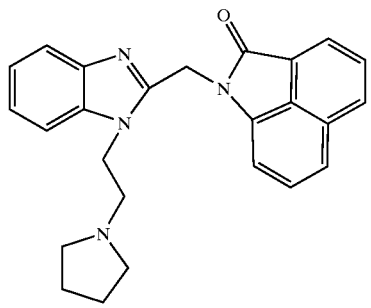

78

Compound 78 was prepared using the same procedure as compound 71 with 1-(2-chloroethyl)pyrrolidine hydrochloride in 46% yield:

$^1$H NMR (CDCl$_3$) δ2.26 (bs, 4H), 3.15–3.30 (m, 2H), 3.70–3.90 (m, 4H), 5.39 (bs, 2H), 6.01 (s, 2H), 7.41 (t, J=7.8 Hz, 1H), 7.50–7.60 (m, 3H), 7.69–7.79 (m, 2H), 8.03–8.12 (m, 3H), 8.35 (d, J=8.3 Hz, 1H);

IR (KBr, cm$^{-1}$) 3445, 2649, 1719, 1635, 1495, 1475, 1307, 969, 783, 747;

MS m/e 397 (MH$^+$);

Anal. Calcd for C$_{25}$H$_{24}$N$_4$O.2HCl.1.5H$_2$O: C, 60.48; H, 5.89; N, 11.28

Found: C, 60.37; H, 5.98; N, 11.19.

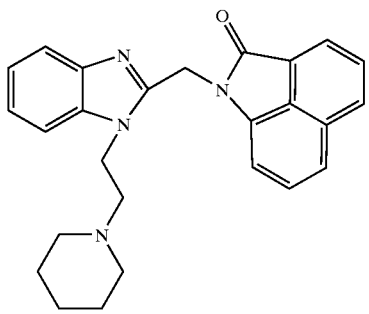

79

Compound 79 was prepared using the same procedure as compound 71 with 1-(2-chloroethyl)piperidine monohydrochloride in 60% yield:

$^1$H NMR(CDCl$_3$) δ1.07–1.37 (m, 6H), 2.20 (bs, 4H), 2.31 (bs, 2H), 4.26 (bs, 2H), 5.35 (s, 2H), 7.09–7.33 (m, 5H), 7.36 (dd, J=1.2, 7.7 Hz, 1H), 7.57 (t, J=7.6 Hz, 1H), 7.61–7.67 (m, 1H), 7.87 (d, J=8.1 Hz, 1H), 7.95 (d, J=7.0 Hz, 1H);

IR (KBr, cm$^{-1}$) 2920, 1707, 1476, 1397, 1309, 1093, 782, 748;

MS m/e 411 (MH$^+$);

Anal. Calcd for C$_{26}$H$_{26}$N$_4$O.0.3H$_2$O: C, 75.08; H, 6.45; N, 13.47

Found: C, 75.09; H, 6.45; N, 13.45.

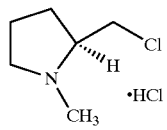

80a (S)-2-(chloromethyl)-1-methylpyrrolidine hydrochloride was prepared according to the procedure reported by S. D. Kimball et al. (*J. Med. Chem.* 1992, 35, 780–793).

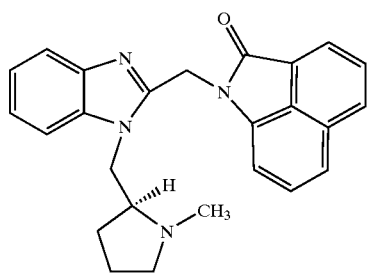

80

Compound 80 was prepared using the same procedure as compound 71 with compound 80a:

$^1$H NMR (CD$_3$OD) δ2.10–2.40 (m, 4H), 3.13 (s, 3H), 3.57–3.73 (m, 1H), 3.85–3.95 (m, 1H), 4.20–4.36 (m, 1H), 5.14 (dd, J=8.9, 15.0 Hz, 1H), 5.36 (dd, J=5.7, 15.0 Hz, 1H), 5.95 (s, 2H), 7.39 (d, J=7.1 Hz, 1H), 7.62–7.79 (m, 5H), 7.87–7.92 (m, 1H), 8.10 (d, J=9.0 Hz, 1H), 8.19 (d, J=6.9 Hz, 1H), 8.26 (d, J=8.1 Hz, 1H);

MS m/e 397 (MH$^+$);

Anal. Calcd for C$_{25}$H$_{24}$N$_4$O.2HCl.2H$_2$O: C, 59.41; H, 5.98; N, 11.08

Found: C, 59.56; H, 5.75; N, 10.90.

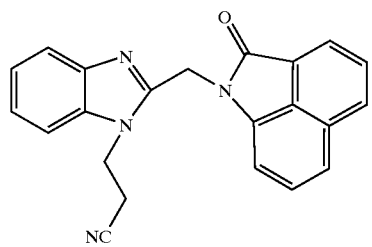

81

A mixture of compound 71a (1.00 g, 3.34 mmol), acrylonitrile (533 mg, 10.06 mmol), and 1,3,4,6,7,8-hexahydro-1-methyl-2H-pyrimido[1,2-a] pyrimidine (MTBD, 29 mg, 0.19 mmol) in CH$_3$CN (35 mL) was stirred at reflux for 18 hours. The solvent was evaporated and the residue was diluted with water and extracted with EtOAc. The organic material was dried over MgSO$_4$ and evaporated. The resulting residue was triturated with Et$_2$O and filtered to give 1.0 g (85% yield) of compound 81 as a yellow solid:

$^1$H NMR (CDCl$_3$) δ2.72 (t, J=6.8 Hz, 2H), 4.75 (t, J=6.8 Hz, 2H), 5.50 (s, 2H), 7.30–7.39 (m, 3H), 7.44–7.50 (m, 2H), 7.54–7.60 (m, 1H), 7.75 (t, J=8.0 Hz, 1H), 7.81–7.85 (m, 1H), 8.07 (d, J=8.1 Hz, 1H), 8.14 (d, J=7.0 Hz, 1H);

IR (KBr, cm$^{-1}$) 3363, 2247, 1686, 1633, 1466, 1395, 1363, 1095, 772, 743;

MS m/e 352 (MH$^+$).

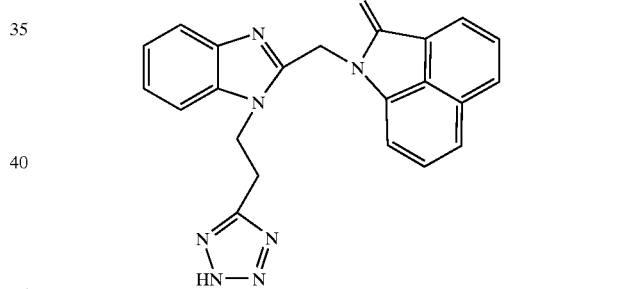

82

A mixture of compound 81 (980 mg, 2.78 mmol), sodium azide (542 mg, 8.34 mmol), and ammonium chloride (446 mg, 8.34 mmol) in DMF (20 mL) was stirred at 95° C. for 72 hours. The solvent was evaporated under reduced pressure. The residue was dissolved in water and washed with EtOAc. The pH of the aqueous layer was adjusted to 7 and the yellow precipitate was collected to give 1.2 g (quantitative yield) of compound 82:

$^1$H NMR (CDCl$_3$) δ3.41 (t, J=6.9 Hz, 2H), 4.83 (t, J=6.9 Hz, 2H), 5.25 (s, 2H), 6.84 (d, J=6.2 Hz, 1H), 6.98 (d, J=7.1 Hz, 1H), 7.18–7.56 (m, 3H), 7.64 (d, J=8.5 Hz, 1H), 7.71 (d, J=8.1 Hz, 1H), 7.82 (t, J=8.0 Hz, 1H), 8.11 (d, J=7.0 Hz, 1H), 8.16 (d, J=8.1 Hz, 1H);

IR (KBr, cm$^{-1}$) 3343, 1693, 1577, 1472, 1397, 775, 742;

MS m/e 396 (MH$^+$);

Anal. Calcd for C$_{22}$H$_{16}$N$_7$O.2.7H$_2$O: C, 56.70; H, 4.63; N, 21.04

Found: C, 56.76; H, 4.53; N, 20.88.

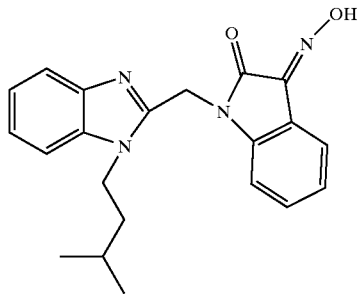

83

A mixture of isatin 54 (100 mg, 0.29 mmol) and hydroxylamine hydrochloride (200 mg 2.87 mmol) in MeOH (5 mL) was stirred at reflux for 1.5 hours. The solvent was evaporated and the residue was suspended in $CH_2Cl_2$. The filtrate was evaporated. The residue was purified by flash column chromatography (gradient, EtOAc:hexanes=1:2 to 1: 1) and the purified material was triturated with $Et_2O$/hexanes to give 13 mg (12% yield) of compound 83:

$^1$H NMR (CD$_3$OD) δ0.94 (d, J=6.6 Hz, 6H), 1.42–1.50 (m, 2H), 1.65–1.74 (m, 1H), 4.28–4.34 (m, 2H), 5.32 (s, 2H), 7.07–7.12 (m, 2H), 7.23–7.35 (m, 3H), 7.45 (d, J=6.8 Hz, 1H), 7.62 (d, J=7.3 Hz, 1H), 8.10 (d, J=8.0 Hz, 1H);

IR (KBr, cm$^{-1}$) 2966, 1726, 1608, 1461, 1347, 1180, 1084, 1015, 738;

MS m/e 363 (MH$^+$);

Anal. Calcd for $C_{21}H_{22}N_4O_2$: C, 69.59; H, 6.12; N, 15.46

Found: C, 69.22, H, 6.29; N, 15.20.

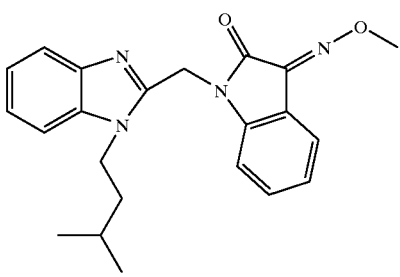

84

Compound 84 was prepared using the same procedure as compound 83 with O-methylhydroxylamine hydrochloride in 88% yield:

$^1$H NMR (CD$_3$OD) δ0.96 (d, J=6.6 Hz, 6H), 1.45–1.53 (m, 2H), 1.66–1.73 (m, 1H), 4.30 (t over bs, 5H), 5.30 (s, 2H), 7.10 (d, J=7.8 Hz, 2H), 7.22–7.38 (m, 3H), 7.46 (d, J=8.4 Hz, 1H), 7.61 (d, J=7.2 Hz, 1H), 7.97 (d, J=7.5 Hz, 1H);

IR (KBr, cm$^{-1}$) 3431, 2952, 1724, 1608, 1468, 1353, 1010, 752;

MS m/e 377 (MH$^+$);

Anal. Calcd for $C_{22}H_{24}N_4O_2$: C, 70.19; H, 6.43; N, 14.88

Found: C, 69.89; H, 6.34; N, 14.80.

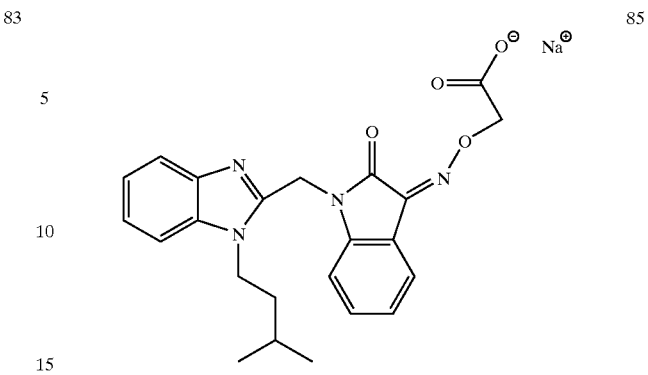

85

Compound 85 was prepared using the same procedure as compound 83 with carboxymethoxylamine hemihydrochloride. The sodium salt was prepared by adding 1 equivalent of 1N NaOH to the acid and evaporating the solvent:

$^1$H NMR (DMSO-d$_6$) δ0.82 (d, J=6.7 Hz, 6H), 1.31–1.41 (m, 2H), 1.50–1.63 (m, 1H), 3.95–4.05 (m, 2H), 4.83 (s, 2H), 4.93 (s, 2H), 6.74–6.86 (m, 1H), 7.00–7.03 (m, 2H), 7.03–7.05 (m, 1H), 7.15 (bs, 2H), 7.63–7.65 (m, 1H), 7.84–7.89 (m, 1H);

MS m/e 421 (MH$^+$).

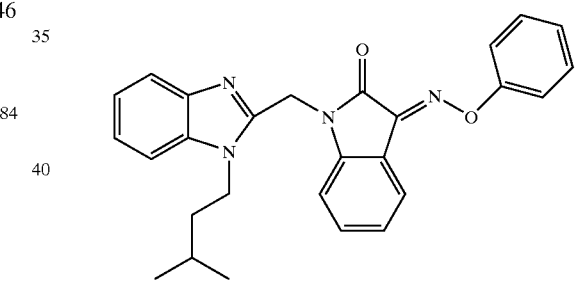

86

Compound 86 was prepared using the same procedure as compound 83 with O-phenylhydroxylamine hydrochloride:

$^1$H NMR (CD$_3$OD) δ0.91 (d, J=6.5 Hz, 6H), 1.44–1.49 (m, 2H), 1.65–1.69 (m, 1H), 4.30 (t, J=8.3 Hz, 5H), 5.32 (s, 2H), 5.52 (s, 2H), 7.07–7.09 (m, 2H), 7.24–7.41 (m, 6H), 7.45–7.50 (m, 3H), 7.61 (d, J=7.4 Hz, 1H), 7.96 (d, J=7.6 Hz, 1H);

IR (KBr, cm$^{-1}$) 3443, 2951, 1731, 1607, 1467, 1372, 1332, 979, 744;

MS m/e 453 (MH$^+$);

Anal. Calcd for $C_{22}H_{24}N_4O_2$: C, 74.31; H, 6.24; N, 12.38

Found: C, 74.02; H, 6.14; N, 12.36.

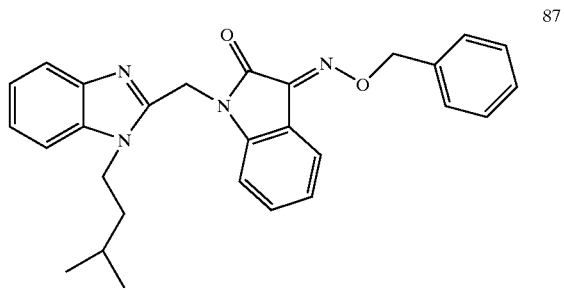

87

Compound 87 was prepared using the same procedure as compound 83 with O-benzylhydroxylamine hydrochloride in 78% yield:

$^1$H NMR (CD$_3$OD) δ0.91 (d, J=6.5 Hz, 6H), 1.44–1.49 (m, 2H), 1.65–1.69 (m, 1H), 4.30 (t, J=8.3 Hz, 5H), 5.32 (s, 2H), 5.52 (s, 2H), 7.07–7.09 (m, 2H), 7.24–7.41 (m, 6H), 7.45–7.50 (m, 3H), 7.61 (d, J=7.4 Hz, 1H), 7.96 (d, J=7.6 Hz, 1H);

IR (KBr, cm$^{-1}$) 3443, 2951, 1731, 1607, 1467, 1372, 1332, 979, 744;

MS m/e 453 (MH$^+$);

Anal. Calcd for C$_{22}$H$_{24}$N$_4$O$_2$: C, 74.31; H, 6.24; N, 12.38 Found: C, 74.02; H, 6.14; N, 12.36.

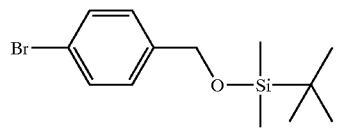

88a

To a solution of 4-bromobenzyl alcohol (56.8 g, 0.304 mol) and imidazole (31.0 g, 0.456 mol) in THF (500 ml) at 0° C. was added TBDMS chloride (50.3 g, 0.334 mol) in one portion. After stirring at room temperature for 1 hour, the suspension was filtered. The filtrate was diluted with EtOAc (500 ml), washed with water and brine, dried over MgSO$_4$, and concentrated. The residue was distilled under vacuum to provide 84.6 g (92% yield) of compound 88a as a colorless oil:

$^1$H NMR (CDCl$_3$) δ0.95 (s, 9H), 4.69 (s, 2H), 7.21 (d, J=7.5 Hz, 2H), 7.44 (d, J=7.5 Hz, 2H);

MS m/e 282 (MH$^+$).

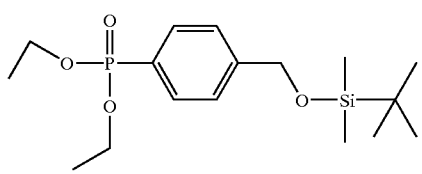

88b

To a solution of bromide 88a (73.0 g, 0.242 mol) in THF (500 ml) at −78 °C. was added t-BuLi (1.7 M in heptane, 314 ml, 0.533 mol) dropwise. The mixture was stirred at −78° C. for 30 minutes before addition of diethyl chlorophosphate (43.9 g, 0.254 mol). The reaction mixture was stirred for 2 hours and was quenched with saturated NH$_4$Cl. The organic layer was washed with brine, dried over MgSO$_4$, and concentrated. The crude product 88b was used for the next reaction without further purification.

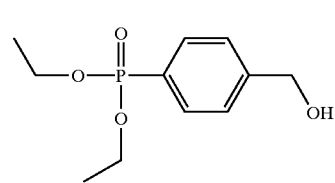

88c

To a solution of compound 88b (31.1 g, 86.8 mmol) in THF (300 ml) at 0° C. was added TBAF (1M in THF, 104 ml, 104 mmol). The reaction mixture was stirred for 2 hours and was quenched with saturated NH$_4$Cl. The organic layer was diluted with EtOAc (300 ml), washed with water and brine, dried over MgSO$_4$, and concentrated. The crude alcohol product 88c was used for the next reaction without further purification:

$^1$H NMR (CDCl$_3$) δ1.28 (t, J=7.2 Hz, 6H), 4.00–4.11 (m, 4H), 4.71 (s, 2H), 7.42 (dd, J=3.6, 8.0 Hz, 2H), 7.70 (dd, J=8.0, 12.9 Hz, 2H).

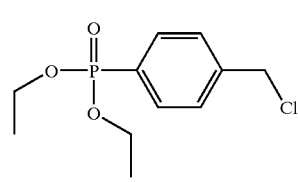

88d

Chloride 88d was prepared using the same procedure as compound 4c with compound 88c and thionyl chloride:

$^1$H NMR (CDCl$_3$) δ1.31 (t, J=7.2 Hz, 6H), 4.05–4.16 (m, 4H), 4.59 (s, 2H), 7.48 (dd, J=3.9, 8.0 Hz, 2H), 7.80 (dd, J=8.0, 13.2 Hz, 2H);

MS m/e 262 (MH$^+$).

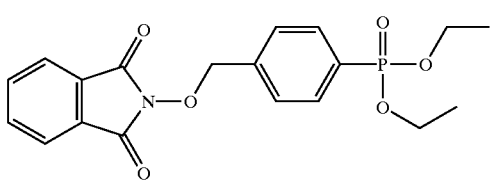

88e

A mixture of N-hydroxyphthalimide (0.90 g, 5.5 mmol), compound 88d (1.32 g, 5.0 mmol), and DIEA (1.26 g, 10 mmol) in CH$_3$CN (50 ml) was stirred at reflux for 4 hours. The resulting solution was diluted with CH$_2$Cl$_2$ (100 mL) and washed with saturated NaHCO$_3$. The organic layer was dried over MgSO$_4$ and concentrated. The residue was purified by flash chromatography (gradient, CH$_2$Cl$_2$:MeOH= 40:1 to 30:1) to give 1.39 g (65% yield) of compound 88e as a viscous oil:

$^1$H NMR (CD$_3$OD) δ1.28–1.33 (m, 6H), 4.08–4.13 (m, 4H), 5.25 (s, 2H), 7.47–7.50(m, 2H), 7.77–7.82 (m, 8H);

MS m/e 390 (MH$^+$).

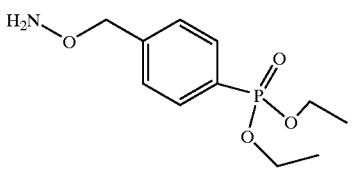

88f

A solution of compound 88e (1.50 g, 3.85 mmol) and hydrazine (0.33 g, 9.6 mmol) in MeOH (50 ml) was stirred at reflux for 12 hours. The mixture was filtered and the filtrate was concentrated. Trituration of the residue with hot CHCl$_3$ (50 ml), followed by filtration and concentration of the filtrate gave 0.90 g (90% yield) of compound 88f as a viscous oil, which was used without further purification.

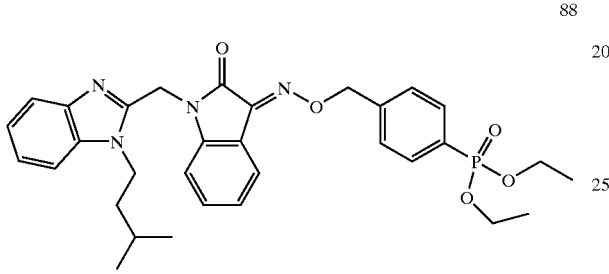

88

A mixture of compound 54 (902 mg, 2.60 mmol), compound 88f (808 mg, 3.12 mmol) and p-toluenesulphonic acid (99 mg, 0.52 mmol) in MeOH (26 ml) was stirred at reflux for 1 hour. The reaction mixture was diluted with CH$_2$Cl$_2$ (100 ml), washed with saturated NaHCO$_3$, dried over MgSO$_4$, and concentrated. The residue was purified by flash chromatography (gradient, CH$_2$Cl$_2$:MeOH=40:1 to 20:1) to give 1.29 g (84% yield) of compound 88 as a yellow foam:

$^1$H NMR (CD$_3$OD) δ0.91 (d, J=6.6 Hz, 6H), 1.34 (t, J=7.2 Hz, 6H), 1.46–1.54 (m, 2H), 1.64–1.71 (m, 1H), 4.07–4.30 (m, 4H), 4.32 (t, J=8.2 Hz, 2H), 5.33 (s, 2H), 5.62 (s, 2H), 7.09–7.16 (m, 2H), 7.26–7.37 (m, 2H), 7.39–7.42 (m, 1H), 7.48–7.50 (m, 1H), 7.62–7.70 (m, 3H), 7.79–7.84 (m, 2H), 8.04–8.07 (m, 1H);

IR (KBr, cm$^{-1}$) 3436, 2957, 1727, 1607, 1468, 1023;

MS m/e 588 (MH$^+$);

Anal. Calcd for C$_{32}$H$_{37}$N$_4$O$_5$P.H$_2$O: C, 63.36; H, 6.48; N, 9.24

Found: C, 63.34; H, 6.48; N, 9.15.

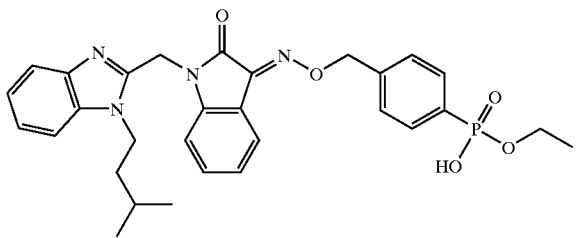

89

Compound 88 (294 mg, 0.5 mmol) and 1 N NaOH (1.50 ml, 1.50 mmol) in a mixture of MeOH and H$_2$O (20 ml, 1:1) was heated to reflux for 12 hours. The mixture was acidified with 1 N HCl to pH 2 and concentrated. The residue was purified by prep-HPLC (gradient, 10% MeOH in H$_2$O with 0.1% TFA to 90% MeOH in H$_2$O with 0.1% TFA) to give 360 mg (56% yield) of compound 89 as a yellow gel:

$^1$H NMR (CD$_3$OD) δ0.94 (d, J=6.6 Hz, 6H), 1.19 (t, J=7.1 Hz, 3H), 1.46–1.53 (m, 2H), 1.66–1.75 (m, 1H), 3.76–3.86 (m, 2H), 4.33 (t, J=8.3 Hz, 2H), 5.34 (s, 2H), 5.57 (s, 2H), 7.08–7.13 (m, 2H), 7.25–7.40 (m, 3H), 7.47–7.55 (m, 3H), 7.64 (d, J=7.3 Hz, 1H), 7.80–7.87 (m, 2H), 8.00–8.03 (m, 1H);

IR (KBr, cm$^{-1}$) 3436, 2959, 1684, 1210, 1135;

MS m/e 561 (MH$^+$);

Anal. Calcd for C$_{30}$H$_{33}$N$_4$O$_5$P.4H$_2$O.0.5TFA: C, 52.32; H, 5.74; N, 7.87

Found: C, 52.66; H, 5.66; N, 7.94.

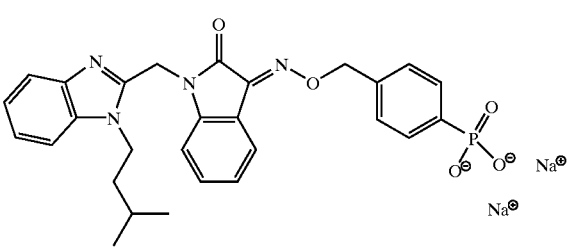

90

To a solution of compound 88 (720 mg, 1.22 mmol) in CH$_3$CN (25 ml) at 0° C. was added TMS bromide (1.86 g, 12.2 mmol) and stirred at room temperature for 12 hours. The mixture was concentrated and the residue was purified by preperative HPLC (gradient, 10% MeOH in H$_2$O with 0.1% TFA to 90% MeOH in H$_2$O with 0.1% TFA) to give 474 mg (73% yield) yellow powder. To a mixture of this yellow solid (60 mg, 0.11 mmol) in MeOH (2 ml) and H$_2$O (1 ml) was added 1N NaOH (0.225 ml, 0.22 mmol). The solution was concentrated and the residue was triturated with hot EtOAc to give 59 mg (90%) of compound 90 as yellow solid:

$^1$H NMR (CD$_3$OD) δ0.98 (d, J=6.6 Hz, 6H), 1.48–1.55 (m, 2H), 1.68–1.77 (m, 1H), 4.34 (t, J=8.2 Hz, 2H), 5.34 (s, 2H), 5.53 (s, 2H), 7.04–7.14 (m, 2H), 7.25–7.39 (m, 3H), 7.42–7.50 (m, 3H), 7.63–7.66 (m, 1H), 7.90–7.96 (m, 3H );

IR (KBr, cm$^{-1}$) 3392, 2953, 1721, 1611, 1469, 970;

MS m/e 533 (MH$^+$);

Anal. Calcd for C$_{28}$H$_{27}$N$_4$Na$_2$O$_5$P.4H$_2$O.0.5TFA: C, 49.37; H, 5.07; N, 7.94

Found: C, 49.50; H, 5.47; N, 7.98.

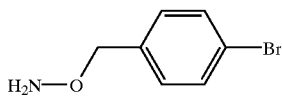

91a

Compound 91a was prepared using the same procedure sequence as compound 88f starting with 4-bromobenzyl bromide:

$^1$H NMR (DMSO-d$_6$) δ6.09 (s, 2H), 7.27–7.30 (m, 2H), 7.52–7.55 (m, 2H);

MS m/e 203, 205 (MH$^+$).

92

Compound 92 was prepared using the same procedure as compound 88 with compound 91a:

$^1$H NMR (DMSO-d$_6$) δ0.92 (d, J=6.6 Hz, 6H), 1.55–1.59 (m, 2H), 1.66–1.69 (m, 1H), 4.38 (t, J=7.7 Hz, 2H), 5.42 (s, 2H), 5.51 (s, 2H), 7.13–7.20 (m, 2H), 7.32–7.44 (m, 2H), 7.45–7.47 (m, 3H), 7.60–7.66 (m, 3H), 7.70–7.71 (m, 1H), 7.97 (d, J=7.2 Hz, 1H);

IR (KBr, cm$^{-1}$) 3445, 2956, 1727, 1607, 1468, 976;

MS m/e 531, 533 (MH$^+$);

Anal. Calcd for C$_{28}$H$_{27}$BrN$_4$O$_2$: C, 63.28; H, 5.12; N, 10.54

Found: C, 63.03; H, 5.14; N, 10.48.

93a

Compound 93a was prepared using the same sequence of procedures as compound 88e starting with methyl 4-(bromomethyl)-benzoate:

$^1$H NMR (CDCl$_3$) δ3.94 (s, 2H), 5.29 (s, 2H), 7.64 (d, J=8.2 Hz, 2H), 7.75–7.85 (m, 4H), 8.08 (d, J=8.2 Hz, 2H);

MS m/e 312 (MH$^+$).

93b

Compound 93b was prepared using the same procedure as compound 88f with compound 93a:

$^1$H NMR (CDCl$_3$) δ3.92 (s, 3H), 4.75 (s, 2H), 5.48 (bs, 2H), 7.43 (d, J=8.3 Hz, 2H), 8.03 (d, J=8.3 Hz, 2H);

MS m/e 182 (MH$^+$).

93

Compound 93 was prepared using the same procedure as compound 88 with compound 93b:

$^1$H NMR (DMSO-d$_6$) δ0.89 (d, J=6.6 Hz, 6H), 1.40–1.70 (m, 3H), 3.86 (s, 3H), 4.25–4.30 (m, 2H), 5.27 (s, 2H), 5.62 (s, 2H), 7.10–7.27 (m, 3H), 7.43–7.62 (m, 6H), 7.97–8.02 (m, 3H);

MS m/e 511 (MH$^+$);

Anal. Calcd for C$_{30}$H$_{30}$N$_4$O$_4$·0.25H$_2$O: C, 69.95; H, 5.97; N, 10.88

Found: C, 69.59; H, 5.68; N, 10.69.

94

Compound 93 (81 mg, 0.13 mmol) and 1N NaOH (0.39 mL, 0.39 mmol) were stirred at reflux in MeOH (5 mL). The solvent was evaporated and the residue was diluted with water. The aqueous material was adjusted to neutral pH with 1N HCl and extracted with EtOAc. The combined extracts were dried over MgSO$_4$ and evaporated. The resulting acid was stirred with exactly 1 equivalent of 1N NaOH in MeOH and then the solvent was evaporated to give 24 mg (36% yield) of the sodium salt 94:

$^1$H NMR (DMSO-d$_6$) δ0.89 (d, J=6.5 Hz, 6H), 1.42–1.66 (m, 3H), 4.26 (bt, J=8.1 Hz, 2H), 5.26 (s, 2H), 5.60 (s, 2H), 7.09–7.52 (m, 8H), 7.58 (d, J=8.1 Hz, 2H), 7.98 (d, J=8.1 Hz, 2H);

MS m/e 497 (MH$^+$).

95a

A solution of isatin (10 g, 68 mmol) and t-butyl bromoacetate (10 mL, 68 mmol) and K$_2$CO$_3$ (18.8 g, 136 mmol) in CH$_3$CN (50 mL) was heated to reflux for 3 hours then cooled, filtered and concentrated. The residue was purified by flash chromatography (heaxanes:EtOAc=9:1) to give 8.38 g (47% yield) of compound 95a as an orange solid:

$^1$H NMR (DMSO-d$_6$) δ1.41 (s, 9H), 4.50 (s, 2H), 7.17 (t, J=8.4 Hz, 2H), 7.60 (d, J=8.5 Hz, 1H), 7.68 (t, J=8.4 Hz, 1H);

MS m/e 261 (MH$^+$);

Anal. Calcd for C$_{14}$H$_{15}$NO$_4$: C, 64.36; H, 5.79; N, 5.36

Found: C, 64.41; H, 5.96; N, 5.28.

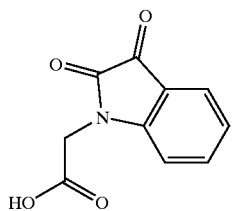

95b

A mixture of ester 95a (5.0 g, 19.10 mmol) and TFA (20 mL) was stirred at room temperature for 12 hours. The solvent was removed and the residue was dried under vacuum to give 3.5 g (77% yield) of compound 95b as an orange solid:

$^1$H NMR (DMSO-d$_6$) δ4.50 (s, 2H), 7.15–7.20 (m, 2H), 7.60 (d, J=8.5 Hz, 1H), 7.68 (t,J=8.4 Hz, 1H);

MS m/e 205 (MH$^+$).

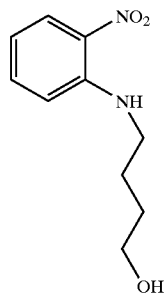

95c

A solution of 2-fluoronitrobenzene (5.0 g, 35.50 mmol) and 1-amino-4-butanol (3.2 g, 35.50 mmol) in CH$_3$CN (100 mL) and triethylamine (4.0 g, 35.5 mmol) was heated to reflux for 12 hours, then cooled and concentrated. The residue was dissolved in EtOAc and washed with 1N HCl. The mixture was dried over MgSO$_4$ and concentrated to give 7.21 g (97% yield) of compound 95c as a dark orange solid:

$^1$H NMR (DMSO-d$_6$) δ1.45–1.56 (m, 2H), 1.58–1.69 (2H), 3.35 (t, J=6.7 Hz, 2H coupled to proton exchangeable in D$_2$O), 3.43 (t, J=6.4 Hz, 2H), 3.90–4.00 (br, 1H, exchanges with D$_2$O), 6.66 (t, J=6.0 Hz, 1H), 7.04 (d, J=9.0 Hz, 1H), 7.52 (t, J=7.2 Hz, 1H), 8.04 (d, J=1.6, 7.2 Hz, 1H), 8.13 (bs, 1H, exchanges with D$_2$O, 1H);

IR (KBr cm$^{-1}$) 1350, 1154;

MS m/e 211 (MH$^+$);

Anal. Calcd for C$_{10}$H$_{14}$N$_2$O$_3$.0.28H$_2$O: C, 55.80; H, 6.82; N, 13.01

Found: C, 55.80; H, 6.62; N, 12.97.

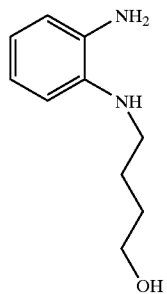

95d

A solution of the nitro compound 95c (5.0 g, 23.80 mmol) in ethanol (50 mL) was hydrogenated at 40 psi with 10% palladium on carbon (100 mg) for 4 hours. The catalyst was removed by filtration and the solvent was evaporated to give 4.3 g (99% yield) of compound 95d as a dark oil:

$^1$H NMR (DMSO-d$_6$) δ1.47–1.66 (m, 4H), 2.99 (t, J=6.6 Hz, 2H), 3.43 (t, J=6.6 Hz, 2H), 4.31–4.50 (br, exchange with D$_2$O, 4H), 6.36–6.42 (m, 2H) 6.54–6.82 (m, 2H);

IR (film cm$^{-1}$) 1055, 739;

MS m/e 181 (MH$^+$);

Anal. Calcd for C$_{10}$H$_{16}$N$_2$O.0.71H$_2$O: C, 62.23; H, 9.10; N, 14.51

Found: C, 62.23; H, 8.78; N, 14.41.

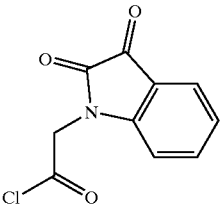

95e

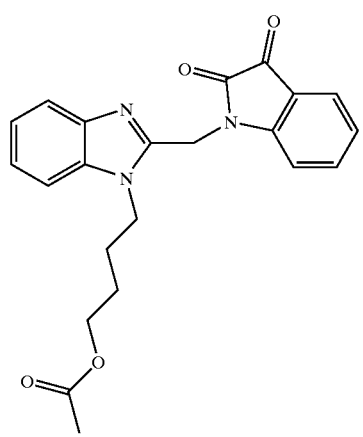

95

To a solution of compound 95d (4.97 g, 27.60 mmol) and triethylamine (3.0 g, 30 mmol) in CH$_2$Cl$_2$ (100 mL) at −78° C. was added compound 95e (freshly prepared from compound 95b (5.66 g, 27.60 mmol) and oxalyl chloride (3.5 g, 27.60 mmol)) in CH$_2$Cl$_2$ (50 mL). The mixture was stirred at −78° C. for 1 hour then warmed to room temperature and stirred for 12 hours. The solvent was removed. The residue was dissolved in AcOH (100 mL) and heated to reflux for 12 hours. The solvent was evaporated and the residue was purifed by flash chromatography (hexanes:EtOAc=3:1) to give 2.2 g (20% yield) of compound 95 as a yellow solid:

$^1$H NMR (DMSO-d$_6$) δ1.63–1.66 (m, 2H), 1.77–1.81 (m, 2H), 1.90 (s, 3H), 1.99 (s, 3H), 4.03 (t, J=6.6 Hz, 2H), 4.34 (t, J=7.5 Hz, 2H), 5.24 (s, 2H), 7.14–7.19 (m, 2H), 7.25 (t, J=8.2 Hz, 1H), 7.31 (d, J=8.0 Hz, 1H), 7.58–7.67 (m, 4H);

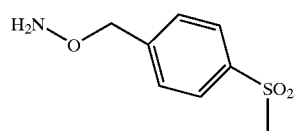

96a

Compound 96a was prepared using the same procedure sequence as compound 88f starting with p-methylsulfonylbenzyl chloride.

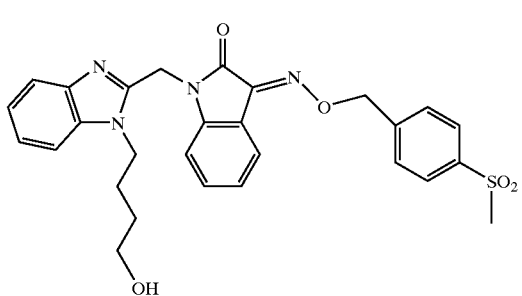

96

A mixture of compound 95 (0.39 g, 0.99 mmol) and 96a (0.2 g, 0.99 mmol) in EtOH (50 mL) was heated to reflux for 12 hours. The solution was concentrated and filtered to give 195 mg (34% yield) of intermediate as a yellow solid. The solid was dissolved in MeOH (50 mL) and treated with p-toluenesulfonic acid (0.21 g, 1.10 mmol) and stirred at reflux for 12 hours. The mixture was cooled, concentrated. The residue was dissolved in EtOAc and washed with saturated aqueous $NaHCO_3$, dried over $MgSO_4$ and concentrated. The residue was dissolved in a minimum of MeOH and diluted with water. After standing for 1 hour, the precipitated product was isolated by filtration to give 0.12 g (66% yield) of compound 96 as a yellow solid:

$^1$H NMR (DMSO-$d_6$) δ1.40–1.55 (m, 2H), 1.70–1.80 (m, 2H), 3.19 (s, 3H), 3.38–3.99 (m, 2H), 4.31–4.33 (m, 2H), 5.26 (s, 2H), 5.65 (s, 2H), 7.11–7.24 (m, 4H), 7.45 (t, J=7.8 Hz, 1H), 7.55 (t, J=6.8 Hz, 2H), 7.73 (d, J=7.6 Hz, 2H), 7.98 (d, J=8.2 Hz, 2H), 7.90–8.00 (m, 1H);

MS m/e 532 (MH$^+$);

Anal. Calcd for $C_{28}H_{28}N_4O_5 \cdot 0.6H_2O$: C, 61.89; H, 5.42; N, 10.31

Found: C, 61.93; H, 5.23; N, 10.33.

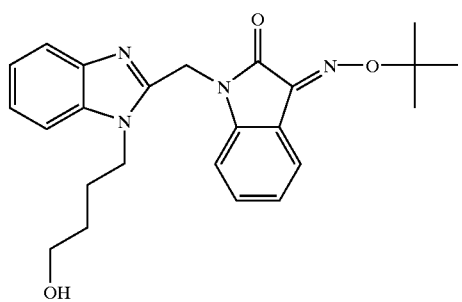

97

Compound 97 was prepared using the same procedure as compound 96 with O-(tert-butyl)hydroxylamine hydrochloride:

$^1$H NMR (DMSO-$d_6$) δ1.15 (s, 9H), 1.45–1.48 (m, 2H), 1.75–1.80 (m, 2H), 3.40 (t, J=6.2 Hz, 2H), 4.29 (t, J=7.6 Hz, 2H), 4.52 (d, J=5.3 Hz, 2H), 4.85–4.96 (bs, 1H), 6.55–6.61 (m, 1H), 6.84–6.87 (m, 1H); 7.04–7.07 (m, 2H), 7.17–7.21 (m, 2H), 7.54 (d, J=7.9 Hz, 1H), 7.61 (d, J=7.7 Hz, 1H);

MS m/e 421 (MH$^+$).

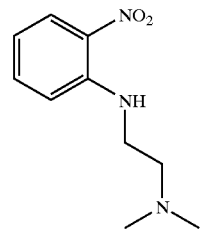

98a

To a mixture of 2-fluoronitrobenzene (16.8 g, 119 mmol) and sodium acetate (300 mg) was added N,N-dimethylethylenediamine (1 2.5 mL, 113 mmol). After heating to 80° C. for 1 hour, the mixture was poured into water, and extracted with EtOAc. The combined organic layers were dried over $MgSO_4$ and evaporated. The crude material was purified by silica gel chromatography (gradient, 1:1 EtOAc:Hexanes to 5% MeOH in EtOAc) to provide 12.0 g (50% yield) of compound 98a as an orange oil:

$^1$H NMR (CDCl$_3$) δ2.30 (s, 6H), 2.63 (t, J=6.3 Hz, 2H), 3.33–3.37 (m, 2H), 6.63 (t, J=8.3 Hz, 1H), 6.82 (d, J=8.3 Hz, 1H), 7.43 (t, J=8.1 Hz, 1H), 8.17 (d, J=8.5 Hz, 1H), 8.33 (bs, 1H);

MS m/e 209 (MH$^+$).

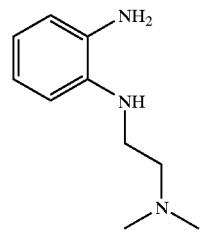

98b

A mixture of compound 98a (10.0 g, 47.7 mmol) and 10% palladium on carbon (500 mg) in EtOH (100 mL) was hydrogenated at 50 psi for 1 hour. The mixture was filtered through a pad of celite and the filtrate was evaporated. The residue was recrystallized from hexanes to give 7.52 g (88% yield) of compound 98b as flaky brown solid:

$^1$H NMR (CDCl$_3$) δ2.26 (s, 6H), 2.60 (t, J=6.1 Hz, 2H), 3.33–3.37 (t, J=6.1 Hz, 2H), 6.65–6.72 (m, 3H), 6.81 (t, J=7.5 Hz, 1H);

MS m/e 179 (MH$^+$).

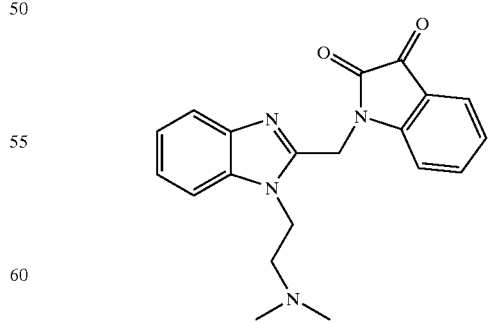

98

To a solution of compound 98b (2.6 g, 14.6 mmol) in $CH_2Cl_2$ (50 mL) at −78° C. was added compound 95e (freshly prepared from 95b (3.0 g, 14.6 mmol) and thionyl chloride, 20 mL) in $CH_2Cl_2$ (50 mL). The mixture was stirred at −78° C. for 1 hour then warmed to room temperature and stirred for 12 hours. The solvent was removed to give 2.8 g of a mixture of mono and diacetylated products. Both compounds can be converted to the desired product by heating the mixture in AcOH (100 mL) and concentrated HCl (2 mL) at reflux for 12 hours. The residue was purified by flash chromatography (gradient, $CH_2Cl_2$:MeOH=99:1 to $CH_2Cl_2$:MeOH=97:3) to give 1.8 g (68% yield) of compound 98 as a yellow solid:

$^1$H NMR (DMSO-$d_6$) δ2.11 (s, 6H), 2.58 (t, J=6.0 Hz, 2H), 4.39 (t, J=6.0 Hz, 2H), 5.27 (s, 2H), 7.11–7.26 (m, 4H), 7.54–7.65 (m, 4H);

MS m/e 348 (MH$^+$);

Anal. Calcd for $C_{20}H_{20}N_4O_2 \cdot 0.7H_2O \cdot 0.5$ AcOH: C, 64.50; H, 6.03; N, 14.33

Found: C, 64.68; H, 5.93; N, 14.32.

99

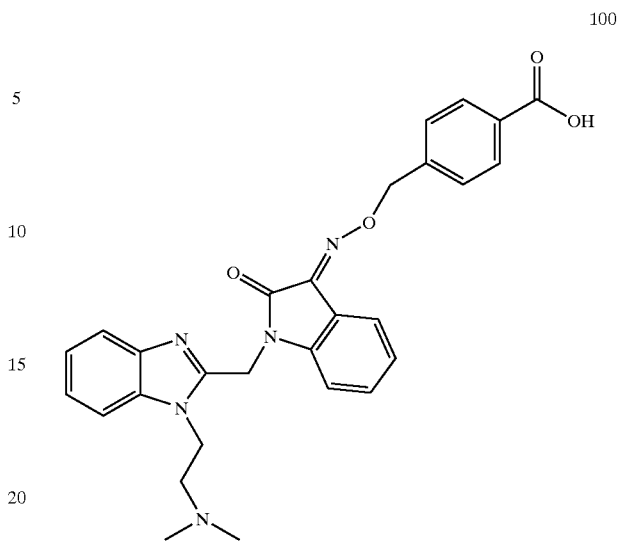

100

A mixture of compound 98 (200 mg, 0.57 mmol), compound 93b (104 mg, 0.57 mmol) and p-toluenesulfonic acid (162 mg, 0.87 mmol) was stirred at reflux for 12 hours. The mixture was concentrated and the residue dissolved in EtOAc, washed with saturated $NaHCO_3$, dried over $MgSO_4$, and concentrated. The dark residue was purified by preparative HPLC (gradient, 80% MeOH/water to 100% MeOH/water) to give 128 mg (44% yield) of compound 99 as a dark oil:

$^1$H NMR (DMSO-$d_6$) δ2.95 (s, 6H), 3.50–3.70 (m, 2H), 3.86 (s, 3H), 4.72–4.77 (m, 2H), 3.38 (s, 2H), 5.62 (s, 2H), 7.10–7.27 (m, 4H), 7.44–7.49 (m, 1H), 7.58–7.63 (m, 3H), 7.63–7.69 (d, J=8.0 Hz, 1H), 7.98–8.03 (m, 3H);

MS m/e 511 (MH$^+$);

Anal. Calcd for $C_{29}H_{29}N_5O_4 \cdot 0.4H_2O$: C, 46.29; H, 3.56; N, 7.38

Found: C, 46.29; H, 3.72; N, 7.49.

A solution of compound 99 in aqueous 1N HCl (50 mL) was heated to reflux for 6 hours then cooled and concentrated. The residue was purified by preparative HPLC ($C_{18}$, gradient, 50–70% MeOH/water) to give a yellow solid. The solid was dissolved in 4N HCl in dioxane (10 mL). The solvent and excess HCl were evaporated to give 95 mg (75% yield) of compound 100 as a hydrochloride salt:

$^1$H NMR (DMSO-$d_6$) δ2.90 (s, 6H), 3.60–3.70 (m, 2H), 5.00–5.03 (m, 2H), 5.62 (s, 2H), 5.66 (s, 2H), 7.18 (t, J=7.6 Hz, 1H), 7.9 (d, J=7.9 Hz, 1H), 7.44–7.54 (m, 3H), 7.60 (d, J=8.2 Hz, 2H), 7.69 (d, J=8.0 Hz, 1H), 7.99–8.03 (m, 3H), 8.10 (d, J=8.2 Hz, 1H);

MS m/e 497 (MH$^+$);

Anal. Calcd for $C_{28}H_{27}N_5O_4 \cdot 2.9H_2O \cdot 1.8HCl$: C, 54.74; H, 5.67, N, 11.40

Found: C, 54.98; H, 5.27; N, 11.00.

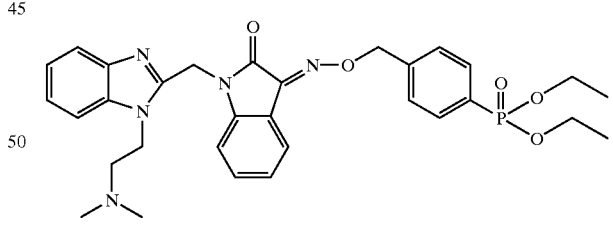

Compound 101 was prepared using the same method as compound 99 with compound 88f:

$^1$H NMR (DMSO-$d_6$) δ1.23 (t, J=7.0 Hz, 6H), 2.91 (d, J=4.8 Hz, 6H), 3.57 (s, 2H), 3.97–4.04 (m, 4H), 4.86 (t, J=7.4 Hz, 2H), 5.47 (s, 2H), 5.62 (s, 2H), 7.17 (t, J=7.7 Hz, 1H), 7.25 (d, J=8.0 Hz, 1H), 7.30 (t, J=7.7 Hz, 1H), 7.39 (t, J=7.4 Hz, 1H), 7.45–7.49 (m, 1H), 7.59–7.65 (m, 3H), 7.72–7.80 (m, 2H), 7.86 (d, J=7.9 Hz, 1H), 8.01 (t, J=7.7 Hz, 1H);

MS m/e 590 (MH$^+$).

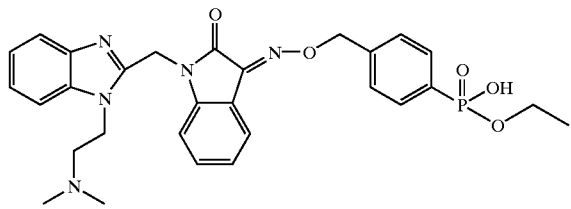

Compound 102 was prepared using the same procedure as compound 89 with compound 101:

$^1$H NMR (DMSO-d$_6$) δ1.09 (t, J=7.0 Hz, 3H), 3.00–3.10 (m, 2H), 3.38 (bs, 6 H), 3.71–3.77 (m, 2H), 4.55–4.70 (m, 2H), 5.27 (s, 2H), 5.50 (s, 2H), 7.10 (t, J=7.6 Hz, 1H), 7.11–7.21 (m, 2H), 7.23 (t, J=7.1 Hz, 1H), 7.40 (t, J=6.7 Hz, 1H), 7.41–7.47 (m, 2H), 7.54 (d, J=8.0 Hz, 1H), 7.63 (d, J=8.1 Hz, 1H), 7.68–7.72 (m, 2H), 7.92 (d, J=6.9 Hz, 1H).

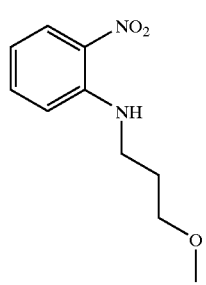

103a

To a mixture of 2-methoxypropylamine (8.45 g, 94.83 mmol) and potassium carbonate (26.21 g, 189.66 mmol) in CH$_2$Cl$_2$ (150 mL) was added 1-fluoro-2-nitrobenzene (13.38 g, 94.83 mmol) dropwise. The resulting mixture was stirred at 65° C. for 20 hours. The potassium carbonate was removed by filtration. The filtrate was washed with water and saturated aqueous sodium chloride, dried over MgSO$_4$, and evaporated to give 19.6 g (98% yield) of intermediate 103a as an orange oil:

$^1$H NMR (CDCl$_3$) δ1.95–2.00 (m, 2H), 3.37 (s, 3H), 3.39–3.43 (m, 2H), 3.52 (t, J=5.7 Hz, 2H), 6.60 (dt, J=1.2, 8.0 Hz, 1H), 6.85 (d,J=1.4, 7.0 Hz, 1H), 8.14 (dd, J=1.4, 7.0 Hz, 1H), 8.28 (bs, 1H).

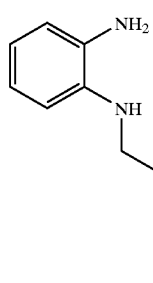

103b

A mixture of 103a (5.87 g, 27.92 mmol) and 10% palladium on carbon (1.17 g) in MeOH (100 mL) was hydrogenated at 50 psi for 4 hours. The catalyst was removed by filtration through a pad of celite. The filtrate was evaporated to give 4.59 g (91% yield) of the diamine 103b.

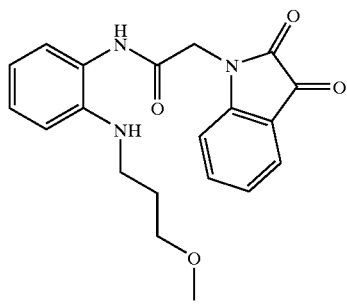

103c

To a mixture of diamine 103b (3.45 g, 19.14 mmol) and DIEA (4.95 g, 38.30 mmol) in anhydrous THF (75 mL) was added a solution of compound 95e (4.28 g, 19.14 mmol) in THF (50 mL) slowly over 15 minutes. The resulting mixture was stirred for 10 minutes at room temperature. The solvent was evaporated to give the intermediate 103c which was used without further purification.

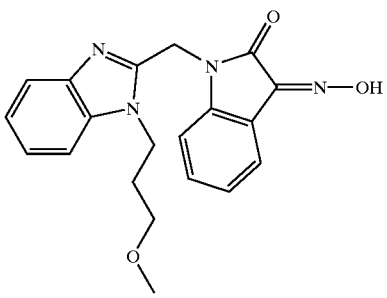

104

A mixture of compound 103c (7.00 g, 19.0 mmol) and hydroxylamine hydrochloride (1.46 g, 21.0 mmol) in glacial acetic acid (150 mL) was stirred at 120° C. for 30 minutes. The mixture was then concentrated in vacuo to a yellow solid. The crude solid was triturated with cold CH$_2$Cl$_2$ and isolated by filtration. The solid was redissolved in EtOAc and washed three times with saturated aqueous NaHCO$_3$ and then with brine. The organic phase was dried over anhydrous Na$_2$SO$_4$ and partially concentrated in vacuo to a point where yellow solid precipitated from solution. The resulting suspension was chilled in an ice bath and filtered to give 3.84 g (55% yield) of compound 104 as a light yellow fluffy powder:

$^1$H NMR (acetone-d$_6$) δ2.81 (s, 2H), 3.30 (s, 3H), 3.35 (t, J=5.9 Hz, 2H), 4.48 (t, J=7.1 Hz, 2H), 5.33 (s, 2H), 7.09–7.12 (m, 1H), 7.18–7.21 (m, 1H), 7.23–7.27 (m, 1H), 7.33 (d, J=7.80 Hz, 1H), 7.37–7.41 (m, 1H), 7.51 (d, J=8.0 Hz, 1H), 7.58 (d, J=8.0 Hz, 1H), 8.11 (d, J=7.5 Hz, 1H), 12.65 (s, 1H);

MS m/e 365 (MH$^+$).

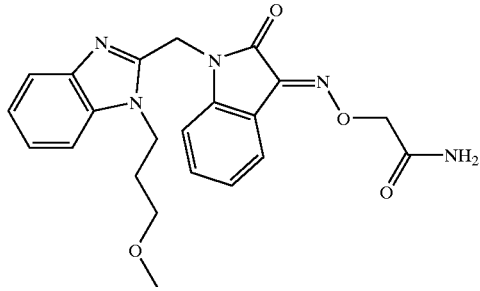

105

Compound 104 (219 mg, 0.60 mmol) and 2-chloro-N-(hydroxymethyl)-acetamide (148 mg, 1.2 mmol) were dissolved in anhydrous CH$_3$CN (50 mL). To the solution was added BEMP on polystyrene (Fluka, 1.0 g, 1.8 mmol), and the mixture was stirred at 60° C. overnight. To the resulting mixture was added PS-thiophenol resin (Argonaut, 1.0 g, 1.2 mmol), MP-carbonate resin (Argonaut, 400 mg, 1.2 mmol) and triethylamine (36 mg, 0.36 mmol) and the mixture was heated to 60° C. for 4 hours. The mixture was filtered to remove all resins and concentrated in vacuo to afford 136 mg (54% yield) of compound 105 as a yellow powder:

$^1$H NMR (DMSO-d$_6$) δ2.00 (t, J=6.4 Hz, 2H), 3.25 (s, 3H), 3.32 (t, J=5.8 Hz, 2H), 4.38 (t, J=6.9 Hz, 2H), 4.84 (s, 2H), 5.28 (s, 2H), 7.11–7.19 (m, 3H), 7.22–7.25 (m, 1H), 7.39 (s, 1H), 7.43–7.47 (m, 1H), 7.49 (s, 1H), 7.53–7.57 (m, 2H), 8.01 (d, J=7.1 Hz, 1H);

MS m/e 422 (MH$^+$).

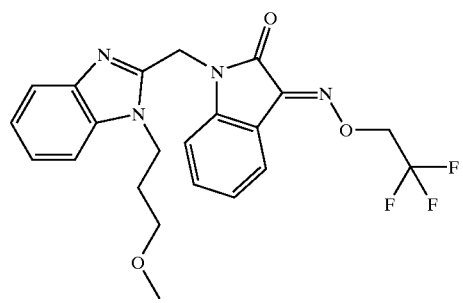

106

Compound 104 (219 mg, 0.60 mmol) and 2,2,2-trifluoroethyl-p-tosylate (305 mg, 1.2 mmol) were combined in anhydrous CH$_3$CN (50 mL). To the solution was added BEMP on polystyrene (Fluka, 1.0 g, 1.8 mmol) and the mixture was stirred at 60° C. overnight. To the resulting mixture was added PS-thiophenol resin (Argonaut, 1.0 g, 1.2 mmol), MP-carbonate resin (Argonaut, 400 mg, 1.2 mmol) and triethylamine (36 mg, 0.36 mmol), and the mixture was heated to 60° C. for 4 hours. The mixture was filtered to remove all resins and concentrated in vacuo. The crude residue was dissolved in minimum CH$_2$Cl$_2$ and was diluted with diethyl ether (15 mL) and hexanes (30 mL). The resulting solution was concentrated in vacuo to a volume of 35 mL when solids precipitated from solution. The suspension was chilled in an ice bath, filtered and rinsed with hexanes to give 140 mg (52% yield) of compound 106 as a canary yellow powder:

$^1$H NMR (DMSO-d$_6$) δ1.99 (t, J=6.5 Hz, 2H), 3.24 (s, 3H), 3.31 (t, J=5.9 Hz, 2H), 4.37 (t, J=7.0 Hz, 2H), 5.19 (q, J=9.0 Hz, 2H), 5.28 (s, 2H), 7.21 (m, 4H), 7.49 (m, 1H), 7.55 (m, 2H), 7.92 (d, J=7.0 Hz, 1H);

MS m/e 447 (MH$^+$).

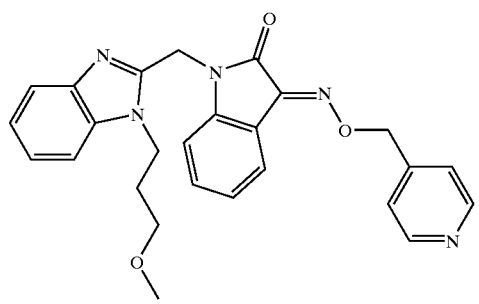

107

Compound 107 was prepared by the same procedure as described for the preparation of compound 105 with 4-(chloromethyl)pyridine hydrochloride. The crude product was purified by silica gel flash chromatography (CH$_2$Cl$_2$:CH$_3$OH=40:1) to give 94 mg (34% yield) of compound 107 as a yellow solid:

$^1$H NMR (DMSO-d$_6$) δ1.98 (t, J=6.5 Hz, 2H), 3.22 (s, 3H), 3.28 (t, J=5.9 Hz, 2H), 4.36 (t, J=7.0 Hz, 2H), 5.27 (s, 2H), 5.59 (s, 2H), 7.13–7.25 (m, 4H), 7.43–7.50 (m, 3H), 7.54 (t, J=8.9 Hz, 2H), 8.02 (d, J=7.0 Hz, 1H), 8.61–8.62 (m, 2H);

MS m/e 456 (MH$^+$).

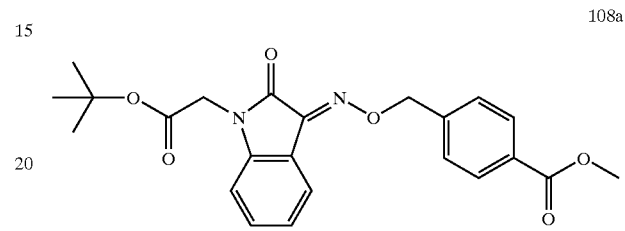

108a

A mixture of compound 95a (3.00 g, 11.23 mmol), compound 93b (2.14 g, 11.79 mmol), and p-toluenesulfonic acid (427 mg, 2.25 mmol) in MeOH (50 mL) was stirred for 1.5 hours at room temperature. The mixture was concentrated and the resulting yellow precipitate was filtered and dried to give 4.45 g (93% yield) of compound 108a:

$^1$H NMR (CDCl$_3$) δ1.40 (s, 9H), 3.85 (s, 3H), 4.50 (s, 2H), 5.59 (s, 2H), 7.09–7.14 (m, 2H), 7.48 (t, J=7.8 Hz, 1H), 7.59 (d, J=8.2 Hz, 2H), 7.95 (d, J=7.4 Hz, 1H), 7.99 (d, J=8.2 Hz, 2H).

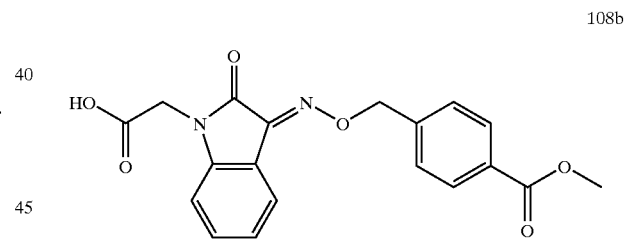

108b

Acid 108b was prepared using the same procedure as compound 95b with compound 108a:

$^1$H NMR (CDCl$_3$) δ3.85 (s, 3H), 4.50 (s, 2H), 5.60 (s, 2H), 7.11–7.14 (m, 2H), 7.48 (dt, J=1.1, 7.8 Hz, 1H), 7.59 (d, J=8.2 Hz, 2H), 7.95 (d, J=6.8 Hz, 1H), 8.00 (d, J=8.3 Hz, 2H).

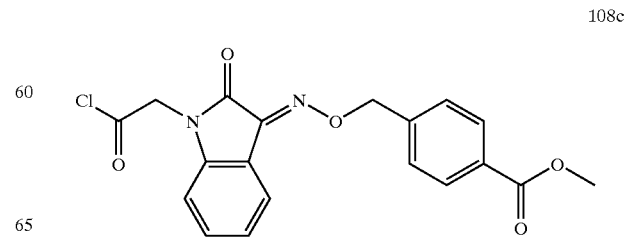

108c

Compound 108c was prepared using the same procedure as compound 95e with compound 108b and was used directly upon isolation.

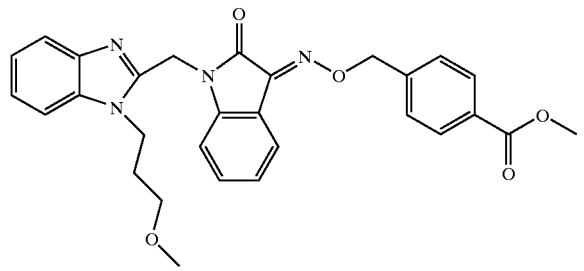

108

To a mixture of compound 103b (233 mg, 1.29 mmol) and poly(4-vinylpyridine) (PVP, 2% cross-linked, 411 mg) in CH$_2$Cl$_2$ (15 mL) was added compound 108c (500 mg, 1.29 mmol). The reaction mixture was stirred at room temperature for 16 hours. The PVP was removed by filtration and washed with CH$_2$Cl$_2$. The filtrate was concentrated to a minimal amount of solvent and was then diluted with Et$_2$O. The brown precipitate was collected by filtration. The brown solid (463 mg) was dissolved in AcOH (10 mL) and stirred at 120° C. for 1 hour. The solvent was evaporated. The residue was dissolved in the minimal amount of MeOH and diluted with Et$_2$O. The yellow solid was collected by filtration to give 434 mg (82% yield over two steps) of compound 108:

$^1$H NMR (DMSO-d$_6$) δ1.96–1.99 (m, 2H), 3.22 (s, 3H), 3.28 (t, J=5.85, 2H), 3.85 (s, 3H), 4.36 (t, J=7.0 Hz, 2H), 5.27 (s, 3H), 5.62 (s, 3H), 7.12 (t, J=7.8 Hz, 2H), 7.17 (t, J=7.2 Hz, 2H), 7.25 (t, J=7.5 Hz, 1H), 7.45 (t, J=7.8 Hz, 1H), 7.54 (t, J=9.4 Hz, 2H), 7.61 (d, 8.2 Hz, 2H), 7.97 (d, 7.6 Hz, 1H), 8.01 (d, J=8.2 Hz, 2H);

MS m/e 531 (MH$^+$).

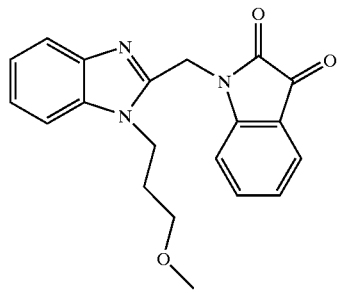

109a

A solution of compound 103c (850 mg, 2.31 mmol) in AcOH (10 mL) was stirred at 120° C. for 1 hour and then at room temperature for 18 hours. The solvent was concentrated and the brown residue was dissolved in CH$_2$Cl$_2$. To this solution was added Et$_2$O and the resulting brown precipitate was filtered. The solid was subjected to flash column chromatography (CH$_2$Cl$_2$/MeOH, 50:1) to give 589 mg (73% yield) of compound 109a:

$^1$H NMR (CDCl$_3$) δ1.94–1.99 (m, 2H), 3.28 (t, J=5.7 Hz, 2H), 3.29 (s, 3H), 4.36 (t, J=7.2 Hz, 2H), 5.27 (s, 2H), 7.11 (t, J=7.6 Hz, 1H), 7.27–7.32 (m, 2H), 7.39–7.41 (m, 1H), 7.47 (d, J=8.2 Hz, 1H), 7.52–7.56 (m, 1H), 7.61 (d, J=7.6 Hz, 1H), 7.77–7.79 (m, 1H).

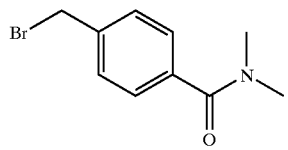

109b

To a solution of α-bromo-p-toluic acid (25 g, 116.25 mmol) in CH$_2$Cl$_2$ (200 mL) was added oxalyl chloride (17.71 g, 139.50 mmol) slowly followed by DMF (450 μL). The reaction was stirred approximately 1 hour until the solution became clear. The solvent was evaporated and the white solid was dried under vacuum to give the acid chloride. A mixture of the acid chloride (7.0 g, 30.24 mmol), poly(4-vinylpyridine) (PVP, 2% cross-linked, 9.6 g), and dimethylamine (2 M in THF, 15.9 mL, 31.75 mmol) in THF (200 mL) were stirred at room temperature for 15 hours. The poly(4-vinylpyridine) was removed by filtration and the filtrate was concentrated to give 7.3 g (99% yield) of compound 109b as a yellow solid:

$^1$H NMR (CDCl$_3$) δ2.99 (s, 3H), 3.09 (s, 3H), 4.48 (s, 2H), 7.38–7.43 (m, 4H).

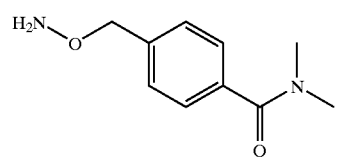

109c

Compound 109c was prepared using the same procedure as compound 88f starting with compound 109b.

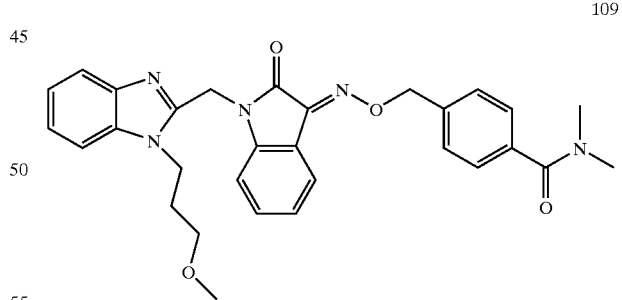

109

Compound 109 was prepared using the same procedure as compound with compounds 109a and 109c:

$^1$H NMR (CDCl$_3$) δ2.04–2.07 (m, 2H), 3.00 (s, 3H), 3.13 (s, 3H), 3.30 (s, 3H), 3.37 (t, J=5.3 Hz, 2H), 4.64 (t, J=6.7 Hz, 2H), 5.55 (s, 2H), 5.66 (s, 2H), 7.10 (t, J=7.3 Hz, 1H), 7.39–7.50 (m, 5H), 7.52–7.56 (m, 2H), 7.58–7.62 (m, 2H), 7.94 (d, J=7.5 Hz, 1H), 7.98 (d, J=7.5 Hz, 1H).

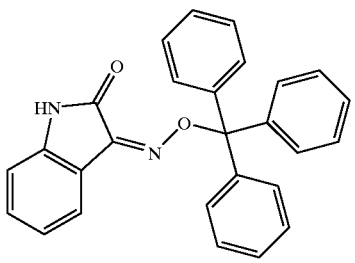

110a

Isatin (2.43 g, 16.50 mmol), O-tritylhydroxylamine (95%, 4.54 g, 16.5 mmol) and 1N aqueous HCl (1.7 mL, 1.70 mmol) were combined in a mixture of 100% ethanol (100 mL) and water (30 mL) and the mixture was stirred at room temperature for 1.5 hours. The reaction mixture gradually changed from a deep red color to yellow. After addition of NaHCO$_3$ (157 mg, 1.87 mmol) to neutralize the HCl, the suspension was chilled in an ice bath and filtered to isolate a yellow powder. Heating the powder at 110° C. under vacuum overnight gave 5.63 g (84% yield) of compound 110a as a canary yellow powder:

$^1$H NMR (CDCl$_3$) δ6.86 (d, J=7.8 Hz, 1H), 7.06–7.09 (m, 1H), 7.25–7.38 (m, 16 H), 7.94 (s, 1H), 8.18 (d, J=7.6 Hz 1H);

MS m/e 427 (M+Na$^+$).

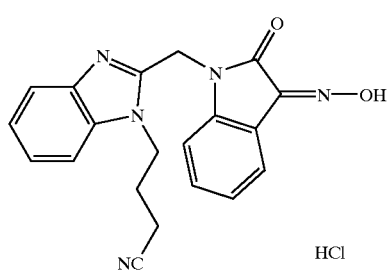

110

A mixture of compound 110a (3.00 g, 7.42 mmol), compound 25b (2.00 g, 7.42 mmol) and Cs$_2$CO$_3$ (7.25 g, 22.3 mmol) in anhydrous CH$_3$CN (70 mL) was stirred at reflux for 2 hours. The mixture was cooled to room temperature, diluted with EtOAc, and washed with water. The organic layer was dried over anhydrous MgSO$_4$ and concentrated in vacuo to a yellow oil. The crude product was dissolved in a minimum of CH$_2$Cl$_2$ and diluted with 15 volumes of MeOH while swirling. Solids precipitated from solution. The suspension was chilled in an ice bath, filtered, rinsed with ice-cold methanol, and allowed to air-dry to give the trityl oxime adduct. A solution of this intermediate (2.00 g, 3.32 mmol) in 1,4-dioxane (50 mL) was treated with 4N HCl in dioxane (8.3 mL, 33.2 mmol) and stirred at room temperature for 3 hours. The reaction mixture was filtered to isolate 1.19 g (88% yield) of compound 110 as a fluffy yellow solid:

$^1$H NMR (DMSO-d$_6$) δ2.20 (t, J=7.4 Hz, 2H), 2.70 (t, J=7.4 Hz, 2H), 4.54 (t, J=7.3 Hz, 2H), 5.52 (s, 2H), 7.15 (t, J=7.5 Hz, 1H), 7.19 (d, J=8.0 Hz, 1H), 7.41–7.48 (m, 3H), 7.65 (d, J=8.0 Hz, 1H), 7.87 (d, J=7.5 Hz, 1H), 8.08 (d, J=7.3 Hz, 1H), 13.65 (s, 1H);

MS m/e 360 (MH$^+$).

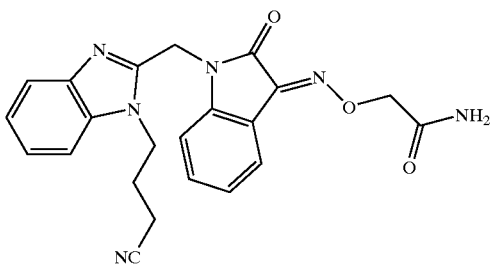

111

Compound 110 (317 mg, 0.80 mmol) and 2-chloro-N-(hydroxymethyl)-acetamide (198 mg, 1.6 mmol) were dissolved in anhydrous CH$_3$CN (35 mL). To the solution was added BEMP on polystyrene (Fluka, 1.2 g, 2.4 mmol), and the mixture was stirred at 60° C. overnight. To the resulting mixture was added PS-thiophenol resin (Argonaut, 1.2 g, 1.6 mmol), MP-carbonate resin (Argonaut, 513 mg, 1.6 mmol) and triethylamine (36 mg, 0.36 mmol) and the mixture was heated to 60° C. for 6 hours. The mixture was filtered to remove all resins and concentrated in vacuo to afford 201 mg (60% yield) of compound 111 as a yellow powder:

$^1$H NMR (DMSO-d$_6$) δ2.13 (t, J=7.5 Hz, 2H), 2.64 (t, J=7.4 Hz, 2H), 4.40 (t, J=7.5 Hz, 2H), 4.84 (s, 2H), 5.31 (s, 2H), 7.12–7.21 (m, 3H), 7.24–7.27 (m, 1H), 7.38 (s, 1H), 7.44–7.49 (m, 2H), 7.56 (d, J=8.0 Hz, 1H), 7.61 (d, J=8.0 Hz, 1H), 8.02 (d, J=7.5 Hz, 1H);

MS m/e 417 (MH$^+$).

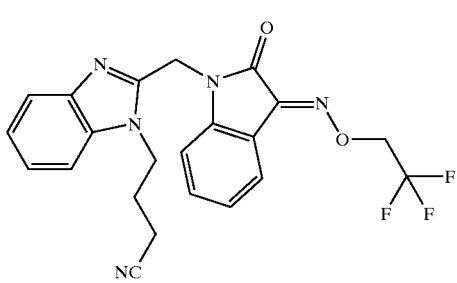

112

Compound 110 (317 mg, 0.80 mmol) and 2,2,2-trifluoroethyl-p-tosylate (407 mg, 1.6 mmol) were dissolved in anhydrous CH$_3$CN (35 mL). To the solution was added BEMP on polystyrene (Fluka, 1.2 g, 2.40 mmol), and the mixture was stirred at 60° C. overnight. To the resulting mixture was added PS-thiophenol resin (Argonaut, 1.2 g, 1.60 mmol), MP-carbonate resin (Argonaut, 513 mg, 1.60 mmol) and triethylamine (36 mg, 0.36 mmol), and the mixture was heated to 60° C. for 6 hours. The mixture was filtered to remove all resins and concentrated in vacuo. The crude residue was purified by silica gel flash chromatography (CH$_2$Cl$_2$:CH$_3$OH=100:1) to give 224 mg (63% yield) of compound 112 as a yellow solid:

$^1$H NMR (DMSO-d$_6$) δ2.13 (t, J=7.5 Hz, 2H), 2.64 (t, J=7.4 Hz, 2H), 4.40 (t, J=7.6 Hz, 2H), 5.19 (q, J=9.0 Hz, 2H), 5.31 (s, 2H), 7.17(t, J=7.6 Hz, 2H), 7.23–7.27 (m, 2H), 7.49–7.52 (m, 1H), 7.55 (d, J=8.0 Hz, 1H), 7.61 (d, J=8.0 Hz, 1H), 7.92 (d, J=7.5 Hz, 1H);

MS m/e 442 (MH$^+$).

113

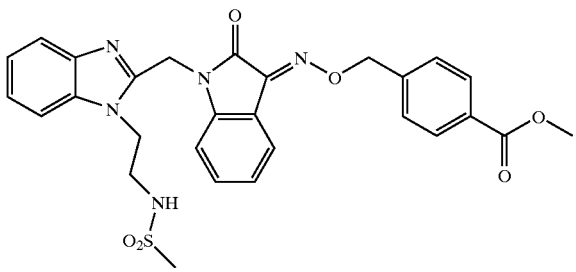

Compound 113 was prepared using the same procedure as compound 108 with compound 108c and compound 23e:

¹H NMR (DMSO-d₆) δ2.81 (s, 3H), 3.42 (t, J=5.8 Hz, 2H), 3.86 (s, 3H), 4.66 (t, J=5.4 Hz, 2H), 5.34 (s, 2H), 5.63 (s, 2H), 7.12–7.19 (m, 3H), 7.27 (t, J=7.3 Hz, 1H), 7.40–7.45 (m, 2H), 7.53 (d, J=8.0 Hz, 1H), 7.63 (d, J=8.3 Hz, 2H), 7.99 (d, J=7.3 Hz, 1H), 8.02 (d, J=8.3 Hz, 2H);

NEW Spectral DATA

1-[1-(4-Fluoro-butyl)-1H-benzoimidazol-2-ylmethyl]-1H-indole-2,3-dione

114a

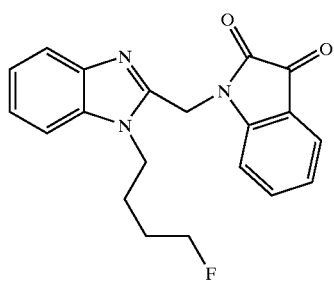

1-[1-(4-Fluoro-butyl)-1H-benzoimidazol-2-ylmethyl]-1H-indole-2,3-dione was prepared as described for compound 25 starting from isatin (1.54 g, 10.5 mmol) and 159c (2.90 g, 10.5 mmol). The product was obtained by precipitation from diethyl ether and methylene chloride to give 1-[1-(4-fluoro-butyl)-1H-benzoimidazol-2-ylmethyl]-1H-indole-2,3-dione (385 mg, 10%) as a yellow solid.

¹H NMR (CDCl₃) δ7.79 (d, J 8.0 Hz, 1H), 7.60 (m, 3H), 7.34 (m, 3H), 7.13 (t, J 7.4 Hz, 1H), 5.28 (s, 2H), 4.46 (dt, J 5.6, 47 Hz, 2H), 4.33 (t, J 7.5 Hz, 2H), 1.82 (m, 4H);

MS m/e 352 (MH⁺).

1-[1-(4-Fluoro-butyl)-1H-benzoimidazol-2-ylmethyl]-1,3-dihydro-indol-2-one

114b

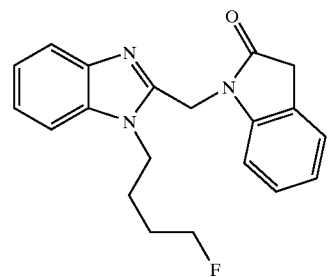

A suspension of 1-[1-(4-Fluoro-butyl)-1H-benzoimidazol-2-ylmethyl]-1H-indole-2,3-dione (607 mg, 1.73 mmol) in hydrazine hydrate (15 mL) was heated at reflux for 18 min. The solution was cooled to room temperature and quenched with ice and ethyl acetate (40 mL). The layers were separated and the aqueous phase extracted with ethyl acetate (2×40 mL). The combined organic phases were washed with brine and dried (MgSO₄). The product was purified by flash column chromatography (eluent 3% methanol in methylene chloride) to give compound 114b 325 mg, 56% as an off white solid.

¹H NMR (CDCl₃) δ7.80 (dd, J 1.9, 5.3 Hz, 1H), 7.43 (d, J 8.0 Hz, 1H), 7.29 (m, 5H), 7.02 (t, J 7.5 Hz, 1H), 5.27 (s, 2H), 4.45 (dt, J 4.9, 47 Hz, 2H), 4.32 (t, J 7.2 Hz, 2H), 3.61 (s, 2H), 1.78 (m, 4H);

MS m/e 338 (MH⁺).

114

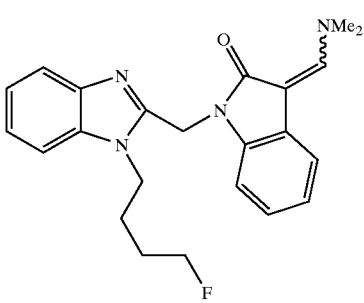

115

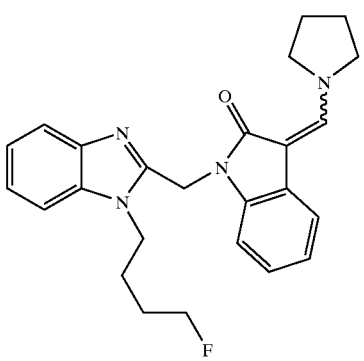

To a solution of the oxindole 114b (26 mg, 0.078 mmol) in DMF (2.5 mL) was added DMF neopentyl acetal (327 μL, 1.17 mmol). The solution was stirred for 1 hour at room temperature. The volatiles were stripped off and the residue purified by flash column chromatography (eluent 3% methanol in methylene chloride). The slow moving product was the enamide 114 (10 mg, 33%) as a 2:1 mixture of geometric isomers (off white solid after trituration from diethyl ether). The fast moving product was the neopentyl enol ether, which was dissolved in methylene chloride and treated with a large excess of pyrrolidine at room temperature. After 2 hours, the volatiles were removed in vacuo, and the residue purified by flash column chromatography (eluent 3% methanol in methylene chloride) to give 7 mg of the enamide 115 (3:1 mixture of geometric isomers) as an oil.

Compound 114: ¹H NMR (CDCl₃) δ7.80 (m, 1H), 7.68 (s, 1H), 7.37 (d, J 7.9 Hz, 1H), 7.29 (m, 4H), 6.95 (m, 2H), 5.39 (s, 2H), 4.34 (m, 4H), 3.36 (s, 6H), 1.67 (m, 4H);

MS m/e 393 (MH⁺);

Compound 115: ¹H NMR (CDCl₃) δ7.84 (s, 1H), 7.79 (m, 1H), 7.49 (d, J=7.7 Hz, 1H), 7.34 (d, J=7.7 Hz, 1H), 7.27 (m, 3H), 7.13 (d, J=7.5 Hz, 1H minor isomer), 6.92 (m, 2H), 5.39, 5.38 (s, 2H), 4.30 (m, 4H), 3.83 (m, 4H), 2.04 (m, 4H), 1.66 (m, 4H);

MS m/e 419 (MH⁺).

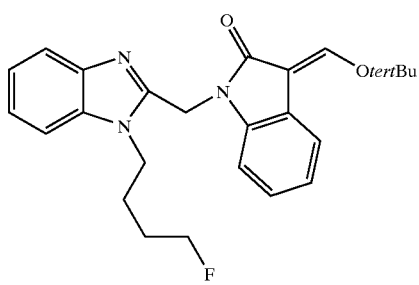

116

A solution of the oxindole 114b (36 mg, 0.11 mmol) and DMF tert-Bu acetal (323 mg, 1.59 mmol) in DMF (2 mL) was stirred at 0° C. for 3 hours. The volatiles were removed in vacuo, and the residue purified by flash column chromatography (eluent 2%, 5% methanol in methylene chloride) to give 12 mg (fast moving product, 27%) of the enol ether 116 as a brownish oil. The slow moving product was the enamide 114 as a 2:1 mixture of geometric isomers (27 mg, 65%).

$^1$H NMR (CDCl$_3$) δ7.93 (s, 1H), 7.79 (m, 1H), 7.61 (d, J 7.3 Hz, 1H), 7.28 (m, 4H), 7.11 (t, J=7.4 Hz, 1H), 7.00 (t, J=7.4 Hz, 1H), 5.31 (s, 2H), 4.35 (m, 4H), 1.68 (m, 4H), 1.53 (s, 9H);

MS m/e 422 (MH$^+$).

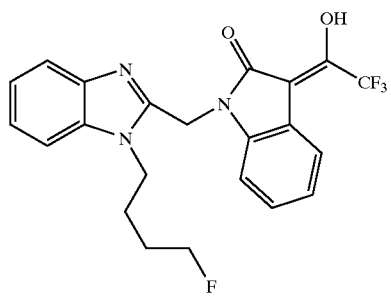

117

To a suspension of NaH (60% in mineral oil, 7.1 mg, 0.18 mmol) in THF (2 mL) was added the oxindole 114b (40 mg, 0.12 mmol) under nitrogen. The mixture was heated at reflux temperature, and ethyl trifluoroacetate (21 μL, 0.18 mmol) was added. After 2 hours of reflux the mixture was cooled to room temperature and poured into 1M aq. HCl. The product was extracted into ethyl acetate (2×15 mL). The combined organic extracts were washed with brine and dried (MgSO$_4$). The pure product 117 was obtained by precipitation from diethyl ether (20 mg, 38%) as a grey solid.

$^1$H NMR (DMSO) δ7.98 (d, J=7.5 Hz, 1H), 7.93 (d, J=6.9 Hz, 1H), 7.79 (d, J=8.4 Hz, 1H), 7.58 (m, 2H), 6.85 (m, 3H), 5.49 (s, 2H), 4.54 (br s, 2H), 4.35 (dt, J=5.7, 47 Hz, 2H), 1.66 (m, 4H);

MS m/e 434 (MH$^+$).

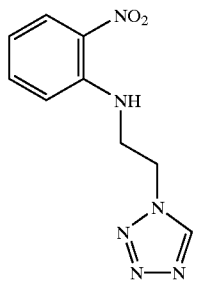

118a

A mixture of amine 23c (40 g, 220 mmol), trimethyl orthoformate (38.5 mL, 352 mmol) and sodium azide (15.7 g, 242 mmol) in acetic acid (400 mL) was heated to reflux for 12 hours. The resulting mixture was cooled to room temperature and poured into 1N HCl in ice (300 mL). The precipitate was filtered and recrystallized from EtOAc to give 19.2 g (37% yield) of compound 118a as bright yellow needles:

$^1$H NMR (DMSO-d$_6$) δ3.90 (J=6.6 Hz, 2H), 4.73 (t, J=6.6 Hz, 2H), 6.72 (t, J=6.9 Hz, 1H), 7.07 (d, J=10.2 Hz, 1H), 7.53 (d, J=6.3 Hz, 1H), 8.06 (d, J=10.1 Hz, 1H), 8.18 (t, J=6.6 Hz, 1H); 9.40 (s, 1H);

IR (KBr, cm$^{-1}$) 1621, 1514, 1347, 740;

MS m/e 235 (MH$^+$);

Anal. Calcd for C$_9$H$_{10}$N$_6$O$_2$: C, 46.15; H, 4.30; N, 35.88 Found: C, 46.17; H, 4.35; N, 35.85.

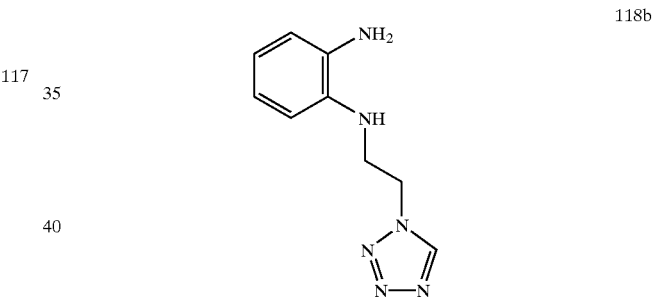

118b

A solution of compound 118a (3.5 g, 14.95 mmol) in EtOH (50 mL) containing 10% palladium on carbon (200 mg) was hydrogenated at 50 psi for 4 hours. The reaction mixture was filtered and concentrated to give 2.8 g (93% yield) of compound 118b as a black solid:

$^1$H NMR (DMSO-d$_6$) δ3.52 (q, J=6.0, 2H), 4.46 (s, 3H), 4.63–4.69 (m, 3H), 6.45–6.57 (m, 4H), 9.4 (s, 1H);

MS m/e 205 (MH$^+$).

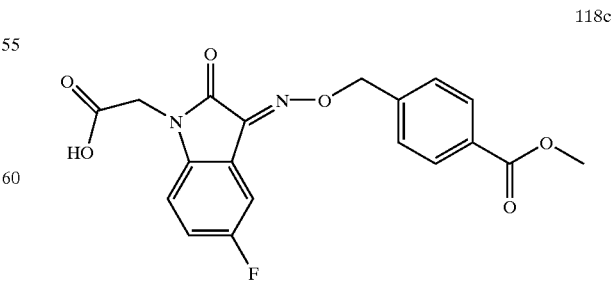

118c

Compound 118c was prepared using the same sequence of procedures as compound 108b starting with 5-fluoroisatin.

¹H NMR (DMSO-d₆) δ3.85 (s, 3H), 4.50 (s, 2H), 5.61 (s, 2H), 7.18 (dd, J=4.1, 8.7 Hz, 1H), 7.60 (d, J=8.2 Hz, 2H), 7.75 (dd, J=2.7, 8.1 Hz, 1H), 7.99 (d, J=8.2 Hz, 2H).

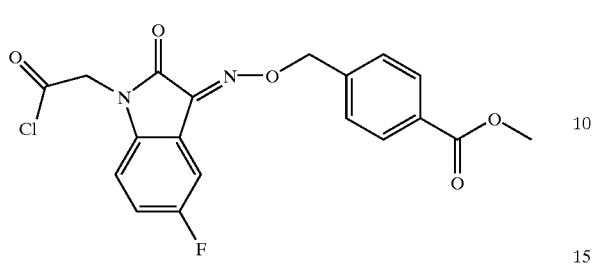

118d

Compound 118d was prepared using the same procedure as compound 98c with compound 118c and was used immediately upon isolation.

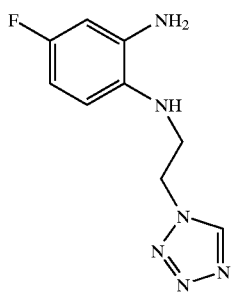

120b

Diamine 120b was prepared using the same procedure as compound 118b with compound 120a and was used directly upon isolation.

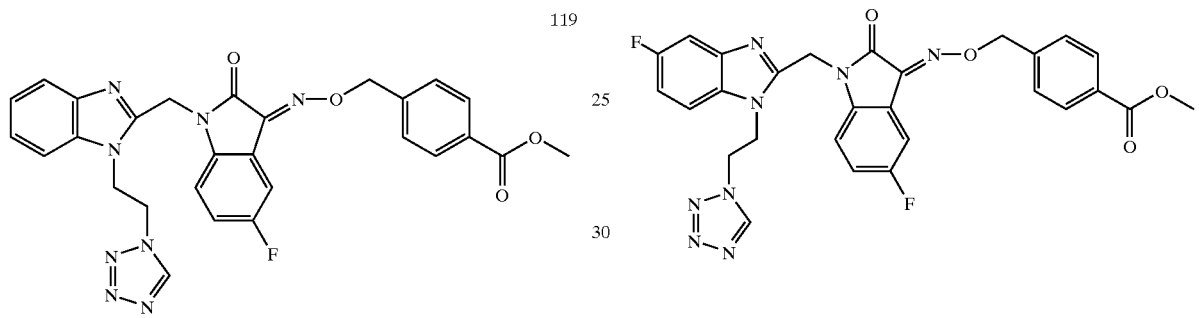

119 / 120

Compound 119 was prepared using the same procedure as compound 108 with compounds 118b and 118d:

¹H NMR (DMSO-d₆) δ3.86 (s, 3H), 4.88 (t, J=5.8 Hz, 2H), 5.02 (t, J=5.9 Hz, 2H), 5.12 (s, 2H), 5.63 (s, 2H), 7.12–7.19 (m, 2H), 7.27–7.29 (m, 1H), 7.35–7.39 (m, 1H), 7.52–7.54 (m, 1H), 7.63 (d, J=8.3 Hz, 2H), 7.77–7.79 (m, 1H), 8.01 (d, J=8.3 Hz, 2H), 9.29 (s, 1H);

MS m/e 555 (MH⁺).

Compound 120 was prepared using the same procedure as compound 108 with compounds 118d and 120b:

¹H NMR (DMSO-d₆) δ3.23 (s, 3H), 4.85–4.89 (m, 2H), 5.01–5.03 (m, 2H), 5.11 (s, 2H), 5.63 (s, 2H), 7.01–7.07 (m, 1H), 7.11–7.16 (m, 1H), 7.25–7.30 (m, 1H), 7.36–7.38 (m, 2H), 7.63 (d, J=8.3 Hz, 2H), 7.80–7.82 (m, 1H), 8.01 (d, J=8.3 Hz, 1H), 9.30 (s, 1H);

MS m/e 573 (MH⁺).

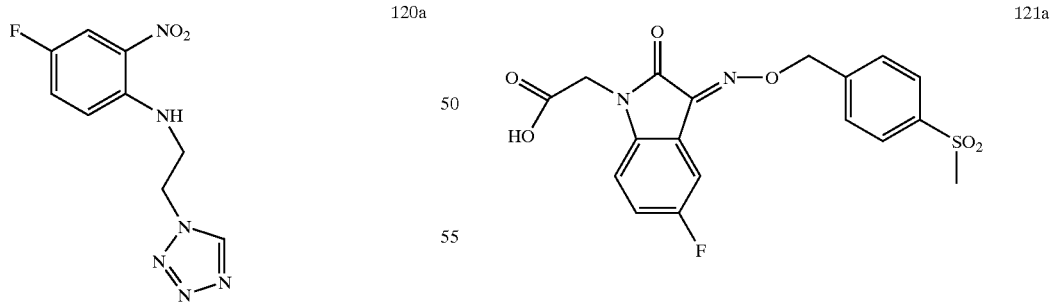

120a / 121a

Compound 120a was prepared using the same procedure as compound 118a starting with 2,5-difluoronitrobenzene:

¹H NMR (DMSO-d₆) δ3.88–3.92 (m, 2H), 4.70–4.72 (m, 2H), 7.13–7.16 (m, 1H), 7.50–7.54 (m, 1H), 7.86–7.89 (m, 1H), 8.12–8.15 (m, 1H), 9.39 (m, 1H);

MS m/e 252 (MH⁺).

Acid 121a was prepared using the same sequence of procedures for compound 108b starting with 5-fluoroisatin and compound 96a:

¹H NMR (DMSO-d₆) δ3.23 (s, 3H), 4.51 (s, 2H), 5.65 (s, 2H), 7.19 (dd, J=4.1, 8.7 Hz, 1H), 7.40 (dt, J=2.7, 8.9 Hz, 1H), 7.73 (d, J=8.4 Hz, 2H), 7.81 (dd, J=2.7, 8.1 Hz, 1H), 7.97 (d, J=8.4 Hz, 2H).

Compound 121b was prepared using the same procedure as compound 108c with compound 121a and was used directly upon isolation.

121

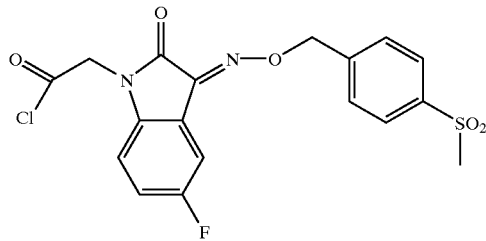

Compound 121 was prepared using the same procedure as compound 108 with compounds 120b and 121b:

¹H NMR (DMSO-d₆) δ3.23 (s, 3H), 4.85–4.89 (m, 2H), 5.01–5.03 (m, 2H), 5.11 (s, 2H), 5.66 (s, 2H), 6.96–7.01 (m, 1H), 7.01–7.07 (m, 1H), 7.12–7.14 (m, 1H), 7.26–7.33 (m, 1H), 7.38–7.41 (m, 2H), 7.75 (d, J=8.3 Hz, 2H), 7.79–7.82 (m, 1H), 7.95–7.99 (m, 3H), 9.29 (s, 1H);

MS m/e 593 (MH⁺).

Compound 122 was prepared using the same procedure as compound 94 with methyl ester 120:

¹H NMR (DMSO-d₆) δ4.40 (s, 1H), 4.79–4.81 (m, 1H), 4.88–4.91 (m, 2H), 5.01–5.03 (m, 1H), 5.12 (s, 1H), 5.36 (s, 1H), 5.62 (s, 2H), 6.89–6.95 (m, 1H), 6.99–7.17 (m, 1H), 7.29–7.32 (m, 1H), 7.35–7.39 (m, 1H), 7.41–7.44 (m, 1H), 7.60 (d, J=8.2 Hz, 1H), 7.77–7.79 (m, 1H), 7.83 (d, J=8.1 Hz, 1H), 7.99 (d, J=8.1 Hz, 2H), 9.17 (s, 1H), 9.30 (s, 1H);

MS m/e 559 (MH⁺).

To a solution of compound 122 (400 mg, 0.72 mmol), dimethylamine hydrochloride (87.6 mg, 1.07 mmol), and DIEA (185.1 mg, 1.43 mmol) in DMF (10 mL) was added bromotripyrrolidineophosphonium hexafluorophosphate (PyBroP®, Fluka, 400.7 mg, 0.86 mmol). The resulting mixture was stirred at room temperature for 18 hours. The mixture was diluted with MeOH (1 mL) and the solvent was evaporated. The residue was dissolved in EtOAc and washed with 5% KHSO₄, 5% NaHCO₃, and brine. The organic layer was dried over Na₂SO₄ and concentrated to give 300 mg (72% yield) of compound 123 as a yellow solid:

¹H NMR (DMSO-d₆) δ2.91 (s, 3H), 2.98 (s, 3H), 4.88–4.90 (m, 2H), 5.01–5.03 (m, 2H), 5.11 (s, 2H), 5.58 (s, 2H), 7.02–7.07 (m, 1H), 7.14–7.17 (m, 1H), 7.27–7.32 (m, 1H), 7.33–7.39 (m, 2H), 7.45 (d, J=8.2 Hz, 2H), 7.54 (d, J=8.1 Hz, 2H), 7.76–7.78 (m, 1H), 9.30 (s, 1H);

MS m/e 586 (MH⁺).

Compound 124a was prepared using the same procedure as compound 98a with 4-fluoro-3-nitrobenzotrifluoride:

¹H NMR (DMSO-d₆) δ2.22 (s, 6H), 2.55 (t, J=6.2 Hz, 2H), 3.43–3.47 (m, 2H), 7.22 (d, J=8.8 Hz, 1H), 7.81 (dd, J=2.2, 9.2 Hz, 1H), 8.32 (s, 1H), 8.60 (t, J=4.5 Hz, 1H);

MS m/e 278 (MH⁺).

Compound 124b was prepared using the same procedure as compound 98b with compound 124a and was used directly upon isolation.

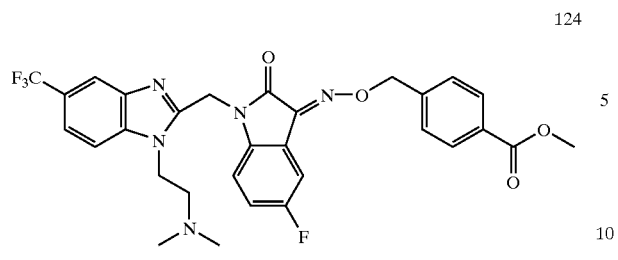

124

Compound 124 was prepared using the same procedure as compound 108 with compound 118d and 124b:

$^1$H NMR (DMSO-d$_6$) δ2.50 (s, 6H), 3.86 (s, 3H), 4.75–4.85 (bs, 2H), 5.41 (s, 2H), 5.64 (s, 2H), 5.58 (s, 2H), 7.17–7.26 (m, 1H), 7.37–7.39 (m,1 H), 7.63 (d, J=8.0 Hz, 3H), 7.80–7.82 (m, 1H), 7.88–7.96 (m, 1H), 7.99–8.03 (m, 3H);

MS m/e 598 (MH$^+$).

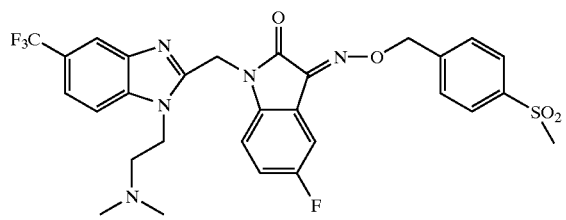

125

Compound 125 was prepared using the same procedure as compound 108 with compound 121b and 124b:

$^1$H NMR (DMSO-d$_6$) δ2.90 (d, J=4.8 Hz, 6H), 3.24 (s, 3H), 4.84–4.86 (m, 4H), 5.44 (s, 2H), 5.67 (s, 2H), 7.24–7.27 (m, 1H), 7.36–7.42 (m, 1H), 7.63–7.64 (m, 1H), 7.76 (d, J=8.3 Hz, 2H), 7.84–7.87 (m, 1H), 7.98–8.00 (m, 4H);

MS m/e 618 (MH$^+$).

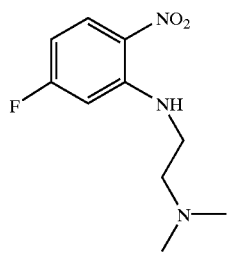

126a

Compound 126a was prepared using the same procedure as compound 98a with 2,4-difluoronitrobenzene:

$^1$H NMR (CDCl$_3$) δ2.21 (s, 6H), 2.53 (t, J=6.1 Hz, 2H), 3.33–3.37 (m, 2H), 6.51–6.56 (m, 1H), 6.85 (dd, J=2.7, 12.2 Hz, 1H), 8.17 (dd, J=6.3, 9.5 Hz, 1H), 8.42 (bs, 1H);

MS m/e 228 (MH$^+$).

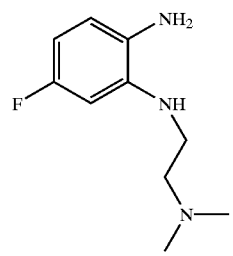

126b

Compound 126b was prepared using the same procedure as compound 98b with compound 126a and was used immediately upon isolation.

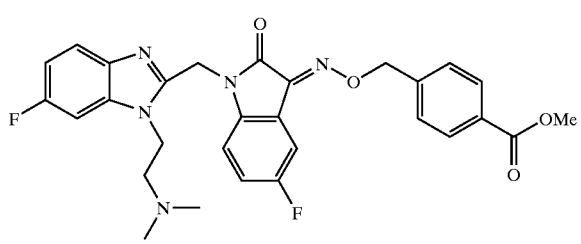

126

Compound 126 was prepared using the same procedure as compound 108 with compound 118d and 126b:

$^1$H NMR (CDCl$_3$) δ2.94 (s, 6H), 3.32 (bs, 2H), 3.94 (s, 3H), 4.97 (bs, 2H), 5.28 (s, 2H), 5.61 (s 2H), 7.05 (t, J=13.6 Hz, 1H), 7.16 (dt, J=4.3, 14.5 Hz, 1H), 7.51 (d, J=13.5 Hz, 3H), 7.69–7.63 (m, 3H), 8.08 (d, J=13.7 Hz, 2H).

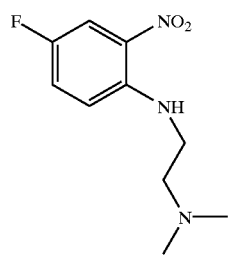

127a

Compound 127a was prepared using the same procedure as compound 98a with 2, 5-difluoronitrobenzene:

$^1$H NMR (DMSO-d$_6$) δ2.21 (s, 6H), 2.53 (t, J=6.05 Hz, 2H), 3.35–3.39 (m, 2H), 7.08 (dd, J=4.8, 9.52 Hz, 1H), 7.50–7.55 (m, 1H), 7.83 (dd, J=3.0, 9.5 Hz, 1H), 8.22 (bs, 1H);

MS m/e 227 (MH$^+$).

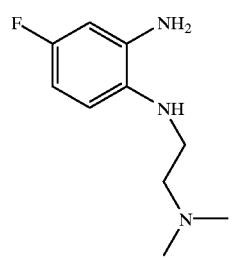

127b

Compound 127b was prepared using the same procedure as compound 98b with compound 127a and was used immediately upon isolation.

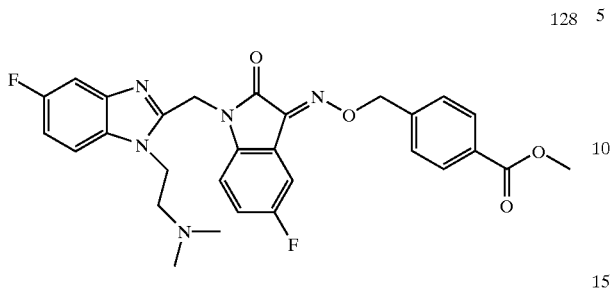
128

Compound 128 was prepared using the same procedure as compound 108 with compound 118d and 127b:

¹H NMR (CDCl₃) δ2.94 (s, 6H), 3.27–3.44 (m, 2H), 3.93 (s, 3H), 5.01 (m, 2H), 5.29 (s, 2H), 5.69 (s, 2H), 7.15 (d, J=9.6 Hz, 2H), 7.41 (d, J=12.4 Hz, 1H), 7.50 (d, J=12.6 Hz, 3H), 7.67 (d, J=9.5 Hz, 1H), 7.88 (bs, 1H), 8.07 (d, J=12.1 Hz, 2H).

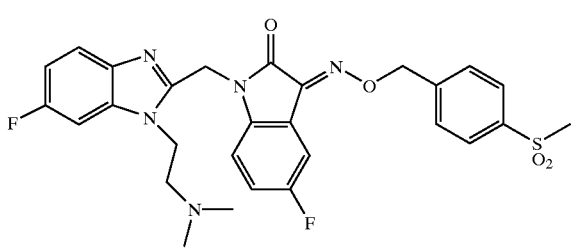
129

Compound 129 was prepared using the same procedure as compound 108 with compound 121b and 126b:

¹H NMR (DMSO-d₆) δ2.85 (s, 6H), 3.23 (s, 3H) 3.52 s, 2H), 4.76 (t, J=7.5, 2H), 5.36 (s, 2H), 5.67 (s, 2H), 7.05 (dt, J=2.2, 9.0 Hz, 1H), 7.26 (dd, J=4.1, 8.7 Hz, 1H), 7.39 (dt, J=2.6, 9.1 Hz, 1H), 7.57 (dd, J=4.9, 8.7 Hz, 1H), 7.71 (d, J=9.4 Hz, 1H), 7.75 (d, J=8.2 Hz, 2H), 7.84 (dd, J=2.6, 8.0 Hz, 1H), 7.98 (d, J=8.2 Hz, 2H).

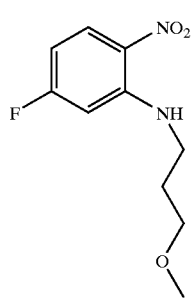
130a

Compound 130a was prepared using the same procedure as compound 103a starting with 2,4-difluoronitrobenzene:

¹H NMR (CDCl₃) δ1.89–2.04 (m, 2H), 3.29, 3.28–3.44 (s over m, 5H), 3.54 (t, J=5.7 Hz, 2H), 6.33–6.37 (m, 1H), 6.52 (dd, J=2.7, 11.5 Hz, 1H), 8.22 (dd, J=6.3, 9.5 Hz, 1H), 8.44 (bs, 1H).

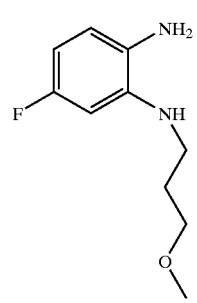
130b

Compound 130b was prepared using the same procedure as compound 103b with compound 130a and was used immediately upon isolation.

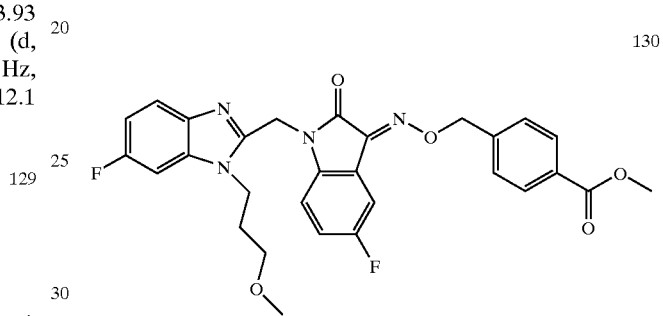
130

Compound 130 was prepared using the same procedure as compound 108 with compounds 118d and 130b:

¹H NMR (CDCl₃) δ1.96–1.99 (m, 2H), 2.12 (s, 3H), 3.32 (s, 3H), 3.32 (t, J=9.0 Hz, 2H), 3.94 (s, 3H), 4.38 (t, J=11.6 Hz, 2H), 5.29 (s, 2H), 5.61 (s, 2H), 7.05–7.13 (m, 3H), 7.42 (dd, J=6.6, 14.3 Hz, 1H), 7.52 (d, J=13.5 Hz, 2H), 7.65–7.73 (m, 2H), 8.08 (d, J=13.6 Hz, 2H).

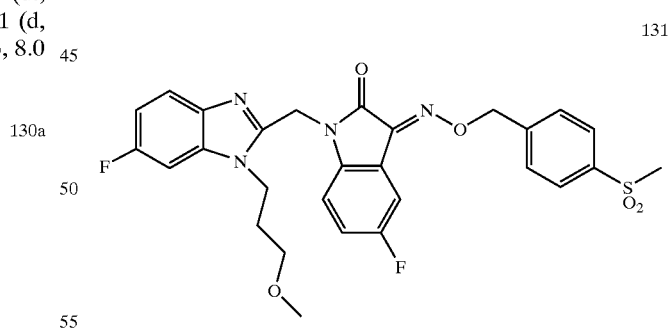
131

Compound 131 was prepared using the same procedure as compound 98 with compounds 121b and 130b:

¹H NMR (DMSO-d₆) δ1.96–1.98 (m, 2H), 3.21 (s, 3H), 3.23 (s, 3H), 3.35 (bs, 2H), 4.33 (t, J=6.2 Hz, 2H), 5.25 (s, 2H), 5.66 (s, 2H), 7.01 (t, J=8.9 Hz, 1H), 7.20 (t, J=4.2 Hz, 1H), 7.37 (t, J=7.7 Hz, 1H), 7.45 (d, J=8.4 Hz, 1H), 7.55 (dd, J=4.5, 8.4 Hz, 1H), 7.75 (d, J=7.7 Hz, 2H), 7.83 (d, J=6.9 Hz, 1H), 7.98 (d, J=7.9 Hz, 2H).

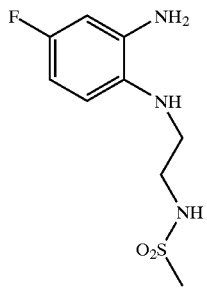
132a

Compound 132a was prepared using the same procedure as compound 23e starting with 2,5-difluoronitrobenzene and was used immediately upon isolation.

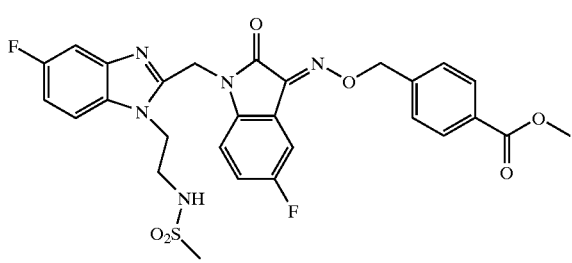
132

Compound 132 was prepared using the same procedure as compound 108 with compounds 118d and 132a:

¹H NMR (DMSO-d₆) δ2.83 (s, 3H), 3.41 (q, J=5.9 Hz, 2H), 3.86 (s, 3H), 4.46 (t, J=5.8 Hz, 2H), 5.33 (s, 2H), 5.64 (s, 2H), 7.13–7.19 (m, 2H), 7.33 (dt, J=2.7, 9.1 Hz, 1H), 7.34–7.44 (m, 2H), 7.64 (d, J=8.2 Hz, 3H), 7.80 (dd, J=2.7, 8.1 Hz, 1H), 8.02 (d, J=8.3 Hz, 2H).

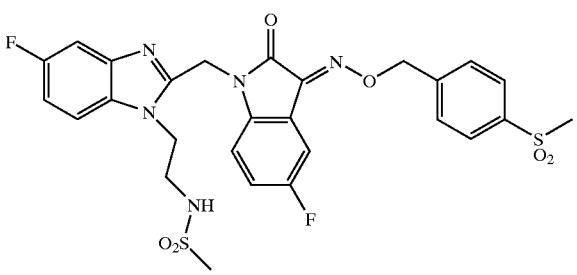
133

Compound 133 was prepared using the same procedure as compound 108 with compounds 121b and 132a:

¹H NMR (DMSO-d₆) δ2.86 (s, 3H), 3.24 (s, 3H), 3.39–3.43 (m, 2H), 4.48 (t, J=5.7 Hz, 2H), 5.36 (s, 2H), 5.67 (s, 2H), 7.17–7.20 (m, 2H), 7.34 (dt, J=2.5, 9.1 Hz, 1H), 7.45–7.39 (m, 2H), 7.68 (dd, J=4.8, 9.0 Hz, 1H), 7.76 (d, J=8.4 Hz, 2H), 7.85 (dd, J=2.7, 8.1 Hz, 1H), 7.99 (d, J=8.4 Hz, 2H).

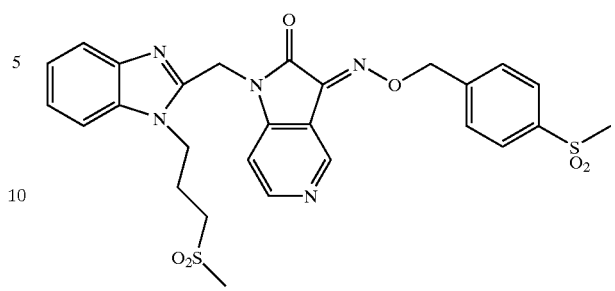
133a

To a solution of 1H-pyrrolo[3,2-c]pyridine-2,3-dione (0.45 g, 3.1 mmol) [prepared as described in Rivalle, *J. Het. Chem.*, 1997, 34, 491.] in MeOH (20 ml) was added p-toluenesulfonic acid (0.6 g, 3.1 mmol) and O-(4-methanesulfonyl-benzyl)-hydroxylamine (0.62 g, 3.1 mmol). The mixture was stirred areflux for 12 h then cooled and filtered. The solid was the desired 1H-pyrrolo[3,2-c]pyridine-2,3-dione 3-[O-(4-methanesulfonyl-benzyl)-oxime which was used without further purification as described for the preparation of 134 using 10d and the compound above with BTPP as base to give 133a.

¹HNMR (DMSO) δ: 2.20–2.23 (m, 2H), 3.00 (s, 3H), 3.25–3.30 (m, 2H), 4.45–4.48 (m, 2H), 5.33 (s, 2H), 5.70 (s, 2H), 7.17 (t, J=7.5 Hz, 1H), 7.26 (t, J=7.7 Hz, 1H), 7.32 (d, J=5.25 Hz, 1H), 7.54 (d, J=8.0 Hz, 1H), 7.63 (d, J=8.1 Hz, 1H), 7.76 (d, J=8.3 Hz, 2H), 7.98 (d, 8.3 Hz, 2H), 8.56 (d, J=5.4 Hz, 1H), 9.02 (s, 1H);

MS m/e 581 (MH⁺).

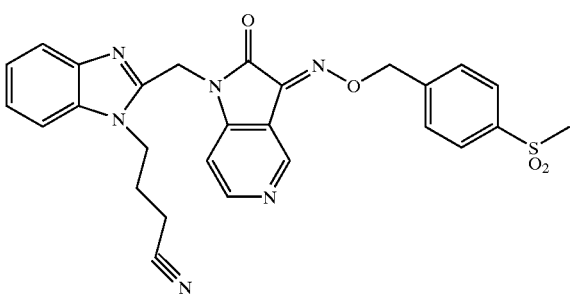
133b

Compound 133b was prepared as described for 133a using compound 25b and BTPP as base.

¹HNMR (DMSO) δ: 2.10–2.17 (m, 2H), 2.60–2.65 (m, 2H), 3.23 (s, 3H), 4.35–4.42 (m, 2H), 5.32 (s, 2H), 5.70 (s, 2H), 7.16 (t, J=7.3 Hz, 1H), 7.29 (t, J=7.3 Hz, 1H), 7.31 (d, J=6.5 Hz, 1H), 7.55 (d, J=8.1 Hz, 1H), 7.62 (d, J=8.1 Hz, 1H), 7.77 (d, J=8.3 Hz, 2H), 7.98 (d, J=8.3 Hz, 2H), 8.56 (d, J=6.5 Hz, 1H), 9.03 (s, 1H);

MS m/e 528 (MH⁺).

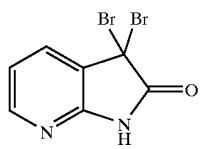
134a 3,3-Dibromo 7-aza oxindole 134a was prepared using a procedure described by Marfat, etc (*Tetrahedron Lett.*, 1987, 28, 4027–4031) or using the procedure below.

To a solution of 7-azaindole (2.0 g, 0.016 mol) in tert. BuOH (120 mL) was added PyBr₃ in portions. The resulting mixture was stirred at room temperature for 15 hours. The solvent was removed in vacuo and the residue was suspended in water (250 mL). The aqueous phase was extracted with ethyl acetate (2×150 mL) and the combined organic fractions were washed with water (2×100 mL) and brine (50 mL). The organic phase was dried (MgSO₄) and evaporated. The residue was triturated in methylene chloride and filtered to afford 3.72 g of compound 134a (80%) as a white-brown solid:

¹H NMR (CDCl₃) δ8.25 (dd, J=1.4, 5.3 Hz, 1H), 7.88 (dd, J=1.4, 7.6 Hz, 1H), 7.16 (dd, J=5.3, 7.6 Hz, 1H);

MS m/e 293 (MH⁺).

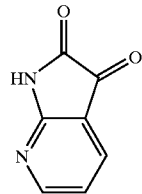

134b

Compound 134b was prepared from the dibromide above according to the procedure described by J. Lloyd et al. (*Bioorganic and Medicinal Chemistry Letters*, 1994, 4, 195–200).

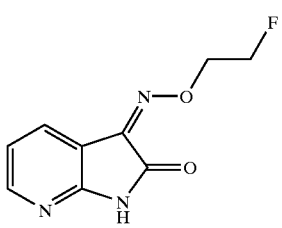

134c

A solution of compound 134b (300 mg, 1.03 mmol) in DMSO (25 mL) was heated at 95° C. under house vacuum for 6.5 hours. The solution containing the corresponding 7-aza isatin was cooled to room temperature, followed by the addition O-(2-Fluoro-ethyl)-hydroxylamine hydrochloride(prepared as described by Ishikawa et al *J. Antibiot.*, 2000, 53, 1071) (131 mg, 1.13 mmol). After stirring for 1 hour at room temperature the mixture was quenched with water and extracted with ethyl acetate (6×25 mL). The combined organic phases were washed with brine and dried over MgSO₄. The solvent was removed in vacuo and the residue purified by flash column chromatography (gradient, 2% MeOH in methylene chloride to 3%) to give compound 134c (200 mg, 93%) as an orange solid that was further purified by trituration from diethyl ether-methylene chloride (1:1).

¹H NMR (DMSO) δ11.5 (s, 1H), 4.57–4.84 (m, 4H), 7.08 (m, 1H), 8.10 (d, J=7.0 Hz, 1H), 8.24 (d, J=4.1 Hz, 1H);

MS m/e 210 (MH⁺).

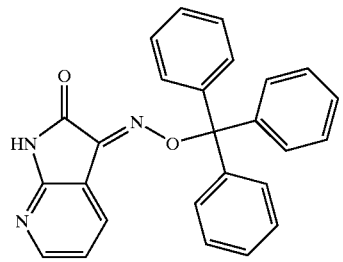

134d

Compound 134b (0.972 g, 6.56 mmol) was combined with o-tritylhydroxylamine (1.90 g, 6.56 mmol) in a mixture of EtOH (20 mL) and water (5 mL). The resulting mixture was briefly heated to boiling with a heat gun and then allowed to cool to room temperature. The suspension was chilled in an ice bath and filtered to isolate the crude pink solid which was rinsed with a mixture of cold 4:1 ethanol-:water. The solid was dissolved with heating in chloroform and the resulting warm solution was passed through a plug of silica gel to remove the pink contaminant. Concentration in vacuo afforded 1.67 g (63% yield) of compound 134d as a yellow powder:

¹H NMR (DMSO-d₆) δ7.15 (dd, J=7.4 Hz, 5.3 Hz, 1H), 7.27–7.28 (m, 6H), 7.34–7.42 (m, 9H), 8.24 (dd, J=7.5 Hz, 1.4 Hz, 1H), 8.27 (dd, J=5.3 Hz, 1.5 Hz), 11.47 (s, 1H);

MS m/e 428 (M+Na⁺), 833 (2M+Na⁺).

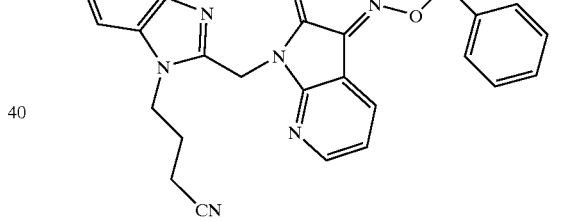

134

Compound 134d (0.75 g, 1.85 mmol) was combined with cesium carbonate (1.81 g, 5.55 mmol) in DMF (20 mL), and the suspension was stirred at room temperature for 10 minutes. Compound 25b (0.50 g, 1.85 mmol) was added. The orange mixture was stirred at room temperature for 4.3 hours and the color of the reaction mixture became olive green all at once. The reaction mixture was diluted with ethyl acetate (100 mL) and water (100 mL). The phases were separated, and the organic layer was washed with water (2×50 mL) and brine (50 mL). The deep olive green mixture was dried over anhydrous MgSO₄ and it slowly became orange in color. The mixture was filtered and the filtrate concentrated in vacuo. The resulting crude solid was recrystallized from EtOAc to give 0.98 g (88% yield) of compound 134 as a yellow powder:

¹H NMR (DMSO-d₆) δ2.13–2.16 (m, 2H), 2.63 (t, J=7.4 Hz, 2H), 4.42 (t, J=7.4 Hz, 2H), 5.24 (s, 2H), 7.13–7.16 (m, 1H), 7.22–7.26 (m, 2H), 7.31–7.32 (m, 6H), 7.36–7.39 (m, 3H), 7.41–7.44 (m, 6H), 7.50 (d, J=8.0 Hz, 1H), 7.59 (d, J=8.1 Hz, 1H), 8.28 (dd, J=1.6, 5.4 Hz, 1H), 8.34 (dd, J=1.6, 7.5 Hz, 1H);

MS m/e 603 (MH⁺).

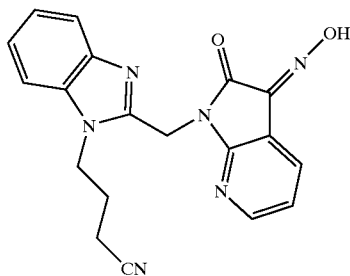

135

Compound 134 (0.50 g, 0.83 mmol) and p-toluenesulfonic acid monohydrate (0.141 g, 0.75 mmol) were combined in anhydrous $CH_3CN$ (8 mL) in a sealed tube and the mixture was heated to 100° C. for 1 hour. Upon cooling, the product came out of solution as spherical crystals. The crystals were filtered from the mixture and rinsed with cold $CH_3CN$ to give 0.39 g (86% yield) of compound 135 as a mono-p-toluenesulfonic acid salt:

$^1$H NMR (DMSO-$d_6$) δ2.26 (t, J=7.6 Hz, 2H), 2.29 (s, 3H), 2.72 (t, J=7.5 Hz, 2H), 4.67 (t, J=7.4 Hz, 2H), 5.60 (s, 2H), 7.11 (d, J=8.1 Hz, 2H), 7.19 (dd, J=5.4, 7.4 Hz, 1H), 7.47 (d, J=8.3 Hz, 2H), 7.56 (t, J=7.7 Hz, 1H), 7.62 (t, J=7.7 Hz, 1H), 7.73 (d, J=8.0 Hz, 1H), 8.04 (d, J=8.3 Hz, 1H), 8.22 (dd, J=1.6, 5.3 Hz, 1H), 8.30 (dd, J=1.6, 7.5 Hz, 1H), 13.99 (s, 1H);

MS m/e 361 (MH$^+$).

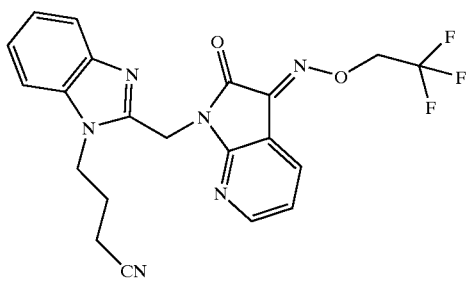

136

Compound 135 (68 mg, 0.12 mmol), 2,2,2-trifluoroethyl p-toluenesulfonate (0.035 g, 0.135 mmol) and BEMP on polystyrene (Fluka, 0.17 g, 0.37 mmol) were combined in anhydrous $CH_3CN$ (3 mL) and the mixture was heated to 70° C. for 48 hours. Solids were removed from the mixture by filtration and rinsed with methanol. The filtrate was concentrated in vacuo, and the crude product was purified by preparative HPLC (gradient, 10% MeOH in $H_2O$ with 0.1% TFA to 90% MeOH in $H_2O$ with 0.1% TFA) to give 25 mg (36% yield) of a trifluoroacetic acid salt of compound 136 as a yellow glassy solid:

$^1$H NMR (DMSO-$d_6$) δ2.18–2.24 (m, 2H), 2.68 (t, J=7.4 Hz, 2H), 4.53 (t, J=7.4 Hz, 2H), 5.24 (q, J=8.9 Hz, 2H), 5.42 (s, 2H), 7.23 (dd, J=5.4, 7.5 Hz, 1H), 7.33 (t, J=7.5 Hz, 1H), 7.41 (t, J=7.4 Hz, 1H), 7.62 (d, J=8.0 Hz, 1H), 7.79 (d, J=8.0 Hz, 1H), 8.19 (dd, J=1.5, 7.5 Hz, 1H), 8.30 (dd, J=1.5, 5.3 Hz, 1H);

MS m/e 443 (MH$^+$).

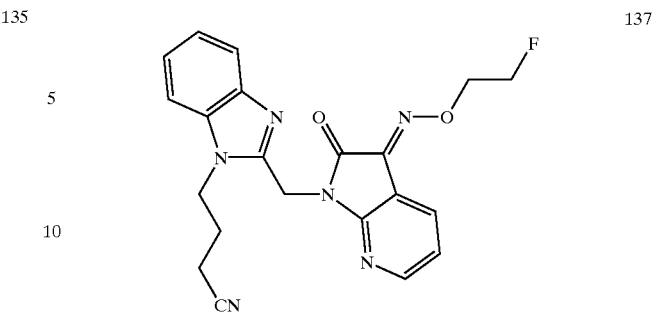

137

Compound 137 was prepared using the same procedure as compound 136. Excess electrophile was scavenged by the addition of PS-thiophenol resin (Argonaut, 100 mg), which was stirred with the reaction mixture for 4 hours. Purification by preparative HPLC (gradient, 10% MeOH in $H_2O$ with 0.1% TFA to 90% MeOH in $H_2O$ with 0.1% TFA) gave 15 mg (23% yield) of a trifluoroacetic acid salt of compound 137 as a red glassy solid:

$^1$H NMR (DMSO-$d_6$) δ2.18–2.24 (m, 2H), 2.68 (t, J=7.4 Hz, 2H), 4.53 (t, J=7.4 Hz, 2H), 4.78–4.80 (m, 2H), 4.81 (dt, J=3.7, 81.8 Hz, 2H), 5.42 (s, 2H), 7.20 (dd, J=5.3, 7.4 Hz, 1H), 7.34 (t, J=7.6 Hz, 1H), 7.41 (t, J=7.6 Hz, 1H), 7.60 (d, J=8.1 Hz, 1H), 7.78 (d, J=7.7 Hz, 1H), 8.24–8.27 (m, 2H);

MS m/e 407 (MH$^+$).

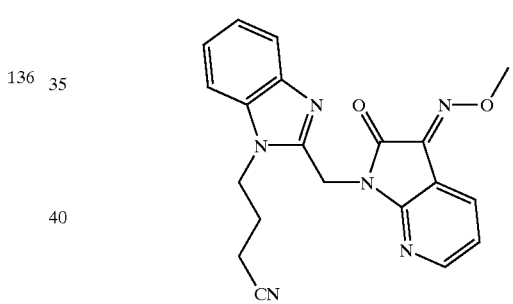

138

A mixture of compound 135 (68 mg, 0.12 mmol), cesium carbonate (0.12 g, 0.37 mmol) and iodomethane (19 mg, 0.14 mmol) in anhydrous $CH_3CN$ (3 mL) was stirred for 18 hours at room temperature. The mixture became a deep olive green color during the course of the reaction. Excess iodomethane was scavenged by the addition of PS-thiophenol resin (Argonaut, 100 mg), which was stirred with the reaction mixture for 2 hours. Solids were removed by filtration and rinsed with MeOH. The filtrate was concentrated in vacuo to a green solid. The crude product was purified by preparative HPLC (gradient, 10% MeOH in $H_2O$ with 0.1% TFA to 90% MeOH in $H_2O$ with 0.1% TFA) to give 12 mg (20% yield) of a trifluoroacetic acid salt of compound 138 as a red glassy solid:

$^1$H NMR (DMSO-$d_6$) δ2.17–2.23 (m, 2H), 2.68 (t, J=7.4 Hz, 2H), 4.29 (s, 3H), 4.53 (t, J=7.4 Hz, 2H), 5.42 (s, 2H), 7.17 (dd, J=5.3, 7.4 Hz, 1H), 7.32 (t, J=7.5 Hz, 1H), 7.40 (t, J=7.5 Hz, 1H), 7.60 (d, J=8.0 Hz, 1H), 7.78 (d, J=8.0 Hz, 1H), 8.21 (dd, J=1.5, 7.4 Hz, 1H), 8.25 (dd, J=1.5, 5.3 Hz, 1H);

MS m/e 375 (MH$^+$).

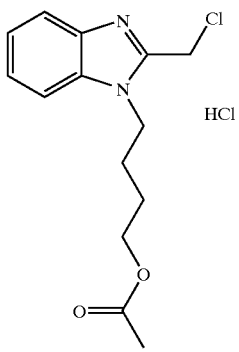

139a

Compound 139a was prepared using the same procedure as compound 25b with 4-bromobutyl acetate:

$^1$H NMR (CDCl$_3$) δ1.80–1.86 (m, 2H), 2.03 (s, 3H), 2.06–2.12 (m, 2H), 4.14 (t, J=6.1 Hz, 2H), 4.55 (t, J=8.1 Hz, 2H), 5.42 (s, 2H), 7.48 (t, J=7.3 Hz, 1H), 7.55 (t, J=7.3 Hz, 1H), 7.64 (d, J=8.5 Hz, 1H), 7.78 (d, J=8.2 Hz, 1H);

MS m/e 281 (MH$^+$).

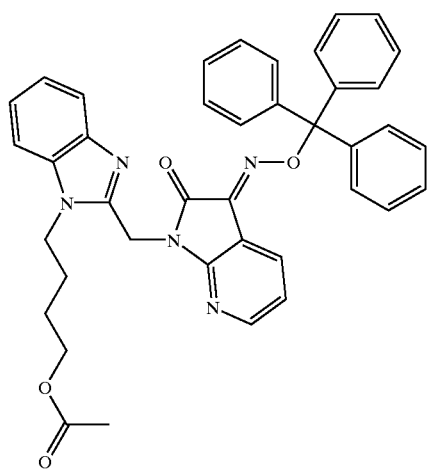

139

A mixture of compound 134b (0.75 g, 1.85 mmol) and cesium carbonate (1.81 g, 5.55 mmol) in DMF (20 mL) was stirred at room temperature for 10 minutes. After addition of compound 139a (0.59 g, 1.85 mmol), the orange mixture was stirred at room temperature for 2.5 hours and the reaction mixture became olive green in color. The reaction mixture was diluted with EtOAc (100 mL) and water (100 mL). The phases were separated and the organic layer was washed with water (2×50 mL) and brine (50 mL). The deep olive green organic layer was dried over anhydrous MgSO$_4$ and it slowly became orange in color. The mixture was filtered and the filtrate concentrated in vacuo. The residue was purified by flash chromatography (CH$_2$Cl$_2$:CH$_3$OH, 50:1) and then recrystallized from EtOAc to give 0.73 g (61% yield) of compound 139 as a yellow powder:

$^1$H NMR (DMSO-d$_6$) δ1.63–1.67 (m, 2H), 1.82–1.85 (m, 2H), 4.03 (t, J=6.5 Hz, 2H), 4.38 (t, J=7.3 Hz, 2H), 5.22 (s, 2H), 7.11–7.14 (m, 1H), 7.20–7.26 (m, 2H), 7.31–7.32 (m, 6H), 7.36–7.39 (m, 3H), 7.41–7.44 (m, 6H), 7.49 (d, J=8.0 Hz, 1H), 7.58 (d, J=8.1 Hz, 1H), 8.28 (dd, J=1.6, 5.4 Hz, 1H), 8.35 (dd, J=1.6, 7.5 Hz, 1H);

MS m/e 650 (MH$^+$).

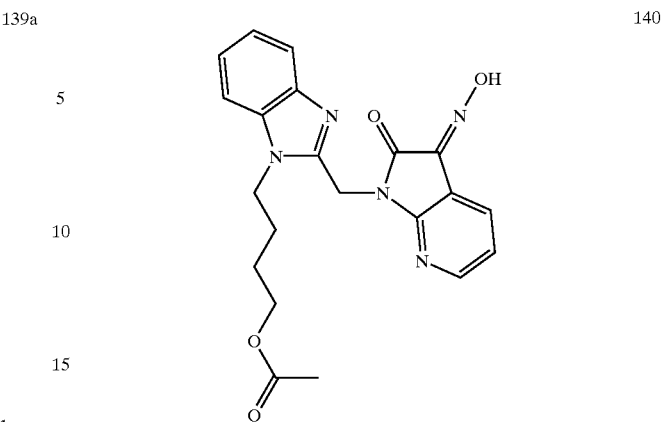

140

Compound 140 was prepared using the same procedure as compound 135. Purification by flash chromatography (gradient, CH$_2$Cl$_2$:CH$_3$OH, 30:1 to 10:1) gave 0.15 g (70% yield) of compound 140 as a yellow glassy solid:

$^1$H NMR (DMSO-d$_6$) δ1.66–1.69 (m, 2H), 1.84–1.87 (m, 2H), 1.99 (s, 3H), 4.05 (t, J=6.5 Hz, 2H), 4.40 (t, J=7.4 Hz, 2H), 5.27 (s, 2H), 7.12–7.15 (m, 2H), 7.22 (t, J=8.1 Hz, 1H), 7.48 (d, J=8.0 Hz, 1H), 7.59 (d, J=8.1 Hz, 1H), 8.21 (dd, J=1.6, 5.3 Hz, 1H), 8.27 (dd, J=1.6, 7.4 Hz, 1H), 13.89 (s, 1H);

MS m/e 408 (MH$^+$).

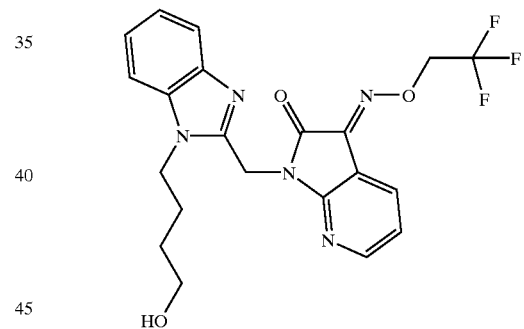

141

A mixture of compound 140 (0.05 g, 0.12 mmol), 2,2,2-trifluoroethyl p-toluenesulfonate (0.035 g, 0.14 mmol) and BEMP on polystyrene (Fluka, 0.17 g, 0.37 mmol) in anhydrous CH$_3$CN (3 mL) was heated to 70° C. for 18 hours. MeOH (1 mL) was added to remove the acetate group and the mixture was heated to 70° C. for 4 hours. Solids were removed by filtration and rinsed with methanol. The filtrate was concentrated in vacuo, and the crude product was purified by preparative HPLC (gradient, 10% MeOH in H$_2$O with 0.1% TFA to 90% MeOH in H$_2$O with 0.1% TFA) to give 0.025 g (37% yield) of a trifluoroacetic acid salt of compound 141 as an off-white powder:

$^1$H NMR (DMSO-d$_6$) δ1.50–156 (m, 2H), 1.85–1.91 (m, 2H), 3.42–3.49(m, 2H), 4.50 (t, J=7.4 Hz, 2H), 5.24 (q, J=9.0 Hz, 2H), 5.43 (s, 2H), 7.23–7.27 (m, 1H), 7.36–7.38 (m, 1H), 7.42–7.45 (m, 1H), 7.63 (d, J=8.1 Hz, 1H), 7.81 (d, J=7.9 Hz, 1H), 8.17–8.21 (m, 1H), 8.28–8.32 (m, 1H);

MS m/e 448 (MH$^+$).

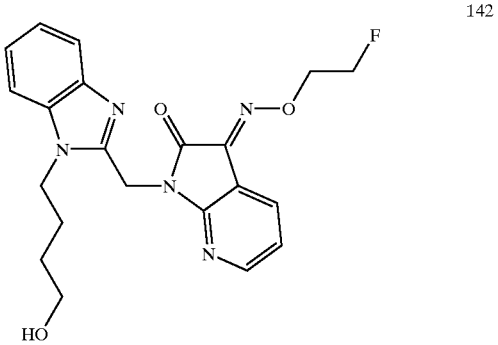

142

Compound 142 was prepared using the same procedure as compound 141. Excess electrophile was scavenged by the addition of PS-thiophenol resin (Argonaut, 100 mg), which was stirred with the reaction mixture for 4 hours. Purification by preparative HPLC (gradient, 10% MeOH in $H_2O$ with 0.1% TFA to 90% MeOH in $H_2O$ with 0.1% TFA) gave 0.012 g (19% yield) of a trifluoroacetic acid salt of compound 142 as an off-white solid:

$^1$HNMR (DMSO-$d_6$) δ1.51–1.56 (m, 2H), 1.85–1.91 (m, 2H), 3.45 (t, J=6.3 Hz, 2H), 4.50 (t, J=7.4 Hz, 2H), 4.74–4.83 (m, 2H), 4.81 (dt, J=2.6, 83.1 Hz, 2H), 7.20–7.22 (m, 1H), 7.36–7.37 (m, 1H), 7.41–7.44 (m, 1H), 7.63 (d, J=8.0 Hz, 1H), 7.81 (d, J=7.9 Hz, 1H), 8.24–8.27 (m, 2H);

MS m/e 412 (MH$^+$).

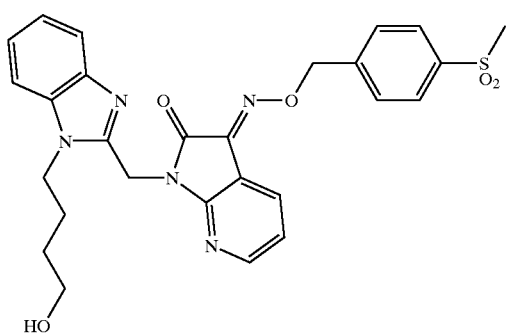

143

Compound 143 was prepared by the same procedure as described for the preparation of compound 141. Excess electrophile was scavenged by the addition of PS-thiophenol resin (Argonaut, 100 mg), which was stirred with the reaction mixture for 4 hours. Purification by preparative HPLC (gradient, 10% MeOH in $H_2O$ with 0.1% TFA to 90% MeOH in $H_2O$ with 0.1% TFA) gave a mixture of compound 143 plus the trifluoroacetate ester of compound 143. This mixture was dissolved in methanol and the resulting solution was treated with MP-carbonate resin (Argonaut) for 18 hours at room temperature. Filtration to remove the resin followed by concentration of the filtrate in vacuo gave 0.022 g (34% yield) of compound 143 as a yellow glassy solid:

$^1$H NMR (DMSO-$d_6$) δ1.48–1.51 (m, 2H), 1.81–1.84 (m, 2H), 3.24 (s, 3H), 3.43–3.45 (m, 2H), 4.36 (t, J=7.3 Hz, 2H), 4.50 (t, J=5.1 Hz, 1H), 5.25 (s, 2H), 5.68 (s, 2H), 7.12 (t, J=8.0 Hz, 1H), 7.17–7.22 (m, 2H), 7.47 (d, J=8.0 Hz, 1H), 7.56 (d, J=8.1 Hz, 1H), 7.76 (d, J=8.3 Hz, 2H), 7.99 (d, J=8.3 Hz, 2H), 8.26–8.28 (m, 2H);

MS m/e 534 (MH$^+$).

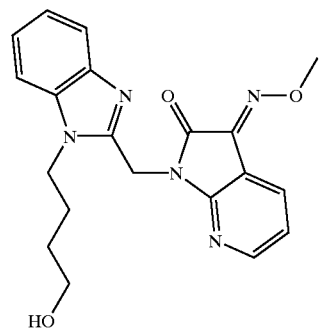

144

A mixture of compound 140 (0.050 g, 0.12 mmol) with cesium carbonate (0.12 g, 0.37 mmol) and iodomethane (0.019 g, 0.14 mmol) in anhydrous $CH_3CN$ (3 mL) was stirred for 18 hours at room temperature. The mixture became a deep olive green color during the course of the reaction. MeOH (1 mL) was added to remove the acetate group, and excess iodomethane was scavenged by the addition of PS-thiophenol resin (Argonaut, 100 mg) which was stirred with the reaction mixture for 2 hours. Solids were removed by filtration and rinsed with MeOH and the filtrate was concentrated in vacuo to a green solid. Purification of the crude product by preparative HPLC (gradient, 10% MeOH in $H_2O$ with 0.1% TFA to 90% MeOH in $H_2O$ with 0.1% TFA) gave a mixture of compound 144 plus the trifluoro acetate ester of compound 144. This mixture was dissolved in MeOH and the resulting solution was treated with MP-carbonate resin (Argonaut) for 18 hours at room temperature. Filtration to remove the resin followed by concentration of the filtrate in vacuo gave 0.007 g (16% yield) of compound 144 as a yellow glassy solid:

$^1$H NMR (DMSO-$d_6$) δ1.49–1.52 (m, 2H), 1.81–1.84 (m, 2H), 3.43–3.46 (m, 2H), 4.28 (s, 3H), 4.37 (t, J=7.4 Hz, 2H), 4.51 (t, J=5.1 Hz, 1H), 5.27 (s, 2H), 7.11–7.17 (m, 2H), 7.20–7.23 (m, 1H), 7.47 (d, J=8.0 Hz, 1H), 7.57 (d, J=8.0 Hz, 1H), 8.20 (dd, J=1.6, 7.4 Hz, 1H), 8.25 (dd, J=1.6, 5.3 Hz, 1H);

MS m/e 380 (MH$^+$).

O-(2-Fluoro-ethyl)-hydroxylamine was prepared using a procedure described by Ishikawa, et al J. Antibiot., 2000, 53, 1071.

1H-Pyrrolo[2,3-b]pyridine-2,3-dione 3-[O-(2-fluoro-ethyl)-oxime]

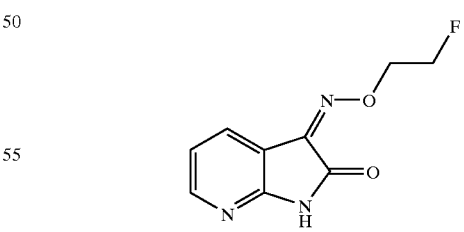

A solution of compound 134a (300 mg, 1.03 mmol) in DMSO (25 mL) was heated at 95° C. at 15 torr for 6.5 hours, The solution containing the corresponding 7-aza isatin was cooled to room temperature, followed by the addition O-(2-Fluoro-ethyl)-hydroxylamine hydrochloride (131 mg, 1.13 mmol). After stirring for 1 hour at room temperature the mixture was quenched with water and extracted with ethyl acetate (6×25 mL). The combined organic phases were washed with brine and dried over MgSO₄. The solvent was removed in vacuo and the residue purified by flash column chromatography (gradient, 2% MeOH in methylene chloride to 3%) to give 1H-Pyrrolo[2,3-b]pyridine-2,3-dione 3-[O-(2-fluoro-ethyl)-oxime] (200 mg, 93%) as an orange solid that was further purified by trituration from diethyl ether-methylene chloride (1:1).

¹H NMR (CDCl₃) δ do 3.48 (s, 3H), 4.97 (s, 2H), 7.40–7.50 (m, 2H), 7.75–7.85 (m, 2H);

MS m/e 209 (MH⁺).

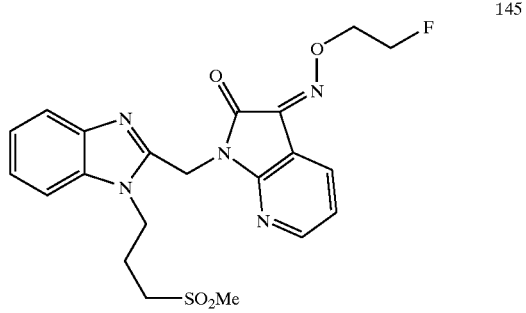

145

Compound 145 was prepared according the procedure for the preparation of compound 134, starting from 1H-pyrrolo[2,3-b]pyridine-2,3-dione 3-[O-(2-fluoro-ethyl)-oxime] (18.9 mg, 0.0904 mmol) and 10d (29.2 mg, 0.0904 mmol). Purification was accomplished by trituration from methylene chloride-methanol) to give compound 145 (18 mg, 43% yield) as a yellow solid.

¹H NMR (DMSO) δ8.26 (dd, J=1.6, 5.3 Hz, 1H), 8.23 (dd, J=1.6, 7.5 Hz, 1H), 7.63 (d, J=8.1 Hz, 1H), 7.50 (d, J=8.0 Hz, 1H), 7.25 (t, J=7.8 Hz, 1H), 7.18 (dd, J=7.5, 5.3 Hz, 1H), 7.14 (t, J=7.9 Hz, 1H), 5.30 (s, 2H), 4.72–4.90 (m, 4H), 4.52 (t, J=7.4 Hz, 2H), 3.30 (t, J=7.5 Hz, 2H), 3.02 (s, 3H), 2.28 (m, 2H);

MS m/e 460 (MH⁺).

(3-tert-Butoxycarbonylamino-pyridin-4-yl)-oxo-acetic Acid Ethyl Ester

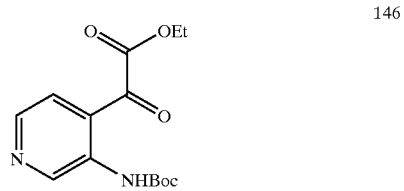

146

(3-tert-Butoxycarbonylamino-pyridin-4-yl)-oxo-acetic acid ethyl ester was prepared according to a procedure described by Estel, etc (*J. Heterocycl. Chem.*, 1989, 26, 105-): To a solution of pyridin-3-yl-carbamic acid tert-butyl ester (8.50 g, 43.8 mmol) and TMEDA (16.5 mL, 109 mmol) in THF (200 mL) at −78° C. was cannulated tert.-BuLi (64.1 mL, 1.7 M in pentane) over 30 min under nitrogen. The mixture was then stirred for 2 hours between −10° C. and −20° C. After cooling to −60° C. diethyl oxalate (17.8 mL, 131 mmol) was added and the mixture allowed to warm to 0° C. After 3 hours the mixture was poured onto ice/1M HCl (120 mL) and extracted with ethyl acetate (3×150 mL). The combined organic extracts were washed with water (100 mL), brine (75 mL), dried over MgSO₄ and concentrated. The residue was purified by flash column chromatography (gradient, hexane/ethyl acetate 5:2, 2:1), to give 3.04 g (24% yield) of compound 146 as a yellow oil.

¹H NMR (DMSO) δ9.80 (s, 1H), 9.70 (br s, 1H), 8.40 (d, J 5.2 Hz, 1H), 7.50 (d, J=5.2 Hz, 1H), 4.44 (q, J=7.2 Hz, 2H), 1.41 (t, J=7.2 Hz, 3H);

MS m/e 327 (M⁺–MeOH⁺).

1H-Pyrrolo[2,3-c]pyridine-2,3-dione

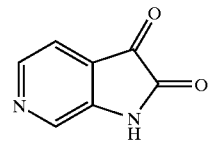

147

Compound 146 (1.62 g, 5.50 mmol) was heated for 7 min at 180–190° C. in a kugelrohr oven at 15 torr. The remaining black solid 147 (823 mg) was used without further purification.

¹H NMR (DMSO) δ11.2 (s, 1H), 8.45 (br s, 1H), 8.34 (br s, 1H), 7.41 (br s, 1H);

MS m/e 180 (M⁺–MeOH⁺).

1H-Pyrrolo [2,3-c]pyridine-2,3-dione 3-[O-(2-fluoro-ethyl)-oxime]

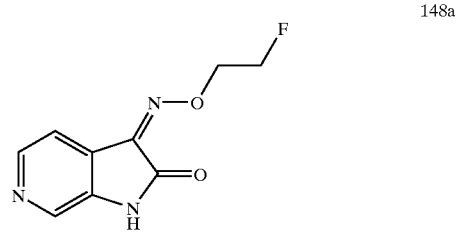

148a

1H-Pyrrolo[2,3-c]pyridine-2,3-dione (208 mg, 1.40 mmol) was dissolved in DMSO (5 mL) and treated with O-(2-Fluoro-ethyl)-hydroxylamine (243 mg, 2.11 mmol). After stirring for 1 hour at room temperature, water (30 mL) was added and the mixture extracted with ethyl acetate (6×20 mL). The combined organic extracts were washed with brine, dried over MgSO₄ and concentrated. The residue was triturated from diethyl ether to give 130 mg (44% yield over 2 steps) of 148a as a yellow solid.

¹H NMR (DMSO) δ11.0 (s, 1H), 8.40 (d, J=4.8 Hz, 1H), 8.28 (s, 1H), 7.73 (d, J=4.7 Hz, 1H), 4.69–4.87 (m, 4H);

MS m/e 210 (MH⁺).

1H-Pyrrolo[2,3-c]pyridine-2,3-dione 3-(O-pyridin-2-ylmethyl-oxime)

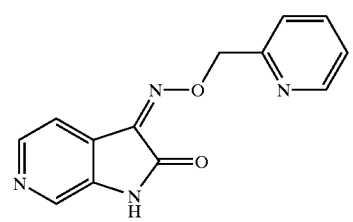

148b

1H-Pyrrolo[2,3-c]pyridine-2,3-dione (110 mg, 0.743 mmol) was dissolved in DMSO (4 mL) and treated with O-pyridin-2-ylmethyl-hydroxylamine (176 mg, 0.892 mmol). After stirring for 1 hour at room temperature, DIPEA (129 μL, 0.743 mmol) was added and the mixture heated to 60° C. and stirred for 2 hours at the same temperature. The mixture was cooled to room temperature, water (20 mL) was added and the mixture extracted with ethyl acetate (7×15 mL). The combined organic extracts were washed with brine, dried over MgSO$_4$ and concentrated. The residue was purified by flash column chromatography (6% methanol in methylene chloride), to give 45 mg (24% yield over 2 steps) of 148b as a yellow solid.

$^1$H NMR (CDCl$_3$) δ9.98 (s, 1H), 8.63 (d, J=4.6 Hz, 1H), 8.42 (d, J=4.8 Hz, 1H), 8.38 (s, 1H), 7.77 (d, J=4.6 Hz, 1H), 7.73 (t, J=7.7 Hz, 1H), 7.43 (d, J=7.8 Hz, 1H), 7.28 (dd, J=4.8, 7.4 Hz, 1H);

MS m/e 255 (MH$^+$);

1H-Pyrrolo[2,3-c]pyridine-2,3-dione 3-(O-allyl-oxime)

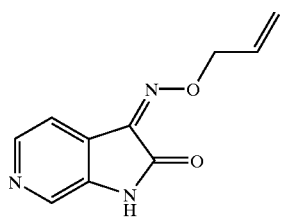

148c

Compound 147 (121 mg, 0.817 mmol) was dissolved in a mixture of MeCN (4 mL) and water (2 mL), and treated with O-Allyl-hydroxylamine (99 mg, 0.90 mmol). After stirring for 75 min at room temperature, another 50 mg of the O-Allyl-hydroxylamine was added. After 30 min. MeCN was stripped off and the residue extracted with ethyl acetate (7×15 mL). The combined organic extracts were washed with brine, dried over MgSO$_4$ and concentrated. The resulting yellow solid 148c (80 mg, 48% over two steps) was sufficiently pure for the next step.

$^1$H NMR (DMSO) δ11.0 (s, 1H), 8.39 (d, J=4.8 Hz, 1H), 8.27 (s, 1H), 7.70 (d, J 4.8 Hz, 1H), 6.10 (m, 1H), 5.43 (d, J=17.3 Hz, 1H), 5.34 (d, J=10.5 Hz, 1H), 5.00 (d, J=5.8 Hz, 1H).

1H-Pyrrolo[2,3-c]pyridine-2,3-dione 3-(O-methyl-oxime)

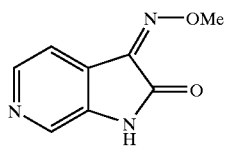

148d

Compound 147 (154 mg, 1.04 mmol) was dissolved in a mixture of MeCN (4 mL) and water (2 mL), and treated with O-methyl-hydroxylamine (96 mg, 1.1 mmol). After stirring for 75 min at room temperature, another 48 mg of the O-methyl-hydroxylamine was added. After 30 min. the solvents were evaporated and the residue purified by flash column chromatography (gradient, 5, 6, 7% methanol in methylene chloride), to give 52 mg (28% yield over 2 steps) 148d as a yellow solid.

$^1$H NMR (DMSO) δ11.0 (s, 3H), 8.37 (d, J=4.7 Hz, 1H), 8.27 (s, 1H), 7.70 (d, J=4.8 Hz, 1H), 4.26 (s, 3H);

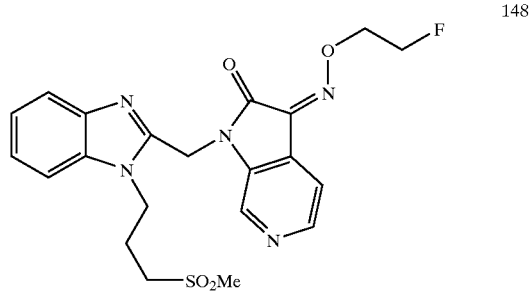

148

Compound 148 was prepared according the procedure for the preparation of compound 134, starting from isatin 148a (19.9 mg, 0.0952 mmol) and 10d (30.8 mg, 0.0952 mmol). Purification was accomplished by preparative TLC (eluens 5% methanol in methylene chloride) to give compound 148 (25 mg, 57% yield) as a yellow solid.

$^1$H NMR (DMSO) δ8.26 (dd, J=1.6, 5.3 Hz, 1H), 8.23 (dd, J=1.6, 7.5 Hz, 1H), 7.63 (d, J=8.1 Hz, 1H), 7.50 (d, J=8.0 Hz, 1H), 7.25 (t, J=7.8 Hz, 1H), 7.18 (dd, J=7.5, 5.3 Hz, 1H), 7.14 (t, J=7.9 Hz, 1H), 5.30 (s, 2H), 4.72–4.90 (m, 4 H), 4.52 (t, J=7.4 Hz, 2H), 3.30 (t, J=7.5 Hz, 2H), 3.02 (s, 3H), 2.28 (m, 2H);

MS m/e 460 (MH$^+$);

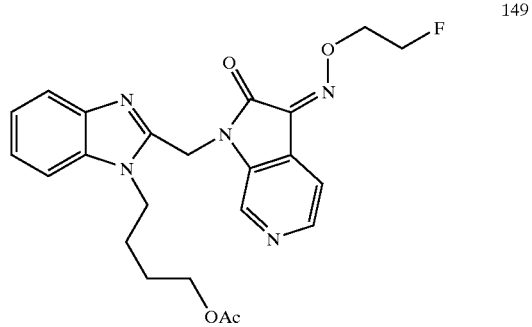

149

Compound 149 was prepared according the procedure for the preparation of compound 134, starting from isatin 148a (28.6 mg, 0.137 mmol) and 139a (43.4 mg, 0.137 mmol). The product 149 was used as it is.

$^1$H NMR (CDCl$_3$) δ8.90 (s, 1H), 8.49 (d, J=4.8 Hz, 1H), 7.76 (m, 2H), 7.30 (m, 2H), 5.30 (s, 2H), 4.75–4.85 (m, 4H), 4.30 (t, J=7.2 Hz, 2H), 4.05 (t, J=6.3 Hz, 2H), 1.98 (s, 3H), 1.76 (m, 4H);

MS m/e 453 (MH$^+$).

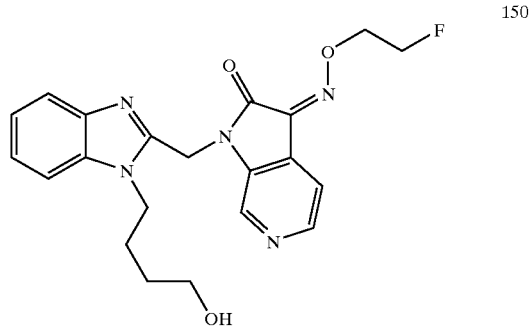

150

Compound 149 (0.137 mmol, assuming quantitative recovery) was dissolved in methanol (3 mL) and 5 drops of thionyl chloride were added. The solution was stirred overnight and the volatiles evaporated. The residue was redissolved in methanol and concentrated. This procedure was repeated three times. Purification was accomplished by preparative TLC (eluant 5% methanol in methylene chloride) to give compound 150 (27 mg, 48% yield over two steps) as a yellow solid.

$^1$H NMR (DMSO) δ8.57 (s, 1H), 8.49 (d, J=4.8 Hz, 1H), 7.83 (d, J=4.8 Hz, 1H), 7.58 (d, J=8.1 Hz, 1H), 7.56 (d, J=8.1 Hz, 1H), 7.24 (t, J=7.4 Hz, 1H), 7.17 (t, J=7.3 Hz, 1H), 5.35 (s, 2H), 4.76–4.90 (m, 4H), 4.48 (t, J=5.2 Hz, 1H), 4.34 (t, J=7.4 Hz, 2H), 3.43 (q, J=6.3 Hz, 2H), 1.77 (m, 2H), 1.49 (m, 2H);

MS m/e 412 (MH$^+$).

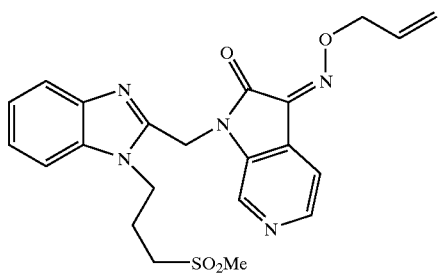

151

Compound 151 was prepared according the procedure for the preparation of compound 134, starting from isatin 148c (84 mg, 0.41 mmol) and 10d (134 mg, 0.41 mmol). Purification was accomplished by flash column chromatography (eluent 5% methanol in methylene chloride), to give 118 mg (63% yield) of compound 151 as a yellow solid.

$^1$H NMR (DMSO) δ8.61 (s, 1H), 8.48 (d, J=4.8 Hz, 1H), 7.80 (d, J=4.8 Hz, 1H), 7.64 (d, J=8.0 Hz, 1H), 7.56 (d, J 8.0 Hz, 1H), 7.28 (t, J 8.0 Hz, 1H), 7.17 (t, J 8.0 Hz, 1H), 6.13 (m, 2H), 5.46 (d, J=17.3 Hz, 1H), 5.36 (d, J=10.5 Hz, 1H), 5.37 (s, 2H), 5.06 (d, J=5.8 Hz, 2H), 4.48 (t, J 7.5 Hz, 2H), 3.26 (t, J=7.6 Hz, 2H), 3.02 (s, 3H), 2.22 (m, 2H);

MS m/e 454 (MH$^+$);

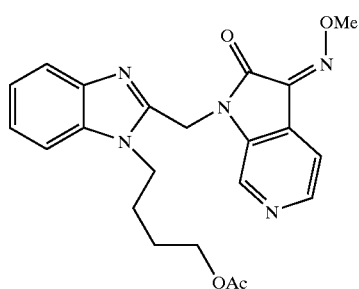

152

Compound 152 was prepared according the procedure for the preparation of compound 134, starting from isatin 148d (14.3 mg, 0.0807 mmol) and 139a (25.6 mg, 0.0807 mmol). The product was used as it is.

MS m/e 422 (MH$^+$).

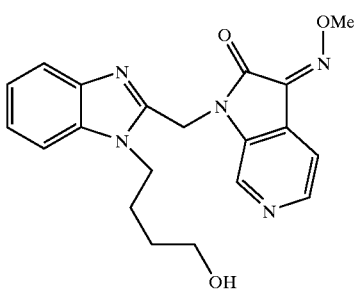

153

Compound 153 (0.0807 mmol, assuming quantitative recovery) was dissolved in methanol (2 mL) and acetyl chloride (58 μL) was added. The solution was stirred for 5 hours and the volatiles evaporated. The residue was redissolved in methanol and concentrated. This procedure was repeated three times. Purification was accomplished by flash column chromatography (eluent 6% methanol in methylene chloride), to give 9 mg (29% yield) of compound 153 as a yellow solid, which was converted into the HCl salt by dissolution in methanol and addition of 4N HCl in dioxane (6 μL), followed by concentration.

$^1$H NMR (CDCl$_3$) δ8.95 (s, 1H), 8.49 (d, J=4.8 Hz, 1H), 7.77 (m, 1H), 7.23 (d, J=4.5 Hz, 1H), 7.33 (m, 3H), 5.35 (s, 2H), 4.39 (s, 3H), 4.33 (m, 2H) 3.69 (t, J=6.1 Hz, 2H), 1.82 (m, 2H), 1.67 (m, 2H);

MS m/e 380 (MH$^+$).

1H-Pyrrolo[2,3-c]pyridine-2,3-dione 3-(O-trityl-oxime)

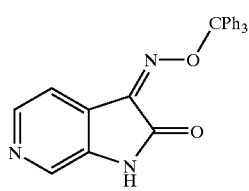

154a

1H-Pyrrolo[2,3-c]pyridine-2,3-dione (298 mg, 2.01 mmol) was dissolved in DMSO (4 mL) and treated with O-Trityl-hydroxylamine (609 mg, 2.21 mmol). After stirring for 20 min. at room temperature, the temperature was raised to 70° C. and 30 min.later to 100° C., and stirring was continued for 2 hours. After cooling to room temperature, water (30 mL) was added and the mixture extracted with ethyl acetate (2×50 mL). The combined organic extracts were washed with water (20 mL), brine (20 mL), dried over MgSO$_4$ and concentrated. Purification was accomplished by flash column chromatography (eluent 5% methanol in methylene chloride), to give 130 mg (13% yield) 154a as a yellow oil.

$^1$H NMR (CDCl$_3$) δ9.57 (br s, 1H), 8.47 (d, J=4.8 Hz, 1H), 8.31 (s, 1H), 7.94 (d, J=4.8 Hz, 1H), 7.32 (m, 15H);

MS m/e 406 (MH$^+$).

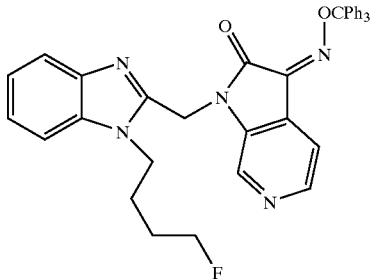

154

Compound 154 was prepared according the procedure for the preparation of compound 134, starting from 154a (121 mg, 0.298 mmol) and 132c (83 mg, 0.298 mmol). The residue after work-up was precipitated from diethyl ether to give 154 (114 mg) as a yellow solid. The rest was purified by flash column chromatography (eluent 3%, 5% methanol in methylene chloride), to give 13 mg of 154 for a combined yield of 127 mg (70%).

$^1$H NMR (CDCl$_3$) δ 8.94 (s, 1H), 8.52 (d, J=4.7 Hz, 1H), 8.93 (d, J=4.7 Hz, 1H), 7.78 (d, J=8.0 Hz, 1H), 7.35 (m, 18H), 5.31 (s, 2H), 4.25–4.28 (m, 4H), 1.69 (m, 4H).

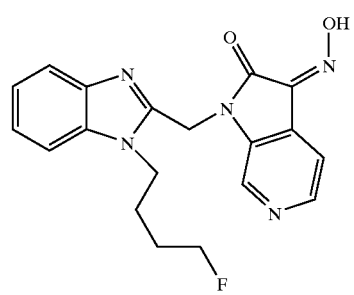

155

To a solution of 154 (127 mg, 0.208 mmol) in acetonitrile (3 mL) and methylene chloride (1 mL) was added p-TsOH.H$_2$O (59 mg, 0.312 mmol). The mixture was heated in a sealed tube at 100° C. for 10 min. The solvents were removed in vacuo and the residue purified by flash column chromatography (eluent 3%, 5%, 8%, 10%, 15% methanol in methylene chloride), to give 58 mg (68%) of 155, that was converted into the HCl salt by dissolving in methanol and addition of excess acetyl chloride. The product was a single configurational isomer in DMSO-d6 (Z-isomer), but was a 5:1 mixture in methanol (CD$_3$OD).

$^1$H NMR (CD$_3$OD) δ 8.97 (s, 1H), 8.76 (d, J=5.7 Hz, 1H), 8.62 (d, J=5.7 Hz, 1H), 8.00 (d, J=8.2 Hz, 1H), 7.75 (d, J=8.2 Hz, 1H), 7.69 (t, J=7.3 Hz, 1H), 7.64 (t, J=7.3 Hz, 1H), 5.86 (s, 2H), 4.71 (t, J=7.9 Hz, 2H), 4.57 (dt, J=5.8, 47 Hz, 2H), 2.18 (m, 2H), 1.94 (m, 2H);

MS m/e 368 (MH$^+$).

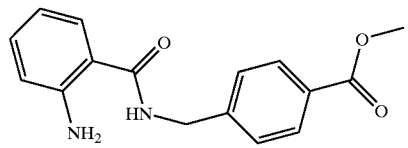

156a

A solution of anthranilic acid (1.66 g, 12.10 mmol), hydroxybenztriazole (1.64 g, 12.10 mmol), and methyl 4-(methylamino)benzoate (2.0 g, 12.10 mmol) in DMF (20 mL) was treated with EDAC (2.32 g, 12.10 mmol) and the mixture was stirred at room temperature for 12 hours. The solvent was removed and the residue was dissolved in EtOAc, washed with 1N HCl, saturated aqueous NaHCO$_3$, dried over MgSO$_4$ and concentrated. The residue was purified by flash chromatography (hexanes:EtOAc=5:1) to give 2.05 g (59% yield) of compound 156a as a white solid:

$^1$H NMR (DMSO-d$_6$) δ 3.82 (s, 3H), 4.49 (d, J=5.9 Hz, 2H), 4.58 (d, J=5.9 Hz, 2H), 6.44–6.59 (m, 3H), 6.70 (d, J=8.2 Hz, 1H), 6.78 (d, J=8.2 Hz, 1H), 7.13–7.22 (m, 2H), 7.44 (d, J=8.2 Hz, 2H), 7.48 (d, J=8.2 Hz, 2H), 7.57 (d, J=6.9 Hz, 2H), 7.88–7.94 (m, 2H), 8.55 (d, J=8.3 Hz, 1H), 8.86 (t, J=5.9 Hz, 1H), 9.46 (t, J=5.9 Hz, 1H);

IR (KBr, cm$^{-1}$) 1706, 1654, 1528;

MS m/e 284 (MH$^+$);

Anal. Calcd for C$_{16}$H$_{16}$N$_2$O$_3$: C, 67.59; H, 5.67; N, 9.85

Found: C, 67.87; H, 5.63; N, 9.87.

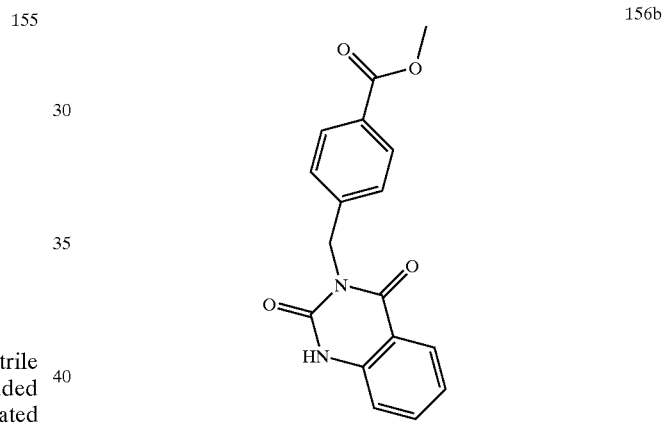

156b

To a mixture of compound 156a (2.0 g, 7.04 mmol) and KHCO$_3$ (1.74 g, 17.30 mmol) in H$_2$O (50 mL) was added methyl chloroformate (1.09 ml, 14.00 mmol) and the mixture was stirred for 12 hours at room temperature. The resulting solid was isolated by filtration to give 2.4 g (99% yield) of the intermediate as a white solid. The solid was dissolved in MeOH (100 mL), treated with sodium methoxide (0.5 M, 1.0 mL) and heated to reflux for 4 hours. The precipitated product was isolated by filtration to give 1.58 g (73% yield) of compound 156b as a white solid:

$^1$H NMR (DMSO-d$_6$) δ 3.83 (s, 3H), 5.16 (s, 2H), 7.23 (t, J=6.9 Hz, 1H), 7.43 (d, J=8.4 Hz, 1H), 7.72 (t, J=7.5 Hz, 1H), 7.69–7.96 (m, 4H);

IR (KBr, cm$^{-1}$) 1718, 1656;

MS m/e 310 (MH$^+$);

Anal. Calcd for C$_{17}$H$_{14}$N$_2$O$_4$: C, 65.80; H, 4.55; N, 9.03

Found: C, 65.77; H, 4.81; N, 8.83.

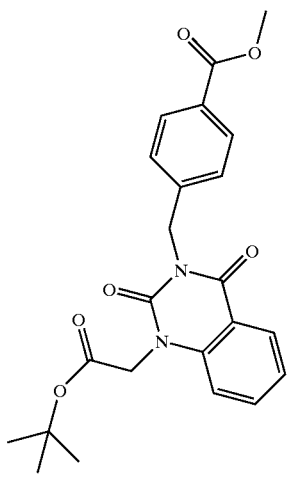

156c

A solution of compound 156b (3.2 g, 10.3 mmol) and K₂CO₃ (2.84 g, 20.3 mmol) in CH₃CN (100 mL) was treated with t-butyl bromoacetate (2.0 g, 10.3 mmol) and stirred at room temperature for 12 hours. The mixture was filtered and the filtrate was concentrated. The residue was purified by flash chromatography (20% EtOAc in hexanes) to give 4.3 g (99% yield) of compound 156c as a clear oil:

¹H NMR (DMSO-d₆) δ1.20 (t, J=7.2 Hz, 3H), 1.41 (s, 9H), 1.15 (q, J=7.2 Hz, 2H), 4.72 (s, 2H), 4.90 (s, 2H), 7.31–7.37 (m, 1H), 7.42 (d, J=8.5 Hz, 3H), 7.78–7.85 (m, 1H), 7.88 (d, J=8.5 Hz, 2H), 8.10 (d, J=6.3 Hz, 1H);

IR (KBr, cm⁻¹) 1746, 1712, 1669;

MS m/e 362 (MH⁺);

Anal. Calcd for $C_{18}H_{22}N_2O_6 \cdot 1.33H_2O$: C, 61.61; H, 5.99; N, 6.25

Found: C, 61.21; H, 5.59; N, 5.91.

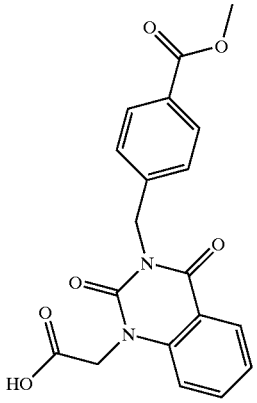

156d

A solution of compound 156c (5.5 g, 14.1 mmol) in TFA (50 mL) was stirred at room temperature for 12 hours. The mixture was concentrated to give 4.3 g (99% yield) of compound 156d as a white solid:

¹H NMR (DMSO-d₆) δ3.82 (s, 3H), 4.88 (s, 2H), 5.21 (s, 2H), 7.33 (t, J=7.8 Hz, 1H), 7.42 (d, J=8.4 Hz, 3H), 7.88 (t, J=7.5 Hz, 1H), 7.92 (d, J=7.5 Hz, 2H), 8.09 (d, J=7.8 Hz, 1H);

IR (KBr, cm⁻¹) 1712, 1664;

MS m/e 368 (MH⁺);

Anal. Calcd for $C_{19}H_{16}N_2O_6 \cdot 0.94H_2O$: C, 59.24; H, 4.68; N, 7.27

Found: C, 59.24; H, 4.45; N, 6.88.

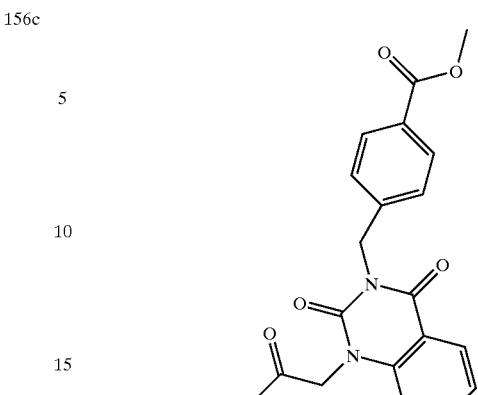

156e

156

A solution of compound 156d (0.5 g, 1.36 mmol) was heated to reflux in thionyl chloride (10 mL) for 30 minutes then cooled and concentrated to give the acid chloride 156e. The compound 98b (0.24 g, 1.36 mmol) was dissolved in CH₂Cl₂ (20 mL), cooled to −78° C. and treated with the acid chloride 156e in CH₂Cl₂ (20 mL). The mixture was warmed to room temperature and stirred for 12 hours. The organic layer was washed with saturated aqueous NaHCO₃, dried, and concentrated. The residue was purified by flash chromatography (CH₂Cl₂: MeOH=20:1) to give 0.42 g (49% yield) of a yellow oil. The oil was dissolved in AcOH (50 mL) and heated to reflux for 2 hours then cooled. The excess acetic acid was removed and the residue purified by flash chromatography (CH₂Cl₂: MeOH=97:3) to give 0.28 g (70% yield) of compound 156 as a white solid:

¹H NMR (DMSO-d₆) δ2.95 (s, 6H), 3.49–3.62 (m, 2H), 3.83 (s, 3H), 4.73–4.80 (m, 2H), 5.26 (s, 2H), 5.79 (s, 2H), 7.26 (t, J=7.5 Hz, 1H), 7.36–7.40 (m, 2H), 7.48 (d, J=7.5 Hz, 2H), 7.54–7.64 (m, 2H), 7.65–7.81 (m, 2H), 7.90 (d, J=7.5 Hz, 2H), 8.15 (d, J=7.5 Hz, 1H);

IR (KBr, cm⁻¹) 1711, 1667, 754;

MS m/e 511 (MH⁺);

Anal. Calcd for $C_{29}H_{29}N_5O_4 \cdot 0.97H_2O$: C, 50.16; H, 4.14; N, 8.60

Found: C, 50.16; H, 3.74; N, 8.23.

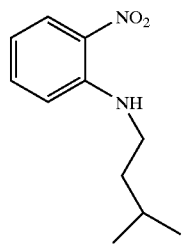

157a

A solution of 2-fluoronitrobenzene (20 g, 142 mmol) and 3-methylbutylamine (12.4 g, 142 mmol) in CH$_3$CN (100 mL) and Et$_3$N (28.5 g, 282 mmol) was heated to reflux for 5 days, then cooled and concentrated. The residue was dissolved in EtOAc and washed with 1N HCl. The mixture was dried over MgSO$_4$ and concentrated to give 27.5 g (93% yield) of compound 157a as a dark orange oil:

$^1$H NMR (CDCl$_3$) δ0.96 (d, J=6.5 Hz, 6H), 1.64 (q, J=7.3 Hz, 2H), 1.65–1.82 (m, 1H), 3.26–3.32 (m, 2H), 6.61 (t, J=8.3 Hz, 1H), 6.83 (d, J=8.4 Hz, 1H), 7.42 (t, J=8.0 Hz, 1H), 8.05 (bs, 1H, exchanges with D$_2$O), 8.15 (d, J=8.7 Hz, 1H);

MS m/e 208 (MH$^+$).

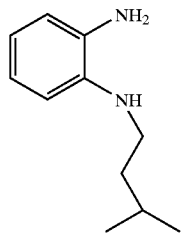

157b

A solution of compound 157a (6.1 g, 29.3 mmol) in EtOH (50 mL) was reduced by catalytic hydrogenation at 40 psi with 10% palladium on carbon (100 mg) for 4 hours. The catalyst was removed by filtration and the solvent was evaporated to give 5.0 g (99% yield) of compound 157b as a dark oil:

$^1$H NMR (DMSO-d$_6$) δ0.91 (d, J=6.7 Hz, 6H), 1.47 (q, J=7.0 Hz, 2H), 3.00 (t, J=7.2 Hz, 2H), 3.28–3.50 (m, 2H), 6.37–6.46 (m, 2H), 6.47–6.53 (m, 2H);

MS m/e 178 (MH$^+$).

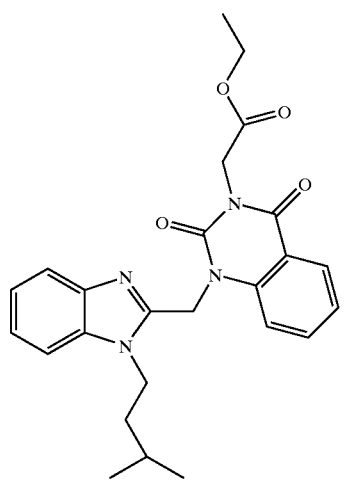

157

Compound 157 was prepared using the same procedures as compound 156 with compounds 157b and 156e:

$^1$H NMR (DMSO-d$_6$) δ1.00 (d, J=6.0 Hz, 6H), 1.20 (t, J=7.2 Hz, 3H), 1.63–1.78 (m, 2H), 4.15 (q, J=6.9 Hz, 2H), 4.36 (t, J=7.5 Hz, 2H), 4.76 (s, 2H), 5.70 (s, 2H), 7.11 (t, J=7.5 Hz, 1H), 7.21 (t, J=7.5 Hz, 1H), 7.17 (t, J=7.5 Hz, 1H), 7.46 (d, J=7.5 Hz, 1H), 7.50–7.60 (m, 2H), 7.78 (t, J=7.5 Hz, 1H), 8.18 (d, J=7.5 Hz, 1H);

IR (KBr, cm$^{-1}$) 1742, 1709, 1669, 740;

MS m/e 448 (MH$^+$);

Anal. Calcd for C$_{25}$H$_{28}$N$_4$O$_4$: C, 66.95; H, 6.29; N, 12.49

Found: C, 66.76; H, 6.14; N, 12.28.

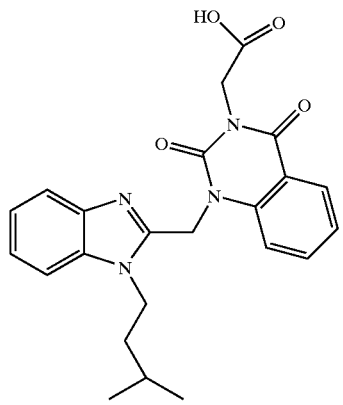

158

A mixture of compound 157 (390 mg, 0.87 mmol) and 1N NaOH (0.88 ml, 0.88 mmol) in MeOH (50 mL) was heated to reflux for 4 hours to give a clear solution. The mixture was concentrated and the residue dissolved in 1N HCl and filtered to give 303 mg (83% yield) of compound 158 as a white solid:

$^1$H NMR (DMSO-d$_6$) δ0.99 (d, J=5.7 Hz, 6H), 1.65–1.82 (m, 2H), 4.25–4.60 (m, 2H), 4.67 (s, 2H), 5.88 (s, 2H), 7.35–7.58 (m, 3H), 7.48 (t, J=7.5 Hz, 2H), 7.79 (t, J=7.5 Hz, 2H)8.16 (d, J=7.5 Hz, 1H);

IR (KBr, cm$^{-1}$) 1711, 1669, 757;

MS m/e 420 (MH$^+$);

Anal. Calcd for C$_{23}$H$_{24}$N$_4$O$_4$.H$_2$O: C, 60.97; H, 6.14; N, 12.37

Found: C, 60.59; H, 5.74; N, 12.18.

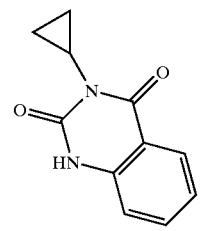

159a

Compound 159a was prepared using the same procedure as compound 156b starting with cyclopropylamine:

$^1$H NMR (DMSO-d$_6$) δ0.70–0.74 (m, 2H), 0.98–1.02 (m, 2H), 2.61–2.65 (m, 1H), 7.11–7.18 (m, 2H), 7.61 (t, J=7.5 Hz, 1H), 7.89 (d, J=7.9 Hz, 1H);

IR (KBr, cm$^{-1}$) 1727, 1666, 1163, 1082;

MS m/e 202 (MH$^+$);

Anal. Calcd for C$_{11}$H$_{10}$N$_2$O$_2$·0.4H$_2$O: C, 63.29; H, 5.18; N, 13.42

Found: C, 63.55; H, 5.44; N, 13.02.

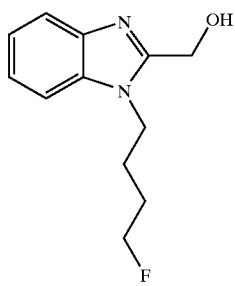

159b

To a solution of 2-hydroxymethylbenzimidazole (1.5 g, 10.12 mmol) in a mixture of DMF and THF (60 mL, 1:1) was added sodium hydride (60% suspension in mineral oil, 425 mg, 10.63 mmol). After stirring for 1 hour at room temperature, 1-bromo-4-fluorobutane (1.56 g, 10.12 mmol) was added and the reaction was stirred at 65° C. for 18 hours. The solvent was evaporated. The residue was diluted with 1N NaOH and extracted with EtOAc. The combined extracts were dried over Na$_2$SO$_4$ and evaporated to give 2.34 g (quantitative yield) of compound 159b as a yellow oil which was used without further purification.

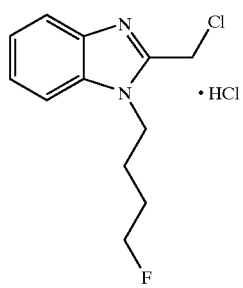

159c

To solution of alcohol 159b (2.30 g, 10.34 mmol) in CH$_2$Cl$_2$ (30 mL) was added thionyl chloride (2.46 g, 20.68 mmol) at 0° C. The reaction was stirred for 2 hours and then the solvent and excess thionyl chloride were evaporated to give 2.8 g (98% yield) of compound 159c.

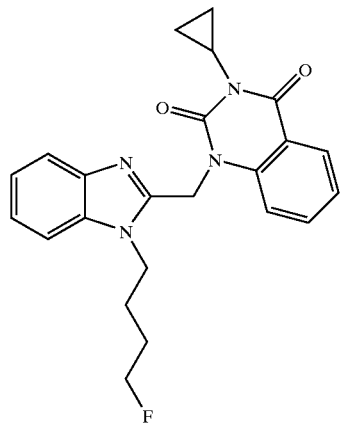

159

Compound 159 was prepared using the same procedure as compound 4 with compound 159a and compound 159c:

$^1$H NMR (DMSO-d$_6$) δ0.73–0.76 (m, 2H), 1.03–1.09 (m, 2H), 1.73–1.83 (m, 2H), 1.86–1.93 (m, 2H), 2.74–2.79 (m, 1H), 4.42 (t, J=7.5 Hz, 2H), 4.47 (t, J=6.0 Hz, 2H), 4.52 (t, 5.1 Hz, 1H), 5.62 (s, 2H), 7.11 (t, J=7.2 Hz, 1H), 7.22 (t, J=8.0 Hz, 1H), 7.23 (t, J=7.5 Hz, 1H), 7.27 (t, J=7.5 Hz, 1H), 7.47–7.49 (m, 1H), 7.58 (d, J=8.0 Hz, H), 7.66 (t, J=7.6 Hz, 1H), 8.06 (d, J=8.0 Hz, 1H);

MS m/e 406 (MH$^+$);

Anal. Calcd for C$_{23}$H$_{23}$FN$_4$O$_2$: C, 67.96; H, 5.70; N, 13.78

Found: C, 67.57; H, 5.51; N, 13.67.

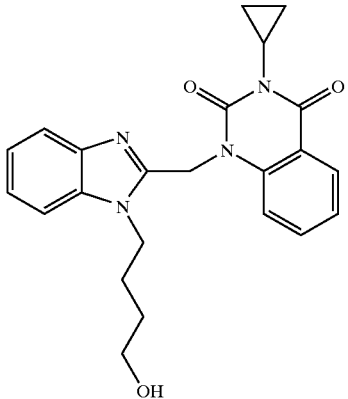

160

To a solution of compound 159a (127 mg, 0.63 mmol) in THF (20 mL) was added BTPP (0.6 mL, 1.98 mmol) and the mixture was stirred for 30 minutes at room temperature. Compound 139a (200 mg, 0.63 mmol) was added and the mixture was stirred for 12 hours at room temperature. The solvent was removed. The residue was dissolved in MeOH (5 mL) and diluted with diethyl ether (20 mL) and water (50 mL). After standing for 30 minutes, the precipitated product was isolated by filtration to give 214 mg (84% yield) of compound 160 as a white solid:

$^1$H NMR (DMSO-d$_6$) δ0.73–0.76 (m, 2H), 1.03–1.09 (m, 2H), 1.50–1.56 (m, 2H), 1.79–1.86 (m, 2H), 2.75–2.79 (m, 1H), 3.46 (q, J=6.3 Hz, 2H), 4.39 (t, J=7.4 Hz, 2H), 4.52 (t, J=5.1 Hz, 2H), 5.62 (s, 2H), 7.11 (t, J=7.2 Hz, 1H), 7.22 (t, J=8.0 Hz, 1H), 7.23 (t, J=7.5 Hz, 1H), 7.27 (t, J=7.5 Hz, 1H), 7.47–7.49 (m, 1H), 7.58 (d, J=8.0 Hz, 1H), 7.66 (t, J=7.6 Hz, 1H), 8.06 (d, J=8.0 Hz, 1H);

IR (KBr) 1702, 1664, 1607, 1481;

MS m/e 404 (MH⁺);

Anal. Calcd for $C_{23}H_{24}N_4O_3$: C, 68.30; H, 5.98; N, 13.85

Found: C, 67.99; H, 6.06; N, 13.92.

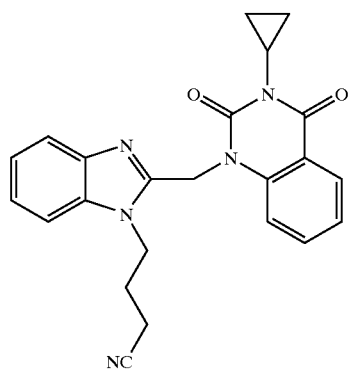

161

Compound 161 was prepared using the same method as compound 160 with compound 159a and compound 25b:

¹H NMR (DMSO-d₆) δ0.72–0.75 (m, 2H), 1.02–1.06 (m, 2H), 2.14–2.20 (m, 2H), 2.69 (t, J=7.4 Hz, 2H), 2.74–2.78 (m, 1H), 4.44 (t, J=7.5 Hz, 2H), 5.63 (s, 2H), 7.13 (t, J=7.9 Hz, 1H), 7.22–7.30 (m, 2H), 7.48–7.53 (m, 2H), 7.61 (d, J=8.17 Hz, 1H), 7.68 (t, J=7 Hz, 1H), 8.06 (d, J=7.5 Hz, 1H);

IR (KBr) 1708, 1667, 1608;

MS m/e 399 (MH⁺);

Anal. Calcd for $C_{23}H_{21}N_5O_2$: C, 69.15; H, 5.29; N, 17.53

Found: C, 69.36; H, 5.20; N, 17.56.

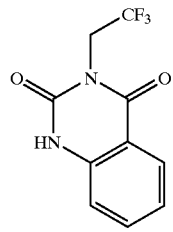

162a

Compound 162a was prepared using the same procedure as compound 156b starting with 2,2,2-trifluoroethylamine hydrochloride:

¹H NMR (DMSO-d₆) δ4.72 (q, J=9.2 Hz, 2H), 7.20–7.26 (m, 2H), 7.08 (t, J=7.6 Hz, 1H), 7.96 (d, J=7.6 Hz, 1H);

IR (KBr, cm⁻¹) 1727, 1666, 1163, 1082;

MS m/e 244 (MH⁺);

Anal. Calcd for $C_{10}H_7F_3N_2O_2$: C, 49.19; H, 2.89; N, 11.47

Found: C, 49.04; H, 2.85; N, 11.42.

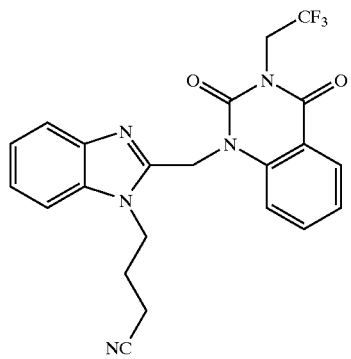

162

Compound 162 was prepared using the same procedure as compound 160 with compound 162a and compound 25b:

¹H NMR (DMSO-d₆) δ2.16–2.18 (m, 2H), 2.69 (t, J=7.4 Hz, 2H), 4.44 (t, J=7.5 Hz, 2H), 4.81–4.87 (m, 2H), 5.71 (s, 2H), 7.14 (t, J=7.2 Hz, 1H), 7.26 (t, J=7.5 Hz, 1H), 7.37 (t, J=7.7 Hz, 1H), 7.49 (d, J=8.0 Hz, 1H), 7.59–7.64 (m, 2H), 7.78 (t, J=9.0 Hz, 1H), 8.15 (d, J=7.5 Hz, 1H);

MS m/e 441 (MH⁺);

Anal. Calcd for $C_{22}H_{18}F_3N_5O_2 \cdot 0.4H_2O$: C, 58.93; H, 4.22; N, 15.62

Found: C, 59.21; H, 4.45; N, 15.41.

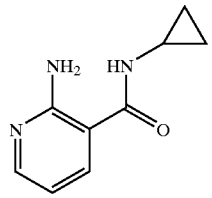

163a

To a solution of 2-aminonicotinic acid (5.0 g, 36.2 mmol), cyclopropylamine (2.0 g, 36.2 mmol), HOBT (4.9 g, 36.2 mmol) in DMF (50 ml) was added EDC (6.9 g, 36.2 mmol) and the mixture stirred for 12 h at 23° C. The solvent was removed and the residue dissolved in EtOAc/H₂O. The organic layer is washed with saturated NaHCO₃, dried over MgSO₄ and concentrated to give 3.2 g (50%) of product as a white solid.

¹H NMR (DMSO-d6) δ: 0.54–0.59 (m, 2H), 0.66–0.69 (m, 2H), 2.77–2.88 (m, 1H), 3.10–3.40 (br s, 1H), 6.53–6.56 (m, 1H), 7.04 (s, 2H), 7.82 (d, J=6.2 Hz, 1H), 8.04–8.08 (m, 1H), 8.36–8.42 (m, 1H);

MS m/e 177 (MH⁺).

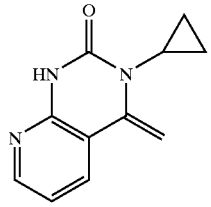

163b

Compound 163b was prepared as described for 156b except CDI in CH₂Cl₂ was used in place of ethylchloroformate.

¹H NMR (DMSO-d6) δ: 0.71–0.77 (m, 2H), 0.99–1.02 (m, 2H), 2.20–2.25 (m, 1H), 7.22–7.24 (m, 2H), 8.25 (dd, J=1.5, 7.7 Hz, 1H), 8.56–8.58 (m, 1H);

MS m/e 203 (MH⁻).

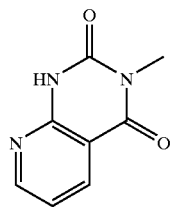

163c

Compound 163c was prepared as described for 163b except CDI in CH₂Cl₂ was used in place of ethylchloroformate.

¹H NMR (DMSO-d6) δ: 3.25 (s, 3H), 7.25–7.28 (m, 1H), 8.29 (d, J=7.8 Hz, 1H), 8.60–8.62 (m, 1H);
MS m/e 177 (MH⁻).

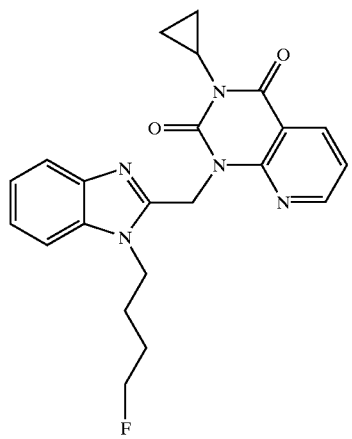

163

3-Cyclopropyl-1-[1-(4-fluoro-butyl)-1H-benzoimidazol-2-ylmethyl]-1H-pyrido[2,3-d]pyrimidine-2,4-dione, 163, was prepared as described for compound using 163b and 159c with BTPP.

¹H NMR (DMSO-d6) δ: 0.75–0.79 (m, 2H), 1.04–1.08 (m, 2H), 1.75–1.84 (m, 2H), 1.91–1.96 (m, 2H), 2.76–2.79 (m, 1H), 4.42–4.48 (m, 2H), 4.53 (dt, J=J=9.7, 41.5 Hz, 2H), 7.11 (t, J=7.7 Hz, 1H), 7.21 (t, J=7.7 Hz, 1H), 7.3 2–7.35 (m, 1H), 7.44 (d, J=8.0 Hz, 1H), 7.58 (d, J=8.0 Hz, 1H), 8.42 (dt, J=1.7, 7.7 Hz, 1H), 8.58–8.59 (m, 1H);
MS m/e 407 (MH⁺).

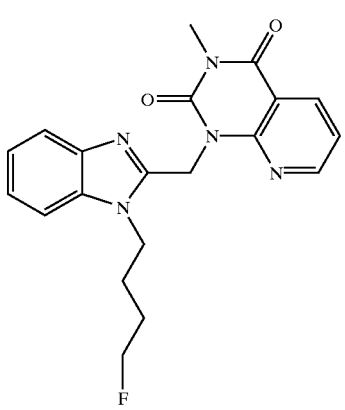

163d

3-Methyl-1-[1-(4-fluoro-butyl)-1H-benzoimidazol-2-ylmethyl]-1H-pyrido [2,3-d]pyrimidine-2,4-dione, 163d, was prepared as described for compound using 3-methyl-1H-pyrido[2,3-d]pyrimidine-2,4-dione 1 63c and 159c with BTPP.

¹H NMR (DMSO-d6) δ: 1.75–1.83 (m, 2H), 1.93–1.97 (m, 2H), 3.37 (s, 3H), 4.43–4.49 (m, 3H), 4.57 (t, J=5.9 Hz, 1H), 5.74 (s, 2H), 7.10 (t, J=7.5 Hz, 1H), 7.20 (t, J=7.5 Hz, 1H), 7.36–7.44 (m, 1H), 7.44 (d, J=8.0 Hz, 1H), 7.58 (d, J=8.0 Hz, 1H), 8.47 (d, J=7.8 Hz, 1H), 8.62 (d, J=4.8 Hz, 1H);
MS m/e 381 (MH⁺).

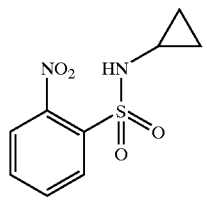

164a

To a −78° C. mixture of cyclopropylamine (10 g, 1.75 mmol) in CH₂Cl₂ (100 mL) was added a solution of 2-nitrobenzene sulfonyl chloride (22.1 g, 85.7 mmol) and the mixture was stirred for 12 h. The mixture was washed with 1N HCl dried over MgSO₄ then concentrated to give 18.7 g, (88%) of a N-Cyclopropyl-2-nitro-benzenesulfonamide as a tan solid.

¹H NMR(CDCl₃) δ: 0.66–0.70 (m, 2H), 0.70–0.75 (m, 2H), 2.32–2.37 (m, 1H), 5.58 (s, 1H), 7.13–7.78 (m, 2H), 7.83–7.87 (m, 1H), 8.18–8.22 (m, 3H);
MS m/e 242 (MH⁺).

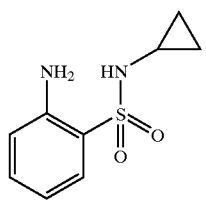

164b

A solution of N-cyclopropyl-2-nitro-benzenesulfonamide (7.9 g, 33.0 mmol) in EtOH (50 ml) was treated with HCl (3.0 ml, 4.0 N in dioxane), Pd/C (10%, 100 mg) and shaken in a Parr Hydrogenator at 50 psi for 48 h. The catalyst was removed by filtration and the solvent evaporated to give 6.9 g (84%) of 2-Amino-N-cyclopropyl-benzenesulfonamide as a light grey solid.

¹H NMR (DMSO-d6) δ: 0.35–0.37 (m, 2H), 0.42–0.44 (m, 2H), 2.0–2.08 (m, 1H), 5.89 (s, 2H), 6.62 (t, J=7.1 Hz, 1H), 6.80 (d, J=8.3 Hz, 1H), 7.27 (t, J=7.1 Hz, 1H), 7.50 (d, j=8.0, 1H), 7.82 (s, 1H);
MS m/e 242 (MH⁺).

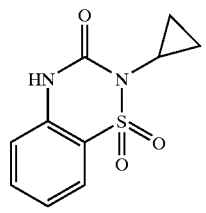

164c

A solution of of 2-amino-N-cyclopropyl-benzenesulfonamide (6.9 g, 32.5 mmol) in CH₂Cl₂ (50 ml)

was treated with CDI (6.5 g, 40 mmol) and stirred for 12 h at reflux. The solution was a washed with HCl (1N), dried over MgSO$_4$ and concentrated to give 6.5 g (84%) of 2-cyclopropyl-1,1-dioxo-1,4-dihydro-2H-1λ$^6$-benzo[1,2,4]thiadiazin-3-one as a brown solid.

$^1$H NMR (DMSO-d6) δ: 0.72–0.80 (m, 2H), 0.90–1.1 (m, 2H), 2.71–2.75 (m, 1H), 7.23 (d. 8.1 Hz, 1H), 7.29 (t, J=7.7 Hz, 1H), 7.68 (t, J=7.5 Hz, 1H), 7.81 (d, J=7.6 Hz, 1H);

MS m/e 238 (MH$^+$).

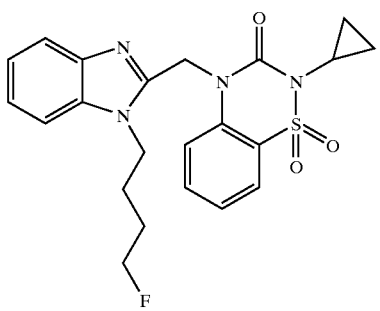

164

2-Cyclopropyl-4-[1-(4-fluoro-butyl)-1H-benzoimidazol-2-ylmethyl]-1,1-dioxo-1,4-dihydro-2H-1λ$^6$-benzo [1,2,4]thiadiazin-3-one as described for compound 25 using 159c and 164c.

$^1$H NMR (DMSO-d6) δ: 0.90–0.96 (m, 2H), 1.06–1.10 (m, 2H), 1.80–1.91 (m, 2H), 2.07–2.13 (m, 2H), 2.91–2.93 (m, 1H), 4.43 (t, J=8.0 Hz, 2H), 4.54 (dd, J=5.5, 47.1 Hz, 2H), 6.03 (s, 2H), 7.26 (s, 1H), 7.35 (t, J=7.6 Hz, 1H), 7.52–7.54 (m, 2H), 7.69 (t, J=7.8 Hz, 1H), 7.80 (d, J=8.6 Hz, 1H), 7.86 (d, J=7.7 Hz, 1H), 7.91–7.93 (m, 1H);

MS m/e 443 (M+).

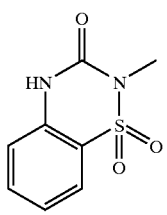

165a

2-Methyl-1,1-dioxo-1,4-dihydro-2H-1λ$^6$-benzo [1,2,4]thiadiazin-3-one was prepared as described above for compound 164c except phosgene was used in place of CDI for the ring closure reaction.

$^1$H NMR (DMSO-d6) δ: 3.34 (s, 3H), 7.27–7.34 (m, 2H), 7.71 (t, J=7.0 Hz, 1H), 7.86 (d, J=7.5 Hz, 1H);

MS m/e 212 (MH$^+$).

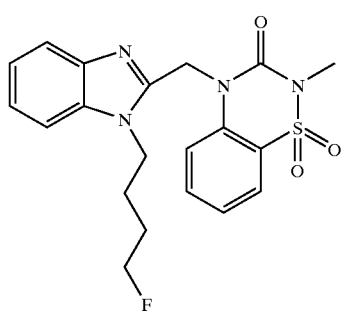

165

Prepared from 165a and 159c as described for compound 25.

$^1$H NMR (DMSO-d6) δ: 1.74–1.82 (m, 2H), 1.88–1.93 (m, 2H), 3.24 (s, 3H), 4.38 (t, J=7.3 Hz, 2H), 4.51 (dt, J=5.9, 47.4 Hz, 2H), 5.57 (s, 2H), 7.15 (t, J=7.5 Hz, 1H), 7.24 (t, J=7.4 Hz, 1H), 7.45 (t, J=7.8 hz, 1H), 7.51 (d, J=7.9 hz, 1H), 7.44–7.47 (m, 2H), 7.78 (t, J=8.1 Hz, 1H), 7.99 (d, J=7.5 Hz, 1H);

MS m/e 416 (MH$^+$).

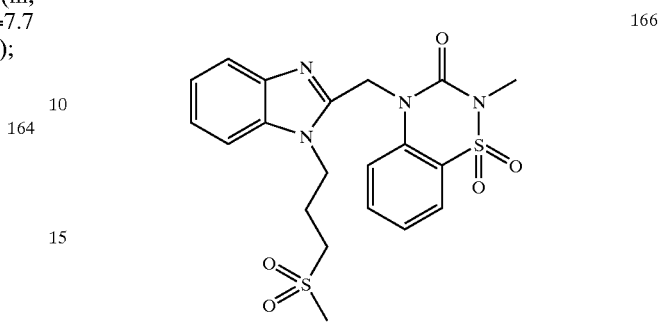

166

A mixture of 2-methyl-1,1-dioxo-1,4-dihydro-2H-1l6-benzo [1,2,4]thiadiazin-3-one (300 mg, 0.71 mmol) and Cs$_2$CO$_3$ (0.69, 2.13 mmol) in DMF (20 mL) was stirred for 30 minutes and then treated with 10d (0.23 g, 0.71 mmol) and stirred for 12 h. The mixture is filtered and concentrated. The residue was purified by preparative thin layer chromatography using 50% EtOAc in hexanes as eluant to give 48 mg (15%) of the product 166 as a clear glass.

$^1$H NMR (DMSO-d6) d: 2.10–2.35 (m, 2H), 2.73 (s, 3H), 2.89 (s, 3H), 3.31–3.39 (m, 2H), 4.40–4.54 (m, 2H), 5.58 (s, 2H);

MS m/e 462 (MH$^+$).

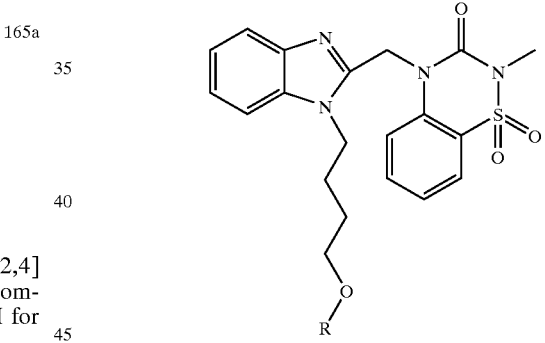

167, R = H
168, R = Ac 2-methyl-1,1-dioxo-1,4-dihydro-2H-1l6-benzo [1,2,4]thiadiazin-3-one (300 mg, 0.71 mmol) and Cs$_2$CO$_3$ (0.69, 2.13 mmol) in DMF (20 mL) was stirred for 30 minutes and then treated 139a (224 mg, 0.71 mmol) and stirred for 12 h. The mixture was filtered and concentrated. The residue was purified by preparative TLC using 30% EtOAc/hexanes as eluant to give 168, 48 mg (15%) of the acetate and 167, 70 mg (24%) of the alcohol. The alcohol could be obtained exclusively by treating the crude reaction mixture with HCl (1N, 10 ml) in MeOH and heating the mixture to reflux for 2 h. Preparative TLC of this reaction gave 147 mg (50%) of 167.

168, R=Ac $^1$H NMR (DMSO-d6) δ: 1.66–1.74 (m, 2H), 1.85–1.89 (m, 2H), 2.00 (s, 3H), 3.24 (s, 3H), 4.07 (t, J=6.5 Hz, 2H), 4.37 (t, J=7.2 Hz, 2H), 5.57 (s, 2H), 7.15 (d, J=7.9 Hz, 1H), 7.24 (t, J=7.2 Hz, 1H), 7.45 (t, J=7.6 Hz, 1H), 7.51 (d, J=7.9 Hz, 1H), 7.60 (t, J=7.2 Hz, 1H), 7.78 (t, J=7.3 Hz, 2H), 7.99 (d, J=7.9 Hz, 1H);

MS m/e 456 (MH+).
167, R=H:
¹H NMR (DMSO-d6) d: 1.52–1.55 (m, 2H), 1.81–1.89 (m, 2H), 3.24 (s, 3H), 3.41–3.52 (m, 2H), 4.35 (t, J=7.5 Hz, 2H), 4.50 (t, J=5.1 Hz, 1H), 5.57 (s, 2H), 7.14 (t, J=8.0 Hz, 1H), 7.23 (t, J=7.2 Hz, 1H), 7.45 (t, J=7.7 Hz, 1H), 7.50 (d, J=7.9 Hz, 1H), 7.55–7.61 (m, 2H), 7.77 (t, J=7.2 Hz, 1H), 7.99 (d, J=6.6 Hz, 1H);
MS m/e 456 (MH+).

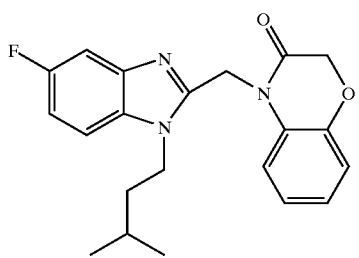

169

Compound 169 was prepared using the same procedure as compound 160 with 2H-1,4-benzoxazin-3(4H)-one and compound 42d:
¹H NMR (CD₃OD) δ1.04 (d, J=6.2 Hz, 6H), 1.76–1.78 (m, 3H), 4.45–4.48 (m, 2H), 4.78 (s, 2H), 5.63 (s, 2H), 7.03–7.09 (m, 3H), 7.14–7.16 (m, 1H), 7.32 (dt, J=2.4, 9.2 Hz, 1H), 7.39 (dd, J=2.4, 8.5 Hz, 1H), 7.75 (dd, J=4.2, 9.1 Hz, 1H);
MS m/e 368 (MH+).

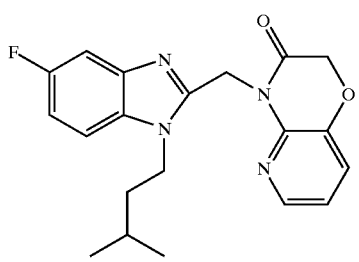

170

Compound 170 was prepared using the same procedure as compound 160 with 2H-pyrido[3,2-B]-1,4-oxazin-3(4H)-one and compound 42d:
¹H NMR (CD₃OD) δ1.06 (d, J=6.4 Hz, 6H), 1.80–1.88 (m, 3H), 4.56–4.60 (m, 2H), 4.90 (s, 2H), 5.76 (s, 2H), 7.08 (dd, J=4.9, 8.0 Hz, 1H), 7.34–7.43 (m, 3H), 7.82 (dd, J=4.3, 9.1 Hz, 1H), 7.92 (dd, J=1.3, 4.9 Hz, 1H);
MS m/e 369 (MH+).

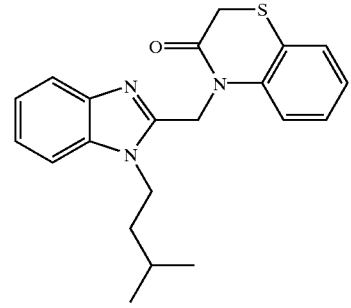

171

A solution of the compound 4b (0.5 g, 2.29 mmol) and 2H-1,4-benzothiazin-3(4H)-one (0.38 g, 2.29 mmol) con-taining tributylphosphine (0.61 g, 3.0 mmol) in benzene (5 ml) was treated with 1,1'-(azodicarbonyl)dipiperidine (0.76 g, 3.0 mmol). The mixture was stirred at room temperature for 12 hours. The solvent was removed. The residue was purified by flash chromatography (15% EtOAc in hexanes) and further purified by preparative HPLC (C18, gradient 30% MeOH/Water to 90% MeOH/water with 0.1% TFA) to give 150 mg (20% yield) of compound 171 as a white solid:
¹H NMR (DMSO-d₆) δ0.97 (d, J=6.2 Hz, 6H), 1.6–1.8 (m, 3H), 3.33 (s, 2H), 3.61 (s, 2H), 3.41–4.13 (m, 2H), 5.43 (s, 2H), 7.01 (t, J=7.5 Hz, 1H), 7.14–7.27 (m, 3H), 7.41 (t, J=7.5, 2H), 7.52 (t, J=7.9 Hz, 2H);
IR (KBr, cm⁻¹) 2955, 1673, 1479, 1449, 1384, 741;
MS m/e 365 (MH+);
Anal. Calcd for C₂₁H₂₃N₃OS: C, 69.01; H, 6.34; N, 11.50
Found: C, 68.84; H, 6.31; N, 11.45.

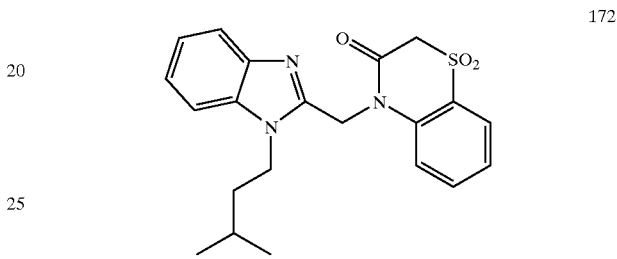

172

A solution of compound 171 (300 mg, 0.8 mmol) and 3-chloroperbenzoic acid (80%, 350 mg, 1.64 mmol) in CH₂Cl₂ (20 ml) was stirred at room temperature for 12 hours. The reaction mixture was washed with saturated aqueous NaHSO₃ and saturated aqueous NaHCO₃ then dried over MgSO₄ and concentrated. The residue was purified by flash chromatography (hexanes:EtOAc=3:2) to give 60 mg (18% yield) of compound 172 as a white solid:
¹H NMR (DMSO-d₆) δ0.98 (d, J=6.1 Hz, 6H), 1.60–1.73 (m, 3H), 4.26–4.34 (m, 2H), 5.00 (s, 2H), 5.52 (s, 2H), 7.13–7.27 (m, 2H), 7.41 (t, J=7.0 Hz, 1H); 7.54 (t, J=8.1 Hz, 2H), 7.73–7.79 (m, 2H), 7.91 (d, J=7.7 Hz, 1H);
IR (KBr, cm⁻¹) 2954, 1692, 1482, 1319, 1171, 738;
MS m/e 397 (MH+);
Anal. Calcd for C₂₁H₂₃N₃O₃S: C, 63.46; H, 5.83; N, 10.57
Found: C, 63.17; H, 5.86; N, 10.30.

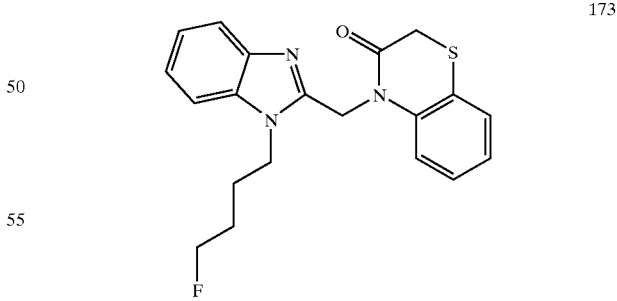

173

Compound 173 was prepared as described for compound 25 with 159c and 2H-1,4-benzothiazin-3(4H)-one using BTPP.
¹H NMR (DMSO-d6) δ: 1.77–1.85 (m, 2H), 1.92–1.97 (m, 2H), 3.50 (s, 2H), 4.30 (t, J=7.6 Hz, 1H), 4.49 (dt, J=5.8, 47.1 Hz, 2H), 5.52 (s, 2H), 7.00 (t, J=8.0 Hz, 1H), 7.22–7.28 (m, 5H), 7.32–7.34 (m, 1H), 7.72 (t, J=7.9 Hz, 1H); MW m/e 369 (MH+).

174

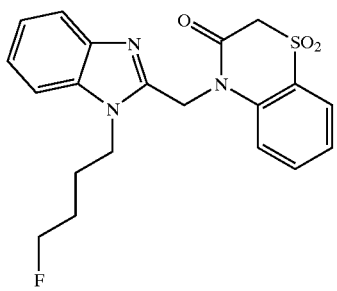

To a solution of sulfide (200 mg, 0.54 mmol) in DMF (20 ml) was treated with MPP (560 mg, 1.14 mmol) and stirred for 12 h. The solvent was removed and the residue was dissolved in EtOAc/H$_2$O. The organic layer was washed with saturated NaHCO$_3$, then dried over MgSO$_4$ and concentrated to give 60 mg (30%), of 4-[1-(4-fluoro-butyl)-1H-benzoimidazol-2-ylmethyl]-1,1-dioxo-1,4-dihydro-2H-1$\lambda^6$-benzo[1,4]thiazin-3-one.

$^1$H NMR (DMSO-d6) δ: 1.73–1.81 (m, 2H), 1.86–1.92 (m, 2H), 4.38 (t, J=5.8 Hz, 2H), 4.50 (dt, J=6.0, 47.3 Hz, 2H), 4.99 (s, 2H), 5.53 (s, 2H), 7.17 (t, J=7.6 Hz, 1H), 7.25 (t, J=7.5 Hz, 1H), 7.42 (t, J=7.6 Hz, 1H), 7.53 (d, J=8.0 Hz, 1H), 7.68 (d, J=8.3 Hz, 1H), 7.7 (t, J=8.1 Hz, 1H), 7.91 (d, J=7.7 Hz, 1H);

175a

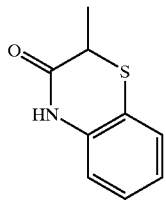

To a mixture of 2-bromopropionic acid (1.21 g, 8.0 mmol), 2-aminothiophenol (1.0 g, 8.0 mmol), HOBT (1.1 g, 8.0 mmol) in DMF (50 ml) was added EDC (1.53 g, 8.0 mmol) and the mixture stirred for 12 h then concentrated. The residue was dissolved in EtOAc/H$_2$O. The organic layer was washed with saturated NaHCO$_3$, dried over MgSO4 and concentrated. The residue solidified on standing to give the product 0.72 g, (50%) as a tan solid.

$^1$H NMR (DMSO-d6) δ: 1.32 (d, J=11.7 Hz, 3H), 3.65 (q, J=7.0 Hz, 1H), 6.96–6.99 (m, 2H), 7.18 (t, J=7.6 Hz, 1H), 7.30 (d, J=7.5 Hz, 1H);

MS m/e 178 (MH$^+$).

175

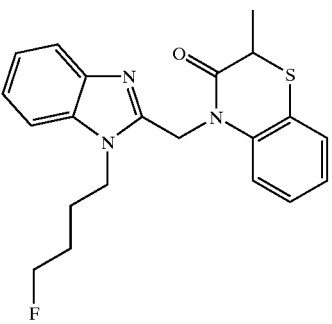

Compound 175 was prepared as described for compound 25 using compound 175a and 159c with BTPP instead of Cs$_2$CO$_3$.

$^1$H NMR (DMSO-d6) δ: 1.37 (d, J=6.9 Hz, 1H), 1.71–1.80 (m, 2H), 1.83–1.87 (m, 2H), 3.76 (q, J=6.8 Hz, 1H), 4.33–4.37 (m, 2H), 4.49 (dt, J=6.0, 47 Hz, 2H), 5.35 (d, J=16.8, Hz, 1H), 5.49 (d, J=16.8 Hz, 1H), 7.07 (t, J=7.6 Hz, 1H), 7.16 (t, J=7.2 Hz, 1H), 7.21–7.28 (m, 2H), 7.42 (t, J=6.4 Hz, 2H), 7.54 (d, J=8.0 hz, 1H), 7.58 (d, j=8.0 Hz, 1H);

MS m/e 383 (MH$^+$).

176

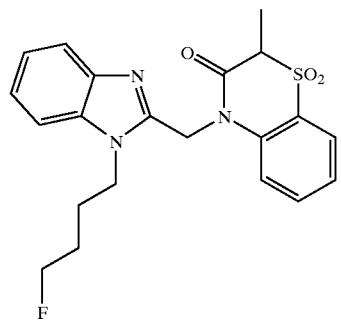

To a solution of sulfide (1.64 g, 0.43 mmol) in DMF (20 ml) was treated with MPP (4.45 mg, 0.90 mmol) and stirred for 12 h. The solvent was removed and the residue was dissolved in EtOAc/H$_2$O. The organic layer was washed with saturated NaHCO$_3$, then dried over MgSO$_4$ and concentrated. The yellow oil was purified by preparative TLC to give 176 60 mg (30%), as a yellow oil.

$^1$H NMR (DMSO-d6) δ: 1.48 (d, J=6.9 Hz, 3H), 1.65–1.79 (m, 2H), 1.80–1.95 (m, 2H), 4.30–4.45 (m, 2H), 4.50 (dt, J=5.9, 47 Hz, 2H), 5.03 (q, J=6.9 Hz, 1H), 5.40 (d, j=17 Hz, 1H), 5.64 (d, J=17 Hz, 1H), 7.17 (t, 7.6 Hz, 1H), 7.25 (t, j=8.0 Hz, 1H), 7.45 (t, J=7.3 Hz, 1H), 7.52 (d, J=8.0 Hz, 1H), 7.60 (d, j=8.0 Hz, 1H), 7.68 (d, J=8.4 Hz, 1H), 7.78 (t, J=8.2 Hz, 1H), 7.93 (d, J=7.6 Hz, 1H);

MS m/e 415 (MH$^+$).

177a

To a slurry of NaH (0.64 g, 16 mmol) in DMF (20 ml) was added 2-aminothiophenol (2.0 g, 16 mmol) and the mixture stirred until gas evolution ceased. 2-methyl-2-bromopropionic acid ethyl ester (3.12 g, 2.34 ml, 16 mmol) and the mixture stirred for 8 h. The solvent was removed and the residue dissolved in toluene and heated to reflux for 12 h. The solvent was removed to give 177a 2.87 g (92%) as a tan solid.

$^1$H NMR (DMSO-d6) δ: 1.49 (s, 6H), 6.88 (d, J=8 Hz, 1H), 7.01 (t, J=7.5 hz, 1H), 7.17 (t, J=6.7 z, 1H), 7.26–7.29 (m, 1H), .72 (br s, 1H);

MS m/e 193 (MH$^+$).

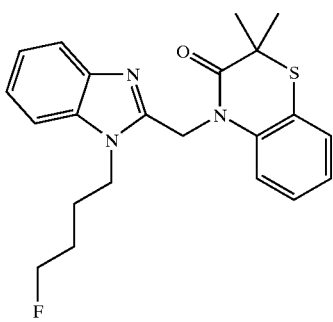

177

Compound 177 was prepared as described for compound 25 using 159c and 177a with BTPP instead Of $CS_2CO_3$.

$^1$H NMR (DMSO-d6) δ: 1.39 (s, 6H), 1.73–1.79 (m, 2H), 1.85–1.88 (m, 2H), 4.35 (t, J=7.1 Hz, 2H), 4.50 (dt, J=5.7, 47.3 Hz, 2H), 5.43 (s, 2H), 7.08 (t, J=7.5 Hz, 1H), 7.15 (t, J=7.8 Hz, 1H), 7.22 (t, J=7.2 Hz, 1H), 7.28 (t, J=7.6 Hz, 1H), 7.40 (t, J=8.9 Hz, 1H), 7.51 (d, J=7.9 Hz, 1H), 7.57 (d, J=7.9 Hz, 1H);

MS m/e 397 (MH$^+$).

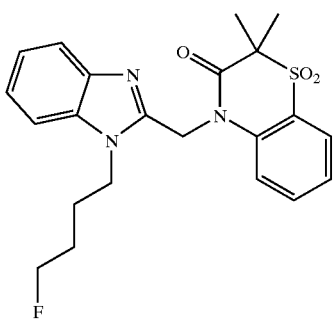

178

4-[1-(4-Fluoro-butyl)-1H-benzoimidazol-2-ylmethyl]-2,2-dimethyl-1,1-dioxo-1,4-dihydro-2H-1λ$^6$-benzo[1,4]thiazin-3-one was prepared as described for compound 176 above.

$^1$H NMR (DMSO-d6) δ: 1.50 (s, 6H), 1.75–1.80 (m, 2H), 1.89–1.92 (m, 2H), 4.37 (t, J=7.3 Hz, 1H), 4.51 (dt, J 5.9, 47.4 Hz, 2H), 5.52 (s, 2H), 7.15 (t, J=7.9 Hz, 1H), 7.24 (t, J=7.7 Hz, 1H), 7.45 (t, J=7.6 Hz, 1H), 7.49 (d, J=7.9 Hz, 1H), 7.56 (d, J=8.4 Hz, 1H), 7.60 (d, J=8.1 Hz, 1H), 7.76 (t, J=7.6 Hz, 1H), 7.95 (d, J=7.7 Hz, 1H);

MS m/e 429 (MH$^+$).

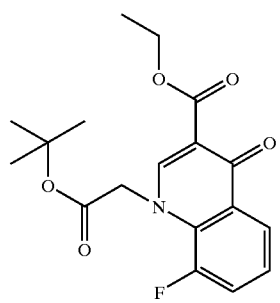

179a

To a slurry of sodium hydride (0.44 g, 8.50 mmol) in DMF (50 mL) was added ethyl 1,4-dihydro-8-fluoro-4-oxoquinoline-3-carboxylate [Maybridge](2.0 g, 8.50 mmol) and the mixture was stirred until gas evolution ceased. T-butyl bromoacetate (1.75 g, 9.00 mmol) was added and the mixture was stirred for 12 hours at room temperature. The solvent was removed. The residue was dissolved in EtOAc and washed with water. The organic extracts were dried with $MgSO_4$ and evaporated. The residue was purified by flash chromatography (3% $MeOH/CH_2Cl_2$) to give 2.35 g (79% yield) of compound 179a as a white solid:

$^1$H NMR (DMSO-d$_6$) δ1.29 (t, J=6.9 Hz, 3H), 1.43 (s, 3H), 4.24 (q, J=6.9 Hz, 2H), 5.21 (d, J=7.5 Hz, 2H), 7.44–7.49 (m, 1H), 7.65 (dd, J=7.8, 16.0 Hz, 1H), 8.10 (d, J=7.2 Hz, 1H), 8.65 (s, 1H);

IR (KBr, cm$^{-1}$) 1739, 1722, 1243;

MS m/e 349 (MH$^+$);

Anal. Calcd for $C_{18}H_{20}FNO_5$: C, 61.88; H, 5.77; N, 4.01

Found: C, 61.73; H, 5.69; N, 4.08.

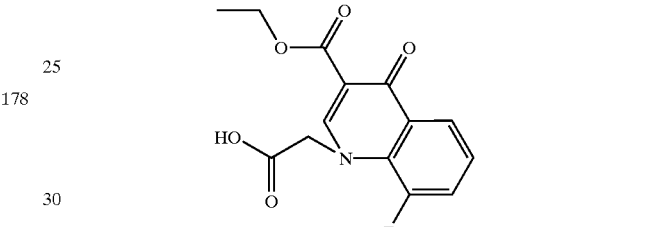

179b

Compound 179a (2.0 g, 5.70 mmol) was stirred with TFA (20 mL) for 12 hours then concentrated to give an oil. The oil was triturated with water and filtered to give 1.6 g (99% yield) of compound 179b as a tan solid:

$^1$H NMR (DMSO-d$_6$) δ1.29 (t, J=7.1 Hz, 3H), 4.25 (d, J=7.1 Hz, 2H), 5.24 (d, J=4.4 Hz, 2H), 7.44–7.48 (m, 1H), 7.47 (dd, J=7.9, 16 Hz, 1H), 8.09 (d, J=7.9 Hz, 1H), 8.66 (s, 1H);

IR (KBr, cm$^{-1}$) 1728, 1688;

MS m/e 293 (MH$^+$);

Anal. Calcd for $C_{14}H_{12}FNO_5$: C, 56.43; H, 4.20; N, 4.73

Found: C, 56.43; H, 4.15; N, 4.75.

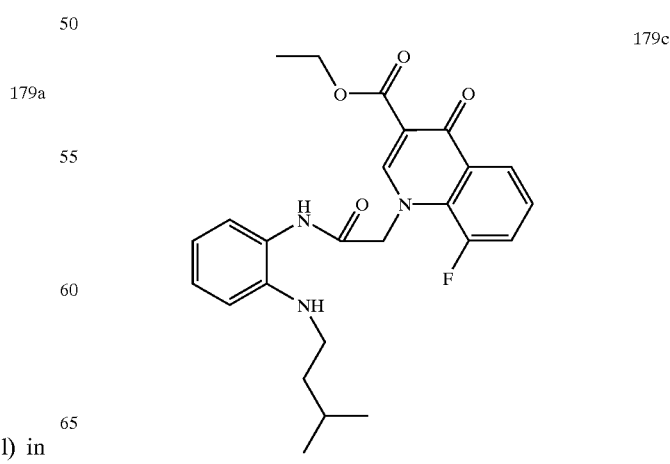

179c

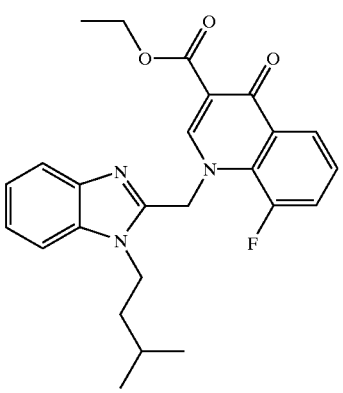

179

To a mixture of compound 179b (1.5 g, 1.70 mmol) and 2-chloro-1-methyl pyridinium iodide (0.522, 2.04 mmol) in CH$_3$CN (50 ml) was added triethylamine (0.48 ml, 1.70 mmol) followed by compound 157b (0.3 g, 1.70 mmol). The mixture was stirred for 12 hours at room temperature. The reaction mixture was filtered to give 0.44 g (57%) of the intermediate 179c as a white solid. The solid 10 (0.44 g, 0.97 mmol) was dissolved in AcOH (25 ml) and heated to reflux for 4 hours then cooled and concentrated. The residue was purified by flash chromatography (3% MeOH in CH$_2$Cl$_2$) to give 289 mg (69% yield) of compound 179 as a white solid:

$^1$H NMR (DMSO-d$_6$) δ1.02 (d, J=5.7 Hz, 6H), 1.29 (t, J=6.9 Hz, 3H), 1.68–1.72 (m, 3H), 4.22–4.31 (m, 4H), 6.09 (d, J=4.5 Hz, 2H), 7.12 (t, J=7.5 Hz, 1H), 7.24 (t, J=7.5 Hz, 1H);

IR (KBr, cm$^{-1}$) 2958, 1718, 1610, 1561, 1260, 1129;

MS m/e 435 (MH$^+$);

Anal. Calcd for C$_{25}$H$_{26}$FN$_3$O$_3$·0.64H$_2$O: C, 67.17; H, 6.15; N, 9.40

Found: C, 67.17; H, 6.14; N, 9.12.

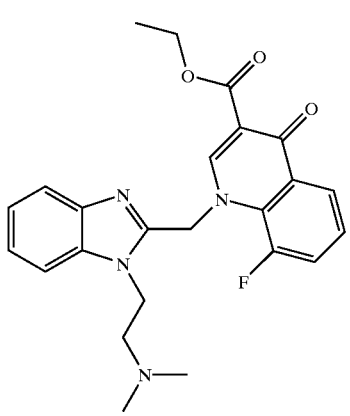

180

Compound 180 was prepared as a tan foam using the same procedure as compound 179 with compound 179b and compound 98b in 51% yield:

$^1$H NMR (DMSO-d$_6$) δ1.29 (t, J=7.2 Hz, 3H), 2.27 (s, 6H), 2.66 (t, J=6.3 Hz, 2H), 4.25 (q, J=7.2 Hz, 2H), 4.38 (t, J=6.3 Hz, 2H), 6.09 (s, 2H), 7.09 (t, J=7.2 Hz, 1H), 7.15 (t, J=7.2 Hz, 1H), 7.40–7.52 (m, 4H), 8.13 (d, J=9 Hz, 1H), 8.78 (s, 1H);

IR (KBr, cm$^{-1}$) 1725, 1695;

MS m/e 436 (MH$^+$);

Anal. Calcd for C$_{24}$H$_{25}$FN$_4$O$_3$·0.72H$_2$O: C, 64.16; H, 5.93; N, 12.47

Found: C, 64.15; H, 5.84; N, 12.11.

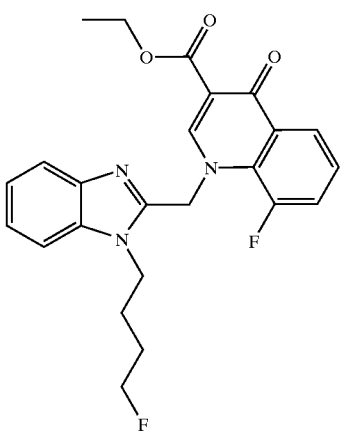

181

Compound 181 was prepared as described for compound 25 using 159c and 4-oxo-1,4-dihydro-quinoline-3-carboxylic acid ethyl ester (prepared as described by Gould, R. G.; Jacobs, W. A.; *J. Am. Chem. Soc.* 1939, 61, 2890) using BTPP as described for compound 25.

$^1$H NMR (DMSO-d6) δ: 1.29 (t, J=7.1 Hz, 2H), 1.70–1.84 (m, 4H), 4.25 (q, J=7.1 hz, 1H), 4.42–4.48 (m, 3H), 4.56 (dt, J=J, 5.9, 47 Hz, 1H), 6.06 (s, 2H), 7.15 (t, J=7.3 Hz, 1H), 7.24 (t, J=7.3 Hz, 1H), 7.44–7.49 (m, 2H), 7.62–7.66 (m, 3H), 8.26 (d, J=7.9 Hz, 1H), 8.93 (s, 1H);

MS m/e 421 (MH$^+$).

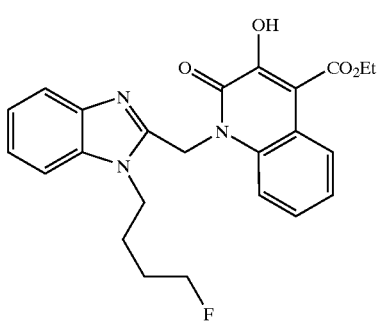

182

A solution containing the isatin 114a (215 mg, 0.61 mmol), diethyl amine (63 µL, 0.61 mmol) and ethyl diazoacetate (128 µL, 1.22 mmol) in DMF-EtOH (1:1, 6 mL) was stirred at room temperature for 15 hours. The solvents were removed in vacuo and to the residue was added 1M HCl (10 mL). After stirring for 30 min. the mixture was extracted with ethyl acetate (2×15 mL). The aqueous phase was neutralized with solid NaHCO$_3$ and extracted with ethyl acetate (2×15 mL). The organic phases were combined and washed with brine (10 mL), and dried (MgSO$_4$) to give 182 (294 mg, 100%) as a yellow solid.

$^1$H NMR (CDCl$_3$) δ8.85 (br s, 1H), 8.16 (d, J=8.5 Hz, 1H), 7.88 (d, J=7.7 Hz 1H), 7.79 (m, 1H), 7.46 (t, J=7.3 Hz, 1H), 7.32 (m, 4H), 6.04 (s, 2H), 4.55 (q, J=7.1 Hz, 2H), 4.40 (dt, J=5.6, 47 Hz, 2H), 4.31 (t, J=7.6 Hz, 2H), 1.68 (m, 4H), 1.47 (t, J=7.1 Hz, 3H);

MS m/e 438 (MH$^+$).

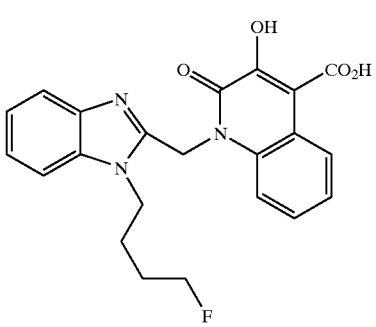

183

A mixture of the ethyl ester 182 (294 mg, 0.672 mmol) in water (5 mL), 1M NaOH (3.4 mL), dioxane (4 mL) was heated at reflux temperature for 3 hours. 1M NaOH (5 mL) was added and heating was continued for 1 hour. The mixture was cooled to room temperature and acidified to pH 3 with 1 M HCl. Extraction with ethyl acetate (4×20 mL) and washing with brine (10 mL), drying (MgSO$_4$) afforded the pure 183, 150 mg (55%) as a white solid.

$^1$H NMR (DMSO) δ7.61 (d, J=8.0 Hz, 1H), 7.52 (d, J=8.4 Hz, 1H), 7.47 (d, J=8.0 Hz, 1H), 7.31 (t, J=7.7 Hz, 1H), 7.23 (m, 2H), 7.14 (t, J 7.5 Hz, 1H), 5.88 (s, 2H), 4.50 (m, 4H), 1.80 (m, 4H);

MS m/e 410 (MH$^+$).

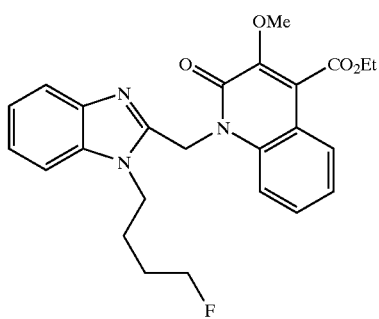

184

To a solution of the quinolone 182(52 mg, 0.12 mmol) in DMF (2 mL) was added Cs$_2$CO$_3$ (82 mg, 0.25 mmol). After stirring for 5 min. MeI (9.0 μL, 0.14 mmol) was added and stirring was continued for 4 hours. The volatiles were removed in vacuo and the residue suspended in water. The product was extracted into ethyl acetate (2×12 mL), the combined organic fractions washed with brine (5 mL) and dried (MgSO$_4$). Purification by flash column chromatography (eluent 2% methanol in methylene chloride) gave 21 mg (39%) of 184 as a white solid.

$^1$H NMR (CDCl$_3$) δ8.17 (d, J=8.6 Hz, 1H), 7.76 (m, 1H), 7.49 (t, J=8.0 Hz, 1H), 7.43 (d, J=8.0 Hz, 1H), 7.27 (m, 4H), 5.92 (s, 2H), 4.51 (q, J=7.2 Hz, 2H), 4.40 (m, 4H), 4.06 (s, 3H), 1.67 (m, 4H), 1.44 (t, J=7.2 Hz, 3H);

MS m/e 452 (MH$^+$).

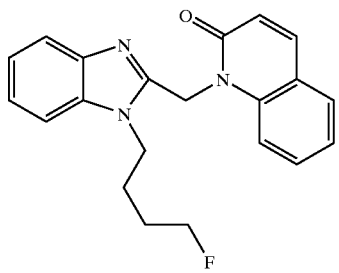

185

Compound 185 was prepared as described for compound 25 from 2-hydroxyquinoline (52 mg, 0.36 mmol) and compound 159c. Compound 185 was obtained after purification by flash column chromatography (eluent 2% methanol in methylene chloride) to give 60 mg (48%) of 185 as an off-white solid.

$^1$H NMR (DMSO) δ8.02 (d, J=9.5 Hz, 1H), 7.77 (d, J=7.7 Hz, 1H), 7.62 (d, J=8.6 Hz, 1H), 7.59 (d, J=8.0 Hz, 1H), 7.55 (t, J 8.2 Hz, 1H), 7.47 (d, J 8.0 Hz, 1H), 7.27 (d, J=7.3 Hz, 1H), 7.22 (t, J=7.3 Hz, 1H), 7.13 (t, J=7.3 Hz, 1H), 6.70 (d, J=9.5 Hz, 1H), 5.80 (s, 2H), 4.49 (m, 4H), 1.80 (m, 4H);

MS m/e 350 (MH$^+$).

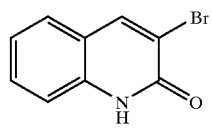

186a

Compound 186a was prepared according to the procedure reported by Sabol et al., *Synth. Commun.*, 2000, 30, 427–432.

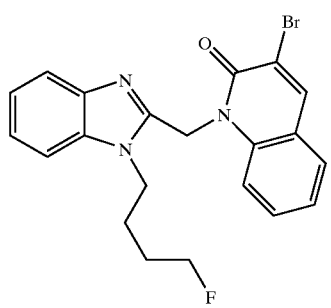

186

Compound 186 was prepared as described for the preparation of compound 25 using 186a (538 mg, 2.40 mmol) and 159c. The crude product 186 was obtained after precipitation from water. Recystallization from ethyl acetate afforded 463 mg (45%) of 186 as an off-white solid.

$^1$H NMR (DMSO) δ8.67 (s, 1H), 7.80 (d, J=7.8 Hz, 1H), 7.62 (m, 3H), 7.45 (d, J=8.0 Hz, 1H), 7.32 (t, J=7.8 Hz, 1H), 7.23 (t, J=8.0 Hz, 1H), 7.13 (t, J=8.0 Hz, 1H), 5.86 (s, 2H), 4.51 (m, 4H), 1.82 (m, 4H);

MS m/e 428 (M$^+$).

187a

To a suspension of 2,4-dihydroxy quinoline (3.00 g, 18.6 mmol) and potassium carbonate (5.14 g, 37.2 mmol) in acetone (500 mL) was added dimethyl sulfate (2.1 mL, 22 mmol) and the resulting mixture heated at reflux during 5 hrs. The solvent was removed in vacuo and the residue triturated in water. The product was collected by filtration, washed with water and triturated from methanol to give 4-methoxy 2-quinolone 187a (1.76 g, 54%) as a white solid, that had identical $^1$H NMR data as reported (Reisch et al., Arch. Pharm., 1980, 313, 751–755).

187

Compound 187 was prepared as described for compound 25 using 187a (529 mg, 3.02 mmol) and 159c. Compound 187 was purified by flash column chromatography (eluent 2% methanol in methylene chloride) to give 200 mg (17%) of 187 as an off-white solid.

$^1$H NMR (DMSO) δ7.93 (d, J=7.5 Hz, 1H), 7.58 (m, 3H), 7.47 (d, J=8.0 Hz, 1H), 7.25 (t, J=7.3 Hz, 1H), 7.22 (t, J=8.0 Hz, 1H), 7.13 (t, J=7.4 Hz, 1H), 6.14 (s, 1H), 5.76 (s, 2H), 4.48 (m, 4H), 4.00 (s, 3H), 1.78 (m, 4H);

MS m/e 380 (MH$^+$).

188

A mixture of the bromide 186 (101 mg, 0.236 mmol), Pd(PPh$_3$)$_4$ (27 mg, 0.024 mmol), vinyl tri-nbutyltin (83 μL, 0.28 mmol) in toluene (1.2 mL) was heated at reflux for 1.5 hours under a nitrogen atmosphere. The mixture was cooled to room temperature, water and ethyl acetate (15 mL) were added and the layers separated. The organic phase was washed with water (2×10 mL), brine and dried with Na$_2$SO$_4$. The remaining yellow solid was washed with hexane and diethyl ether to give 100 mg product that was further purified by reverse phase preparative HPLC to give 40 mg (45%) of 188.

$^1$H NMR (CD$_3$OD) δ8.12 (s, 1H), 7.73 (d, J 7.9 Hz, 1H), 7.50 (m, 4H), 7.27 (m, 2H), 7.18 (t, J 7.5 Hz, 1H), 6.97 (dd, J 11.3, 17.7 Hz, 1H), 6.14 (d, J 17.7 Hz, 1H), 5.89 (s, 2H), 5.42 (d, J 11.3, 1H), 4.43 (m, 4H), 1.80 (m, 4H);

MS m/e 376 (MH$^+$).

189

A mixture of the alkene 188 (21 mg, 0,056 mmol) and Pd-C (10%, 3 mg) in THF (1 mL) was stirred under a hydrogen atmosphere for 3 hours. The catalyst was filtered off and the filtrate concentrated to give compound 189 (21 mg, 100%) as a brownish solid.

$^1$H NMR (DMSO) δ7.86 (s, 1H), 7.73 (d, J=7.7 Hz, 1H), 7.60 (m, 2H), 7.48 (m, 2H), 7.23 (m, 2H), 7.13 (t, J=7.7 Hz, 1H), 5.82 (s, 2H), 4.49 (m, 4H), 2.58 (q, J=7.4 Hz, 2H), 1.77 (m, 4H), 1.21 (t, J=7.4 Hz, 3H);

MS m/e 378 (MH$^+$);

190

A mixture of the bromide 186 (51 mg, 0.119 mmol), Pd(PPh$_3$)$_4$ (14 mg, 0.012 mmol), ethoxyvinyl tri-n-butyltin (48 μL, 0.14 mmol) in toluene (1.2 mL) was heated at reflux for 2.5 hours under a nitrogen atmosphere. The mixture was cooled to room temperature, water and ethyl acetate (15 mL) were added and the layers separated. The organic phase was washed with water (2×10 mL), brine and dried with Na$_2$SO$_4$. The remaining yellow solid was triturated from diethyl ether overnight to give compound 190 (34 mg, 68%) product.

$^1$H NMR (DMSO) δ8.33 (s, 1H), 7.87 (d, J=7.9 Hz, 1H), 7.59 (m, 2H), 7.45 (d, J=8.0 Hz, 1H), 7.30 (m, 2H), 7.22 (t, J=7.3 Hz, 1H), 7.12 (t, J=7.3 Hz, 1H), 5.85 (s, 2H), 5.71 (s, 1H), 4.61 (s, 1H), 4.50 (m, 4H), 3.91 (q, J=7.0 Hz, 2H), 1.80 (m, 4H), 1.39 (t, J=7.0 Hz, 3H);

MS m/e 420 (MH$^+$);

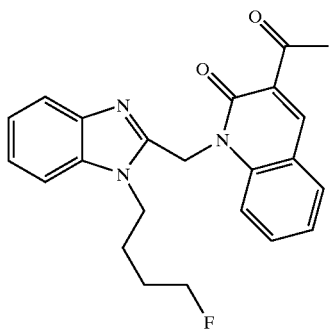

191

A solution of the vinyl ether 190 (12 mg, 0. 029 mmol) in 1:1 1M HCl-THF (2 mL) was stirred at room temperature for 1 hour. The solvents were removed and the residue precipitated from diethyl ether to give 8 mg (70%) of 191 as an off-white solid.

$^1$H NMR (DMSO) δ8.65 (s, 1H), 8.07 (d, J=7.7 Hz, 1H), 7.74 (t, J=7.9 Hz, 1H), 7.68 (d, J=8.6 Hz, 1H), 7.60 (m, 2H), 7.40 (m, 2H), 7.25 (t, J=7.3 Hz, 1H), 6.02 (s, 2H), 5.71 (s, 1H), 4.54 (m, 2H), 2.61 (s, 3H), 1.89 (m, 4H);

MS m/e 392 (MH$^+$);

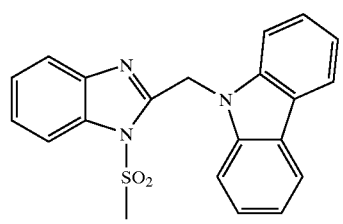

192a

To a suspension of carbazole (226 mg, 1.35 mmol) in CH$_3$CN (8 mL) was added sodium hydride (60% suspension in mineral oil, 54 mg, 1.35 mmol). This mixture was stirred at room temperature for 30 minutes prior to addition of compound 1b (500 mg, 1.45 mmol). After 3 hours, the reaction mixture was diluted with water and the orange solid was filtered. The solid was dissolved in CH$_2$Cl$_2$ and washed with brine solution. The organic layer was dried over MgSO$_4$ and evaporated. Flash column chromatography (3:1 hexanes/EtOAc) gave 53 mg (10% yield) of compound 192a:

$^1$H NMR (CDCl$_3$) δ2.58 (s, 3H), 5.92 (s, 2H), 7.17–7.21 (m, 4H), 7.31–7.38 (m, 2H), 7.51 (d, J=8.3 Hz, 2H), 7.72–7.79 (m, 2H), 8.02 (d, J=7.7 Hz, 2H);

IR (KBr, cm$^{-1}$) 3436, 2918, 1455, 1370, 1210, 1159, 1148, 744, 545;

MS m/e 376 (MH$^+$);

Anal. Calcd for C$_{21}$H$_{17}$N$_3$O$_2$S .0.25H$_2$O: C, 66.38; H, 4.64; N, 11.06

Found: C, 66.49; H, 4.64; N, 10.81.

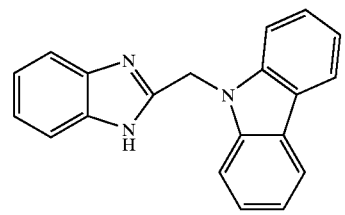

192b

Compound 192a (166 mg, 0.44 mmol) was dissolved in CH$_3$OH/CH$_2$Cl$_2$ (20 mL, 1:1 ratio). Hydrazine (1.53 g, 47.78 mmol) was added and the reaction mixture was stirred at reflux for 48 hours. The solvent was evaporated to give a white residue which was triturated with water and then filtered to give 117 mg (89% yield) of compound 192b:

$^1$H NMR (CD$_3$OD) δ5.82 (s, 2H), 7.16–7.25 (m, 4H), 7.42 (td, J=1.2, 7.1 Hz, 3H), 7.52 (d, J=8.2 Hz, 3H), 8.12 (d, J=7.6 Hz, 2H);

IR (KBr, cm$^{-1}$) 3049, 2642, 1625, 1460, 1326, 1210, 1034, 748, 722;

MS m/e 298 (MH$^+$);

Anal. Calcd for C$_{20}$H$_{15}$N$_3$.0.40H$_2$O: C, 78.87; H, 5.23; N, 13.80

Found: C, 78.88; H, 5.23; N, 13.44.

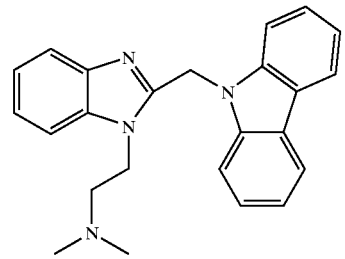

192

To compound 192b (50 mg, 0.17 mmol) suspended in THF (5 mL) was added NaH (60% suspension in mineral oil, 20 mg, 0.50 mmol). After stirring at room temperature for 20 minutes, 2-chloro-N,N-dimethylethylamine hydrochloride (27 mg, 0.19 mmol) was added and the reaction mixture was stirred at 60° C. for 16 hours. The reaction was quenched with saturated aqueous NaHCO$_3$ and was extracted with Et$_2$O. The combined organic extracts were dried over MgSO$_4$ and evaporated. Column chromatography (gradient hexanes/EtOAc, 1:1 to straight EtOAc) gave 29 mg (47% yield) of compound 192:

$^1$H NMR (CDCl$_3$) δ1.77 (s, 6H), 1.80 (t, J=7.5 Hz, 2H), 3.97 (t, J=7.5 Hz, 2H), 5.83 (s, 2H), 7.24–7.31 (m, 5H), 7.41–7.46 (m, 2H), 7.58 (d, J=8.2 Hz, 2H), 7.85 (d, J=6.4 Hz, 1H), 8.10 (dd, J=0.6, 7.2 Hz, 2H);

IR (KBr, cm$^{-1}$) 3413, 2933, 1597, 1485, 1461, 1323, 1258, 1209, 742, 718;

MS m/e 369 (MH$^+$);

Anal. Calcd for C$_{24}$H$_{24}$N$_4$.0.70H$_2$O: C, 75.64; H, 6.72; N, 14.70

Found: C, 75.87; H, 6.64; N, 14.32.

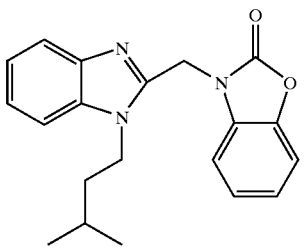

193

Compound 194 was prepared using the same procedure as compound 4 with compound 4c and 2-benzoxazolinone:
$^1$H NMR (CDCl$_3$) δ0.98 (d, J=6.6 Hz, 6H), 1.44–1.52 (m, 2H), 1.68–1.79 (m, 1H), 4.26–4.32 (m, 2H), 5.35 (s, 2H), 7.05–7.22 (m, 3H), 7.29–7.35 (m, 3H), 7.38–7.41 (m, 1H), 7.79–7.82 (m, 1H);
IR (KBr, cm$^{-1}$): 2958, 1760, 1486, 1241, 1021, 755, 741;
MS m/e 336 (MH$^+$);
Anal. Calcd for C$_{20}$H$_{21}$N$_3$O$_2$·0.25H$_2$O: C, 70.67; H, 6.38; N, 12.36
Found: C, 70.89; H, 6.41; N, 12.30.

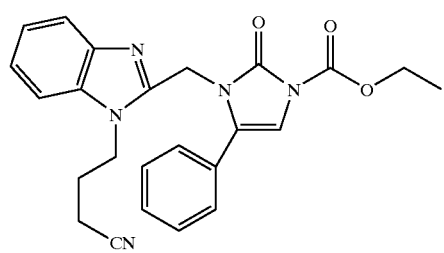

194

Compound 194 was prepared using the same procedure as compound 69 starting with compound 25b and 3-ethoxycarbonyl-5-phenyl-imidazolone (Meanwell, N. A. et al, *J. Org. Chem*, 1995, 60, 1565–82).
$^1$H NMR (d$_6$-DMSO) δ1.31 (t, J=7.0 Hz, 3H), 1.95–2.00 (m, 2H), 2.51–2.54 (m, 2H), 4.27–4.31 (m, 2H), 4.32–4.36 (m, 2H), 5.09 (s, 2H), 7.03 (d, J=6.8 Hz, 1H), 7.19–7.26 (m, 2H), 7.39–7.42 (m, 3H), 7.54–7.60 (m, 4H);
MS m/e 430 (MH$^+$).

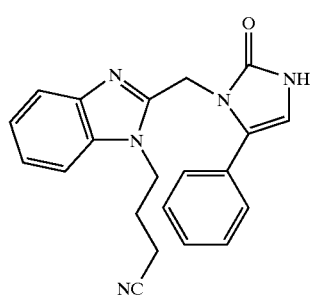

195

To a solution of 194 (62 mg, 0.14 mmol) in THF (1 mL) was added dimethylamine (2M in THF, 0.5 mL, 0.5 mmol) and stirred for 1 h. The product precipitated out the solution was collected by filtration to give 46 mg (89%) of 195 as a white solid.
$^1$H NMR (d$_6$-DMSO) δ1.99–2.02 (m, 2H), 2.56 (t, J=7.4 Hz, 2H), 4.32 (t, J=7.4 Hz, 2H), 5.07 (s, 2H), 6.65 (d, J=2.4 Hz, 1H), 7.16–7.19 (m, 1H), 7.22–7.30 (m, 2H), 7.34 (t, J=7.4 Hz, 2H), 7.50 (d, J=7.2 Hz, 2H), 7.56–7.58 (m, 2H), 10.38 (s, 1H);
MS m/e 358 (MH$^+$).

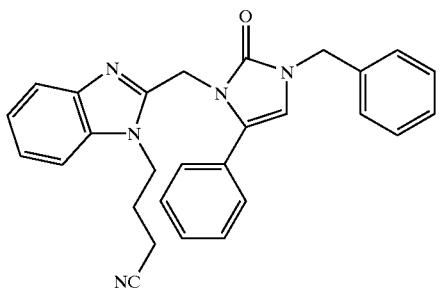

196

Compound 196 was prepared as described for compound 25.
$^1$H NMR (CDCl$_3$) δ2.05–2.10 (m, 2H), 2.32 (t, J=7.0 Hz, 2H), 4.39 (t, J=7.2 Hz, 2H), 4.86 (s, 2H), 5.14 (s, 2H), 6.24 (d, J=5.4 Hz, 1H), 7.24–7.47 (m, 13H), 7.71 (d, J=7.5 Hz, 1H);
MS m/e 448 (MH$^+$).

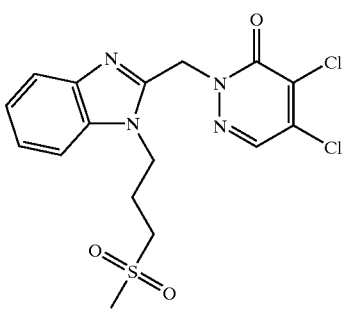

197

Compound 197 was prepared using the same procedure as compound 25 starting with compound 10d and 4,5-dichloro-3-hydroxypyridazine.
$^1$H NMR (CDCl$_3$) δ2.45–2.49 (m, 2H), 2.99 (s, 3H), 3.17 (t, J=6.9 Hz, 2H), 4.59 (t, J=7.1 Hz, 2H), 5.66 (s, 2H), 7.25–7.32 (m, 2H), 7.40 (d, J=7.8 Hz, 1H), 7.74 (d, J=7.6 Hz, 1H), 7.92 (s, 1H);
MS m/e 415 (MH$^+$);
Anal. Calcd for C$_{16}$H$_{16}$Cl$_2$N$_4$O$_3$S: C, 46.27; H, 3.88; N, 13.49. Found: C, 46.25; H, 3.90; N, 13.49.

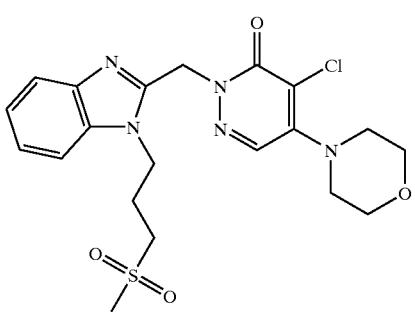

198

A solution of 197 (41 mg, 0.10 mmol) and morpholine (87 mg, 1.00 mmol) in ethanol (1 ml) was heated to reflux for 1 h. The solid formed after cooling was collected and washed by ethanol to give 31 mg (75%) of 198 as a white solid.

¹H NMR (CDCl₃) δ2.36–2.40 (m, 2H), 2.98 (s, 3H), 3.42–3.45 (m, 4H), 3.81–3.84 (m, 4H), 4.60 (t, J=7.1 Hz, 2H), 5.67 (s, 2H), 7.27–7.33 (m, 2H), 7.41 (d, J=7.7 Hz, 1H), 7.74 (s, 1H), 7.80 (d, J=7.7 Hz, 1H);

MS m/e 466 (MH⁺);

Anal. Calcd for $C_{20}H_{24}ClN_5O_4S$: C, 51.55; H, 5.19; N, 13.03. Found: C, 51.35; H, 5.05; N, 14.86.

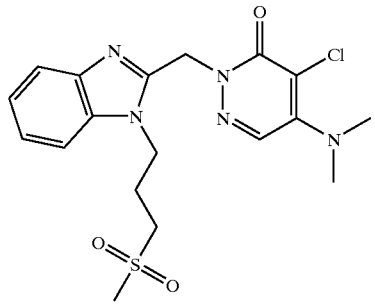

199

A solution of 197 (41 mg, 0.10 mmol) and dimethylamine (40% aq, 0.2 ml) in ethanol (1 ml) was heated to 120° C. in a sealed tube for 1 h. The solvent was removed and the residue purified by reverse phasepreparative HPLC (gradient, 10% MeOH in H₂O with 0.1% TFA to 90% MeOH in H₂O with 0.1% TFA) to give 29 mg (68%) of 199.

¹H NMR (CDCl₃) δ2.33–2.38 (m, 2H), 2.97 (s, 3H), 3.14–3.17 (m, 8H), 4.58 (t, J=7.1 Hz, 2H), 5.63 (s, 2H), 7.27–7.32 (m, 2H), 7.39 (d, J=7.7 Hz, 1H), 7.72 (s, 1H), 7.78 (d, J=7.7 Hz, 1H);

MS m/e 424 (MH⁺);

Anal. Calcd for $C_{18}H_{22}ClN_5O_3S$: C, 50.99; H, 5.23; N, 16.52;

Found: C, 50.91; H, 4.97; N, 16.37.

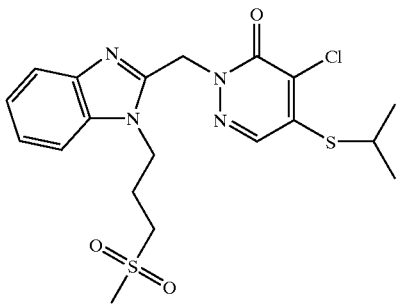

200

A solution of 197 (41 mg, 0.10 mmol), 2-propanethiol (76 mg, 1.00 mmol) and TEA (20 mg, 0.20 mmol) in ethanol (1 ml) was heated to reflux for 1 h. The solvent was removed and the residue purified by reverse phase preparative HPLC (gradient, 10% MeOH in H₂O with 0.1% TFA to 90% MeOH in H₂O with 0.1% TFA) to give 26 mg (57%) of 200.

¹H NMR (CDCl₃) δ1.44 (d, J=6.6 Hz, 6H), 2.39–2.44 (m, 2H), 2.97 (s, 3H), 3.16 (t, J=7.0 Hz, 2H), 3.64–3.69 (m, 1H), 4.58 (t, J=7.1 Hz, 2H), 5.63 (s, 2H), 7.24–7.31 (m, 2H), 7.39 (d, J=7.8 Hz, 1H), 7.75 (d, J=7.8 Hz, 1H), 7.81 (s, 1H);

MS m/e 455 (MH⁺).

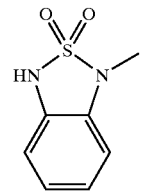

201

A solution of N-methyl-1,2-phenylenediamine (2.44 g, 20.0 mmol) and sulfamide (2.11 g, 22.0 mmol) in diglyme (20 mL) was heated to reflux for 1 h. The solvent was removed and the residue taken up in EtOAc (300 ml) and washed with 1N HCl then saturated sodium chloride. The organic layer was dried over MgSO₄ and evaporated to give 3.680 g (99%) of 201 as a red viscous oil. The crude product was used for the next reaction without further purification.

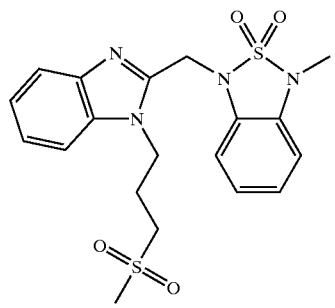

202

Compound 202 was prepared using the same precedure as Compound 25 starting with Compound 10d and 201.

¹H NMR (CDCl₃) δ2.23–2.30 (m, 2H), 2.80 (s, 3H), 3.09 (t, J=7.5 Hz, 2H), 3.50 (s, 3H), 4.52 (t, J=8.0 Hz, 2H), 5.13 (s, 2H), 6.76 (d, J=7.7 Hz, 1H), 6.93 (t, J=7.7 Hz, 1H), 7.02 (t, J=7.6 Hz, 1H), 7.23 (d, J=7.8 Hz, 1H), 7.32–7.44 (m, 2H), 7.44–7.46 (m, 1H), 7.82–7.84 (m, 1H);

MS m/e 435 (MH⁺).

N-Hydroxy-4-(2-hydroxymethyl-benzoimidazol-1-yl)-butyramidine

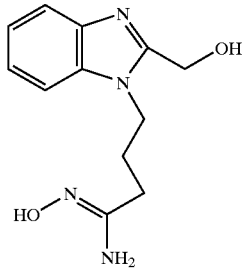

203

A mixture containing 4-(2-hydroxymethyl-benzoimidazol-1-yl)-butyronitrile, 25a, (40.0 g, 186 mmol), hydroxylamine hydrochloride (46.5 g, 0.689 mole) and potassium carbonate (51.4 g, 0.372 mole) in ethanol (400 mL) and water (200 mL) was heated at 80° C. and stirred overnight. The solvents were removed in vacuo and water was added. The white precipitate was collected by filtration, washed with water and dried in vacuo to afford N-hydroxy-4-(2-hydroxymethyl-benzoimidazol-1-yl)-butyramidine (35.8 g, 78%) as a white solid:

¹H NMR (DMSO) δ1.97–2.06 (m, 4H), 4.27 (t, 2H, J=7.4 Hz), 4.72 (s, 2H), 5.44 (br s, 2H), 5.64 (br s, 1H), 7.18 (t, 1H, J=7.5 Hz), 7.23 (t, 1H, J=7.5 Hz), 7.57 (d, 1H, J=7.5 Hz), 7.59 (d, 1H, J=7.5 Hz), 8.83 (s, 1H);

MS m/e 249 (MH⁺);

[1-(3-[1,2,4]Oxadiazol-3-yl-propyl)-1H-benzoimidazol-2-yl]-methanol

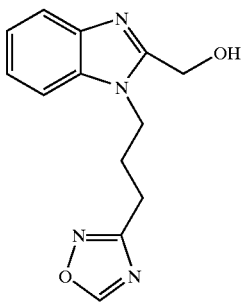

204

A suspension of N-hydroxy-4-(2-hydroxymethyl-benzoimidazol-1-yl)-butyramidine, 203, (500 mg, 2.01 mmol) in trimethyl orthoformate (5 mL) in the presence of BF₃.OEt₂ (50 μL) in a sealed tube was placed in a microwave oven (Smith Creator, Personal Chemistry) and heated at 100° C. for 15 min while stirring, resulting in the dissolution of all the material. The reaction was repeated 5 times. The 6 batches were combined and concentrated in vacuo. The residue was treated with 1M HCl (15 mL) and THF (15 mL) and left overnight. Concentration followed by trituration from dichloromethane and recrystallization from isopropyl alcohol and methanol afforded [1-(3-[1,2,4]oxadiazol-3-yl-propyl)-1H-benzoimidazol-2-yl]-methanol (2.28 g, 73%) as a white solid:

¹H NMR (DMSO) δ2.27 (quint, 2H, J=7.4 Hz), 2.95 (t, 2H, J=7.5 Hz), 4.52 (t, 2H, J=7.6 Hz), 5.06 (s, 2H), 6.65 (br s, 1H), 7.57 (t, 1H, J=7.5 Hz), 7.60 (t, 1H, J=7.3 Hz), 7.79 (d, 1H, J=7.8 Hz), 8.01 (d, 1H, J=7.6 Hz), 9.54 (s, 1H);

MS m/e 259 (MH⁺);

2-Chloromethyl-1-(3-[1,2,4]oxadiazol-3-yl-propyl)-1H-benzoimidazole, HCl Salt

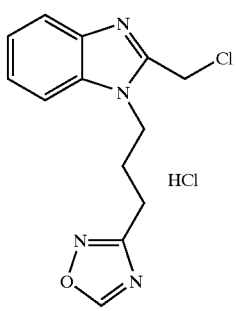

205

To a cooled (0° C.) suspension of [1-(3-[1,2,4]oxadiazol-3-yl-propyl)-1H-benzoimidazol-2-yl]-methonal, 204, (850 mg, 3.29 mmol) in dichloro methane (20 mL) was added thionyl chloride (360 μl, 4.94 mmol). The solution was stirred at 0° C. for 15 min. and then for 1.5 h at ambient temperature. The solution was concentrated in vacuo to give 2-chloromethyl-1-(3-[1,2,4]oxadiazol-3-yl-propyl)-1H-benzoimidazole, HCl salt as a white solid in quantitative yield, which was used without further purification:

¹H NMR (DMSO) δ2.27 (quint, 2H, J=7.5 Hz), 2.95 (t, 2H, J=7.5 Hz), 4.55 (t, 2H, J=7.1 Hz), 5.27 (s, 2H), 7.46–7.53 (m, 2H), 7.78 (d, 1H, J=7.9 Hz), 7.89 (d, 1H, J=7.9 Hz), 9.55 (s, 1H);

MS m/e 277 (MH⁺);

3-Cyclopropyl-1-[1-(3-[1,2,4]oxadiazol-3-yl-propyl)-1H-benzoimidazol-2-ylmethyl]-1H-quinazoline-2,4-dione

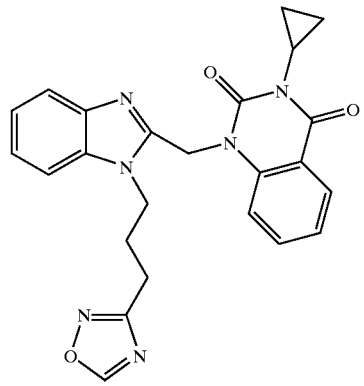

206

To a solution of 3-cyclopropyl-1H-quinazoline-2,4-dione, 159a, (83 mg, 0.41 mmol) in DMF (6 mL) was added BTPP (269 mg, 0.86 mmol) and the solution was stirred for 15 min. 2-Chloromethyl-1-(3-[1,2,4]oxadiazol-3-yl-propyl)-1H-benzoimidazole, 205, HCl salt (128 mg, 0.41 mmol) was added and stirring was continued for 1 h. The solution was concentrated and water was added to the residue. The white precipitate was collected by filtration, washed with water and purified by flash chromatography (eluent dichloromethane-ethyl acetate 2:1, 1:1) to afford 3-cyclopropyl-1-[1-(3-[1,2,4]oxadiazol-3-yl-propyl)-1H-benzoimidazol-2-ylmethyl]-1H-quinazoline-2,4-dione (26 mg, 14%) as a white solid:

¹H NMR (DMSO-d₆) δ0.72–0.75 (m, 2H), 1.02–1.06 (m, 2H), 2.26 (quint, 2H, J=7.4 Hz), 2.74–2.78 (m, 1H), 2.95 (t, 2H, J=7.4 Hz), 4.49 (t, 2H, J=7.4 Hz), 5.64 (s, 2H), 7.14 (t, 1H, J=7.6 Hz), 7.24 (t, 1H, J 7.6 Hz), 7.28 (t, 1H, J 7.5 Hz), 7.49 (t, 1H, J=8.0 Hz), 7.51 (d, 1H, J=8.5 Hz), 7.62 (d, 1H, J=8.1 Hz), 7.68 (t, 1H, J=7.9 Hz), 8.07 (d, 1H, J=7.9 Hz), 9.55 (s, 1H);

MS m/e 443 (MH⁺);

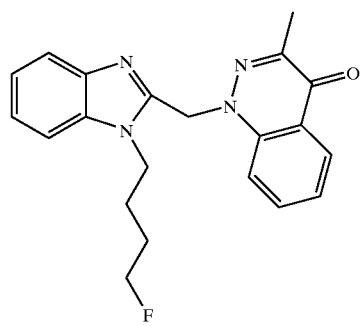

207

To a solution of 3-methyl-1H-cinnolin-4-one (200 mg, 1.25 mmol) (prepared as described by B. Singh, J. Het. Chem. 1991, 881–883) in THF (2 ml) was added BTPP (1.15 ml, 3.75 mmol) and the mixture stirred for 15 minutes at 23° C. Compound 159c was added and the mixture stirred for 12 h. The solvent is removed and the residue triturated with water. A tan solid was isolated by filtration. The solid is further purified by column chromatography (50% EtOAc in hexanes) as elutant to give 170 mg (37%) of 207.

¹H NMR (DMSO-d₆) δ:1.68–1.77 (m, 4H), 2.30 (s, 3H), 4.40–4.42 (m, 3H), 4.50–4.52 (m, 1H), 6.04 (s, 2H), 7.16 (t, J=7.6 Hz, 1H), 7.25 (t, J=7.7 Hz, 1H), 7.44 (t, J=7.2 Hz, 1H), 7.55 (d, J=7.7 Hz, 1H), 7.60 (d, J=8.0 Hz, 1H), 7.78 (t, 7.4 Hz, 1H), 7.90 (d, J=8.9 Hz, 1H), 8.14 (d, J=8.1 Hz, 1H); MS m/e 364 (MH⁺).

208

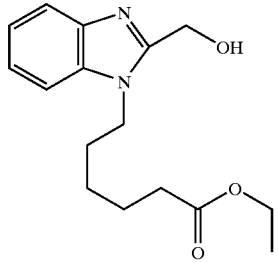

Compound 208 was prepared as described for compound 25, using 2-hydroxymethylbenzimidazole and ethyl 6-bromohexanoate.

¹H NMR (CD₃OD) δ1.18–1.22 (m, 3H), 1.42–1.45 (m, 2H), 1.66–1.69 (m, 2H), 1.90–1.92 (m, 2H), 2.30–2.33 (m, 2H), 4.06–4.10 (m, 2H), 4.35–4.38 (m, 2H), 4.89 (s, 2H), 7.23–7.32 (m, 2H), 7.51–7.53 (m, 1H), 7.60–7.63 (m, 1H); MS m/e 291 (MH⁺).

209

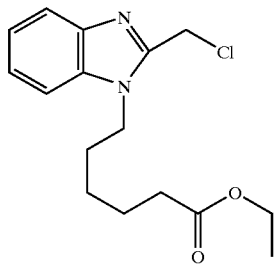

Compound 209 was prepared as described for compound 4c.

¹H NMR (CD₃OD) δ1.21 (t, J=7.1 Hz, 3H), 1.47–1.54 (m, 4H), 1.65–1.74 (m, 2H), 1.95–2.05 (m, 2H), 2.34 (t, J=7.2 Hz, 2H), 4.03–4.12 (m, 2H), 4.58 (t, J=7.7 Hz, 2H), 5.31 (s, 2H), 7.68–7.72 (m, 2H), 7.83–7.85 (m, 1H), 7.97–8.00 (m, 1H); MS m/e 309 (MH⁺).

210

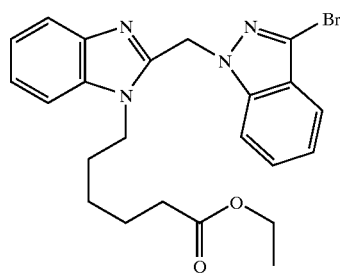

Compound 210 was prepared as described for compound 25 using compound 4a.

¹H NMR (CD₃OD) δ1.18–1.32 (m, 5H), 1.46–1.61 (m, 4H), 2.21 (t, J=7.3 Hz, 2H), 4.04–4.11 (m, 2H), 4.49 (t, J=7.8 Hz, 2H), 6.20 (s, 2H), 7.33–7.37 (m, 1H), 7.54–7.60 (m, 3H), 7.64–7.68 (m, 1H), 7.73–7.83 (m, 3H); MS m/e 469, 471 (MH⁺).

Biological Activity

The antiviral activity of these compounds against respiratory syncytial virus was determined in HEp-2 (ATCC CCL 23) cells that were seeded in 96 well microtiter plates at 1.5×10⁴ cells/100 μL/well in DMEM (Dulbecco's Modified Eagle's Medium) supplemented with penicillin, streptomycin, glutamine, and 10% fetal bovine serum. The cells were incubated overnight at 37° C., the culture medium was removed, and cells were infected (100 μL volume in medium containing 2% fetal bovine serum) with respiratory syncytial virus Long strain at 5000 plaque forming units/mL. The compounds, 100 μL at appropriate dilution, were added to the cells 1 hour post infection. After incubation for 4 days at 37° C., the plates were stained with MTT solution (3-[4,5-dimethlythiazol-2-yl]-2,5-diphenyltetrazolium bromide) and incubated for 4 hours at 37° C. The media was aspirated from the cells and 100 μL/well of acidified isopropanol (per liter: 900 mL isopropanol, 100 mL Triton X100, and 4 mL conc. HCl) was added. Plates were incubated for 15 minutes at room temperature with shaking, and an optical density (OD 540) reading at 540 nanometer (nm) was obtained. The optical density reading is proportional to the number of viable cells. The increase in the number of viable cells reflects the protective, antiviral activity of the compound. Assays comparing MTT staining in uninfected cells containing compound with uninfected cells in the absence of compound provide a measure of cellular toxicity. The control compound in this assay is Ribavirin which exhibits 100% cell protection at 2.5 g/mL (corresponding to 10.2 μM).

The antiviral activity of compounds, designated as EC₅₀, is presented as a concentration that produces 50% cell protection in the assay. The compounds disclosed in this application show antiviral activity with EC₅₀'s between 50 μM and 0.001 μM. Ribavirin has an EC₅₀ of 3 μM in this assay.

What is claimed is:

1. A compound of Formula I, and pharmaceutically acceptable salts thereof,

Formula I

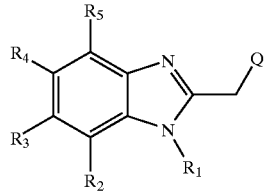

wherein:

R₁ is —(CR$^a$R$^b$)$_n$—X;

R$^a$, R$^b$ are each independently selected from the group consisting of H, C₁₋₆ alkyl; each of said C₁₋₆ alkyl being optionally substituted with one to six same or different halogen;

X is H or C₁₋₆ alkyl; said C₁₋₆ alkyl being optionally substituted with a member selected from the group consisting of one to six same or different halogen or hydroxy;

n is 1–6;

R₂ and R₅ are independently halogen or H;

R₃ and R₄ are each independently selected from the group consisting of H, halogen and C₁₋₆ alkyl; said C₁₋₆ alkyl can be optionally substituted with one to six same or different halogen;

Q is a member selected from the group consisting of

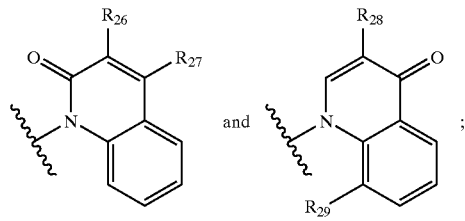

$R^h$ is H or $C_{1-6}$ alkyl;

$R_{26}$ is selected from the group consisting of H, halogen, $C_{1-6}$ alkyl; $C_{2-6}$ alkenyl, $OR^h$ and $COR^h$; said $C_{2-6}$ alkenyl being optionally substituted with $OR^h$;

$R_{27}$ is H, $OR^h$ or $CO_2R^h$;

$R_{28}$ is $CO_2R^h$; and $R_{29}$ is H or halogen.

2. A compound of claim 1 wherein:

$R^a$ and $R^b$ are hydrogen.

3. A compound of claim 1 wherein:

$R_1$ is —$(CH_2)_n$—X and n is 2–4.

4. A compound of claim 1 wherein $R_3$ and $R_4$ are each indepently selected from the group consisting of H, flourine and $C_{1-2}$ alkyl; said $C_{1-2}$ alkyl being optionally substituted with one to three flourine atoms.

5. A compound of claim 1 wherein:

$R_1$ is 3-methyl-2-butyl or —$(CH_2)_n$—X and; wherein n is 2–4.

6. A compound in claim 1 wherein:

$R_2$ and $R_5$ are each independently H.

7. A pharmaceutical composition which comprises a therapeutically effective amount of one or more of the aforementioned compounds as claimed in any one of claim 1, 2, 3, 4, 5, or 6, and a pharmaceutically acceptable carrier.

* * * * *